United States Patent
Takemoto et al.

(10) Patent No.: US 7,026,334 B1
(45) Date of Patent: Apr. 11, 2006

(54) THIAZOLIDINE COMPOUNDS AND PHARMACEUTICAL COMPOSITIONS EXHIBITING THROMBOPOIETIN RECEPTOR AGONISM

(75) Inventors: Hiroshi Takemoto, Osaka (JP); Masami Takayama, Osaka (JP); Takeshi Shiota, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 441 days.

(21) Appl. No.: 10/048,008

(22) PCT Filed: Jul. 24, 2000

(86) PCT No.: PCT/JP00/04909

§ 371 (c)(1),
(2), (4) Date: Jan. 25, 2002

(87) PCT Pub. No.: WO01/07423

PCT Pub. Date: Feb. 1, 2001

(30) Foreign Application Priority Data

Jul. 26, 1999 (JP) ............................. 11-211164

(51) Int. Cl.
*A61K 31/427* (2006.01)
*C07D 417/12* (2006.01)

(52) U.S. Cl. ........................ 514/314; 514/342; 514/369; 546/167; 546/270.4; 548/183

(58) Field of Classification Search ................. 548/183; 546/167, 270.4; 514/314, 342, 369
See application file for complete search history.

(56) References Cited

U.S. PATENT DOCUMENTS

| | | | |
|---|---|---|---|
| 5,330,998 A | 7/1994 | Clark et al. | 514/369 |
| 5,955,616 A | 9/1999 | Ohtani et al. | 548/183 |
| 6,147,100 A | 11/2000 | Seno et al. | 514/369 |

FOREIGN PATENT DOCUMENTS

| | | |
|---|---|---|
| AU | 8931077 | 3/1990 |
| EP | 0 389 699 A1 | 10/1990 |
| FI | 9004413 | 6/1990 |
| JP | 1-299289 | 12/1989 |
| NO | 178068 | 10/1995 |
| PT | 89922 | 11/1989 |
| WO | WO 89/08652 | 9/1989 |

OTHER PUBLICATIONS

B. Hulin et al., "Novel Thiazolidine–2,4–diones as Potent Euglycemic Agents," J. Med. Chem., 25, 1992, pp. 1853–1864.
M. Ebisawa et al., "Novel Thiazolidinedione Derivatives with Retinoid Synergistic Activity," Biol. Pharm. Bull 21(5), May 1998, pp. 547–549.
H. Sugimoto et al., "Metabolic Changes of Prostaglandis in Diabetic Rats and Restoration by Insulin Therapy," Fukuoka Acta Med. 73(2), 1982, pp. 76–83.

*Primary Examiner*—Laura L. Stockton
(74) *Attorney, Agent, or Firm*—Finnegan, Henderson, Farabow, Garrett & Dunner, L.L.P.

(57) ABSTRACT

Pharmaceutical compositions containing as an active ingredient compounds of the general formula (I), prodrugs of the same, pharmaceutically acceptable salts of both, or solvates of them and exhibiting thrombopoietin receptor agonism:

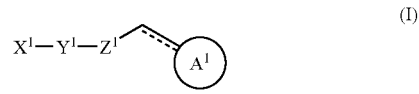

(I)

wherein $X^1$ is optionally substituted heteroaryl or the like; $Y^1$ is —$NR^4CO$—$(CH_2)_{0-2}$— or the like (wherein $R^4$ is a hydrogen or the like); $Z^1$ is optionally substituted arylene or the like; and $A^1$ is a ring represented by general formula (II) or (III):

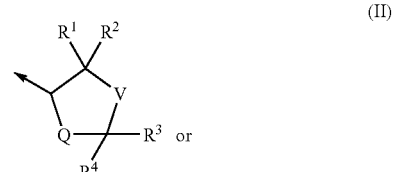

(II)

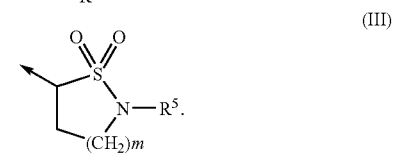

(III)

18 Claims, 2 Drawing Sheets

THIAZOLIDINE COMPOUNDS AND PHARMACEUTICAL COMPOSITIONS EXHIBITING THROMBOPOIETIN RECEPTOR AGONISM

DESCRIPTION

Pharmaceutical compositions exhibiting thrombopoietin receptor agonism

1. Technical Field

The present invention relates to pharmaceutical compositions exhibiting thrombopoietin receptor agonism.

2. Background Art

Thrombopoietin, polypeptide cytokine composed of 332 amino acids, activates the production of platelets by stimulating the differentiation and proliferation of megakaryocytes through the receptor and is expected as a medicine for hemopathy accompanied with the unusual number of platelets, for example, thrombocytopenia and the like. DNA sequences encoding the thrombopoietin receptor have been described in Proc. Natl. Acad. Sci., 189:5640–5644 (1992). Low molecular peptides having an affinity for the thrombopoietin receptor is also known (JP98/72492A, and W096/40750), but these peptide derivatives are not generally practical for oral administration.

1,4-Benzodiazepine derivatives as a low molecule compound having an affinity to the thrombopoietin receptor is described in JP99/1477A.

The compounds having a similar structure of the present invention compound are described in JP92/99770A, Chem. Pharm. Bull., 1982, 30, 3580, JP94/172339A (EP512899), JP90/308240A, W097/32863, Arzneim. Forsch/Drug Res., 1998, 48, 651, JP95/173143A, JP93/85551A, JP85/443A, JP96/245602A JP96/157462A, JP96/143556A and the like, but the affinity for thrombopoietin receptor is not described therein.

Disclosure of Invention

The object of the present invention is to prepare pharmaceutical compositions exhibiting thrombopoietin receptor agonism and provide orally administrable platelet production modifiers.

In the above situation, the inventors of the present invention have found that the following compounds exhibit strong thrombopoietin receptor agonism.

The present invention relates to:
I) A pharmaceutical composition exhibiting thrombopoietin agonism which contains as an active ingredient a compound of the formula (I):

(I)

wherein $X^1$ is optionally substituted aryl, optionally substituted aralkyl, optionally substituted heteroaryl, optionally substituted heteroarylalkyl, or optionally substituted non-aromatic heterocyclic group; $Y^1$ is —$NR^A CO$—$(CH_2)_{0-2}$—, —$NR^A CO$—$(CH_2)_{0-2}$—W—, —$NR^A CO$—$CH=CH$—, —W—$(CH_2)_{1-5}$—$NR^A CO$—$(CH_2)_{0-2}$—, —W—$(CH_2 CH_{1-5}$—$CONR^A$—$(CH_2)_{0-2}$—, —$CONR^A$—$(CH_2)_{0-2}$—, —$(CH_2 CH_{0-5}$—$NR^A$—$SO_2$—$(CH_2 CH_{0-5}$—, —$(CH_2 CH_{0-5}$—$SO_2$—$NR^A$—$(CH_2 CH_{0-5}$—, —$NR^A$—$(CH_2)_{0-2}$—, —$NR^A$—$CO$—$NR^A$—, —$NR^A$—$CS$—$NR^A$—, —$N=C(-SR^A)$—$NR^A$—, —$NR^A CSNR^A CO$—, —$N=C(-SR^A)$—$NR^A CO$—, —$NR^A$—$(CH_2 CH_{1-2}$—$NR^A$—$CO$—, —$NR^A CONR^A NR^F CO$—, or —$N=C(-NR^A R^A)$—$NR^A$—$CO$—, wherein $R^A$ is each independently a hydrogen atom, optionally substituted lower alky, optionally substituted aryl, optionally substituted aralkyl, optionally substituted heteroaryl, or optionally substituted heteroarylalkyl, $R^F$ is a hydrogen atom or optionally substituted aryl, W is an oxygen atom or a sulfur atom;

$Z^1$ is optionally substituted arylene, optionally substituted heteroarylene, optionally substituted non-aromatic heterocycle-diyl, or optionally substituted cycloalkyl-diyl;

$A^1$ is a ring represented by the formula:

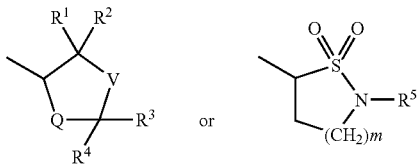

wherein $R^1$ and $R^2$ are both hydrogen atoms or taken together may form an oxygen atom or a sulfur atom; $R^3$ and $R^4$ are both hydrogen atoms or taken together may form an oxygen atom or a sulfur atom; $R^5$ is a hydrogen atom or lower alkyl; Q and V are each independently —O—, —S—, —$NR^B$— (wherein $R^B$ is a hydrogen atom or lower alkyl), or —$CH_2$—; m is 1, 2, or 3;

a broken line (- - -) represents the presence or absence of a bond, its prodrug, or their pharmaceutically acceptable salt, or solvate thereof.

In more detail, the invention relates to the following II) to XX).

II) A pharmaceutical composition exhibiting thrombopoietin agonism which contains a compound of I), wherein $X^1$ is optionally substituted 5-member heteroaryl or a group represented by the formula:

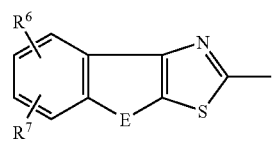

wherein E is —$(CH_2)_{1-3}$—, —O—$CH_2$—, or —S—$CH_2$—; $R^6$ and $R^7$ are each independently a hydrogen atom, optionally substituted lower alkyl, carboxy, lower alkyloxycarbonyl, optionally substituted aminocarbonyl, optionally substituted thienyl, or optionally substituted phenyl.

Preferred is a pharmaceutical composition exhibiting thrombopoietin agonism which contains a compound of I), wherein $X^1$ is phenyl optionally substituted with one or more group(s) selected from lower alkyl, lower alkyloxy, lower alkylthio, arylazo, aralkyloxy, aryl, halo(lower)alkyl, halogen, and hydroxy.

III) A pharmaceutical composition exhibiting thrombopoietin agonism which contains a compound of I), wherein $X^1$ is a group represented by the formula:

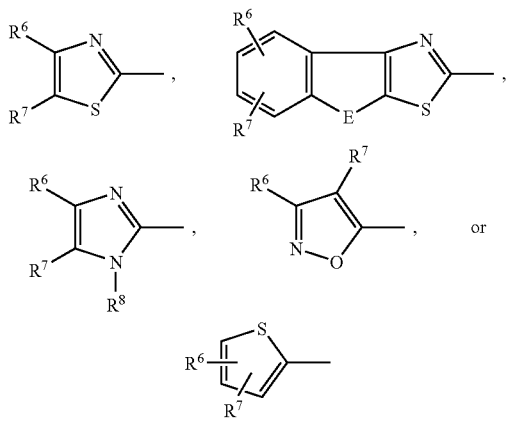

wherein E is $-(CH_2)_{1-3}-$, $-O-CH_2-$, or $-S-CH_2-$; $R^6$ and $R^7$ are each independently a hydrogen atom, optionally substituted lower alkyl, carboxy, lower alkyloxycarbonyl, optionally substituted aminocarbonyl, optionally substituted thienyl, or optionally substituted phenyl; $R^8$ is a hydrogen atom or lower alkyl.

IV) A pharmaceutical composition of any one of I) to III), wherein $Y^1$ is $-NHCO-$, $-CONH-$, $-NHCH_2-$, or $-NHSO_2-$.

V) A pharmaceutical composition of any one of I) to IV), wherein $Z^1$ is 1,4-phenylene.

VI) A pharmaceutical composition of any one of I) to V), wherein $A^1$ is a ring represented by the formula:

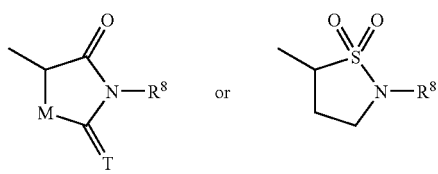

wherein $R^8$ is a hydrogen atom or lower alkyl; M is $-S-$, $-O-$, $-N(R^c)-$, or $-CH_2-$ (wherein $R^c$ is a hydrogen atom or lower alkyl); T is an oxygen atom or a sulfur atom.

A pharmaceutical composition exhibiting thrombopoietin agonism of any one of I) to V), wherein $A^1$ is a ring represented by the formula:

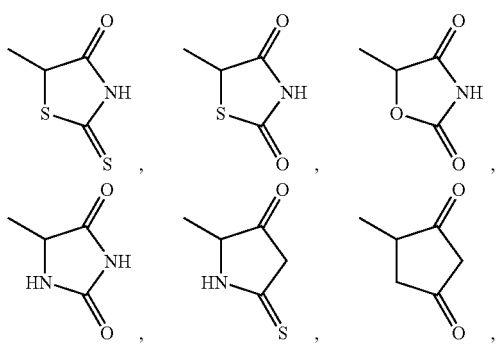

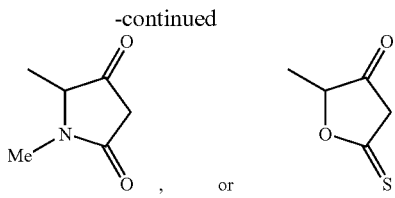

is preferred.

VII) A pharmaceutical composition of any one of I) to VI), wherein the broken line represents the presence of a bond.

VIII) A pharmaceutical composition exhibiting thrombopoietin agonism of any one of I) to VII), which is for treating or preventing hemopathy.

IX) A pharmaceutical composition exhibiting thrombopoietin agonism of any one of I) to VII), which is a platelet production modifier.

X) Use of a compound of any one of I) to VII), for preparation of a pharmaceutical composition for treating hemopathy.

XI) A method for treating hemopathy of a mammal, including a human, which comprises administration to said mammal of a compound of any one of I) to VII) in a pharmaceutically effective amount.

XII) A compound represented by the formula (II)

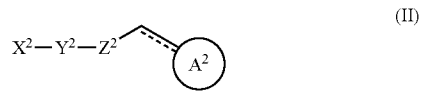

(II)

wherein $X^2$ is optionally substituted 5-member heteroaryl or a group represented by the formula:

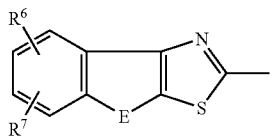

wherein E is $-(CH_2)_{1-3}-$, $-O-CH_2-$, or $-S-CH_2-$; $R^6$ and $R^7$ are each independently a hydrogen atom, optionally substituted lower alkyl, carboxy, lower alkyloxycarbonyl, optionally substituted aminocarbonyl, optionally substituted thienyl, or optionally substituted phenyl;

$Y^2$ is $-NR^GCO-(CH_2)_{0-2}-$, $-NR^GCO-(CH_2)_{0-2}-W-$, $-NR^GCO-CH=CH-$, $-W-(CH_2)_{1-5}-NR^GCO-(CH_2)_{0-2}-$, $-W-(CH_2)_{1-5}-CONR^G-(CH_2)_{0-2}-$, $-CONR^G-(CH_2)_{0-2}-$, $-(CH_2)_{0-5}-NR^G-SO_2-(CH_2)_{0-5}-$, $-(CH_2)_{0-5}-SO_2-NR^G-(CH_2)_{0-5}-$, $-NR^G-(CH_2)_{0-2}-$, $-NR^G-CO-NR^G-$, $-NR^G-CS-NR^G-$, $-N=C(-SR^G)-NR^G-$, $-NR^GCSNR^GCO-$, $-N=C(-SR^G)-NR^GCO-$, $-NR^G-(CH_2)_{1-2}-NR^G-CO-$, $-NR^GCONR^GNR^FCO-$, or $-N=C(-NR^GR^G)-NR^G-CO-$, wherein $R^G$ is each independently a hydrogen atom or optionally substituted lower alkyl, $R^F$ is a hydrogen atom or optionally substituted aryl, W is an oxygen atom or a sulfur atom;

$Z^2$ is optionally substituted phenylene, optionally substituted 2,5-pyridine-diyl, optionally substituted 2,5-thiophene-diyl, or optionally substituted 2,5-furan-diyl;

$A^2$ is a ring represented by the formula:

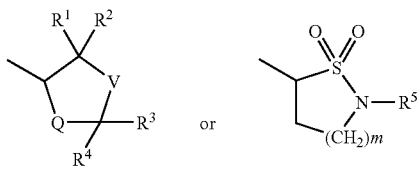

wherein $R^1$ and $R^2$ are both hydrogen atoms or taken together may form an oxygen atom or a sulfur atom; $R^3$ and $R^4$ are both hydrogen atoms or taken together may form an oxygen atom or a sulfur atom; $R^6$ is a hydrogen atom or lower alkyl; Q and V are each independently —O—, —S—, —NRB— (wherein $R^B$ is a hydrogen atom or lower alkyl), or —CH$_2$—; m is 1, 2, or 3; a broken line (- - -) represents the presence or absence of a bond, provided that $X^2$ is not oxazole, its prodrug, or their pharmaceutically acceptable salt, or solvate thereof.

XIII) A compound of XII), wherein $X^2$ is a group represented by the formula:

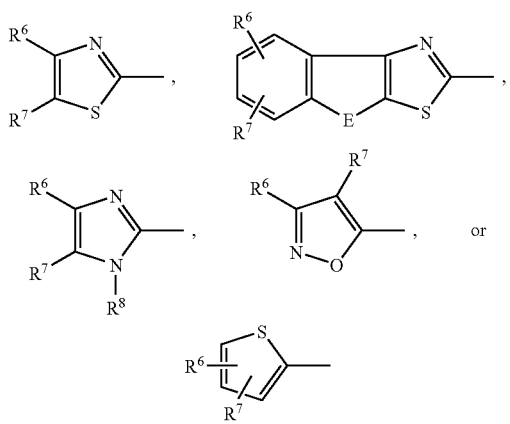

wherein E is —(CH$_2$)$_{1-3}$—, —O—CH$_2$—, or —S—CH$_2$—; $R^6$ and $R^7$ are each independently a hydrogen atom, optionally substituted lower alkyl, carboxy, lower alkyloxycarbonyl, optionally substituted aminocarbonyl, optionally substituted thienyl, or optionally substituted phenyl; $R^8$ is a hydrogen atom or lower alkyl, its prodrug, or their pharmaceutically acceptable salt, or solvate thereof.

XIV) A compound of XII), wherein $X^2$ is a group represented by the formula:

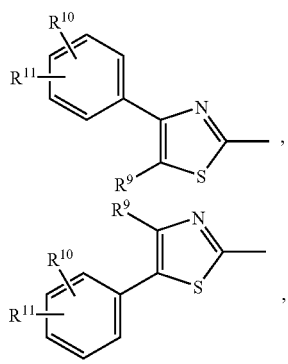

-continued

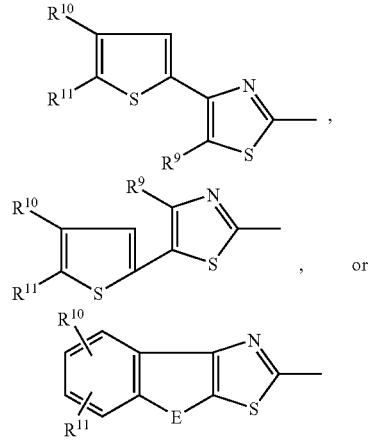

wherein E is as defined in XII;
$R^9$ is a hydrogen atom, optionally substituted lower alkyl, carboxy, lower alkyloxycarbonyl, or optionally substituted aminocarbonyl;
$R^{10}$ and $R^{11}$ are each independently a hydrogen atom, halogen, carboxy, lower alkyloxycarbonyl, optionally substituted aminocarbonyl, nitro, or optionally substituted amino, its prodrug, or their pharmaceutically acceptable salt, or solvate thereof.

XV) A compound of any one of XII) to XIV), wherein $Y^2$ is —NHICO—, —CONH—, —NHCH$_2$—, or —NHSO$_2$—, its prodrug, or their pharmaceutically acceptable salt, or solvate thereof.

XVI) A compound of any one of XII) to XIV), wherein $Z^2$ is 1,4-phenylene, its prodrug, or their pharmaceutically acceptable salt, or solvate thereof.

XVII) A compound of any one of XII) to XVI), wherein A2 is a ring represented by the formula:

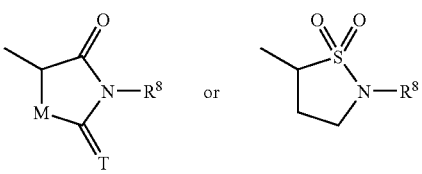

wherein $R^8$ is a hydrogen atom or lower alkyl; M is —S—, —O—, —N($R^c$)—, or —CH$_2$— (wherein $R^c$ is a hydrogen atom or lower alkyl); T is an oxygen atom or a sulfur atom, its prodrug, or their pharmaceutically acceptable salt, or solvate thereof.

XVIII) A compound of any one of XII) to XVII), wherein the broken line represents the presence of a bond, its prodrug, or their pharmaceutically acceptable salt, or solvate thereof.

XIX) A compound represented by the formula III-A:

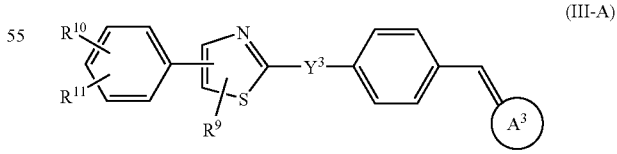

(III-A)

wherein, $R^9$ is a hydrogen atom, optionally substituted lower alkyl, carboxy, lower alkyloxycarbonyl, or optionally substituted aminocarbonyl;
$R^{10}$ and $R^{11}$ are each independently a hydrogen atom, halogen, carboxy, lower alkyloxycarbonyl, optionally substituted aminocarbonyl, nitro, or optionally substituted amino;

$Y^3$ is —NHCO— or —CONH—;

$A^3$ is a ring represented by the formula:

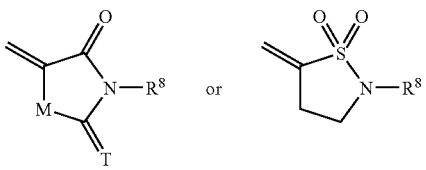

wherein $R^8$ is a hydrogen atom or lower alkyl; M is —S—, —O—, —N($R^c$)—, or —CH$_2$— (wherein $R^c$ is a hydrogen atom or lower alkyl); T is an oxygen atom or a sulfur atom, its prodrug, or their pharmaceutically acceptable salt, or solvate thereof. XX) A compound represented by the formula III-B:

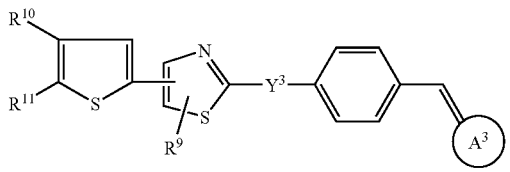

wherein $R^9$, $R^{10}$, $R^{11}$, $Y^3$ and $A^3$ ring are as defined in XIX, its prodrug, or their pharmaceutically acceptable salt, or solvate thereof.

XXI) A pharmaceutical composition containing a compound of any one of XII) to XX) as an active ingredient.

XXII) A pharmaceutical composition which contains as an active ingredient a compound of any one of XII) to XX), which is for exhibiting for thrombopoietin agonism.

XXIII) A pharmaceutical composition containing as the active ingredient a compound of any one of XII) to XX), which is a platelet production modifier XXIV) A platelet production modifier which contains as the active ingredient a compound of any one of XII) to XX).

XXV) Use of a compound of any one of XII) to XX) for preparation of a pharmaceutical composition for treating hemopathy.

XXVI) A method for treating hemopathy of a mammal, including a human, which comprises administration to said mammal of a compound of any one of XII) to XX) in a pharmaceutically effective amount.

In the present specification, the term "halogen" means fluoro, chloro, bromo, and iodo.

In the present specification, the term "lower alkyl" employed alone or in combination with other terms means a straight- or branched chain monovalent hydrocarbon group having 1 to 8 carbon atom(s). Examples of alkyl include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl and the like. C1 to C6 alkyl is preferred. C1 to C3 alkyl is more preferred.

The term "alkenyl" in the present specification means a straight- or branched chain monovalent hydrocarbon group having 2 to 8 carbon atoms and at least one double bond. Examples of the alkenyl include vinyl, allyl, 1-propenyl, 2-propenyl, crotonyl, isopentenyl, a variety of butenyl isomers and the like. C2 to C6 alkenyl is preferred. C2 to C4 alkenyl is more preferred.

The term "lower alkynyl" used in the present specification means a straight or branched chain monovalent hydrocarbon group having 2 to 8 carbon atoms and at least one triple bond. The alkynyl may contain (a) double bond(s). Examples of the alkynyl include ethynyl, 2-propynyl, 6-heptynyl, 7-octynyl and the like.

In the present specification, the term "cycloalkyl" employed alone or in combination with other terms means cycloalkyl group having 3 to 8 carbon atoms. Examples of cycloalkyl group include cyclopropyl, cyclobutyl, cyclopentyl, cyclohexyl, cycloheptyl, cyclooctyl and the like. C3 to C6 cycloalkyl is preferred.

In the present specification, the term "aryl" employed alone or in combination with other terms means monocyclic or condensed ring aromatic hydrocarbons. Examples of aryl include phenyl, 1-naphtyl, 2-naphtyl, anthryl, and the like.

The term "aralkyl" herein used means the above mentioned "lower alkyl" substituted with the above mentioned "aryl" at any possible position. Examples of the aralkyl are benzyl, phenethyl (e.g., 2-phenethyl and the like), phenylpropyl (e.g., 3-phenylpropyl and the like), naphthylmethyl (e.g., 1-naphthylmethyl and 2-naphthylmethyl and the like), anthrylmethyl (e.g., 9-anthrylmethyl and the like), and the like. Benzyl and phenylethy are preferred.

In the present specification, the term heteroaryl" employed alone or in combination with other terms means a 5 to 6 membered aromatic heterocyclic group which contains one or more hetero atoms selected from the group consisting of oxygen, sulfur, and nitrogen atoms in the ring and may be fused with cycloalkyl, aryl, non-aromatic heterocyclic group, and other heteroaryl at any possible position. Examples of the heteroaryl are pyrrolyl (e.g., 1-pyrrolyl, 2-pyrrolyl, 3-pyrrolyl), furyl (e.g., 2-furyl, 3-furyl), thienyl (e.g., 2-thienyl 3-thienyl), imidazolyl (e.g., 2- imidazolyl, 4- imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl(e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, 6-indolizinyl), isoindolyl (2-isoindolyl), indolyl (e.g., 1-indolyl, 2-indolyl, 3-indolyl), indazolyl (e.g., 3-indazolyl), puriyl (e.g., 8-puriyl), quinolizinyl (e.g., 2-quinolizinyl), isoquinolyl (e.g., 3-isoquinolyl), quinolyl (e.g., 3-quinolyl, 5-quinolyl), phthalazinyl (e.g., 1-phthalazinyl), naphthyridinyl (e.g., 2-naphthyridinyl), quinolanyl (2-quinolanyl), quinazolinyl (e.g., 2-quinazolinyl), cinnolinyl (e.g., 3-cinnolinyl), pteridinyl (e.g., 2- pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl) and the like.

Preferable are thiazolyl, isoxazolyl, isothiazolyl, thienyl, furyl, pyrrolyl, imidazolyl, carbazolyl benzothiazolyl, pyridyl, and pyrazolyl as "heteroaryl" for $X^1$.

In the present specification, the term "5-membered heteroaryl" means a 5 membered aromatic heterocyclic group which contains one or more hetero atoms selected from the group consisting of oxygen, sulfur, and nitrogen atoms. Examples of the 5-membered heteroaryl are thienyl, furyl, pyrrolyl, imidazolyl, pyrazolyl, isothiazolyl, isoxazolyl, thiazolyl and the like. Preferable is thiazolyl.

The term "heteroarylalkyl" herein used means the above-mentioned lower alkyl" substituted with the above-mentioned "heteroaryl" at any possible position. Examples of the heteroarylalkyl are thiazolylmethyl (e.g., 2-thiazolylmethyl), thiazolylethyl (e.g., 2-thiazolyl-2-ethyl), imidazolylmethyl (e.g., 4-imidazolylmethyl), pyridylmethyl (e.g., 2-pyridylmethyl , 3-pyridylmethyl, 4-pyridylmethyl), pyridylethyl (e.g., 2-pyridylethyl) and the like.

In the present specification, the term "non-aromatic heterocyclic group" employed alone or in combination with other terms means a 5 to 7 membered non-aromatic ring which contains one or more hetero atoms selected from the group consisting of oxygen, sulfur, and nitrogen atoms in the ring and the 5 to 7 membered non-aromatic ring may be condensed with two or more rings selected from the group consisting of cycloalkyl, aryl, heteroaryl, and the 5 to 7 membered non-aromatic ring. Examples of the non-aromatic heterocyclic group are pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidinyl (e.g., piperidino, 2-piperidinyl), piperazinyl (e.g., 1-piperazinyl), indolynyl (e.g., 1-indolynyl), isoindolinyl (e.g., isoindolinyl), morpholinyl (e.g., morpholino, 3-morpholinyl), indenothiazole (e.g., 8H-indenol[1,2-d] thiazole), dihydronaphtothiazole (4,5- dihydronaphto[1,2-d] thiazole), dihydrothiazabenzoazlene (e.g.,5,6-dihydro-4H-3-thia-1-aza-benzo[e]azulene), chromenothiazole (e.g., 4H-chromeno[4,3-d]thiazole), thiochromenothiazole (e.g., 4H-thiochromeno[4,3-d]thiazole), and the like.

The term "arylene" herein used means a divalent group of the above-mentioned "aryl". Examples of the arylene are phenylene, naphthylene, and the like. Mentioned in more detail, it is examplified by 1,2-phenylene, 1,3-phenylen, 1,4-phenylene, and the like. Preferable is 1,4-phenylene.

The term "heteroarylene" herein used means a divalent group of the above-mentioned "heteroaryl". Examples of the heteroarylene are thionphene-diyl, furan-diyl, pyridine-diyl, and the like. Mentioned in more detail, it is exemplified by 2,5-thionphene-diyl, 2,5-furan-diyl, 2,5-pyridine-diyl, and the like.

The term "non-aromatic heterocycle-diyl" herein used means a divalent group of an above-mentioned "non-aromatic heterocyclic group". Examples of the non-aromatic heterocycle-diyl are pyrrolidine-diyl, piperidine-diyl, pyrazine-diyl and the like The term "cycloalkyl-diyl" herein used means a divalent group of the above-mentioned "cycloalkyl". Examples of the cycloalkyl-diyl are cylopentyl-diyl, cyclohexyl-diyl and the like.

The term "lower alkyloxycarbonyl" herein used are methyloxycarbonyl, ethyloxycarbonyl, n-propyloxycarbonyl, isopropyloxycarbonyl, n-butyloxycarbonyl, t-butyloxycarbonyl, n-pentyloxycarbonyl and the like.

In the present specification, the term "acyl" employed alone or in combination with other terms means alkylcarbonyl in which alkyl group is the above-mentioned "lower alkyl" and arylcarbonyl in which aryl group is the above-mentioned "aryl". Examples of the acyl are acetyl, propyonyl, benzoyl, and the like. "Lower alkyl" and "aryl" may be substituted respectively with substituents mentioned below.

The term "lower alkyloxy" herein used are methyloxy, ethyloxy, n-propyloxy, i-propyloxy, n-butyloxy, i-butyloxy, sec-butyloxy, tert-butyloxy, and the like. Methyloxy, ethyloxy, n-propyloxy, i-propyloxy and n-butyloxy are preferred.

The term "lower alkylthio" herein used are methylthio, ethylthio, and the like.

In the present specification, the term "halo(lower)alkyl" employed alone or in combination with other terms means the above-mentioned "lower alkyl" which is substituted with the above mentioned "halogen" at 1 to 8 positions, preferably, at 1 to 5. Examples of the halo(lower)alkyl are trifluoromethyl, trichloromethyl, difluoroethyl, trifluoroethyl, dichloroethyl, trichloroethyl, and the like. Preferable is trifluoromethyl.

Examples of the term "acyloxy" herein used are acetyloxy, propionyloxy, benzoyloxy and the like.

In the present specification, the term "optionally substituted amino" employed alone or in combination with other terms includes amino substituted with one or two of the above mentioned "lower alkyl", "aralkyl", "heteroarylalkyl" or "acyl". Examples of the optionally substituted amino are amino, methylamino, dimethylamino, ethylmethylamino, diethylamino, benzylamino, acetylamino, benzoylamino and the like. Preferable are amino, methylamino, dimethylamino, ethylmethylamino, diethylamino and acetylamino.

Examples of the term "optionally substituted aminocarbonyl" herein used are aminocarbonyl, methylaminocarbonyl, dimethylaminocarbonyl, ethylmethylaminocarbonyl, diethylaminocarbonyl and the like. Preferable are aminocarbonyl, methylaminocarbonyl, and dimethylaminocarbonyl.

The substituents of "optionally substituted lower alkyl" are cycloalkyl, -lower alkenyl, lower alkyliden, hydroxy, lower alkyloxy, mercapto, lower alkylthio, halogen, nitro, cyano, carboxy, lower alkyloxycarbonyl, halo(lower)alkyl, halo(lower)alkyloxy, substituted or unsubstituted amino, substituted or unsubstituted aminocarbonyl, acyl, acyloxy, optionally substituted non-aromatic heterocyclic group, aryloxy (e.g., phenyloxy), aralkyloxy (e.g., benzyloxy), lower alkylsulfonyl, guanidino, azo group, optionally substituted ureide, =N—O-(acyl) and the like. These substituents are able to locate at one or more of any possible positions.

Preferable are lower alkyloxycarbonyl, ethyliden, or =N—O—COCH$_3$, as substituents of "optionally substituted lower alkyl" for $R^{6,}$ $R^7$ and $R^9$.

Preferable are unsubstituted alkyl, as "optionally substituted lower lkyl" for $R^4$. Lower alkyloxycarbonyl as substituents is preferred.

The substituents of "optionally substituted arylene", "optionally substituted phenylene". "optionally substituted heteroarylene", "optionally substituted 2,5-pyridine-diyl", "optionally substituted 2,5-thiophene-diyl", "optionally substituted 2,5-furan-diyl", "optionally substituted non-aromatic heterocycle-diyl", "optionally substituted cycloalkyl-diyl", "optionally substituted aryl", "optionally substituted thienyl", "optionally substituted phenyl", "optionally substituted heteroaryl", "optionally substituted 5-membered heteroaryl", "optionally substituted aralkyl", "optionally substituted heteroarylalkyl", "optionally substituted non-aromatic heterocyclic group", and "optionally substituted ureide" herein used are optionally substituted lower alkyl, cycloalkyl, lower alkenyl, lower alkynyl, hydroxy, lower alkyloxy, aralkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino, azo group, —N═N-(optionally substituted phenyl) or optionally substituted ureide and the like. These substituents are able to locate at one or more of any possible positions.

Preferable are unsubstituted groups as substituents of "optionally substituted arylene", "optionally substituted phenylene", "optionally substituted heteroarylene", "optionally substituted 2,5-pyridine-diyl", "optionally substituted 2,5-thiophene-diyl", "optionally substituted 2,5-furan-diyl", "optionally substituted non-aromatic heterocycle-diyl", "optionally substituted cycloalkyl-diyl". Halogen, nitro, cyano, lower alkyl, lower alkyloxy as substituents are preferred.

The examples of substituents of "optionally substituted aryl" and "optionally substituted aralkyl" for $X^i$ are lower alkyl, hydroxy lower alkyl, hydroxy, lower alkyloxy, lower alkylthio, halogen, nitro, cyano, carboxy, lower halo(lower)alkyl, halo(lower)alkyloxy, aralkyloxy, unsubstituted or substituted amino, unsubstituted or substituted aminocarbonyl, aryl, heteroaryl, non-aromatic heterocyclic group, arylazo (e.g., phenylazo), and the like. Preferable substituents are lower alkyl, hydroxy, lower alkyloxy, lower alkylthio, halogen, halo(lower)alkyl, halo(lower)alkyloxy, aralkyloxy, —N═N-(phenyl), alkylendioxy, and the like.

The examples of "optionally substituted aryl" for $X^1$ are phenyl, 2-methylphenyl, 3-methylphenyl, 4-methylphenyl, 3,4-dimethylphenyl, 4-ethylphenyl, 4-t-buylphenyl, 4-n-buylphenyl, 4-n-hexylphenyl, 4-n-octylphenyl, 3,5-di-t-butyl-4-hydroxyphenyl, 4-ethyloxyphenyl, 4-fluorophenyl, 3,4-dichlorophenyl, 3,5-dichlorophenyl, 4-iodophenyl, 4-trifluoromethylphenyl, 4-methylthiophenyl, 4-phenylmethyloxyphenyl, 4-phenyazophenyl, 4-phenylphenyl, 2-naphtyl, benzodioxoryl (e.g., 1,3-benzodioxoryl), and the like.

The substituents of "optionally substituted thienyl" and "optionally substituted phenyl" for $R^6$ and $R^7$ are lower alkyl, lower alkyl substituted with unsubstituted or substituted amino, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, formyl, acyloxy, optionally substituted phenyl, aryl (e.g., phenyl), heteroaryl (imidazolyl), non-aromatic heterocyclic group (e.g., morpholino, piperazinyl), aralkyl, arylazo, and the like. Preferable are lower alkyl, lower alkyloxy, halogen, nitro, carboxy, lower alkyloxycarbonyl, halo(lower)alkyl, halo(lower)alkyloxy, unsubstituted or substituted amino, unsubstituted or substituted aminocarbonyl, aryl, arylazo and the like.

The examples of "optionally substituted phenyl" for $R^6$ and $R^7$ are phenyl, 3-methylphenyl, 4-methylphenyl, 4-t-buylphenyl, 4-n-pentyllphenyl, 3-methyloxyphenyl, 4-methyloxyphenyl, 4-carboxyphenyl, 4-methyloxycarbonylphenyl, 4-ethyloxycarbonylphenyl, 4-isopropyloxycarbonyl, 4-n-butyloxycarbonyl, 4-t-butyloxycarbonyl, 2-fluorophenyl, 3-fluorophenyl, 4-fluorophenyl, 2,4-difluorophenyl, 2,6-difluorophenyl, 3,4-difluorophenyl, 2,4,5-trifluorophenyl, 2,3,4,5,6-pentafluorophenyl, 4-chlorophenyl, 2,4-dichlorophenyl, 3,4-dichlorophonyl, 3,5-dichlorophenyl, 3-bromophenyl, 4-bromophenyl, 4-iodophenyl, 3-fuluro-4-methyloxyphenyl, 3-trifluoromethylphenyl, 4-trifluoromethylphenyl, 2-trifluoromethyloxyphenyl, 4-acetylaminophenyl, 4-aminocarbonylphenyl, 4-N-methylaminocarbonylphenyl, 4-N,N-dimethylaminocarbonyl, 2-nitrophenyl, 4-nitrophenyl, 4-phenylphenyl, 4-phenyazophenyl, and the like.

Preferable are lower alkyl, cycloalkyl, lower alkenyl, lower alkynyl, hydroxy, lower alkyloxy, aralkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, acyloxy, guanidino, azo group, and the like as substituents of "optionally substituted aryl", "optionally substituted heteroaryl", "optionally substituted aralkyl", and "optionally substituted heteroarylalkyl" for $R^4$. These substituents are able to locate at one or more of any possible positions.

Preferable is phenyl as "optionally substituted aryl" for $R^F$.

The substituents of "optionally substituted hetroaryl", "optionally substituted hetroarylalkyl", "optionally substituted non-aromatic heterocyclic group" for $X^1$ and the substituents of "optionally substituted 5-membered beteroaryl" for $X^2$ are optionally substituted lower alkyl, lower alkenyl (e.g., ═Cl—I—CH$_3$), lower alkynyl, hydroxy, lower alkyloxy, mercapto, lower alkylthio, halogen, nitro, cyano, carboxy, lower alkyloxyccarbonyl, halo(lower)alkyl, halo(lower)alkyloxy, substituted or unsubstituted amino, substituted or unsubstituted aminocarbonyl, acyl (e.g., aryloxycarbonyl optionally substituted with halogen, nitro, cyano and the like), acyloxy, optionally substituted phenyl, aryl, optionally substituted heteroaryl (e.g., 2-pyridyl, 3-pyridyl, 4-pyridyl, 3-thienyl, 5-methylpyridine-2-yl, 3-quinolyl, 5-chlorothiophene-2-yl, 5-bromothiophene-2-yl), non-aromatic heterocyclic group, aralkyl, ═N—O-(acyl), and the like. Preferable are optionally substituted lower alkyl, lower alkenyl, lower alkyloxycarbonyl, optionally substitute phenyl, heteroaryl, ═N—O-(acyl), and the like.

When hetero atom is nitrogen atom, the nitrogen atom may be substituted with alkyl, oxo and the like.

In the present specification, the term "hemopathy" means hemopathy accompanied with the unusual number of platelet. For example the hemopathy is thrombocytopenia (after bone marrow transplantation, after chemotherapy, anaplastic anemia, bone marrow dysplasia syndrome, acquired thrombopenia of intractable sudden thrombocy topenic purpura and the like, congenital thrombopenia of thrombopoictin deficiency and the like) and the like.

BEST MODE FOR CARRYING OUT THE INVENTION

Figure 1:
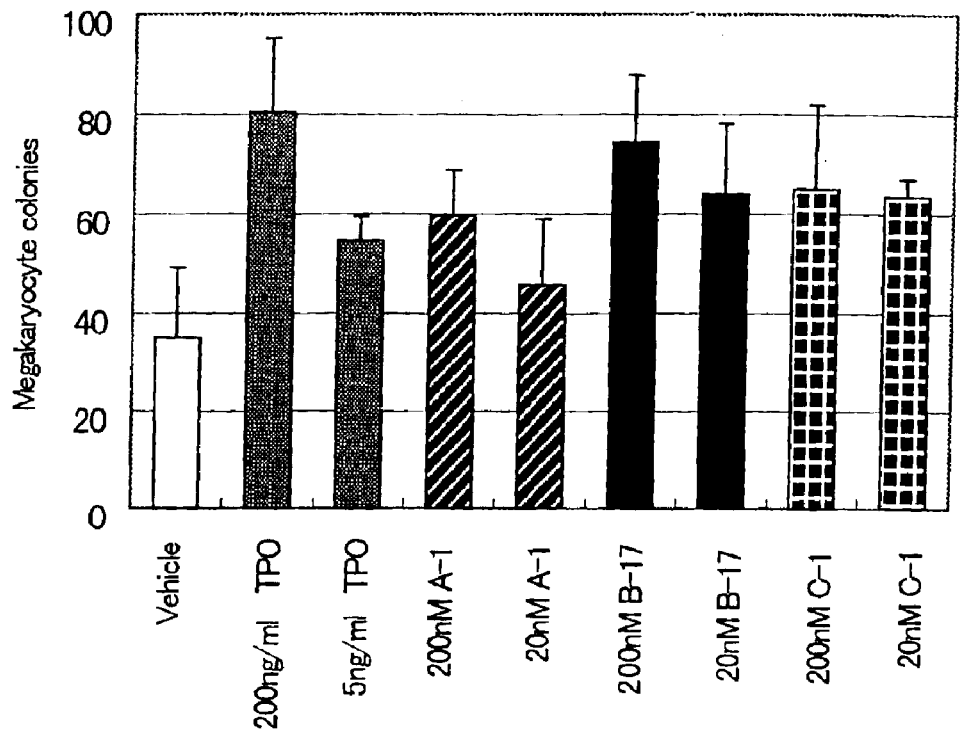
FIG. 1: The chart shows the stimulation activity of a present invention for the proliferation and differentiation of megakaryocyte precursor cells, by counting megakaryocyte colonies formed from human bone marrow cells.

Compounds (I) of the invention can be synthesized by the following methods A–C and the similar process. And it is possible to produce the compounds in accordance with the procedure described in WO97/05135 and WO97/39737.
(Method A)

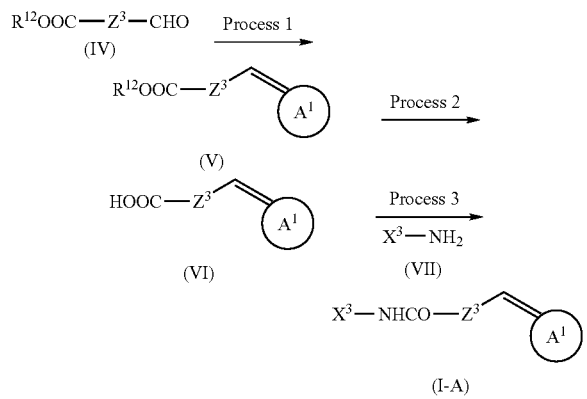

wherein $A^1$ is as defined above, $Z^3$ is optionally substituted arylene, optionally substituted heteroarylene, optionally substituted non-aromatic heterocyle-diyl, or optionally substituted cycloalkyl-diyl, $X^3$ is optionally substituted aryl, optionally substituted aralkyl, optionally substituted heteroaryl, or optionally substituted heteroarylalkyl, $R^{12}$ is lower alkyl.
(Process 1)

Commercial available compound $Z^1$ (compound (IV)) having lower alkyloxycarbonyl and aldehyde groups as substituents is used as a starting material.

The compound (IV) is also obtained by the following methods 1)-3). 1) A carboxy group of the compound having lower alkyloxycarbonyl and carboxy groups as substituents is treated with ethyl chlorocarbonate to give mixed acid anhydride. 2) A usual reductive reaction (e.g., reductive reaction with sodium borohydride) gives a compound having lower alkyloxycarbonyl and hydroxy groups. 3) A usual oxidative reaction (e.g., Swern oxidation, Dess-Martin Oxidation and the like) obtains compound (IV) having alkyloxycarbonyl and aldehyde groups.

This is the process of obtaining bezyliden derivatives by the reaction of aldehyde derivatives with 2,4-thiazolidine-dione. Compound (IV) is reacted with 2,4-thiazolidine-dione under reflux in the presence of acetic acid and piperidine as a catalyst in a solvent such as benzene, toluene to obtain the desired compound. (Knoevenagel Reaction).

A derived double bond may be reduced by a usual reductive reaction (e.g., hydrogenation) at any appropriate process. In case of a presence of a functional group(s) possibly interfering the reaction, the group(s) can be protected in accordance with a method described in "Protective Groups in Organic Synthesis" ( Theodora W. Green (John Wiley & Sons)) and the like, and then deprotected at an appropriate process.
(Process 2)

This is the conversion of alkyloxy derivatives to carboxylic acid derivatives by the hydrolysis. It can be carried out by usual hydrolysis. For example, compound (V) is reacted in the presence of acetic acid, hydrochloric acid, and the like to give the carboxylic acid derivative (compound (VI)).
(Process 3)

This process is the reaction of carboxylic acid derivatives (VI) and amine derivatives (VII) to obtain amide derivative (I–A) by an active ester method, an acid chloride method, a mixed acid anhydride method, and the like. This process is performed in a solvent such as tetrahydrofuran, dioxane, dichloromethane, toluene, benzene. An active ester method can be carried out by using 1-hydroxybenzotriazlole, hydroxysuccinimide, dimethylaminopyridine and the like, dicyclohexylcarbodiimide 1-ethyl-3-(dimethylamionpropyl) carbodiimide hydrochloride, and the like as a condensing agent. A acid chloride method can be performed by conversion of a free carboxylic acid with thionyl chloride, oxalyl chloride as a reagent to an acid chloride. A mixed acid anhydride method can be carried out by the reaction of carboxylic acid with ethyl chloroformate isobutyl chloroformate and the like to obtain acid mix anhydride. Bases such as triethylamine, pyridine may be used in the reaction, if necessary.

Commercial available compound $Z^1$ (compound (IV)) having lower alkyloxycarbonyl and aldehyde groups as substituents is used as a starting material.

The compound (VII) is commercial available but it is also obtained by means of the following methods. 1) Compound (VII) having two successive rings can be obtained by Suzuki Reaction when $X^3$ is optionally substituted aryl, optionally substituted aryl, or the like and when above-mentioned substituents are aryl or heteroaryl. 2) Compound (VII') can be given by the following method when $X^3$ is optionally substituted thiazole.

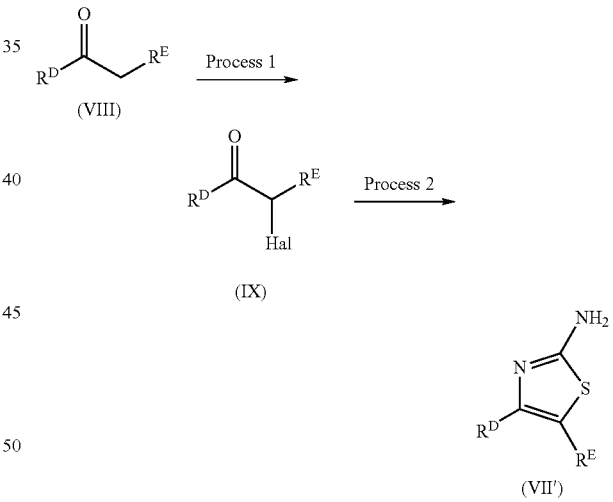

wherein $R^D$ and $R^E$ are hydrogen atoms, optionally substituted lower alkyl, carboxy, lower alkyloxycarbonyl, optionally substituted aminocarbonyl, or optionally substituted phenyl and the like, Hal is halogen.
(Process 1)

This process is halogenation. It can be carried out by a usual halogenation. For example, bromination can be performed by the reaction with bromine in mixed solvent of methanol and chloroform.
(Process 2)

This is a process of constructing a thiazole ring. For example, the desired thiazole (VII') derivative can be obtained by the reaction with thiourea in a solvent such as methanol.

(Method B)

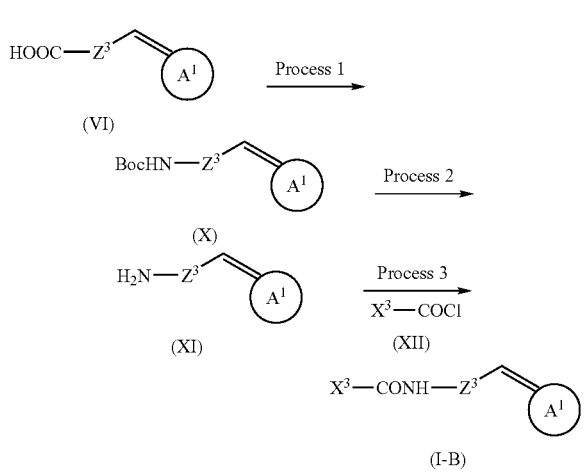

wherein $A^1$, $X^3$, and $Z^3$ are as defined above, Boc is t-butyloxycarbonyl (Process 1)

The present process is the conversion of a carboxy group to an amino group protected with Boc. For example, the desired compound can be obtained by the reaction of the compound (IV) with diphenylphosphoryl azide in a solvent such as dimethylformamide, toluene, ether, dioxane in a presence t-butanol and a base such as tritehylamine.

(Process 2)

The present process is a deprotection of Boc. It can be deprotected in accordance of a method described in Protective Groups in Organic Synthesis, Theodora W Green (John Wiley & Sons) and the like. For example, compound (X) is treated with trifluoroacetic acid to give the desired deprotected compound (XI).

(Process 3)

This process may be carried out in the same manner as that described in process 3 of method A.

(Method C)

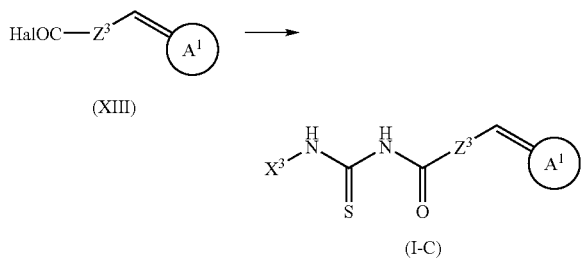

wherein $A^1$, $X^3$, $Z^3$, and Hal are as defined above

The present process is the treating acid halogenide (XIII) of compound (VI) with ammonium isothiocyanate and the following reaction of the above-mentioned compound (VII) to give the desired compound (I–C).

A compound represented by the formula (I), wherein $Y^1$ is not —CONH—, —NHCO—, or —NHC(=S)NHC(=O)—, can be synthesized in the same manner as that described in above mentioned methods A–C. N-alkylation can be carried by a usual alkylation.

When $Y^1$ is —N(—alkyl)—CO—, $Z^1$ is optionally substituted thiazole, the said ompound is represented by equilibrium as follows.

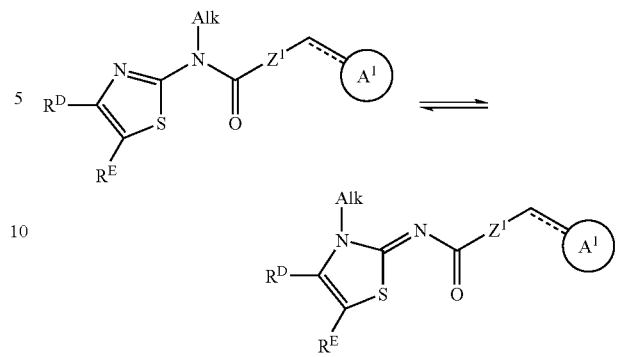

($A^1$, $Z^1$, $R^D$, $R^E$, and a broken line are as defined above, Alk is lower alkyl)

Both a cis isomer and a trans isomer are included when a broken line represents a presence of a bond in the formulae (I), (II), and (III). For example, a cis isomer and a trans isomer can be as follows, when $A^1$ ring is thiazolidine-dione.

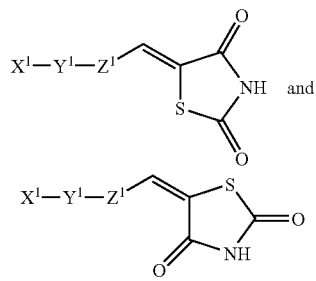

wherein $X^1$, $Y^1$, and $Z^1$ are as defined above.

The term "solvate" includes, for example, solvates with organic solvents, hydrates, and the like.

The term "compound of the present invention" herein used includes a pharmaceutically acceptable salt or solvate thereof. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, maleic acid, fumaric acid, benzenesulfonic acid, p-toluenesulfonic acid, and the like). These salts can be formed by the usual method. These hydrates can coordinate with any water molecules when hydrates are formed.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. The method of both selection and manufacture of appropriate prodrug derivatives is described in, for example. Design of Prodrugs, Elsevier, Amsterdam, 1985). For instance, prodrugs such as an ester derivative which is prepared by reacting a basal acid compound with a suitable alcohol, or an amide derivative which is prepared by reacting a basal acid compound with a suitable amine are exemplified when the compounds according to present invention have a carboxylic group. Particularly preferred esters as prodrugs are methyl, ethyl, n-propyl, isopropyl, n-butyl, isobutyl, tert-butyl, morpholinoethyl, and N,N-diethylglycolamido, and the like. For instance, prodrugs such as an acyloxy derivative which is prepared by reacting a basal hydroxy compound with a suitable acyl halide or a suitable acid anhydride, or an amide derivative which is prepared by reacting a basal acid compound with a suitable amine are exemplified when the compounds according to present invention have a hydroxy group. Particularly preferred acyloxy derivatives as prodrugs —OCOC$_2$H$_5$, —OCO(t-Bu), —OCOC$_{15}$H$_{31}$, —OCO(m—COONa—Ph), —COCH$_2$CH$_2$COONa, —OCOCH(NH$_2$)CH$_3$, —OCOCH$_2$N(CH$_3$)$_2$, and the like. For instance, prodrugs such as an amide derivative which is prepared by reacting a basal amino compound with a suitable acid halide or a suitable acid anhydride are exemplified when the compounds according to present invention have an amino group. Particularly preferred amide as prodrugs are —NHCO (CH$_2$)$_{20}$CH$_3$, —NHCOCH(NH$_2$)CH$_3$, and the like.

The compound of the present invention is not restricted to any particular isomers but includes all possible isomers and racemic modifications.

The present invention compounds show excellent thrombopoietin receptor agonism as described in examples mentioned later, and may be used as a pharmaceutical composition (platelet production modifier) for hemopathy accompanied with the unusual number of platelet, for example thrombocytopenia and the like. And the present compound may be used as a peripheral blood stem cell releasing promoter, a differetiation-inducer of megakaryocytic leukemic cell, a platelet increasing agent of a platelet donor and the like.

When the compound of the present invention is administered to a person for the treatment of the above diseases, it can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the dosage can generally be between 0.1 to 100 mg/kg/day, and preferably 1 to 20 mg/kg/day for adult.

The following examples are provided to further illustrate the present invention and are not to be constructed as limiting the scope thereof.

P Abbreviations described below are used in the following examples.

Me: methyl
Et: ethyl
$^i$Pr: isopropyl
$^n$Bu: butyl
$^t$Bu: tert-butyl
$^i$Bu: isobutyl
$^n$Pen n-pentyl
$^n$Hex: n-hexyl
$^n$Oct: n-octyl
Ph: phenyl
Bn: benzyl
Bz: benzoyl
Py: pyridyl
Ac: acetyl
Boc: t-butyloxycarbonyl DMF: dimethylformamide ジメチルホルムアミド
DMSO: dimethylsulfoxide

EXAMPLE

Example 1

The preparation of compound (A-1)

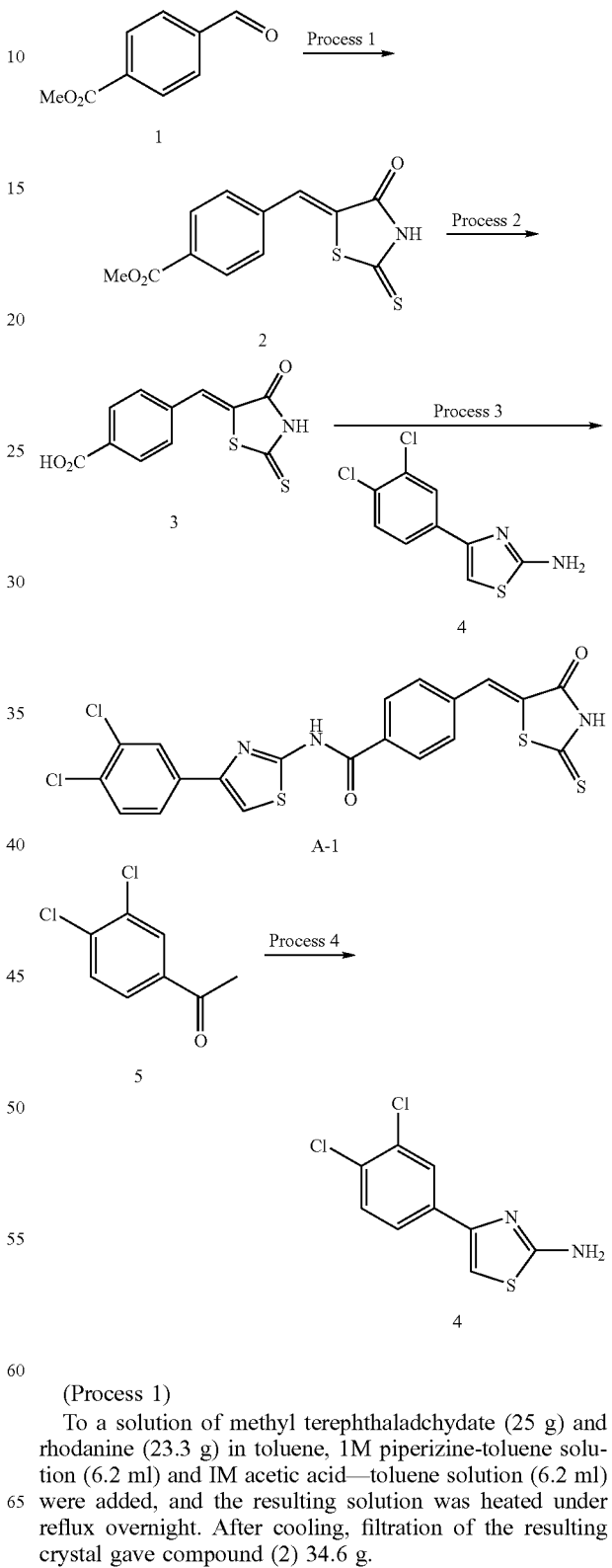

(Process 1)

To a solution of methyl terephthaladchydate (25 g) and rhodanine (23.3 g) in toluene, 1M piperizine-toluene solution (6.2 ml) and IM acetic acid—toluene solution (6.2 ml) were added, and the resulting solution was heated under reflux overnight. After cooling, filtration of the resulting crystal gave compound (2) 34.6 g.

¹H NMR(DMSO-d₆, δ ppm) 13.18 (bs, 1H), 8.07 (d, 2H, J=8.7 Hz), 7.73 (d, 2H, J=8.7 Hz), 7.68 (s, 1H), 3.88 (s, 1H).

(Process 2)

A suspension of compound (2) (34.6 g) in dioxane (160 ml), acetic acid (250 ml), and 6N hydrocholoric acid (88 ml) was refluxed at 120° C. for 5 h. Water (350 ml) was poured into the reaction mixture and after cooling the filtration of crystal gave compound (3) 30.0 g.

¹H NMR (DMSO-d₆, δ (5 ppm): 13.95 (bs, 1H), 13.24 (bs, 1H), 8.06 (d, 2H, J=8.4 Hz), 7.72 (d, 2H, J=8.4 Hz), 7.69 (s, 1H).

(Process 3)

A mixture of compound (3)(3 g) in dioxane (20 ml) and thionyl chloride (10 ml) was heated to dissolve at 100° C. Evaporation of the solvent under the reduced pressure gave carboxylic acid chloride. The obtained carboxylic acid chloride was not purified to proceed to a further reaction. To the solution of carboxylic acid chloride (286 mg) and compound (4) (368 mg) synthesized by process 4 in dioxane (50 ml), pyridine (162 μl) was added and the reaction mixture heated at 100° C. for 2 h. After cooling and evaporation of the solvent under the reduced pressure, methanol (6 ml) and water (2 ml) were added to the residue and then the resulting crystal was filtrated. Recrystallization from DMF yielded 220 mg of compound (A-1).

¹H NMR (DMSO-d₆, δ ppm): 13.94 (bs, 1H), 12.93 (s, 11H), 8.23 (d, 2H, J=8.5 Hz), 8.21 (d, 1H, J=2.1 Hz), 7.91–7.97 (m, 1H), 7.93 (s, 1H), 7.76 (d, 2H, J=8.5 Hz), 7.73 (s, 1H), 7.70 (s, 1H).

(Process 4)

To a solution of 3', 4'-dichloroacetophenone (5) (5.67 g) in 10% methanol-chloroform, bromine (1.52 ml) was added, and then the reaction solution was stirred at room temperature until the color of bromine disappeared. After evaporation of the solvent under the reduced pressure, the residue was dissolved in ethanol, thiourea (2.28 g) was added and the mixture was refluxed for 2 hours. After removing the solvent by evaporation under reduced pressure, ethyl acetate—water was added to the residue, then the precipitated crystal was collected by filtration. To the crystal was added ethyl acetate—a saturated sodium carbonate solution, then the ethyl acetate layer was separated, dried, and evaporated to obtain 3.38 g of compound (4).

¹H NMR (CDCl δ ppm): 7.89 (d, 1H, J=2.2 Hz), 7.69 (dd, 1H, J=8.5 Hz, 2.2 Hz), 7.43 (d, 1H, J=8.2 Hz), 6.74 (s, 1H), 5.06 (bs, 1H).

Compound (A-2) to Compound (A-73) were synthesized in a manner similar to Example 1. Their physical data were shown in Tables 1 to 8.

TABLE 1

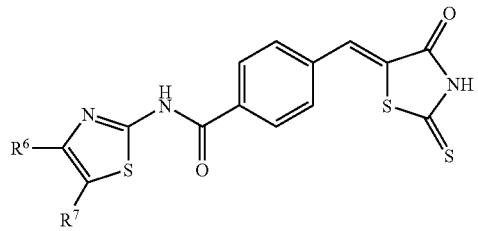

| Example No. | Compound No. | R⁶ | R⁷ | ¹H-NMR (δ) ppm (DMSO d-6) |
|---|---|---|---|---|
| 2 | A-2 | phenyl | H | 13.90(bs, 1H), 12.94(s, 1H), 8.25(d, 2H, J=8.1Hz), 7.96(d, 1H, J=6.9 Hz), 7.77(d, 1H, J=8.1Hz), 7.73(s, 1H), 7.71(s, 1H), 7.46(t, 2H, J=7.5 Hz), 7.35(t, 2H, J=6.9Hz) |
| 3 | A-3 | 4-F-phenyl | H | 13.95(bs, 1H), 12.92(s, 1H), 8.24(d, 2H, J=8.1Hz), 7.97–8.02(m, 2H), 7.76(d, 1H, J=8.1Hz), 7.72(s, 1H), 7.70(s, 1H), 7.26–7.31(m, 2H) |
| 4 | A-4 | 4-Br-phenyl | H | 13.90(bs, 1H), 12.95(s, 1H), 8.24(d, 2H, J=8.4Hz), 7.92(d, 2H, J=8.7 Hz), 7.80(s, 1H), 7.76(d, 2H, J=8.4 Hz), 7.70(s, 1H), 7.66(d, 2H, J=8.7 Hz) |
| 5 | A-5 | 4-Cl-phenyl | H | 13.90(bs, 1H), 12.92(s, 1H), 8.24(d, 2H, J=7.8Hz), 7.98(d, 2H, J=8.7 Hz), 7.79(s, 1H), 7.76(d, 2H, J=8.4 Hz), 7.71(s, 1H), 7.52(d, 2H, J=7.8 Hz) |
| 6 | A-6 | 4-Me-phenyl | H | 13.92(bs, 1H), 12.89(s, 1H), 8.25(d, 2H, J=8.2Hz), 7.76(d, 1H, J=8.2 Hz), 7.71(s, 1H), 7.26(d, 2H, J=8.5Hz), 2.34(s, 3H) |

TABLE 1-continued

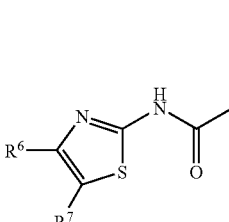

| Example No. | Compound No. | R⁶ | R⁷ | ¹H-NMR (δ) ppm (DMSO d-6) |
|---|---|---|---|---|
| 7 | A-7 | 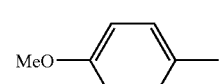 Ph— | H | 13.90(bs, 1H), 12.95(s, 1H) 8.26(d, 2H, J=8.4Hz), 8.06(d, 2H, J=7.5 Hz), 7.92–8.12(m, 8H), 7.47–7.52 (m, 2H), 7.36–7.41(m, 2H) |
| 8 | A-8 | 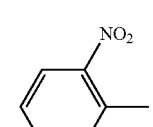 MeO— | H | 13.90(bs, 1H), 12.88(s, 1H), 8.24(d, 2H, J=8.4Hz), 7.89(d, 2H, J=7.8 Hz), 7.76(d, 2H, J=7.8Hz), 7.70(s, 1H), 7.55(s, 1H), 7.01(d, 2H, J=8.4 Hz), 3.80(s, 3H) |
| 9 | A-9 | 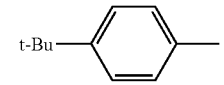 NO₂ | H | 13.90(bs, 1H), 12.93(s, 1H), 8.21(d, 2H, J=8.1Hz), 7.94(d, 1H, J=7.5 Hz), 7.79–7.83(m, 2H), 7.75(d, 2H, J=8.1Hz), 7.70(s, 1H), 7.61–7.66 (m, 1H), 7.59(S, 1H) |
| 10 | A-10 | t-Bu | H | 13.85(bs, 1H), 12.30(s, 1H), 8.21(d, 2H, J=8.1Hz), 7.73(d, 2H, J=8.1 Hz), 7.70(s, 1H), 6.84(S, 1H), 1.31 (s, 9H) |

TABLE 2

| Example No. | Compound No. | R⁶ | R⁷ | ¹H-NMR (δ) ppm (DMSO d-6) |
|---|---|---|---|---|
| 11 | A-11 | 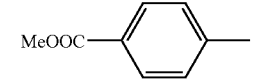 t-Bu— | H | 13.92(bs, 1H), 12.93(s, 1H), 8.25(d, 2H, J=8.5Hz), 7.87(d, 2H, J=8.5 Hz), 7.75(d, 2H, J=8.5Hz), 7.72(s, 1H), 7.65(s, 1H), 7.47(d, 2H, J=8.5 Hz), 1.32(s, 9H) |
| 12 | A-12 | 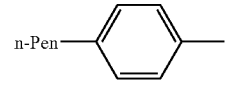 MeOOC— | H | 13.97(bs, 1H), 13.00(s, 1H), 8.25(d, 2H, J=8.5Hz), 8.08(dd, 4H, J= 19.2Hz, 8.5Hz), 7.94(s, 1H), 7.76(d, 2H, J=8.5Hz), 7.72(s, 1H), 3.81(s, 3H) |
| 13 | A-13 | 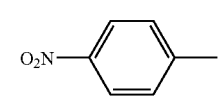 n-Pen— | H | 13.88(bs, 1H), 12.91(s, 1H), 8.24(d, 2H, J=8.5Hz), 7.86(d, 2H, J=8.1 Hz), 7.76(d, 2H, J=8.5Hz), 7.72(s, 1H), 7.64(s, 1H), 7.27(d, 2H, J=8.1 Hz), 2.60(t, 2H, J=7.8Hz), 1.60(q, 2H, J=6.6Hz), 1.27–1.36(m, 2H), 0.87(t, 3H, J=6.6Hz) |
| 14 | A-14 | O₂N— | H | 13.90(bs, 1H), 13.05(s, 1H), 8.34(d, 2H, J=8.5Hz), 8.24(t, 4H, J=8.2 Hz), 8.10(s, 1H), 7.77(d, 2H, J=8.5 Hz), 7.71(s, 1H) |
| 15 | A-15 | 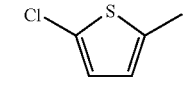 Cl—[thiophene]— | H | 13.92(bs, 1H), 12.99(s, 1H), 8.23(d, 2H, J=8.5Hz), 7.75(d, 1H, J=8.5 Hz), 7.71(s, 1H), 7.64(s, 1H), 7.44 (d, 1H, J=4.1Hz), 7.14(d, 1H, J= 4.1Hz) |

TABLE 2-continued

| Example No. | Compound No. | R⁶ | R⁷ | ¹H-NMR (δ) ppm (DMSO d-6) |
|---|---|---|---|---|
| 16 | A-16 | 2-thienyl | H | 13.90(bs, 1H), 12.93(s, 1H), 8.24(d, 2H, J=8.5Hz), 7.84(bs, 1H), 7.76 (d, 2H, J=8.5Hz), 7.72(s, 1H), 7.61–7.62(m, 2H), 7.56(s, 2H) |
| 17 | A-17 | 2-pyridyl | H | 13.95(bs, 1H), 13.00(s, 1H), 8.65–8.67(m, 1H), 8.26(d, 2H, J=8.4 Hz), 8.09–8.12(m, 1H), 7.80–8.05 (m, 1H), 8.03(s, 1H), 7.78(d, 2H, J= 8.4Hz), 7.70(s, 1H), 7.55(s, 1H), 7.73(s, 1H), 7.43–7.47(m, 3H) |
| 18 | A-18 | 3-pyridyl | H | 13.01(s, 1H), 9.22(d, 1H, J=2.1 Hz), 8.62(dd, 1H, J=5.1Hz, 1.2 Hz), 8.45(d, 1H, J=8.4Hz), 8.25(d, 2H, J=8.1Hz), 7.98(s, 1H), 7.77(d, 2H, J=8.1Hz), 7.72(S, 1H), 7.64 (dd, 1H, J=8.1Hz, 5.1Hz) |
| 19 | A-19 | 4-pyridyl | H | 13.15(s, 1H), 8.92(d, 2H, J=6.3Hz), 8.56(s, 1H), 8.40(d, 2H, J=6.3Hz), 8.25(d, 2H, J=8.5Hz), 7.77(d, 2H, J=8.5Hz), 7.72(s, 1H) |

TABLE 3

| Example No. | Compound No. | R⁶ | R⁷ | ¹H-NMR (δ) ppm (DMSO d-6) |
|---|---|---|---|---|
| 20 | A-20 | 3,4-difluorophenyl | H | 13.93(bs, 1H), 12.93(s, 1H), 8.23(d, 2H, J=8.4Hz), 7.93–8.01(m, 1H), 7.82(s, 1H), 7.80–7.82(m, 1H), 7.76 (d, 2H, J=8.4Hz), 7.71(s, 1H) |
| 21 | A-21 | 5-bromo-2-thienyl | H | 13.97(bs, 1H), 13.00(s, 1H), 8.23(d, 2H, J=8.5Hz), 7.75(d, 2H, J=8.5 Hz), 7.71(s, 1H), 7.64(s, 1H), 7.41 (d, 1H, J=3.8Hz), 7.24(d, 1H, J= 3.8Hz) |
| 22 | A-22 | 4-(H₂N-CO-)phenyl | H | 13.94(bs, 1H), 12.97(s, 1H), 8.25(d, 2H, J=8.5Hz), 8.04(d, 2H, J=8.7 Hz), 7.96(d, 2H, J=8.7Hz), 7.99 (bs, 2H), 7.88(s, 1H), 7.77(d, 2H, J= 8.5Hz), 7.73(s, 1H) |
| 23 | A-23 | 4-(MeHN-CO-)phenyl | H | 13.94(bs, 1H), 12.97(s, 1H), 8.25(d, 2H, J=8.5Hz), 8.04(d, 2H, J=8.7 Hz), 7.96(d, 2H, J=8.7Hz), 7.99 (bs, 2H), 7.88(s, 1H), 7.77(d, 2H, J= 8.5Hz), 7.73(s, 1H), 2.81(d, 3H, J= 4.2Hz) |
| 24 | A-24 | 4-(Me₂N-CO-)phenyl | H | 14.01(bs, 1H), 12.94(s, 1H), 8.25(d, 2H, J=8.5Hz), 8.01(d, 2H, J=8.2 Hz), 7.82(s, 1H), 7.77(d, 2H, J=8.5 Hz), 7.72(s, 1H), 7.49(d, 2H, J=8.2 Hz), 2.98(s, 6H) |
| 25 | A-25 | 4-(i-Pr-O-CO-)phenyl | H | 13.90(bs, 1H), 13.01(s, 1H), 8.25(d, 2H, J=8.5Hz), 8.01–8.12(m, 4H), 7.93(s, 1H), 7.76(d, 2H, J=8.5Hz), 7.72(s, 1H), 5.16(quint, 1H, J=6.0 Hz), 1.35(d, 6H, J=6.0Hz) |
| 26 | A-26 | 4-(n-Bu-O-CO-)phenyl | H | 13.92(bs, 1H), 13.01(s, 1H), 8.25(d, 2H, J=8.4Hz), 8.03–8.12(m, 4H), 7.93(s, 1H), 7.77(d, 2H, J=8.4Hz), 7.72(s, 1H), 4.30(t, 2H, J=6.6Hz), 1.67–1.76(m, 2H), 1.41–1.51(2-m, 2H), 0.95(t, 3H, J=7.2Hz) |

TABLE 3-continued

| Example No. | Compound No. | R⁶ | R⁷ | ¹H-NMR (δ) ppm (DMSO d-6) |
|---|---|---|---|---|
| 27 | A-27 | 5-Me-2-pyridyl | H | 13.05(s, 1H), 9.16(s, 1H), 8.80(d, 1H, J=7.8Hz), 8.24(d, 2H, J=8.4 Hz), 7.16(s, 1H), 7.90(d, 1H, J=8.7 Hz), 7.77(d, 2H, J=8.4Hz), 7.72(s, 1H), 2.74(d, 3H) |
| 28 | A-28 | —CH₂COOEt | H | 13.94(bs, 1H), 12.82(s, 1H), 8.21(d, 2H, J=8.7Hz), 7.74(d, 2H, J=8.7 Hz), 7.71(s, 1H), 7.08(s, 1H), 4.09 (q, 2H, J=6.9Hz), 3.75(s, 2H), 1.20 (t, 3H, J=7.2Hz) |

TABLE 4

| Example No. | Compound No. | R⁶ | R⁷ | ¹H-NMR (δ) ppm (DMSO d-6) |
|---|---|---|---|---|
| 29 | A-29 | C(Me)=C(COOMe), see structure | H | 13.91(bs, 1H), 12.86(s, 1H), 8.22(d, 2H, J=8.5Hz), 7.75(d, 2H, J=8.5 Hz), 7.71(s, 1H), 7.22(s, 1H), 7.09 (q, 1H, J=6.9Hz), 3.68(s, 3H), 1.89 (d, 3H, J=6.9Hz) |
| 30 | A-30 | C(COOEt)=N-OAc, see structure | H | 13.94(bs, 1H), 13.23(s, 1H), 8.24(d, 2H, J=8.1Hz), 7.98(s, 1H), 7.75(d, 2H, J=8.1Hz), 7.71(s, 1H), 4.46(q, 1H, J=7.2Hz), 2.10(s, 3H), 1.35(t, 3H, J=7.2Hz) |
| 31 | A-31 | 3-quinolyl | H | 13.90(bs, 1H), 13.08(s, 1H), 9.64(d, 1H, J=2.1Hz), 9.10(s, 1H), 8.27(d, 2H, J=8.5Hz), 8.20(d, 2H, J=8.1 Hz), 8.17(s, 1H), 7.92(td, 1H, J= 8.7Hz, 1.8Hz), 7.76–7.81(m, 3H), 7.72(s, 1H) |
| 32 | A-32 | phenyl | —COOEt | 14.04(bs, 1H), 13.30(s, 1H), 8.25(d, 2H, J=8.5Hz), 7.73–7.76(m, 4H), 7.70(s, 1H), 7.44–7.46(m, 3H), 4.22 (q, 2H, J=6.9Hz), 1.23(t, 3H, J= 6.9Hz) |
| 33 | A-33 | phenyl | —COOMe | 13.97(bs, 1H), 13.31(s, 1H), 8.24(d, 2H, J=8.4Hz), 8.76(d, 2H, J=8.4 Hz), 7.73–7.76(m, 2H), 7.70(s, 1H), 7.44–7.46(m, 3H), 3.75(s, 1H) |
| 34 | A-34 | phenyl | —CH₂COOMe | 13.88(bs, 1H), 12.89(s, 1H), 8.24(d, 2H, J=8.5Hz), 7.76(d, 2H, J=8.5 Hz), 7.71(s, 1H), 7.60–7.63(m, 2H), 7.38–7.51(d, 3H), 3.99(s, 2H), 3.68 (s, 3H) |
| 35 | A-35 | phenyl | —(CH₂)₂CO₂Me | 13.93(bs, 1H), 12.80(s, 1H), 8.22(d, 2H, J=8.5Hz), 7.75(d, 2H, J=8.5 Hz), 7.71(s, 1H), 7.46–7.51(m, 2H), 7.46–7.51(m, 2H), 7.36–7.42(m, 1H), 3.6(s, 3H), 3.17(t, 2H, J=7.4 Hz), 2.72(t, 2H, J=7.4Hz) |
| 36 | A-36 | phenyl | —(CH₂)₂CO₂Et | 13.93(bs, 1H), 12.80(s, 1H), 8.22(d, 2H, J=8.5Hz), 7.75(d, 2H, J=8.5 Hz), 7.71(s, 1H), 7.46–7.51(m, 2H), 7.46–7.51(m, 2H), 7.36–7.42(m, 1H), 4.05(q, 2H, J=7.1Hz), 3.17(t, 2H, J=7.4Hz), 2.72(t, 2H, J=7.4 Hz), 1.16(t, 2H, J=7.1Hz) |

TABLE 5

| Example No. | Compound No. | R⁶ | R⁷ | ¹H-NMR (δ) ppm (DMSO d-6) |
|---|---|---|---|---|
| 37 | A-37 | 4-Cl-C₆H₄- | CH₃ | 13.90(bs, 1H), 12.80(s, 1H), 8.22(d, 2H, J=8.5Hz), 7.74(d, 2H, J=8.5 Hz), 7.72(d, 2H, J=8.2Hz), 7.71(s, 1H), 7.53(d, 2H, J=8.2Hz), 2.51(s, 3H) |
| 38 | A-38 | C₆H₅- | Et | 13.87(bs, 1H), 12.76(s, 1H), 8.22(d, 2H, J=8.5Hz), 7.75(d, 2H, J=8.5 Hz), 7.70(s, 1H), 7.62–7.65(m, 2H), 7.45–7.50(m, 2H), 7.35–7.40(m, 1H), 2.93(q, 2H, J=7.7Hz), 1.29(t, 3H, J=7.7Hz) |
| 39 | A-39 | Me | 4-O₂N-C₆H₄- | 13.93(bs, 1H), 12.98(s, 1H), 8.30(d, 2H, J=9.0Hz), 8.23(d, 2H, J=8.2 Hz), 7.79(d, 2H, J=9.0Hz), 7.75(d, 2H, J=8.2Hz), 7.70(s, 1H), 2.50(s, 1H) |
| 40 | A-40 | 4-O₂N-C₆H₄-CH₂CH₂- | H | 13.92(bs, 1H), 12.76(s, 1H), 8.19(d, 4H, J=8.8Hz), 7.72(d, 2H, J=8.2 Hz), 7.69(s, 1H), 7.54(d, 2H, J=8.2 Hz), 7.05(s, 1H), 4.17(s, 2H) |
| 41 | A-41 | C₆H₅-CH₂CH₂- | Me | 13.15(s, 1H), 8.92(d, 2H, J=6.3Hz), 8.56(s, 1H), 8.40(d, 2H, J=6.3Hz), 8.25(d, 2H, J=8.5Hz), 7.77(d, 2H, J=8.5Hz), 7.72(s, 1H) |
| 42 | A-42 | 4-F-C₆H₄- | COOMe | 13.90(bs, 1H), 13.31(s, 1H), 8.24(d, 2H, J=8.7Hz), 7.80–7.84(m, 2H), 7.75(d, 1H, J=8.7Hz), 7.70(s, 1H), 7.26–7.32(m, 2H), 3.76(s, 3H) |
| 43 | A-43 | 4-F-C₆H₄- | CH₂CH₂Cl | 13.92(bs, 1H), 12.86(s, 1H), 8.22(d, 2H, J=8.5Hz), 7.75(d, 1H, J=8.5 Hz), 7.71(s, 1H), 7.65–7.69(m, 2H), 7.28–7.34(m, 2H), 3.91(t, 2H, J=6.6Hz), 3.33(t, 2H, J=6.6Hz) |
| 44 | A-44 | 4-F-C₆H₄- | Me | 13.92(bs, 1H), 12.81(s, 1H), 8.22(d, 2H, J=8.5Hz), 7.74(d, 2H, J=8.5 Hz), 7.70(s, 1H), 7.52–7.63(m, 2H), 7.28–7.34(m, 2H), 2.38(s, 3H) |
| 45 | A-45 | C₆H₅- | CON(Me)₂ | 13.96(bs, 1H), 13.15(s, 1H), 8.25(d, 2H, J=8.5Hz), 7.77(d, 2H, J=8.5 Hz), 7.23(s, 1H), 7.65–7.69(m, 2H), 7.37–7.51(m, 3H), 2.97(s, 3H), 2.67(s, 3H) |
| 46 | A-46 | C₆H₅- | CONH₂ | 13.94(bs, 1H), 13.10(s, 1H), 8.25(d, 2H, J=8.5Hz), 7.72–7.81(m, 5H), 7.52(bs, 2H), 7.41–7.49(m, 3H) |

TABLE 6

| Example No. | Compound No. | R⁶ | R⁷ | ¹H-NMR (δ) ppm (DMSO d-6) |
|---|---|---|---|---|
| 47 | A-47 | C₆H₅- | CONHMe | 13.90(bs, 1H), 13.11(s, 1H), 8.25(d, 2H, J=8.5Hz), 8.18(q, 1H, J=4.7 Hz), 7.76(d, 2H, J=8.5Hz), 7.71–7.74(m, 3H), 7.37–7.48(m, 3H), 2.71(d, 3H, J=4.7Hz) |
| 48 | A-48 | 2-substituted-C₆H₄- | *—CH₂— | 13.95(bs, 1H), 13.00(s, 1H), 8.25(d, 2H, J=8.5Hz), 7.75(d, 2H, J=8.5 Hz), 7.71(s, 1H), 7.56–7.60(m, 2H), 7.36–7.41(m, 1H), 7.23–7.29(m, 1H), 3.92(s, 2H) |

TABLE 6-continued

| Example No. | Compound No. | R⁶ | R⁷ | ¹H-NMR (δ) ppm (DMSO d-6) |
|---|---|---|---|---|
| 49 | A-49 | 1,2-phenylene | *—(CH$_2$)$_2$— | 13.92(bs, 1H), 12.85(s, 1H), 8.24(d, 2H, J=8.5Hz), 7.72–7.77(m, 4H), 7.18–7.32(m, 3H), 2.96–3.05(m, 4H) |
| 50 | A-50 | 1,2-phenylene | *—(CH$_2$)$_3$— | 13.89(bs, 1H), 12.76(s, 1H), 8.23(d, 2H, J=8.5Hz), 7.99(d, 1H, J=7.1 Hz), 7.75(d, 2H, J=8.1Hz), 7.71(s, 1H), 7.19–7.34(m, 3H), 72.96(t, 2H, J=7.1Hz), 2.78–2.81(m, 2H), 2.07–2.15(m, 2H) |
| 51 | A-51 | 4-Br-C$_6$H$_4$— | CH$_2$CH$_2$Cl | 13.95(bs, 1H), 12.90(s, 1H), 8.22(d, 2H, J=8.5Hz), 7.75(d, 2H, J=8.5 Hz), 7.71(s, 1H), 7.66–7.71(m, 2H), 7.57–7.62(m, 2H), 3.91(t, 2H, J= 6.8Hz), 3.33(t, 2H, J=6.8Hz) |
| 52 | A-52 | 4-AcHN-C$_6$H$_4$— | H | 13.99(bs, 1H), 12.92(s, 1H), 10.03 (s, 1H), 8.24(d, 2H, J=8.5Hz), 7.88 (d, 2H, J=8.5Hz), 7.75(d, 2H, J= 8.5Hz), 7.72(s, 1H), 7.66(d, 2H, J= 8.5Hz), 7.59(s, 1H), 2.07(s, 3H) |
| 53 | A-53 | 3-CF$_3$-C$_6$H$_4$— | H | 13.98(bs, 1H), 12.95(s, 1H), 8.33(s, 1H), 8.25(d, 2H, J=8.5Hz), 8.23–8.27(m, 1H), 7.98(s, 1H), 7.77(d, 2H, J=8.5Hz), 7.69–7.72(m, 3H) |
| 54 | A-54 | H | 3,4-Cl$_2$-C$_6$H$_3$— | 13.90(bs, 1H), 8.22(d, 2H, J=8.5 Hz), 8.14(s, 1H), 7.76(d, 2H, J=8.5 Hz), 775(s, 1H), 7.62–7.70(m, 2H) |
| 55 | A-55 | H | C$_6$H$_5$— | 13.87(bs, 1H), 12.86(s, 1H), 8.23(d, 2H, J=8.5Hz), 7.98(s, 1H), 7.76(d, 2H, J=8.5Hz), 7.71(s, 1H), 7.68–7.52(m, 2H), 7.42–7.47(m, 2H), 7.30–7.35(m, 1H) |
| 56 | A-56 | 5-Br-2-Me-3-Me-thiophene | H | 13.89(bs, 1H), 12.95(s, 1H), 8.23(d, 2H, J=8.5Hz), 7.75(d, 2H, J=8.5 Hz), 7.71(s, 1H), 7.36(s, 1H), 7.11 (s, 1H), 2.40(s, 3H) |

TABLE 7

| Example No. | Compound No. | R⁶ | R⁷ | ¹H-NMR (δ) ppm (DMSO d-6) |
|---|---|---|---|---|
| 57 | A-57 | 2,5-Me$_2$-3-Me-thiophene | H | 13.89(bs, 1H), 12.77(s, 1H), 8.23(d, 2H, J=8.5Hz), 7.76(d, 2H, J=8.5 Hz), 7.71(s, 1H), 7.29(s, 1H), 7.07 (d, 1H, J=1.1Hz), 2.60(s, 3H), 2.40 (s, 3H) |
| 58 | A-58 | 4-Cl-C$_6$H$_3$— (2-substituted) | *—OCH$_2$— | 14.03(bs, 1H), 12.99(s, 1H), 8.23(d, 2H, J=8.2Hz), 7.75(d, 2H, J=8.2 Hz), 7.69(s, 1H), 7.54(d, 1H, J=2.5 Hz), 7.24(dd, 1H, J=8.5Hz, 2.5 Hz), 6.97(d, 1H, J=8.5Hz), 5.54(s, 2H) |

TABLE 7-continued

| Example No. | Compound No. | R⁶ | R⁷ | ¹H-NMR (δ) ppm (DMSO d-6) |
|---|---|---|---|---|
| 59 | A-59 | (2-substituted phenyl) | *—SCH₂— | 13.84(bs, 1H), 12.95(s, 1H), 8.34(d, 2H, J=8.5Hz), 7.86–7.90(m, 1H), 7.76(d, 2H, J=8.5Hz), 7.72(s, 1H), 7.34–7.37(m, 1H), 7.19–7.30(m, 2H), 4.32(s, 2H). |
| 60 | A-60 | 3,4-difluorophenyl | H | 13.93(bs, 1H), 12.93(s, 1H), 8.23(d, 2H, J=8.4Hz), 7.93–8.01(m, 1H), 7.82(s, 1H), 7.80–7.82(m, 1H), 7.76(d, 2H, J=8.4Hz), 7.71(s, 1H) |
| 61 | A-61 | 4-CF₃-phenyl | H | 13.94(bs, 1H), 13.01(s, 1H), 8.25(d, 2H, J=8.2Hz), 8.18(d, 2H, J=8.2 Hz), 7.96(s, 1H), 7.82(d, 2H, J=8.2 Hz), 7.76(d, 2H, J=8.2Hz), 7.71(s, 1H) |
| 62 | A-62 | 4-MeO-3-F-phenyl | H | 13.94(bs, 1H), 12.91(s, 1H), 8.24(d, 2H, J=8.5Hz), 7.96(s, 1H), 7.67–7.80(m, 6H), 7.22–7.28(m, 1H), 3.88(s, 3H) |
| 63 | A-63 | 3-F₃CO-phenyl | H | 13.95(bs, 1H), 12.97(s, 1H), 8.25(d, 2H, J=8.5Hz), 8.00–8.02(m, 1H), 7.94–7.96(m, 6H), 7.77(d, 2H, J=8.5Hz), 7.73(s, 1H), 7.60(t, 1H, J=7.8Hz), 7.34–7.36(m, 1H) |
| 64 | A-64 | 3-F-phenyl | H | 13.97(bs, 1H), 12.97(s, 1H), 8.24(d, 2H, J=8.5Hz), 7.87(s, 1H), 7.26–7.84(m, 6H), 7.72(s, 1H), 7.47–7.54(m, 1H), 7.15–7.21(m, 1H) |
| 65 | A-65 | 4-CF₃-phenyl | CO₂Me | 13.40(s, 1H), 8.24(d, 2H, J=8.2 Hz), 7.97(d, 2H, J=8.5Hz), 7.83(d, 2H, J=8.0Hz), 7.76(d, 2H, J=8.0 Hz), 7.70(s, 1H), 3.77(s, 3H) |
| 66 | A-66 | pentafluorophenyl | H | 8.24(d, 2H, J=8.5Hz), 7.77(d, 2H, J=8.5Hz), 7.73(s, 1H), 7.72(s, 1H) |

TABLE 8

| Example No. | Compound No. | R⁶ | R⁷ | ¹H-NMR (δ) ppm (DMSO d-6) |
|---|---|---|---|---|
| 67 | A-67 | 2-F-phenyl | H | 13.96(bs, 1H), 12.98(s, 1H), 8.25(d, 2H, J=8.2Hz), 8.09–8.15(m, 1H), 7.77(d, 2H, J=8.5Hz), 7.73(s, 1H), 7.63(d, 1H, J=2.5Hz), 7.31–7.45 (m, 3H) |

TABLE 8-continued

| Example No. | Compound No. | R⁶ | R⁷ | ¹H-NMR (δ) ppm (DMSO d-6) |
|---|---|---|---|---|
| 68 | A-68 | 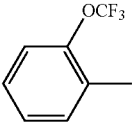 2-OCF₃-phenyl | H | 13.96(bs, 1H), 12.96(s, 1H), 8.23(d, 2H, J=8.2Hz), 7.86(d, 1H, J=7.9 Hz), 7.62–7.78(m, 6H), 7.35(s, 1H) |
| 69 | A-69 | 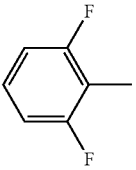 2,6-diF-phenyl | H | 13.93(bs, 1H), 13.03(s, 1H), 8.24(d, 2H, J=8.2Hz), 7.76(d, 2H, J=8.5 Hz), 7.72(s, 1H), 7.47–7.57(m, 1H), 7.55(s, 1H), 7.17–7.28(m, 2H) |
| 70 | A-70 | 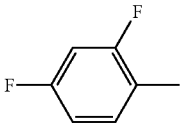 2,4-diF-phenyl | H | 13.95(bs, 1H), 12.97(s, 1H), 8.25(d, 2H, J=8.2Hz), 8.09–7.18(m, 1H), 7.76(d, 2H, J=8.2Hz), 7.72(m, 1H), 7.60(d, 1H, J=2.7Hz), 7.36–7.44(m, 1H), 7.20–7.27(m, 1H) |
| 71 | A-71 | 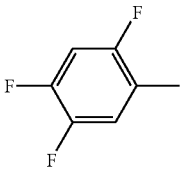 2,4,5-triF-phenyl | H | 13.96(bs, 1H), 12.94(s, 1H), 8.23(d, 2H, J=8.2Hz), 7.97–8.06(m, 1H), 7.75(d, 2H, J=8.2Hz), 7.67–7.72(m, 1H), 7.69(s, 1H), 7.67(d, 1H, J=2.5Hz) |
| 72 | A-72 | 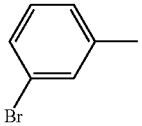 3-Br-phenyl | H | 13.99(bs, 1H), 12.92(s, 1H), 8.24(d, 2H, J=8.5Hz), 8.19(t, 2H, J=1.6 Hz), 7.95–7.98(m, 1H), 7.87(s, 1H), 7.77(d, 2H, J=8.5Hz), 7.52–7.56 (m, 1H), 7.42(t, 1H, J=8.0Hz) |
| 73 | A-73 | 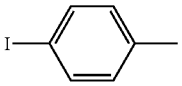 4-I-phenyl | H | 13.97(bs, 1H), 12.95(s, 1H), 8.24(d, 2H, J=8.5Hz), 7.72–7.84(m, 8H), |

Compound (B-1) to Compound (B-25) were synthesized in a manner similar to Example 1 by using 1,4-thiazolidine-dione instead of rhodanine. Their physical data were shown in Tables 9 to 11.

TABLE 9

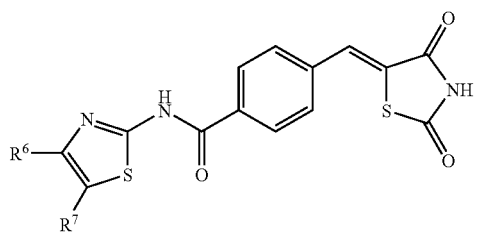

| Example No. | Compound No. | R⁶ | R⁷ | ¹H-NMR (δ) ppm (DMSO d-6) |
|---|---|---|---|---|
| 74 | B-1 | 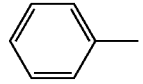 phenyl | H | 12.92(s, 1H), 12.72(bs, 1H), 8.24(d, 2H, J=8.4Hz), 7.95–7.98(m, 2H), 7.87(s, 1H), 7.76(d, 2H, J=8.4Hz), 7.73(s, 1H), 7.43–7.48(m, 2H), 7.32–7.37(m, 1H) |

TABLE 9-continued

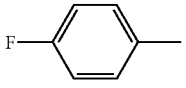

| Example No. | Compound No. | R⁶ | R⁷ | ¹H-NMR (δ) ppm (DMSO d-6) |
|---|---|---|---|---|
| 75 | B-2 | 4-F-C₆H₄- | H | 12.89(s, 1H), 12.75(bs, 1H), 8.24(d, 2H, J=8.4Hz), 7.97–8.02(m, 2H), 7.87(s, 1H), 7.76(d, 2H, J=8.4Hz), 7.70(s, 1H), 7.26–7.32(m, 2H) |
| 76 | B-3 | 4-Br-C₆H₄- | H | 12.92(s, 1H), 12.73(bs, 1H), 8.24(d, 2H, J=8.5Hz), 7.94(d, 2H, J=7.1 Hz), 7.90(s, 1H), 7.86(s, 1H), 7.76 (d, 2H, J=8.5Hz), 7.65(d, 2H, J= 7.1Hz) |
| 77 | B-4 | 4-Cl-C₆H₄- | H | 12.91(s, 1H), 12.72(bs, 1H), 8.24(d, 2H, J=8.5Hz), 7.98(d, 2H, J=8.5 Hz), 7.86(s, 1H), 7.79(s, 1H), 7.76 (d, 2H, J=8.5Hz), 7.52(d, 2H, J= 8.5Hz) |
| 78 | B-5 | 4-Me-C₆H₄- | H | 12.89(s, 1H), 12.75(bs, 1H), 8.24(d, 2H, J=8.5Hz), 7.87(s, 1H), 7.85(d, 1H, J=8.1Hz), 7.76(d, 2H, J=8.5 Hz), 7.64(s, 1H), 7.26(d, 1H, J=8.1 Hz), 2.34(s, 3H) |
| 79 | B-6 | 4-Ph-C₆H₄- | H | 12.94(s, 1H), 12.74(bs, 1H), 8.25(d, 2H, J=8.4Hz), 8.06(d, 2H, J=8.1 Hz), 7.87(s, 1H), 7.72–7.79(m, 7H), 7.49(t, 2H, J=7.5Hz), 7.38(t, 2H, J= 7.5Hz) |
| 80 | B-7 | 4-MeO-C₆H₄- | H | 12.89(s, 1H), 12.76(bs, 1H), 8.24(d, 2H, J=8.4Hz), 7.99(d, 2H, J=8.7 Hz), 7.86(s, 1H), 7.76(d, 2H, J=8.4 Hz), 7.56(s, 1H), 7.01(d, 2H, J= 8.7Hz), 3.80(s, 3H) |
| 81 | B-8 | 2-NO₂-C₆H₄- | H | 12.85(s, 1H), 12.73(bs, 1H), 8.21(d, 2H, J=8.7Hz), 7.94(dd, 1H, J=7.8 Hz, 1.2Hz), 7.86(s, 1H), 7.78–7.83 (m, 2H), 7.74(d, 2H, J=8.7Hz), 7.61–7.67(m, 1H), 7.59(S, 1H) |

TABLE 10

| Example No. | Compound No. | R⁶ | R⁷ | ¹H-NMR (δ) ppm (DMSO d-6) |
|---|---|---|---|---|
| 82 | B-9 | t-Bu | H | 12.70(s, 1H), 8.20(d, 2H, J=8.7 Hz), 7.84(s, 1H), 7.73(d, 2H, J=8.7 Hz), 6.84(S, 1H), 1.31(s, 9H) |
| 83 | B-10 | 4-t-Bu-C₆H₄- | H | 12.90(s, 1H), 12.73(bs, 1H), 8.24(d, 2H, J=8.5Hz), 7.88(d, 2H, J=8.5 Hz), 7.87(s, 1H), 7.76(d, 2H, J=8.5 Hz), 7.64(s, 1H), 7.47(d, 2H, J=8.5 Hz), 1.32(s, 9H) |

TABLE 10-continued

| Example No. | Compound No. | R<sup>6</sup> | R<sup>7</sup> | <sup>1</sup>H-NMR (δ) ppm (DMSO d-6) |
|---|---|---|---|---|
| 84 | B-11 | 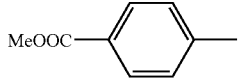 MeOOC— | H | 12.97(s, 1H), 12.72(bs, 1H), 8.25(d, 2H, J=8.5Hz), 8.08(dd, 4H, J= 18.9Hz, 8.8Hz), 7.94(s, 1H), 7.87(s, 1H), 7.76(d, 2H, J=8.5Hz), 3.81(s, 3H) |
| 85 | B-12 | 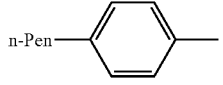 n-Pen— | H | 12.89(s, 1H), 12.72(bs, 1H), 8.24(d, 2H, J=8.7Hz), 7.87(s, 1H), 7.85(d, 2H, J=8.4Hz), 7.75(d, 2H, J=8.4 Hz), 7.63(s, 1H), 7.26(d, 2H, J=8.7 Hz), 2.60(t, 2H, J=7.8Hz), 1.55–1.65(m, 2H), 1.27–1.36(m, 2H), 0.87(t, 3H, J=7.8Hz) |
| 86 | B-13 | 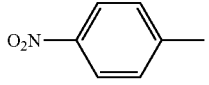 O<sub>2</sub>N— | H | 13.03(s, 1H), 12.73(bs, 1H), 8.34(d, 2H, J=8.5Hz), 8.24(d, 2H, J=8.7 Hz), 8.22(d, 2H, J=8.7Hz), 8.09(s, 1H), 7.86(s, 1H), 7.76(d, 2H, J=8.5 Hz) |
| 87 | B-14 | 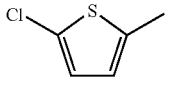 Cl— | H | 12.89(s, 1H), 12.73(bs, 1H), 8.23(d, 2H, J=8.7Hz), 7.87(s, 1H), 7.75(d, 2H, J=8.7Hz), 7.64(s, 1H), 7.44 (d, 1H, J=3.9Hz), 7.15(d, 1H, J= 3.9Hz) |
| 88 | B-15 | 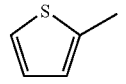 | H | 12.89(s, 1H), 12.72(bs, 1H), 8.24(d, 2H, J=8.5Hz), 7.87(s, 1H), 7.83–7.84(m, 1H), 7.75(d, 2H, J=8.5 Hz), 7.62–7.63(m, 2H), 7.56(s, 1H) |
| 89 | B-16 | 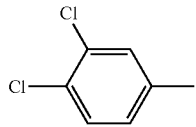 Cl, Cl | H | 12.92(s, 1H), 12.73(bs, 1H), 8.24(d, 2H, J=8.7Hz), 8.22(d, 1H, J=2.4 Hz), 7.95(dd, 1H, J=8.4Hz, 2.4 Hz), 7.94(s, 1H), 7.86(s, 1H), 7.77 (d, 2H, J=8.7Hz), 7.73(d, 1H, J= 8.4Hz) |
| 90 | B-17 | 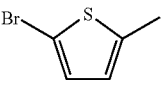 Br— | H | 12.99(s, 1H), 12.75(bs, 1H), 8.38(m, 1H), 8.25(m, 2H), 7.99(m, 2H), 7.87 (s, 1H), 7.77(d, 2H, J=8.4Hz), 7.55 (m, 4H), 7.73(m, 1H), |
| 91 | B-18 | 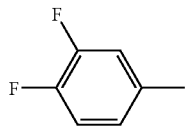 F, F | H | 12.91(s, 1H, ), 12.76(bs, 1H), 8.86(s, 1H), 8.23(d, 2H, J=8.7Hz), 7.96(m, 1H), 7.83(m, 1H), 7.82(s, 1H), 7.75 (d, 2H, J=8.7Hz), 7.52(m, 1H) |

TABLE 11

| Example No. | Compound No. | R<sup>6</sup> | R<sup>7</sup> | <sup>1</sup>H—NMR (δ) ppm (DMSO d-6) |
|---|---|---|---|---|
| 92 | B-19 | 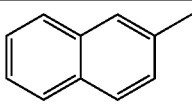 | H | 12.99(s, 1H), 12.75(bs, 1H), 8.38 (1H, m), 8.26(d, 2H, J=8.7 Hz), 7.99 (m, 2H), 7.87(s, 1H), 7.77(d, 2H, J=8.7 Hz), 7.56(m, 4H), 7.73(m, 1H) |
| 93 | B-20 | H | H | 12.72(bs, 2H), 8.22(d, 2H, J=8.7 Hz), 7.86(s, 1H), 7.58(d, 1H, J=3.6 Hz), 7.75(d, 2H, J=8.7 Hz), 7.31(d, 1H, J=3.6 Hz), |
| 94 | B-21 | 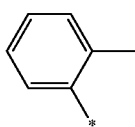 | *—(CH<sub>2</sub>)<sub>2</sub>— | 12.84(s, 1H), 12.73(bs, 1H), 8.23(d, 2H, J=8.5 Hz), 7.86(s, 1H), 7.75(d, 2H, J=8.5 Hz), 7.74(d, 1H, J=6.9 Hz), 7.18–7.32(m, 3H), 2.96–3.05 (m, 4H) |

TABLE 11-continued

| Example No. | Compound No. | R⁶ | R⁷ | ¹H—NMR (δ) ppm (DMSO d-6) |
|---|---|---|---|---|
| 95 | B-22 | (2-substituted phenyl, forming ring) | *—(CH₂)₃— | 12.75(s, 2H), 8.23(d, 2H, J=8.5 Hz), 8.00(d, 2H, J=7.4 Hz), 7.86(s, 1H), 7.75(d, 2H, J=8.5 Hz), 7.19–7.33(m, 3H), 2.96(t, 2H, J=6.8 Hz), 2.78–2.82(m, 2H), 2.06–2.15(m, 2H) |
| 96 | B-23 | 4-F-C₆H₄— | CH₂CH₂Cl | 12.86(s, 1H), 12.74(bs, 1H), 8.22(d, 2H, J=8.5 Hz), 7.86(s, 1H), 7.75(d, 2H, J=8.5 Hz), 7.65–7.69(m, 2H), 7.29–7.35(m, 2H), 3.91(t, 2H, J=6.8 Hz), 3.32(t, 2H, J=6.8 Hz) |
| 97 | B-24 | 4-Cl-C₆H₄— | Me | 12.76(s, 1H), 12.70(bs, 1H), 8.22(d, 2H, J=8.5 Hz), 7.85(s, 1H), 7.74(d, 2H, J=8.5 Hz), 7.72(d, 2H, J=8.5 Hz), 7.53(d, 2H, J=8.5 Hz), 2.51(s, 1H) |
| 98 | B-25 | C₆H₅— | CH₂Me | 12.77(s, 1H), 12.70(bs, 1H), 8.22(d, 2H, J=8.5 Hz), 7.86(s, 1H), 7.75(d, 2H, J=8.5 Hz), 7.62–7.65(m, 2H), 7.45–7.50(m, 2H), 7.35–7.40(m, 1H), 2.93(q, 2H, J=7.4 Hz), 1.29(t, 3H, J=7.4 Hz) |

Compound (C-1) to Compound (C-9) were synthesized in a manner similar to Example 1 by using 1,4-oxazolidine-dione instead of rhodanine. Their physical data were shown in Tables 12.

TABLE 12

| Example No. | Compound No. | R⁶ | R⁷ | ¹H-NMR (δ) ppm (DMSO d-6) |
|---|---|---|---|---|
| 99 | C-1 | 3,4-diCl-C₆H₃— | H | 12.88(s, 1H,), 12.54(bs, 1H), 8.22(s, 1H), 8.20(d, 2H, J=5.8Hz), 7.91–7.97(m, 4H), 7.72(d, 1H, J=8.5Hz), 6.83(s, 1H) |
| 100 | C-2 | 4-MeOOC-C₆H₄— | H | 12.96(s, 1H), 12.54(bs, 1H), 8.22(d, 2H, J=8.7Hz), 8.04–8.13(m, 1H), 7.94(s, 1H), 7.93(d, 2H, J=6.9Hz), 6.84(s, 1H), 3.88(s, 3H) |
| 101 | C-3 | 3,4-diF-C₆H₃— | H | 12.89(s, 1H,), 12.55(bs, 1H), 8.21(d, 2H, J=8.5Hz), 7.89–8.03(m, 1H), 7.93(d, 2H, J=8.5Hz), 7.89–7.86(m, 1H), 7.82(s, 1H), 7.48–7.57(m, 1H), 6.83(s, 1H) |
| 102 | C-4 | 5-Cl-thien-2-yl | H | 12.96(s, 1H), 12.55(bs, 1H), 8.20(d, 2H, J=8.5Hz), 7.92(d, 2H, J=8.5Hz), 7.34(s, 1H), 7.42(d, 1H, J=3.8Hz), 7.24(d, 2H, J=3.8Hz), 6.83(s, 1H) |

TABLE 12-continued

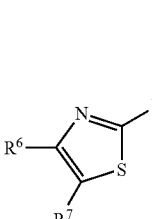

| Example No. | Compound No. | R⁶ | R⁷ | ¹H-NMR (δ) ppm (DMSO d-6) |
|---|---|---|---|---|
| 103 | C-5 | 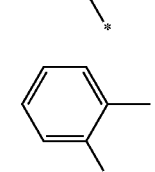 | *—(CH$_2$)$_2$— | 12.81(s, 1H), 12.54(bs, 1H), 8.21(d, 2H, J=8.5Hz), 7.92(d, 2H, J=8.5Hz), 7.74(d, 2H, J=7.4Hz), 7.18–7.32(m, 3H), 6.83(s, 1H), 2.95–3.05(m, 4H) |
| 104 | C-6 | 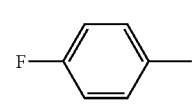 | *—(CH$_2$)$_3$— | 12.72(s, 1H), 12.56(bs, 1H), 8.20(d, 2H, J=8.5Hz), 8.01(d, 1H, J=7.4Hz), 7.92(d, 2H, J=8.5Hz), 7.20–7.34(m, 3H), 6.82(s, 1H), 2.97(t, 2H, J=6.8Hz), 2.79–2.81(m, 2H), 2.09–2.13(m, 2H) |
| 105 | C-7 | 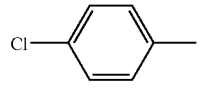 | CH$_2$CH$_2$Cl | 12.83(s, 1H), 12.55(bs, 1H), 8.19(d, 2H, J=8.5Hz), 7.92(d, 2H, J=8.5Hz), 7.65–7.70(m, 2H), 8.28–7.35(m, 2H), 6.83(s, 1H), 3.91(t, 2H, J=6.9Hz), 3.34(t, 2H, J=6.9Hz) |
| 106 | C-8 | 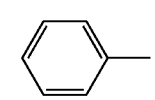 | Me | 12.75(s, 1H), 12.53(bs, 1H), 8.19(d, 2H, J=8.5Hz), 7.91(d, 2H, J=8.5Hz), 7.72(d, 2H, J=8.5Hz), 7.53(d, 2H, J=8.5Hz), 6.82(s, 1H), 2.51(s, 3H) |
| 107 | C-9 | 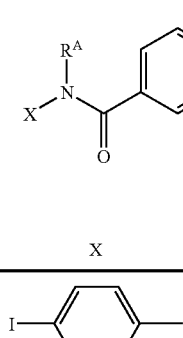 | CH$_2$Me | 12.74(s, 1H), 12.55(bs, 1H), 8.19(d, 2H, J=8.5Hz), 7.92(d, 2H, J=8.5Hz), 7.62–7.65(m, 2H), 7.45–7.50(m, 2H), 7.35–7.40(m, 1H), 6.83(s, 1H), 2.93(q, 2H, J=7.4Hz), 1.30(t, 3H, J=7.4Hz) |

Compound (D-1) to Compound (D-20) were synthesized in a manner similar to Example 1 by using commercial available amines instead of compound (4) in process 3. Their physical data were shown in Tables 13 to 15.

TABLE 13

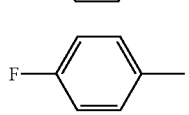

| Example No. | Compound No. | X | R^A | ¹H-NMR (δ) ppm (DMSO d-6) |
|---|---|---|---|---|
| 108 | D-1 |  | H | 7.64(2H, d, J=8.7Hz), 7.71(2H, d, J=8.7Hz), 7.74(2H, d, J=8.7Hz), 7.86(1H, s), 8.06(2H, d, J=8.1Hz), 12.70(1H, br.s) |
| 109 | D-2 |  | H | 7.21(2H, dd, J=8.7Hz, J$_{H–F}$=8.7Hz), 7.75(2H, d, J=8.7Hz), 7.80(2H, m), 7.86(1H, s), 8.06(2H, d, J=8.7Hz), 10.42(1H, s), 12.72(1H, bs) |

TABLE 13-continued

| Example No. | Compound No. | X | R^A | $^1$H-NMR (δ) ppm (DMSO d-6) |
|---|---|---|---|---|
| 110 | D-3 | 4-methyl-9-ethylcarbazol-? (9-ethylcarbazolyl) | H | 1.33(3H, t, J=6.9Hz), 4.45(2H, q, J=6.9Hz), 7.20(1H, dd, J=8.1Hz, 8.1Hz), 7.46(1H, dd, J=8.1Hz, 8.1Hz), 7.60(2H, m), 7.75(1H, m), 7.76(2H, d, J=8.7Hz), 7.88(1H, s), 8.15(2H, d, J=8.7Hz), 8.58(1H, s), 10.43(1H, s), 12.72(1H, bs) |
| 111 | D-4 | 3-methyl-N-ethyl-N-propyl-aniline | H | 1.16(3H, t, J=7.2Hz), 2.30(3H, s), 3.40(2H, q, J=7.2Hz), 3.56(2H, t, 5.4Hz), 3.68(2H, m), 6.44(1H, bs), 6.58(1H, d, J=7.5Hz), 6.63(1H, s), 6.64(1H, d, J=7.5Hz), 7.14(1H, dd, J=7.5Hz, 7.5Hz), 7.52(2H, d, J=8.7Hz), 7.77(2H, d, J=8.7Hz), 7.83(1H, s) |
| 112 | D-5 | N-phenyl-N'-methylurea | Ph | 6.95(1H, dd, J=7.5Hz, 7.5Hz), 7.23(3H, m), 7.38(6H, m), 7.60(2H, m), 7.69(2H, m), 7.77(1H, s), 9.02(1H, s), 9.25(1H, s), 12.66(1H, bs) |
| 113 | D-6 | 4-(phenylazo)tolyl | Me | 3.47(3H, s), 7.41(2H, d, J=9.0Hz), 7.47(4H, m), 7.58(3H, m), 7.78(2H, d, J=9.0Hz), 7.84(2H, m), 12.62(1H, bs) |
| 114 | D-7 | 5-methoxy-2-methylbenzothiazol-? | H | 3.83(3H, s), 7.07(1H, dd, J=2.4Hz, 9.0Hz), 7.62(1H, d, J=2.4Hz), 7.68(1H, d, J=9.0Hz), 7.76(2H, d, J=8.4Hz), 7.87(1H, s), 8.23(2H, d, J=8.4Hz), 12.75(1H, s), 12.88(1H, s) |
| 115 | D-8 | 4-(phenylazo)phenyl | H | 7.58(3H, m), 7.77(2H, d, J=8.7Hz), 7.88(2H, m), 7.95(3H, m), 8.06(2H, m), 8.11(2H, d, J=8.7Hz), 10.72(1H, s), 12.72(1H, bs) |
| 116 | D-9 | benzyl | H | 4.49(2H, d, J=6.0Hz), 7.25(1H, m), 7.33(4H, m), 7.69(2H, d, J=8.1Hz), 7.83(1H, s), 8.01(2H, d, J=8.1Hz), 9.17(1H, t, J=6.0Hz), 12.69(1H, bs) |

TABLE 14

| Example No. | Compound No. | X | R^A | $^1$H-NMR (δ) ppm (DMSO d-6) |
|---|---|---|---|---|
| 117 | D-10 | 4-(methylthio)tolyl | H | 2.47(3H, s), 7.27(2H, d, J=9.0Hz), 7.74(4H, m), 7.85(1H, s), 8.06(2H, d, J=9.0Hz), 12.60(1H, bs) |

TABLE 14-continued

| Example No. | Compound No. | X | R^A | $^1$H-NMR ($\delta$) ppm (DMSO d-6) |
|---|---|---|---|---|
| 118 | D-11 | n-Bu-C6H4- | H | 12.45(bs, 1H), 10.29(s, 1H), 8.07(d, 2H, J=8.1Hz), 7.87(s, 1H), 7.74(d, 2H, J=8.1Hz), 7.67(d, 2H, 8.7Hz), 7.18(d, 2H, J=8.7Hz), 2.56(t, 2H, J= 7.5Hz), 1.50–1.61(m, 2H), 1.25–1.37 (m, 2H), 0.91(t, 3H, J=7.5Hz) |
| 119 | D-12 | 3-phenyl-5-methylisoxazol-yl | H | 13.94(bs, 1H), 12.25(s, 1H), 8.17(d, 2H, J=8.4Hz), 7.88–7.92(m, 2H), 7.77(d, 2H, J=8.4Hz), 7.72(s, 1H), 7.52–7.53(m, 3H), 6.96(s, 3H) |
| 120 | D-13 | 3-(4-methoxycarbonylphenyl)-5-methylisoxazol-yl | H | 3.893(3H, s), 7.026(1H, s), 7.756(2H, d, J=8.4Hz), 7.851(1H, s), 8.028–8.100 (4H, m), 8.156(2H, d, J=8.4Hz), 12.277 (1H, s), 12.714(1H, br) |
| 121 | D-14 | 4-(2,4-dichlorophenyl)-2-methylthiazol-yl | H | 7.556(1H, dd, J=2.1, 8.4Hz), 7.730–7.769(4H, m), 7.865(1H, s), 7.943(1H, d, J=8.4Hz), 8.236(2H, d, J=8.4Hz), 12.732(1H, s), 12.963(1H, br) |
| 122 | D-15 | 3-phenyl-5-methyl-1H-pyrazol-yl | H | 7.019(1H, br), 7.332–7.381(1H, m), 7.467(2H, t, J=7.7Hz), 7.711–7.785(4H, m), 7.862(1H, s), 8.147(2H, d, J=8.7 Hz) 11.024(1H, s), 12.5(1H, br) |
| 123 | D-16 | 3-(4-methoxycarbonylphenyl)-5-methyl-1H-pyrazol-yl | H | 3.879(3H, s), 7.107(1H, s), 7.732(2H, d, J=8.4Hz), 7.861(1H, s), 7.933(2H, d, J=8.7Hz), 8.036(2H, d, J=8.7Hz), 8.152(2H, d, J=8.4Hz), 11.124(1H, s), 12.711(1H, br) |
| 124 | D-17 | 5-(4-fluorophenyl)-2-methylpyridin-yl | H | 7.31–7.37(2H, m), 7.735(2H, d, J=9.0 Hz), 7.86–7.83(2H, m), 7.871(1H, s), 8.149–8.178(3H, m), 8.298(2H, d, J=8.7 Hz), 8.73(1H, s), 11.058(1H, s), 12.707 (1H, br) |
| 125 | D-18 | 5-(4-ethoxycarbonylphenyl)-2-methylpyridin-yl | H | 1.352(3H, t, J=7.2Hz), 4.350(2H, q, J=7.2Hz), 7.728(2H, d, J=8.4Hz), 7.862(1H, s), 7.919(2H, d, J=8.4Hz), 8.062(2H, d, J=8.4Hz), 8.164(2H, d, J=8.7Hz), 11.119(1H, s), 12.716(1H, br) |

TABLE 15

| Example No. | Compound No. | X | $^1$H-NMR ($\delta$) ppm (DMSO d-6) |
|---|---|---|---|
| 126 | D-19 | 4-phenylthiophen-2-yl | 13.98(bs, 1H), 11.82(s, 1H), 8.15(d, 2H, J=8.2Hz), 7.80(d, 2H, J=8.2Hz), 7.72(s, 1H), 7.65(d, 2H, J=8.0Hz), 7.43(t, 2H, J=8.0Hz), 7.39(s, 1H), 7.30(t, 1H, J=8.0Hz), 7.30(s, 1H). |

TABLE 15-continued

| Example No. | Compound No. | X | ¹H-NMR (δ) ppm (DMSO d-6) |
|---|---|---|---|
| 127 | D-20 | 4-chlorophenyl-imidazole | 12.1(bs, 2H), 11.9(bs, 1H), 8.19(d, 2H, J=8.5Hz), 7.79(d, 2H, J=8.5Hz), 7.74(d, 2H, J=8.5Hz), 7.71(s, 1H), 7.46(s, 1H) 7.40(d, 2H, J=8.5Hz) |

Compound (E-1) to Compound (E-5) were synthesized in a manner similar to Example 1 by using methyl 5-formyl-furancarboxylate, methyl 5-formyl-thiophenecarboxylate, and methyl 4-formyl-nicotinate instead of methyl terephthaldehydate. Their physical data were shown in Tables 16.

TABLE 16

| Example No. | Compound No. | X | Z | ¹H-NMR (δ) ppm (DMSO d-6) |
|---|---|---|---|---|
| 128 | E-1 | 3,4-dichlorophenyl-2-methylthiazole | 2,5-furan | 7.23(1H, d, J=3.9Hz), 7.65(1H, s), 7.71(1H, d, J=8.4Hz), 7.88–7.94(3H, m), 8.19(1H, d, J=2.4Hz), 12.6(1H, br), 12.92(1H, s) |
| 129 | E-2 | 3,4-dichlorophenyl-2-methylthiazole | 2,5-thiophene | 7.69–7.73(2H, m), 7.90–7.94(2H, m), 8.05(1H, s), 8.19(1H, d, J=2.1Hz), 8.33(1H, d, J=4.2Hz), 12.7(1H, br), 13.06(1H, s) |
| 130 | E-3 | 4-(MeOC(O))phenyl-2-methylthiazole | 2,5-thiophene | 3.87(3H, s), 7.72(1H, d, J=4.2Hz), 7.91(1H, s), 8.02–8.10(5H, m), 8.34(1H, d, J=4.2Hz), 12.7(1H, br), 13.11(1H, s) |
| 131 | E-4 | 3,4-dichlorophenyl-2-methylthiazole | pyridine | 13.75(bs, 1H), 13.08(s, 1H), 9.37(d, 1H, J=2.1Hz), 8.56(dd, 1H, J=8.2Hz, 2.4Hz), 8.21(d, 1H, J=1.8Hz), 8.05(d, 1H, J=7.9Hz), 7.95(s, 1H), 7.94(dd, 1H, J=9.1Hz, 2.1Hz), 7.75(s, 1H), 7.33(d, 1H, J=8.5Hz) |

TABLE 16-continued

| Example No. | Compound No. | X | Z | $^1$H-NMR ($\delta$) ppm (DMSO d-6) |
|---|---|---|---|---|
| 132 | E-5 | 4-(2-methylthiazol-4-yl)-benzoyl, MeO-C(=O)-C₆H₄-(2-methylthiazol-4-yl) | 5-pyridyl (2-methyl) | 13.77(bs, 1H), 13.15(s, 1H), 9.48 (d, 1H, J=2.7Hz), 8.57(dd, 1H, J= 8.4Hz, 2.4Hz), 8.02–8.12(m, 4H), 7.96(s, 1H), 7.92–8.02(m, 1H), 7.75(s, 1H), 3.88(s, 3H) |

Compound (F-1) to Compound (F-4) were synthesized in a manner similar to Example 1 by using methyl 4-formyl-phenoxyacetate, methyl 4-formyl-cinnamate, instead of methyl terephthaldehydate. Their physical data were shown in Tables 17.

TABLE 17

| Example No. | Compound No. | R$^6$ | Y | $^1$H-NMR ($\delta$) ppm (DMSO d-6) |
|---|---|---|---|---|
| 133 | F-1 | 3,4-dichlorophenyl | -NH-C(=O)-CH$_2$-O- | 4.50(2H, s), 7.15(2H, d, J=8.7 Hz), 7.58(2H, d, J=8.7Hz), 7.76(1H, s), 7.88–7.918(2H, m), 8.15(1H, d, J=1.8Hz), 12.52(1H, br), 12.60 (1H, s) |
| 134 | F-2 | 4-(methoxycarbonyl)phenyl | -NH-C(=O)-CH$_2$-O- | 3.87(3H, s), 5.00(2H, s), 7.16(2H, d, J=8.7Hz), 7.59(2H, d, J=8.7 Hz), 7.76(1H, s), 7.88(1H, s), 8.01–8.08(4H, m), 12.50(1H, br), 12.65 (1H, s) |
| 135 | F-3 | 4-(methoxycarbonyl)phenyl | -NH-C(=O)-CH=CH- | 3.87(3H, s), 7.01(1H, d, J=16.2 Hz), 7.66–7.88(7H, m), 8.01–8.10 (4H, m), 12.64(1H, s) |
| 136 | F-4 | 3,4-dichlorophenyl | -NH-C(=O)-CH=CH- | 6.99(1H, d, J=15.9Hz), 7.65–7.79 (7H, m), 7.86(1H, s), 7.89(1H, dd, J=2.1Hz, 8.7Hz), 8.13(1H, d, J= 2.1Hz), 12.58(1H, s) |

Example 137

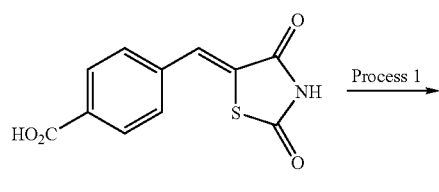

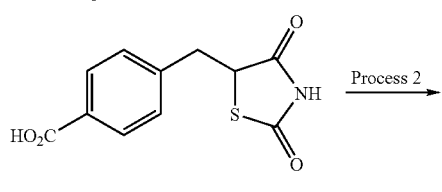

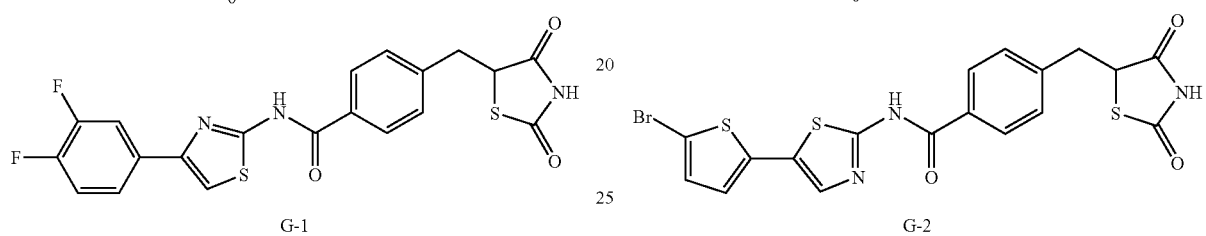

G-1

(Process 1)

To a suspension of compound (3)(1.10 g) synthesized by Process 2 in Example 1 in methanol (300 ml), 10% Palladium-Carbon (0.55 g) was added and the reaction mixture was stirred under hydrogen atmosphere. Removing Palladium-Carbon by filtration and evaporation of the solvent under reduced pressure yielded 1.05 g of compound (6).

$^1$H NMR (DMSO-$d_6$, δ ppm): 12.46 (bs, 1H), 7.99 (d, 2H, J=8.4 Hz), 7.37 (d, 2H, J=8.4 Hz), 4.95 (dd, 1H, J=9.0 Hz, 4.5 Hz), 3.45 (dd, 1H, J=14.4 Hz, 4.5 Hz), 3.22 (dd, 1H, J=14.4 Hz, 9.0 Hz)

(Process 2)

A mixture of compound (6)(1.0 g) in dioxane (20 ml) and thionyl chloride (10 ml) was heated to dissolve at 100° C. Evaporation of the solvent under reduced pressure gave carboxylic acid chloride. The obtained carboxylic acid chloride was not purified to proceed to the further reaction. To the solution of the carboxylic acid chloride (286 mg), and 2-amino-4-(3',4'-difluorophenyl)thiazole (212 mg) in dioxane (50 ml), pyridine (121 μl) was added and the reaction mixture was heated at 100° C. for 2 hours. After evaporation of the solvent under reduced pressure, the residue was purified by silica gel column chromatography (hexane—ethyl acetate; 2:1) to obtain compound (G-1).

$^1$H NMR (DMSO-$d_6$, δ ppm): 12.75 (s, 1H), 12.11 (bs, 1H), 8.08 (d, 2H, J=8.2 Hz), 7.93–8.01 (m, 1H), 7.80–7.84 (m, 1H), 7.80 (s, 1H), 7.48–7.59 (m, 1H), 7.44 (d, 2H, J=8.2 Hz), 5.01 (dd, 1H, J=8.8 Hz, 4.7 Hz), 3.48 (dd, 1H, J=14.0 Hz, 4.7 Hz), 3.26 (dd, 1H, J=14.0 Hz, 8.8 Hz)

Example 138

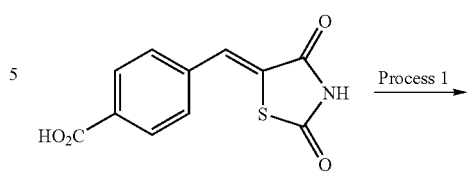

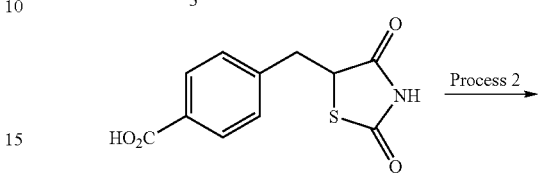

G-2

Compound (G-2) was synthesized in a manner similar to Example 137 by using 2-amino-5-(5'-bromothiophenyl)thiazole instead of 2-amino-4-(3',4'-difluorophenyl)thiazole.

$^1$H NMR (DMSO-$d_6$, δ ppm): 12.81 (s, 1H), 12.10 (bs, 1H), 8.08 (d, 2H, J=8.2 Hz), 7.61 (s, 1H), 7.43 (d, 2H, J=8.2 Hz), 7.40 (d, 1H, J=4.1 Hz), 7.24 (d, 1H, J=4.1 Hz), 5.01 (dd, 1H, J=8.8 Hz, 4.4 Hz), 3.58 (dd, 1H, J=14.0 Hz, 4.4 Hz), 3.25 (dd, 1H, J=14.0 Hz, 8.8 Hz)

Example 139

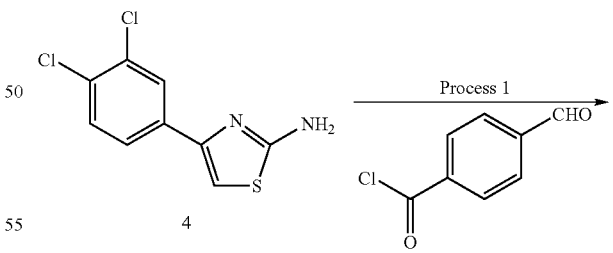

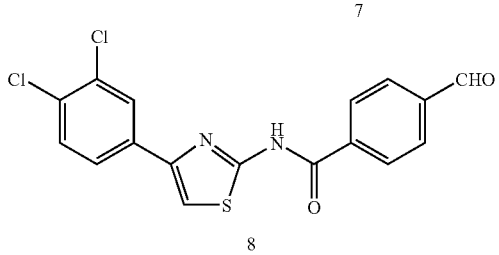

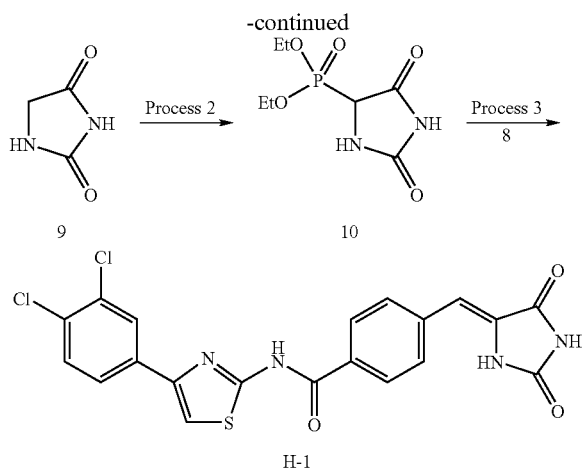

(Process 1)

To a suspension of p-formyl-benzoic acid (3.0 g) in chloroform (30 ml) and thionyl chloride (6 ml), one drop of DMF was added and the mixture was refluxed. After confirmation of the dissolution of the mixture, evaporation of the solvent under reduced pressure gave 3.0 g of compound (7). The obtained compound (7) was subjected to the reaction without further purification. To the solution of compound (4)(2.52 g) in DMF, sodium hydride (0.45 mg) was added in an ice bath. After the reaction mixture was stirred at room temperature for 30 min, 1.36 g of compound (7) was added. After stirring for further 30 min, the resulting mixture was quenched with methanol and acidified with 1N hydrochloric acid. Extraction with ethyl acetate, evaporation of the solvent, and recrystallization from chloroform gave 1.06 g of compound (8).

$^1$H NMR(DMSO-$d_6$, δ ppm) 13.04 (bs, 1H), 10.13 (s, 1H), 8.30 (d, 2H, J=8.4 Hz), 8.22 (d, 1H, J=2.1 Hz), 8.07 (d, 2H, J=8.4 Hz), 7.95 (dd, 1H, J=8.4 Hz, 2.1 Hz), 7.95 (s, 1H), 7.73 (d, 1H, J=8.4 Hz).

(Process 2)

To a solution of hydantoin (2.0 g) in acetic acid, bromine (1.3 ml) was added at 85° C. The reaction solution was stirred at 85° C. for 30 min and then cooled to 30° C., triethyl phosphite (4.8 ml) was added to the solution maintaining the temperature from 40 to 45° C. After the reaction mixture is stirred at room temperature for 90 min, ether was added and then filtration of the precipitated crystal gave 1.1 g of the compound.

$^1$H NMR(DMSO-$d_6$, δ ppm) 10.91 (s, 1H), 8.41 (s, 1H), 4.76 (dd, 1H, J=14.7 Hz, 1.2 Hz), 4.04–4.13 (m, 4H), 1.25 (t, 6H, J=7.2 Hz).

(Process 3)

A mixture of sodium (10 mg) in ethanol (1 ml) was stirred at room temperature. After confirmation of dissolution of sodium, compound (10)(108 mg) was added and the reaction mixture was stirred at room temperature for 10 min. After compound (10)(159 mg) was added, the reaction mixture was stirred at room temperature. Evaporation of the solvent under reduced pressure and recrystallization of the residue from methanol obtained compound (H-1). Compound (H-1) was obtained as the mixture of E isomer and Z isomer.

E isomer:

$^1$H NMR (DMSO-$d_6$, δ ppm): 12.81 (bs, 1H), 10.76 (bs, 1H), 10.46 (s, 1H), 8.22 (d, 1H, J=2.4 Hz), 8.15 (d, 2H, J=8.7 Hz), 7.96 (dd, 1H, J=8.7 Hz, 2.4 Hz), 7.91 (s, 1H), 7.78 (d, 2H, J=8.7 Hz), 7.73 (d, 1H, J=8.7 Hz), 6.48 (s, 1H).

Z isomer:

$^1$H NMR (DMSO-$d_6$, δ ppm): 11.35 (bs, 1H), 11.26 (bs, 1H), 10.13 (s, 1H), 8.22 (d, 1H, J=2.4 Hz), 8.10 (d, 2H, J=9.0 Hz), 8.05 (d, 2H, J=9.0 Hz), 7.95 (dd, 1H, J=8.7 Hz, 2.4 Hz), 7.91 (s, 1H), 7.73 (d, 1H, J=8.7 Hz), 6.38 (s, 1H).

Compound (H-2) to Compound (H-5) were synthesized in a manner similar to above-mentioned method. Their physical data were shown in Tables 18.

TABLE 18

| Example No. | Compound No. | M | T | $^1$H-NMR (δ) ppm (DMSO d-6) |
|---|---|---|---|---|
| 140 | H-2 | NH | S | 12.85(bs, 1H), 12.47(bs, 1H), 12.33 (bs, 1H), 8.22(d, 1H, J=1.8Hz), 8.16(d, 2H, J=8.2Hz), 7.91–7.97 (m, 4H), 7.73(d, 1H, J=8.5Hz), 6.54(s, 1H) |
| 141 | H-3 | CH$_2$ | O | 12.88(s, 1H), 11.51(s, 1H), 8.21(d, 1H, J=2.1Hz), 8.20(d, 2H, J=9.3 Hz), 7.95(dd, 1H, J=8.1Hz, 2.1 Hz), 7.92(s, 1H), 7.80(d, 2H, J=9.3 Hz), 7.72(d, 1H, J=8.1Hz), 7.46(t, 1H, J=2.1Hz), 3.74(d, 1H, J=2.1 Hz) |
| 142 | H-4 | NMe | O | 9.48(bs, 1H), 8.21(s, 1H), 8.19(dd, 4H, J=13.2Hz, 7.8Hz), 7.94(d, 1H, J=6.6Hz), 7.89(s, 1H), 7.72(d, 1H, J=8.1Hz), 6.47(s, 1H), 2.71(d, 3H, J=4.8Hz) |
| 143 | H-5 | O | S | 12.91(s, 1H), 8.21–8.24(m, 3H), 7.93–8.01(m, 4H), 7.72(d, 1H, J= 8.2Hz), 6.57(s, 1H) |

Example 144, 145

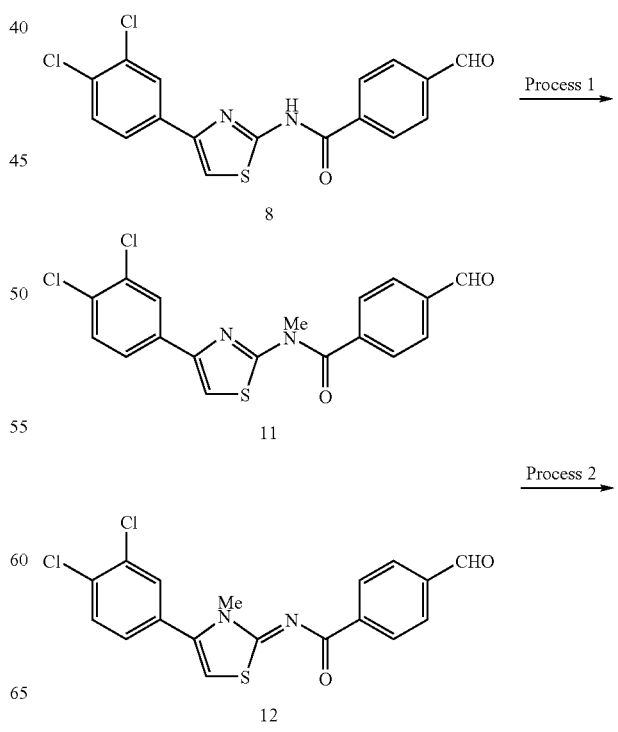

-continued

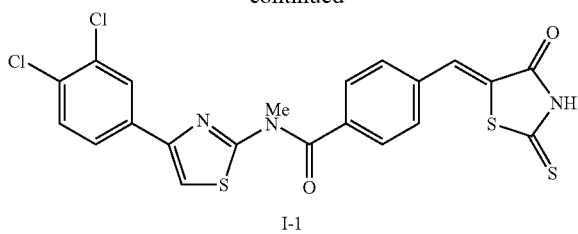

I-1

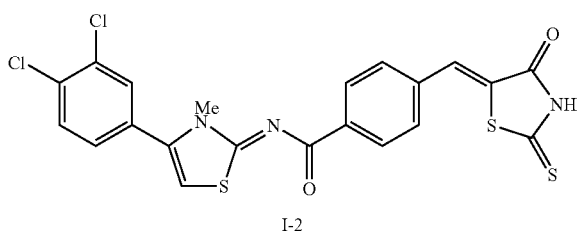

I-2

(Process 1)

To a solution of the compound (8)(0.2 g) prepared in accordance to Example 139—Process 1 in DMF was added sodium hydride (32 mg) in an ice bath and the reaction solution was stirred at room temperature for 30 min. To the solution was added methyl iodide (0.2 ml) and then the reaction mixture was stirred for one hour. The reaction mixture was quenched with iced water and extracted with ethyl acetate. After evaporation of the solvent under reduced pressure, the residue was purified with a column chromatography (hexane-ethyl acetate; 4:1) to give 100 mg of the compound (11) and 33 mg of the compound (12).

Compound (11)
$^1$H NMR (DMSO-d$_6$, δ ppm) 10.12 (s, 1H), 8.22 (d, 1H, J=2.1 Hz), 8.07 (d, 2H, J=8.1 Hz), 8.03 (s, 1H), 7.97 (dd, 1H, J=8.1 Hz, 2.1 Hz), 7.89 (d, 2H, J=8.4 Hz), 7.72 (d, 1H, J=8.4 Hz), 3.63 (s, 3H).

Compound (12)
$^1$H NMR (CDCl$_3$, δ ppm) 10.16 (s, 1H), 8.49 (d, 2H, J=8.0 Hz), 7.97 (d, 2H, J=8.0 Hz), 7.61 (d, 1H, J=8.2 Hz), 7.55 (d, 1H, J=2.2 Hz), 7.27 (dd, 1H, J=8.2 Hz, 2.2 Hz), 6.67 (s, 1H), 3.78 (s, 3H).

(Process 2)

To a solution of the compound (11) (84 mg), and rhodanine (32 mg) in toluene (4 ml) were added 1M piperidine-toluene solution (20 μl) and 1M acetic acid-toluene (20 μl), and then the reaction mixture was refluxed for one hour. After cooling, filtration of the precipitated crystal gave 77 mg of compound (I-1).

$^1$H NMR (DMSO-d$_6$, δ ppm) 13.85 (bs, 1H), 8.21 (d, 1H, J=1.8 Hz), 8.003 (s, 1H), 7.97 (dd, 1H, J=8.7 Hz, 2.1 Hz), 7.83 (d, 2H, J=8.1 Hz), 7.76 (d, 2H, J=8.1 Hz), 7.72 (s, 1H), 7.71 (d, 1H, J=8.7 Hz), 3.65 (s, 3H).

To a solution of the compound (12) (42 mg), and rhodanine (16 mg) in toluene (2 ml) were added 1M piperidine-toluene solution (10 μl) and 1M acetic acid-toluene (10 μl), and then the reaction mixture was refluxed for two hours. After cooling, filtration of the precipitated crystal gave 36 mg of compound (I-2).

$^1$H NMR (DMSO-d$_6$, δ ppm) 13.90 (bs, 1H), 8.36 (d, 2H, J=8.5 Hz), 7.93 (d, 1H, J=1.9 Hz), 7.83 (d, 1H, J=8.2 Hz), 7.72 (d, 2H, J=8.5 Hz), 7.70 (s, 1H), 7.62 (dd, 1H, J=8.2 Hz, 1.9 Hz), 3.75 (s, 3H).

Example 146, 147, 148

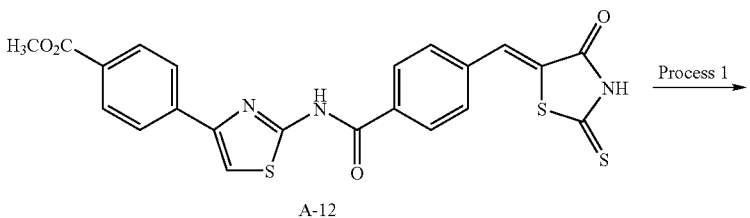

A-12

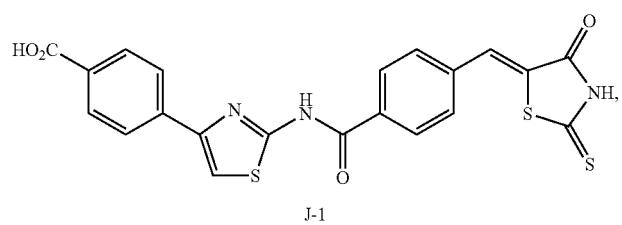

J-1

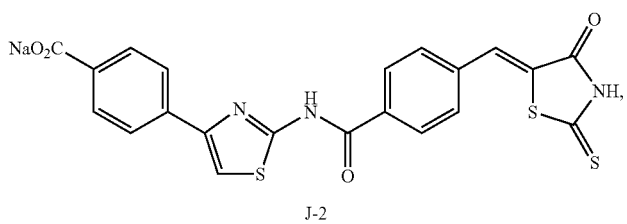

J-2

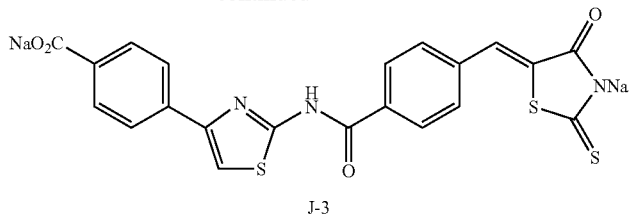

J-3

The compound (A-12)(120 mg) prepared in a manner of Example 1 was dissolved in dioxane (5 ml) and 1N sodium hydroxide (5 ml) and the reaction solution was stirred at room temperature for 30 min. And then the mixture was acidified with 1N hydrochloric acid (5 ml) and evaporated under reduced pressure. The residue was washed with water and recrystallization from DMF-methanol obtained 72 mg of (J-1).

$^1$H NMR (DMSO-d$_6$, δ ppm): 8.20 (d, 2H, J=8.5 Hz), 7.98 (s, 4H), 7.74 (s, 1H), 7.64 (d, 2H, J=8.5 Hz), 7.22 (s, 1H).

Neutralization of compound (I-1) with one equivalent of sodium hydroxide obtained (J-2)

$^1$H NMR (DMSO-d$_6$, δ ppm): 13.92 (bs, 1H), 12.98 (s, 1H), 8.25 (d, 2H, J=8.4 Hz), 8.01–8.10 (m, 4H), 7.92 (s, 1H), 7.77 (d, 2H, J=8.4 Hz), 7.71 (s, 1H).

Neutralization of compound (J-1) with two equivalents of sodium hydroxide obtained (I-3)

$^1$H NMR (DMSO-d$_6$, δ ppm): 8.20 (d, 2H, J=8.1 Hz), 7.93 (dd, 4H, J=11.4 Hz, 8.4 Hz), 7.71 (s, 1H), 7.61 (d, 2H, J=8.1 Hz), 7.21 (s, 1H).

Example 149

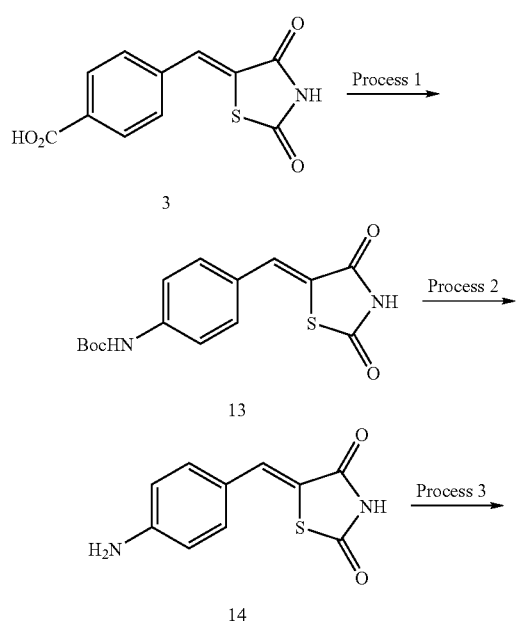

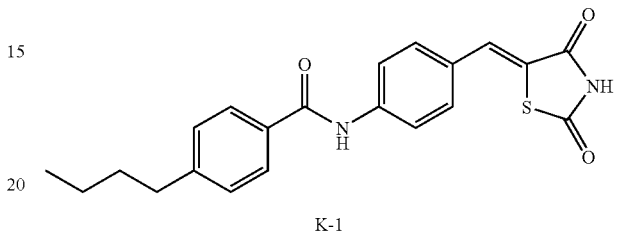

K-1

(Process 1)

To a solution of compound (3)(10 g) synthesized in Example 1—Process 2 in tert-buthanol (200 ml) and dioxane (66 ml) was added triethylamine (5.6 ml) and diphenylphosphoryl azide (8.63 ml), and the reaction solution was refluxed for 2 hours. After evaporation of the solvent under reduced pressure, water was added to the mixture and extracted with ethyl acetate. After evaporation of the solvent under reduced pressure, the residue was purified with recrystallization (ethyl acetate) to yield 4.41 g of the compound (13).

$^1$H NMR (DMSO-d$_6$, δ ppm) 12.50 (bs, 1H), 9.78 (s, 1H), 7.69 (s, 1H), 7.61 (d, 2H, J=9.0 Hz), 7.51 (d, 2H, J=9.0 Hz), 1.49 (s, 9H).

(Process 2)

The compound (13)(3.15 g) was dissolved in trifluoroacetic acid (15 ml) and the solution was stirred at room temperature for 15 min. After evaporation of the solvent under reduced pressure, recrystallization of the residue from diisoprpyl ether gave 2.10 g of (14).

$^1$H NMR (DMSO-d$_6$, δ ppm) 12.29 (bs, 1H), 7.60 (s, 1H), 7.29 (d, 2H, J=8.7 Hz), 6.67 (d, 2H, J=8.7 Hz).

(Process 3)

To a solution of the compound (14)(220 mg) in dioxane (50 ml) were added pyridine (121 μl) and 4-n-butyl benzoyl chloride (187 μl) and the reaction solution was stirred at room temperature for 3 hours. After evaporation of the solvent, to the residue were added methanol (6 ml) and water (2 ml) and then the precipitated crystal was filtrated. Recrystallization from methanol yielded 232 mg of the compound (K-1).

$^1$H NMR (DMSO-d$_6$, δ ppm) 12.56 (bs, 1H), 10.47 (s, 1H), 7.75 (s, 1H), 7.78 (d, 2H, J=8.7 Hz), 7.63 (d, 2H, J=8.7 Hz), 2.67 (t, 2H, J=7.5 Hz), 1.59 (quant, 2H, J=7.5 Hz), 1.32 (sexth, 2H, J=7.2 Hz), 0.91 (t, 3H, J=7.5 Hz)

Compound (K-2) to Compound (K-29) were synthesized in a manner similar to above-mentioned method. Their physical data were shown in Tables 19–22.

TABLE 19

Structure: X-C(=O)-NH-C₆H₄-CH=C(thiazolidinone with T substituent)

| Example No. | Compound No. | X | T | ¹H-NMR (δ) ppm (DMSO d-6) |
|---|---|---|---|---|
| 150 | K-2 | 2-naphthyl | O | 12.56(bs, 1H), 10.73(s, 1H), 8.61(s, 1H), 8.01–8.12(m, 6H), 7.78(s, 1H), 7.63–7.69(m, 4H) |
| 151 | K-3 | benzo[1,3]dioxol-5-yl | O | 10.35(s, 1H), 7.95(d, 2H, J=8.8Hz), 7.75(s, 1H), 8.52–7.75(m, 4H), 7.08(d, 1H, J=8.2Hz), 6.15(s, 2H) |
| 152 | K-4 | 4-(benzyloxy)phenyl | O | 12.55(bs, 1H), 10.39(s, 1H), 7.98(d, 2H, J=8.9Hz), 7.96(d, 2H, J=8.9Hz), 7.75(s, 1H), 7.59(d, 2H, J=8.9Hz), 7.32–7.50(m, 5H), 7.16(d, 2H, J=8.9 Hz), 8.22(s, 2H) |
| 153 | K-5 | 4-Ph-phenyl | O | 12.56(bs, 1H), 10.59(s, 1H), 8.08(d, 2H, J=8.5Hz), 7.86(d, 2H, J=8.2Hz), 7.76–7.79(m, 2H), 7.76(s, 1H), 7.62(d, 2H, J=8.8Hz), 7.50–7.55(m, 2H), 7.41–7.46(m, 1H) |
| 154 | K-6 | 4-n-Hex-phenyl | O | 12.56(bs, 1H), 10.47(s, 1H), 7.97(d, 2H, J=9.0Hz), 7.89(d, 2H, J=8.1Hz), 7.76(s, 1H), 7.63(d, 2H, J=9.0Hz), 7.35(d, 2H, J=8.1Hz), 2.66(t, 2H, J=7.2Hz), 1.60(quant, 2H, J=7.2Hz), 1.29(bs, 6H), 0.84–0.88(m, 3H) |
| 155 | K-7 | 4-EtO-phenyl | O | 12.55(bs, 1H), 10.38(s, 1H), 7.96(d, 4H, J=9.0Hz), 7.75(s, 1H), 7.69(d, 2H, J=9.0Hz), 7.06(d, 2H, J=9.0Hz), 4.12(q, 2H, J=6.9Hz), 1.36(t, 3H, J=6.9Hz) |
| 156 | K-8 | 4-n-Oxt-phenyl | O | 12.56(bs, 1H), 10.46(s, 1H), 7.97(d, 2H, J=8.7Hz), 7.89(d, 2H, J=8.4Hz), 7.75(s, 1H), 7.60(d, 2H, J=8.4Hz), 7.36(d, 2H, J=8.7Hz), 2.66(t, 2H, J=7.2Hz), 1.58–1.62(m, 2H), 1.24–1.27(m, 8H), 0.83–0.88(m, 3H) |
| 157 | K-9 | 3,4-diMe-phenyl | O | 12.55(bs, 1H), 10.42(s, 1H), 7.97(d, 2H, J=8.7Hz), 7.70–7.76(m, 3H), 7.60(d, 2H, J=8.7Hz), 7.30(d, 2H, J=8.1Hz), 2.32(s, 1H), 2.31(s, 1H) |
| 158 | K-10 | 4-F₃C-phenyl | O | 12.55(bs, 1H), 10.75(s, 1H), 8.17(d, 2H, J=8.0Hz), 7.97(d, 2H, J=8.8Hz), 7.93(t, 1H, J=8.0Hz), 7.76(s, 1H), 7.63(d, 2H, J=8.8Hz) |

TABLE 20

| Example No. | Compound No. | X | T | ¹H-NMR (δ) ppm (DMSO d-6) |
|---|---|---|---|---|
| 159 | K-11 | 4-t-Bu-phenyl | O | 12.56(bs, 1H), 10.47(s, 1H), 7.97(d, 2H, J=9.0Hz), 7.90(d, 2H, J=8.4Hz), 7.76(s, 1H), 7.60(d, 2H, J=9.0Hz), 7.57(d, 2H, J=8.4Hz), 1.33(s, 9H) |

TABLE 20-continued

| Example No. | Compound No. | X | T | ¹H-NMR (δ) ppm (DMSO d-6) |
|---|---|---|---|---|
| 160 | K-12 | 3,5-dichlorophenyl | O | 12.57(bs, 1H), 10.69(s, 1H), 7.99(d, 2H, J=2.1Hz), 7.94(d, 2H, J=9.0Hz), 7.89(t, 1H, J=1.8Hz), 7.76(s, 1H), 7.63(d, 2H, J=9.0Hz) |
| 161 | K-13 | 4-ethylphenyl | O | 12.55(bs, 1H), 10.46(s, 1H), 7.97(d, 2H, J=8.8Hz), 7.90(d, 2H, J=8.1Hz), 7.76(s, 1H), 7.50(d, 2H, J=8.8Hz), 7.38(d, 2H, J=8.1Hz), 2.69(q, 2H, J=7.7Hz), 1.22(t, 3H, J=7.7Hz) |
| 162 | K-14 | 3,4-dichlorophenyl | O | 12.59(bs, 1H), 10.67(s, 1H), 8.23(d, 1H, J=2.1Hz), 7.95(d, 1H, J=8.4Hz), 7.94(d, 2H, J=8.4Hz), 7.84(d, 2H, J=8.4Hz), 7.76(s, 1H), 7.62(d, 1H, J=9.0Hz) |
| 163 | K-15 | 4-methylphenyl | O | 12.55(bs, 1H), 10.45(s, 1H), 7.97(d, 2H, J=8.7Hz), 7.89(d, 2H, J=8.4Hz), 7.75(s, 1H), 7.60(d, 2H, J=8.7Hz), 7.35(d, 1H, J=8.4Hz), 2.37(s, 3H) |
| 164 | K-16 | 3-methylphenyl | S | 13.79(bs, 1H), 10.53(s, 1H), 7.98(d, 2H, J=8.8Hz), 7.74–7.78(m, 2H), 7.62(d, 2H, J=8.8Hz), 7.61(s, 1H), 7.24–7.44(m, 2H), 2.41(s, 3H) |
| 165 | K-17 | 3,5-di-t-butyl-4-hydroxyphenyl | S | 13.79(bs, 1H), 10.36(s, 1H), 7.93(d, 2H, J=8.7Hz), 7.68(s, 1H), 7.60(d, 2H, J=8.7Hz), 7.59(d, 1H, J=6.9Hz), 5.75(s, 1H), 1.44(s, 1H) |
| 166 | K-18 | 4-t-butylphenyl | S | 10.50(s, 1H), 7.98(d, 2H, J=8.7Hz), 7.90(d, 2H, J=8.7Hz), 7.61(d, 2H, J=8.7Hz), 7.59(d, 2H, J=8.5Hz), 7.55(s, 1H), 1.33(s, 9H) |
| 167 | K-19 | 4-phenylphenyl | S | 13.79(bs, 1H), 10.62(s, 1H), 8.09(d, 2H, J=8.5Hz), 7.86(d, 2H, J=8.5Hz), 7.77(d, 2H, J=8.5Hz), 7.63(d, 2H, J=8.5Hz), 7.62(s, 1H), 7.50–7.55(m, 2H), 7.41–7.46(m, 1H) |
| 168 | K-20 | 2-naphthyl | S | 13.81(bs, 1H), 10.77(s, 1H), 8.61(s, 1H), 8.02–8.13(m, 6H), 7.63–7.68(m, 5H) |

TABLE 21

| Example No. | Compound No. | X | T | ¹H-NMR (δ) ppm (DMSO d-6) |
|---|---|---|---|---|
| 169 | K-21 | 1,3-benzodioxol-5-yl | S | 13.79(bs, 1H), 10.39(s, 1H), 7.97(d, 2H, J=8.8Hz), 7.61(s, 1H), 7.60(d, 2H, J=8.8Hz), 7.59(d, 1H, J=9.9Hz), 7.53(d, 1H, J=1.8Hz), 7.07(d, 1H, J=8.2Hz), 6.15(s, 2H) |

TABLE 21-continued

| Example No. | Compound No. | X | T | $^1$H-NMR (δ) ppm (DMSO d-6) |
|---|---|---|---|---|
| 170 | K-22 | Et—C₆H₄— | S | 13.79(s, 1H), 10.49(s, 1H), 7.99(d, 2H, J=8.8Hz), 7.91(d, 2H, J=8.2Hz), 7.61(d, 2H, J=8.8Hz), 7.61(s, 1H), 7.38(d, 2H, J=8.2Hz), 2.70(q, 2H, J=7.4Hz), 1.22(t, 3H, J=7.4Hz) |
| 171 | K-23 | n-Bu—C₆H₄— | S | 13.79(bs, 1H), 10.49(s, 1H), 7.99(d, 2H, J=8.8Hz), 7.89(d, 2H, J=8.2Hz), 7.61(d, 2H, J=8.8Hz), 7.61(s, 1H), 7.37(d, , 2H, J=8.2Hz), 2.37(t, 2H, J=7.4Hz), 1.57–1.64(m, 2H), 1.26–1.38(m, 2H), 0.91(t, 3H, J=7.1Hz) |
| 172 | K-24 | F₃C—C₆H₄— | S | 13.80(bs, 1H), 10.79(s, 1H), 8.17(d, 2H, J=8.4Hz), 7.99(d, 2H, J=8.7Hz), 7.94(d, 2H, J=8.4Hz), 7.64(d. 1H, J=8.7Hz), 7.65(s, 1H) |
| 173 | K-25 | 3,5-Cl₂-C₆H₃— | S | 13.80(bs, 1H), 10.71(s, 1H), 7.99(d, 2H, J=1.6Hz), 7.95(d, 2H, J=8.5Hz), 7.89(t, 1H, J=1.9Hz), 7.63(d, 2H, J=8.5Hz), 7.61(s, 1H), |
| 174 | K-26 | Me—C₆H₄— | S | 13.78(bs, 1H), 10.48(s, 1H), 7.98(d, 2H, J=9.0Hz), 7.89(d, 2H, J=8.1Hz), 7.61(d, 2H, J=9.0Hz), 7.61(s, 1H), 7.36(d, 2H, J=8.1Hz), 2.40(s, 3H) |

TABLE 22

R⁶-thiazole-C(O)NH-C₆H₄-CH=C(thiazolidinone with T)

| Example No. | Compound No. | X | T | $^1$H-NMR (δ) ppm (DMSO d-6) |
|---|---|---|---|---|
| 175 | K-27 | C₆H₅— | O | 12.57(bs, 1H), 10.88(s, 1H), 8.53(s, 1H), 8.15–8.19(m, 2H), 8.07(d, 2H, J=8.8Hz), 7.78(s, 1H), 7.65(d, 2H, J=8.8Hz), 7.50–7.55(m, 2H), 7.40–7.45 (m, 1H) |
| 176 | K-28 | 3,4-Cl₂-C₆H₃— | O | 12.58(bs, 1H), 10.91(s, 1H), 8.69(s, 1H), 8.48(d, 1H, J=1.9Hz), 8.15(dd, 1H, J=8.8Hz, 1.9Hz), 8.04(d, 2H, J=8.8Hz), 7.78(d, 1H, J=8.8Hz), 7.76 (s, 1H), 7.64(d, 1H, J=8.8Hz) |
| 177 | K-29 | 3,4-Cl₂-C₆H₃— | S | 13.82(bs, 1H), 10.95(s, 1H), 8.72(s, 1H), 8.50(d, 1H, J=1.9Hz), 8.16(dd, 1H, J=8.5Hz, 1.9Hz), 8.08(d, 2H, J=8.8Hz), 7.80(d, 1H, J=8.5Hz), 7.67(d, 1H, J=8.8Hz), 7.63(s, 1H) |

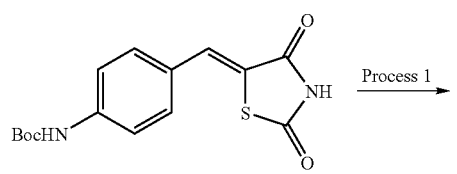

13

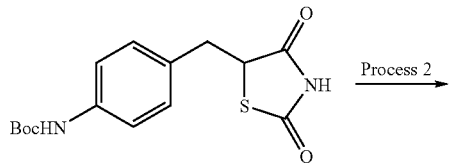

15

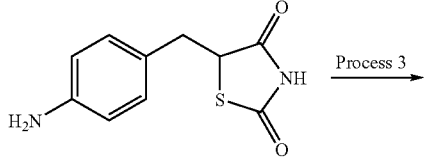

16

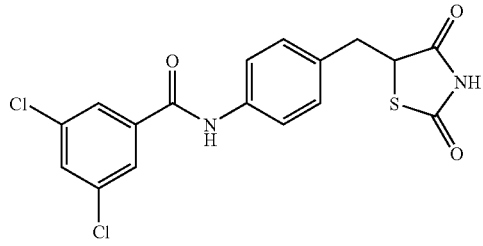

L-1

(Process 1)

To a solution of the compound (13)(1.7 g) synthesized in Example 149—Process 1 in dioxane (200 ml) was added 10% palladium-carbon (0.7 g) and the reaction mixture was stirred under hydrogen atmosphere. Filtration of palladium-carbon and evaporation of the solvent under reduced pressure obtained 1.39 g of the compound (15).

$^1$H NMR (CDCl$_3$, δ ppm): 8.38 (s, 1H), 7.32 (d, 2H, J=8.4 Hz), 7.26 (s, 1H), 7.15 (d, 2H, J=8.4 Hz), 6.54 (s, 1H), 4.50 (dd, 1H, J=9.3 Hz, 3.9 Hz), 3.46 (dd, 1H, J=14.4 Hz, 3.9 Hz), 3.22 (dd, 1H, J=14.4 Hz, 9.3 Hz), 1.52 (s, 9H).

(Process 2)

A solution of the compound (15)(4.23 g) in dichloromethane (20 ml) and trifluoroacetic acid (10 ml) was stirred at room temperature for 15 min. After evaporation of the solvent under reduced pressure, the residue was recrystallized from diisopropyl ether to give 3.8 g of the compound (16).

$^1$H NMR (DMSO-d$_6$, δ ppm) 7.25 (d, 2H, J=8.4 Hz), 7.09 (d, 2H, J=8.4 Hz), 4.90 (dd, 1H, J=8.7 Hz, 4.5 Hz), 4.35 (dd, 1H, J=14.4 Hz, 4.5 Hz), 3.12 (dd, 1H, J=14.4 Hz, 8.7 Hz).

(Process 3)

To a solution of the compound (16)(220 mg) in dioxane (50 ml) were added pyridine (121 μl) and 3,5-dichlorobezoyl chloride (180 μl) and then the reaction solution was stirred at room temperature for 3 hours. After evaporation of the solvent under reduced pressure, the residue was purified with a column chromatography (hexane-ethyl acetate; 2:1) to yield 103 mg of the compound (L-1).

$^1$H NMR (DMSO-d$_6$, δ ppm) 12.02 (bs, 1H), 10.41 (s, 1H), 7.97 (d, 2H, J=1.9 Hz), 7.87 (t, 1H, J=1.9 Hz), 7.69 (d, 2H, J=8.5 Hz), 7.24 (d, 2H, J=8.5 Hz), 4.91 (dd, 1H, J=8.8 Hz, 4.4 Hz), 3.36 (dd, 1H, J=14.3 Hz, 4.4 Hz), 3.12 (dd, 1H, J=14.3 Hz, 8.8Hz)

Compound (L-2) to Compound (L-3) were synthesized in a manner similar to above-mentioned method. Their physical data were shown in Table 23.

TABLE 23

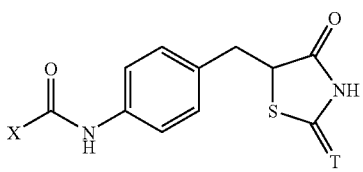

| Example No. | Compound No. | X | T | $^1$H-NMR (δ) ppm (DMSO d-6) |
|---|---|---|---|---|
| 179 | L-2 | F$_3$C-⟨phenyl⟩- | O | 12.04(bs, 1H), 10.47(s, 1H), 8.14(d, 2H, J=8.2Hz), 7.92(d, 2H, J=8.2 Hz), 7.72(d, 2H, J=8.5Hz), 7.25(d, 2H, J=8.5Hz), 4.92(dd, 1H, J=8.9 Hz, 4.4Hz), 3.36(dd, 1H, J=14.4Hz, 4.4Hz), 3.12(dd, 1H, J=14.4Hz, 8.9 Hz) |
| 180 | L-3 | n-Bu-⟨phenyl⟩- | O | 12.05(bs, 1H), 10.56(s, 1H), 7.86(d, 2H, J=8.4Hz), 7.71(d, 2H, J=8.7 Hz), 7.34(d, 2H, J=8.7Hz), 7.22(d, 2H, J=8.4Hz), 4.91(dd, 1H, J=9.0 Hz, 4.5Hz), 3.34(dd, 1H, J=13.8Hz, 4.5Hz), 3.10(dd, 1H, J=13.8Hz, 9.0 Hz), 2.66(t, 2H, J=7.5Hz), 1.58 (quant, 2H, J=8.1Hz), 1.26–1.37(m, 2H), 0.91(t, 3H, J=7.5Hz) |

Example 181

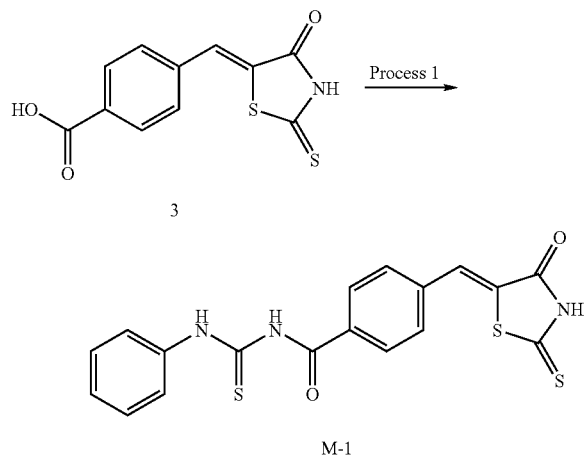

(Process 1)
A mixture of the compound (3)(3 g) prepared in Example 1—Process 2 in dioxane (20 ml) and thionyl chloride (10 ml) was heated and dissolved at 100° C. Evaporation of the solvent under reduced pressure gave carboxylic acid chloride. The carboxylic acid chloride was not purified and used in further reactions. After a solution of the carboxylic acid chloride (143 mg), ammonium thiocyanate (42 mg) in dioxane (25 ml) was stirred at room temperature for 15 min, 3,4-dichloroaniline was added thereto. The reaction solution was stirred at room temperature for 1 hour and the solvent was evaporated under reduced pressure. To the residue were added methanol (6 ml) and water (2 ml) and the precipitated crystal was filtrated. Recrystallization from DMF obtained 104 mg of the compound (M-1).

$^1$H NMR (DMSO-d$_6$, δ ppm): 13.91 (bs, 1H), 12.49 (s, 1H), 11.83 (s, 1H), 8.07–8.12 (m, 3H), 7.63–7.76 (m, 5H).

The following compound was synthesized in a manner similar to above-mentioned method.

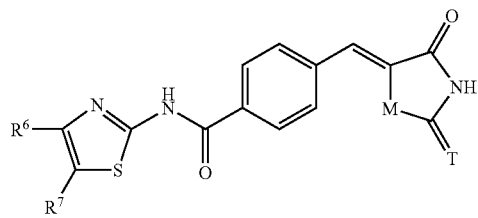

Abbreviation described below are used. Me:methyl, Et:ethyl, nPr:n-propyl, iPr:isobutyl, nBu:n-butyl, iBu:isobutyl, tBu:t-butyl, Pen:n-pentyl, Ph:phenyl, Bn:benzyl, Bz:benzoyl, Ac:acetyl, diF:difluoro, diCl:dichloro, diBr:dibromo, diI:diiodo, diMe:dimethyl, thiophene:thiophene, thienyl:thienyl, Py:pyridil, pyridine:pyridine, pyridinium: pyridinium, Quinoline: Quinoline, Benzodioxole: Benzodioxole, pyrazinyl: pyrazinyl, pyrrolyl: pyrrolyl, pyrrole: pyrrole, oxide: oxide, indole: indole, imidazolyl: imidazolyl, morpholino: morpholino, piperazinyl: piperazinyl, furyl: furyl, furan: furan, thiazolyl: thiazolyl, benzodioxin: benzodioxin, and benzo[b]furan:benzo[b]furan (Compound No: R$^6$, R$^7$, M, T)=(N-1: Ph, Me, S, S), (N-3: 4-Br-Ph, Me, S, S), (N-4: 4-Me-Ph, Me, S, S), (N-5: 4-Ph-Ph, Me, S, S), (N-6: 4-OMe-Ph, Me, S, S), (N-7: 4-tBu-Ph, Me, S, S), (N-8: 4-COOMe-Ph, Me, S, S), (N-9: 4-Pen-Ph, Me, S, S), (N-10: 4-NO$_2$-Ph, Me, S, S), (N-11: 5-Cl-thiophene-2-yl, Me, S, S), (N-12: 3-Thienyl, Me, S, S), (N-13: 2-Py, Me, S, S),(N-14: 3-Py, Me, S, S), (N-15: 4-Py, Me, S, S), (N-16: 3,4-diF-Ph, Me, S, S), (N-17: 5-Br-thiophene-2-yl, Me, S, S), (N-18: 4-CONH$_2$-Ph, Me, S, S), (N-19: 4-CON(Me)H-Ph, Me, S, S), (N-20: 4- CON(Me)$_2$-Ph, Me, S, S), (N-21: 4-iPrOC(=O)-Ph, Me, S, S), (N-22: 4- nBuOC(=O)-Ph, Me, S, S), (N-23: 6-Me-pyridine-3-yl, Me, S, S), (N-24: Quinoline-3-yl, Me, S, S), (N-25: 4-NH$_2$-Ph, Me, S, S), (N-26: 4-N(Ac)H-Ph, Me, S, S), (N-27: 4-OH-Ph, Me, S, S), (N-28: 3,4-di(OH)$_2$-Ph, Me, S, S), (N-29: 3,4- di(NH$_2$)-Ph, Me, S, S), (N-30: 3:4-[N(Ac)H]$_2$-Ph, Me, S, S), (N-31: 4-SH-Pb, Me, S, S), (N-32: 4-SMe-Ph, Me, S, S), (N-33: 3,4-diBr-Ph, Me, S, S), (N-34: 4- N(Me)H-Ph, Me, S, S), (N-35: 4-N(Me)$_2$-Ph, Me, S, S), (N-36: 4-N(Me)$_3$+-Ph, Me, S, S), (N-37: 4-Et-Ph, Me, S, S), (N-38: 4-iPr-Ph, Me, S, S), (N-39: 4-nPr-Ph, Me, S, S), (N-40: 4-nBu-Ph, Me, S, S), (N-41: 4-iBu-Ph, Me, S, S), (N-42: 3,4- diMe-Ph, Me, S, S), (N-43: 1,3-Benzodioxole-5-yl, Mc, S, S), (N-44: N-Me-pyridinium-4-yl, Me, S, S), (N-45: N-Me-pyridinium-3-yl, Me, S, S), (N-46: 5- Me-Pyridine-2-yl, Me, S, S), (N-47: 2-Pyrazinyl, Me, S, S), (N-48: 3-Pyrrolyl, Me, S, S), (N-49: 1-Me-pyrrole-3-yl, Me, S, S), (N-50: Pyridine N-oxide-4-yl, Me, S, S), (N-51: Pyridine N-oxide-3-yl, Me, S, S), (N-52: 6-OH-pyridine-3-yl, Me, S, S), (N-53: 6-SH-pyridine-3-yl, Me, S, S), (N-54: 1-Ac-pyrrole-3-yl, Me, S, S), (N-55: 4-CF$_3$-Ph, Me, S, S), (N-56: 4-CN-Ph, Me, S, S), (N-57: 4-CHO-Ph, Me, S, S), (N-58: 3-Cl-Ph, Me, S, S), (N-59: 3-Br-Ph, Me, S, S), (N-60: 3-F-Ph, Me, S, S), (N-61: 3-I-Ph, Me, S, S), (N-62: 4-1-Pb, Me, S, S), (N-63: 4-OCF$_3$-Ph, Me, S, S), (N-64: 3,4-diI-Ph, Me, S, S), (N-65: Indole-6-yl, Me, S, S), (N-66: 1- Ac-indole-6-yl, Me, S, S), (N-67: 1-Me-indole-6-yl, Me, S, S), (N-68: 4-(1- Imidazolyl)-Ph, Me, S, S), (N-69: 4-Morphorino-Ph, Me, S, S), (N-70: 4-(1-Piperazinyl)-Ph, Me, S, S), (N-71: 2:5-diMe-thiophene-3-yl, Me, S, S), (N-72: 2-Furyl, Me, S, S), (N-73: 5-Me-furan-2-yl, Me, S, S), (N-74: 5-Me-furan-2-yl, Me, S, S), (N-75: 2-Thiazolyl, Me, S, S), (N-76: 1:4-Benzodioxin-6-yl, Me, S, S), (N-77: Benzo[b]furan-2-yl, Me, S, S), (N-78: 4-NH$_2$CH$_2$-Ph, Me, S, S), (N-79: 4-N(Me)HCH$_2$-Ph, Me, S, S), (N-80: 4-N(Me)$_2$CH$_2$-Ph, Me, S, S), (N-81: 6-Cl-pyridine-3-yl, Me, S, S), (N-82: 5,6-diCl-pyridine-3-yl, Me, S, S), (N-83: 5-Cl- pyridine-2-yl, Me, S, S), (N-84: 4:5-diCl-pyridine-2-yI, Me, S, S), (N-85: 4- ClCH$_2$-Bn, Me, S, S), (N-86: Bn, Me, S, S), (N-87: 4-Cl-Bn, Me, S, S), (N-88: 4-Br-Bn, Me, S, S), (N-89: 4-F-Bn, Me, S, S), (N-90: 3,4-diCl-Bn, Me, S, S), (N-91: 3,4-diBr-Bn, Me, S, S), (N-92: 3,4-diF-Bn, Me, S, S), (N-93: 4-Cl-Bz, Me, S, S), (N-94: 3,4-diCl-Bz, Me, S, S), (N-95: 4-Br-Bz, Me, S, S), (N-96: 3,4- diBr-Bz, Me, S, S), (N-97: 4-F-Bz, Me, S, S), (N-98: 3,4-diF-Bz, Me, S, S), (N- 99: 4-NO$_2$-Bn, Me, S, S), (N-100: 4-CN-Bn, Me, S, S), (N-101: Ph, Et, S, S), (N-102: 4-F-Ph, Et, S, S), (N-103: 4-Br-Ph, Et, S, S), (N-104: 4-Me-Ph, Et, S, S), (N-105: 4-Ph-Ph, Et, S, S), (N-106: 4-OMe-Ph, Et, S, S), (N-107: 4-tBu-Ph, Et, S, S), (N-108: 4-COOMe-Ph, Et, S, S), (N-109: 4-Pen-Ph, Et, S, S), (N-110: 4- NO$_2$-Ph, Et, S, S), (N-111: 5-Cl-thiophene-2-yl, Et, S, S), (N-112: 3-Thienyl, Et, S, S), (N-113: 2-Py, Et, S, S), (N-114: 3-Py, Et, S, S), (N-115: 4-Py, Et, S, S), (N-116: 3,4-diF-Ph, Et, S, S), (N-117: 5-Br-thiophene-2-yl, Et, S, S), (N-118: 4-CONH$_2$-Ph, Et, S, S), (N-119: 4-CON(Me)H-Ph, Et, S, S), (N-120: 4- CON(Me)$_2$-Ph, Et, S, S), (N-121: 4-iPrOC(=O)-Ph, Et, S, S), (N-122: 4- nBuOC(=O)-Ph, Et, S, S), (N-123: 6-Me-pyridine-3-yl, Et, S, S), (N-124: Quinoline-3-yl, Et, S, S), (N-125: 4-NH$_2$-Ph, Et, S, S), (N-126: 4-N(Ac)H-Ph, Et, S, S), (N-127: 4-OH-Ph, Et, S, S), (N-128: 3,4-di(OH)$_2$-Ph, Et, S, S), (N-129: 3,4-di(NH$_2$)-Ph, Et, S, S), (N-130: 3:4-[N(Ac)H]$_2$-Ph, Et, S, S), (N-131: 4-SH-Ph, Et, S, S), (N-132: 4-SMe-Ph, Et, S, S), (N-133: 3,4-diBr-Ph, Et, S, S), (N-134: 4-N(Me)H-Ph, Et, S, S), (N-135: 4-N(Me)$_2$-Ph, Et, S, S), (N-136: 4-N(Me)$_3$+-Ph, Et, S, S), (N-137: 4-Et-Ph, Et, S, S), (N-138: 4-iPr-Ph, Et, S, S), (N-139: 4-nPr-Ph, Et, S, S), (N-140: 4-nBu-Ph, Et, S, S), (N-141: 4-iBu-Ph, Et, S, S), (N-142: 3,4-diMe-Ph, Et, S, S), (N-143: 1,3-Benzodioxole-5-yl, Et, S, S), (N-144: N-Me-pyridinium-4-yl, Et, S, S), (N-145: N-Me-pyridinium-3-yl, Et, S, S), (N-146: 5-Me-Pyridine-2-yl, Et, S, S), (N-147: 2-Pyrazinyl, Et, S, S), (N-148: 3-Pyrrolyl, Et, S, S), (N-149: 1-Me-pyrrole-3-yl, Et, S, S), (N-150: Pyridine N-oxide-4-yl, Et, S, S), (N-151: Pyridine N-oxide-3-yl, Et, S, S), (N-152: 6-OH-pyridine-3-yl, Et, S, S), (N-153: 6-SH-pyridine-3-yl, Et, S, S), (N-154: 1-Ac-pyrrole-3-yl, Et, S, S), (N-155: 4-CF$_3$-Ph, Et, S, S), (N-156: 4-CN-Ph, Et, S, S), (N-157: 4-CHO-Ph, Et, S, S), (N-158: 3-Cl-Ph, Et, S, S), (N-159: 3-Br-Ph, Et, S, S), (N-160: 3-F-Ph, Et, S, S), (N-161: 3-I-Ph, Et, S, S), (N-162: 4-I-Ph, Et, S, S), (N-163: 4-OCF$_3$-Ph, Et, S, S), (N-164: 3,4-diI-Ph, Et, S, S), (N-165: Indole-6-yl, Et, S, S), (N-166: 1-Ac-indole-6-yl, Et, S, S), (N-167: 1-Me-indole-6-yl, Et, S, S), (N-168: 4-(1-Imidazolyl)-Ph, Et, S, S), (N-169: 4-Morphorino-Ph, Et, S, S), (N-170: 4-(1-Piperazinyl)-Ph, Et, S, S), (N-171: 2:5-diMe-thiophene-3-yl, Et, S, S), (N-172: 2-Furyl, Et, S, S), (N-173: 5-Me-furan-2-yl, Et, S, S), (N-174: 5-Me-furan-2-yl, Et, S, S), (N-175: 2-Thiazolyl, Et, S, S), (N-176: 1:4-Benzodioxin-6-yl, Et, S, S), (N-177: Benzo[b]furan-2-yl, Et, S, S), (N-178: 4-NH$_2$CH$_2$-Ph, Et, S, S), (N-179: 4-N(Me)HCH$_2$-Ph, Et, S, S), (N-180: 4-N(Me)$_2$CH$_2$-Ph, Et, S, S), (N-181: 6-Cl-pyridine-3-yl, Et, S, S), (N-182: 5,6-diCl-pyridinc-3-yl, Et, S, S), (N-183: 5-Cl-pyridine-2-yl, Et, S, S), (N-184: 4:5-diCl-pyridine-2-yl, Et, S, S), (N-185: 4-ClCH$_2$-Bn, Et, S, S), (N-186: Bn, Et, S, S), (N-187: 4-Cl-Bn, Et, S, S), (N-188: 4-Br-Bn, Et, S, S), (N-189: 4-F-Bn, Et, S, S), (N-190: 3,4-diCl-Bn, Et, S, S), (N-191: 3,4-diBr-Bn, Et, S, S), (N-192: 3,4-diF-Bn, Et, S, S), (N-193: 4-Cl-Bz, Et, S, S), (N-194: 3,4-diCl-Bz, Et, S, S), (N-195: 4-Br-Bz, Et, S, S), (N-196: 3,4-diBr-Bz, Et, S, S), (N-197: 4-F-Bz, Et, S, S), (N-198: 3,4-diF-Bz, Et, S, S), (N-199: 4-NO2-Bn, Et, S, S), (N-200: 4-CN-Bn, Et, S, S), (N-201: Ph, COOMe, S, S), (N-203: 4-Br-Ph, COOMe, S, S), (N-204: 4-Me-Ph, COOMe, S, S), (N-205: 4-Ph-Ph, COOMe, S, S), (N-206: 4-OMe-Ph, COOMe, S, S), (N-207: 4-tBu-Ph, COOMe, S, S), (N-208: 4-COOMe-Ph, COOMe, S, S), (N-209: 4-Pen-Ph, COOMe, S, S), (N-210: 4-NO$_2$-Ph, COOMe, S, S), (N-211: 5-Cl-thiophene-2-yl, COOMe, S, S), (N-212: 3-Thienyl, COOMe, S, S), (N-213: 2-Py, COOMe, S, S), (N-214: 3-Py, COOMe, S, S), (N-215: 4-Py, COOMe, S, S), (N-216: 3,4-diF-Ph, COOMe, S, S), (N-217: 5-Br-thiophene-2-yl, COOMe, S, S), (N-218: 4-CONH$_2$-Ph, COOMe, S, S), (N-219: 4-CON(Me)H-Ph, COOMe, S, S), (N-220: 4-CON(Me)$_2$-Ph, COOMe, S, S), (N-221: 4-iPrOC(=O)-Ph, COOMe, S, S), (N-222: 4-nBuOC(=O)-Ph, COOMe, S, S), (N-223: 6-Me-pyridine-3-yl, COOMe, S, S), (N-224: Quinoline-3-yl, COOMe, S, S), (N-225: 4-NH$_2$-Ph, COOMe, S, S), (N-226: 4-N(Ac)H-Ph, COOMe, S, S), (N-227: 4-OH-Ph, COOMe, S, S), (N-228: 3,4-di(OH)$_2$-Ph, COOMe, S, S), (N-229: 3,4-di(NH$_2$)-Ph, COOMe, S, S), (N-230: 3:4-[N(Ac)H]$_2$-Ph, COOMe, S, S), (N-231: 4-SH-Ph, COOMe, S, S), (N-232: 4-SMe-Ph, COOMe, S, S), (N-233: 3,4-diBr-Ph, COOMe, S, S), (N-234: 4-N(Me)H-Ph, COOMe, S, S), (N-235: 4-N(Me)$_2$-Ph, COOMe, S, S), (N-236: 4-N(Me)$_3$+-Ph, COOMe, S, S), (N-237: 4-Et-Ph, COOMe, S, S), (N-238: 4-iPr-Ph, COOMe, S, S), (N-239: 4-nPr-Ph, COOMe, S, S), (N-240: 4-nBu-Ph, COOMe, S, S), (N-241: 4-iBu-Ph, COOMe, S, S), (N-242: 3,4-diMe-Ph, COOMe, S, S), (N-243: 1,3-Benzodioxole-5-yl, COOMe, S, S), (N-244: N-Me-pyridinium-4-yl, COOMe, S, S), (N-245: N-Me-pyridinium-3-yl, COOMe, S, S), (N-246: 5-Me-Pyridine-2-yl, COOMe, S, S), (N-247: 2-Pyrazinyl, COOMe, S, S), (N-248: 3-Pyrrolyl, COOMe, S, S), (N-249: 1-Me-pyrrole-3-yl, COOMe, S, S), (N-250: Pyridine N-oxide-4-yl, COOMe, S, S), (N-251: Pyridine N-oxide-3-yl, COOMe, S, S), (N-252: 6-OH-pyridine-3-yl, COOMe, S, S), (N-253: 6-SH-pyridine-3-yl, COOMe, S, S), (N-254: 1-Ac-pyrrole-3-yl, COOMe, S, S), (N-255: 4-CF$_3$-Ph, COOMe, S, S), (N-256: 4-CN-Ph, COOMe, S, S), (N-257: 4-CHO-Ph, COOMe, S, S), (N-258: 3-Cl-Ph, COOMe, S, S), (N-259: 3-Br-Ph, COOMe, S, S), (N-260: 3-F-Ph, COOMe, S, S), (N-261: 3-1-Ph, COOMe, S, S), (N-262: 4-I-Ph, COOMe, S, S), (N-263: 4-OCF$_3$-Ph, COOMe, S, S), (N-264: 3,4-dil-Ph, COOMe, S, S), (N-265: Indole-6-yl, COOMe, S, S), (N-266: 1-Ac-indole-6-yl, COOMe, S, S), (N-267: 1-Me-indole-6-yl, COOMe, S, S), (N-268: 4-(1-lmidazolyl)-Ph, COOMe, S, S), (N-269: 4-Morphorino-Ph, COOMe, S, S), (N-270: 4-(1-Piperazinyl)-Ph, COOMe, S, S), (N-271: 2:5-diMe-thiophene-3-yl, COOMe, S, S), (N-272: 2-Furyl, COOMe, S, S), (N-273: 5-Me-furan-2-yl, COOMe, S, S), (N-274: 5-Me-furan-2-yl, COOMe, S, S), (N-275: 2-Thiazolyl, COOMe, S, S), (N-276: 1:4-Benzodioxin-6-yl, COOMe, S, S), (N-277: Benzo[b]furan-2-yl, COOMe, S, S), (N-278: 4-NH$_2$CH$_2$-Ph, COOMe, S, S), (N-279: 4-N(Me)HCH$_2$-Ph, COOMe, S, S), (N-280: 4-N(Me)$_2$CH$_2$-Ph, COOMe, S, S), (N-281: 6-Cl-pyridine-3-yl, COOMe, S, S), (N-282: 5,6-diCl-pyridine-3-yl, COOMe, S, S), (N-283: 5-Cl-pyridine-2-yl, COOMe, S, S), (N-284: 4:5-diCl-pyridine-2-yl, COOMe, S, S), (N-285: 4-ClCH$_2$-Bln, COOMe, S, S), (N-286: Bn, COOMe, S, S), (N-287: 4-Cl-Bn, COOMe, S, S), (N-288: 4-Br-Bn, COOMe, S, S), (N-289: 4-F-Bn, COOMe, S, S), (N-290: 3,4-diCl-Bn, COOMe, S, S), (N-291: 3,4-diBr-Bn, COOMe, S, S), (N-292: 3,4-diF-Bn, COOMe, S, S), (N-293: 4-Cl-Bz, COOMe, S, S), (N-294: 3,4-diCl-Bz, COOMe, S, S), (N-295: 4-Br-Bz, COOMe, S, S), (N-296: 3,4-diBr-Bz, COOMe, S, S), (N-297: 4-F-Bz, COOMe, S, S), (N-298: 3,4-diF-Bz, COOMe, S, S), (N-299: 4-NO$_2$-Bn, COOMe, S, S), (N-300: 4-CN-Bn, COOMe, S, S), (N-302: H, 4-F-Ph, S, S), (N-303: H, 4-Br-Pb, S, S), (N-304: H, 4-Me-Ph, S, S), (N-305: H, 4-Ph-Pb, S, S), (N-306: H, 4-OMe-Ph, S, S), (N-307: H, 4-tBu-Ph, S, S), (N-308: H, 4-COOMe-Ph, S, S), (N-309: H, 4-Pen-Ph, S, S), (N-310: H, 4-NO$_2$-Ph, S, S), (N-311: H, 5-Cl-thiophene-2-yl, S, S), (N-312: H, 3-Thienyl, S, S), (N-313: H, 2-Py, S, S), (N-314: H, 3-Py, S, S), (N-315: H, 4-Py, S, S), (N-316: H, 3,4-diF-Ph, S, S), (N-317: H, 5-Br-thiophene-2-yl, S, S), (N-318: H, 4-CONH$_2$-Ph, S, S), (N-319: H, 4-CON(Me)H-Ph, S, S), (N-320: H, 4-CON(Me)$_2$-Ph, S, S), (N-321: H, 4-iPrOC(=O)-Ph, S, S), (N-322: H, 4-nBuOC(=O)-Ph, S, S), (N-323: H, 6-Me-pyridine-3-yl, S, S), (N-324: H, Quinoline-3-yl, S, S), (N-325: H, 4-NH$_2$-Ph, S, S), (N-326: H, 4-N(Ac)H-Ph, S, S), (N-327: H, 4-OH-Ph, S, S), (N-328: H, 3,4-di(OH)$_2$-Ph, S, S), (N-329: H, 3,4-di(NH$_2$)-Ph, S, S), (N-330: H, 3:4-[N(Ac)H]$_2$-Ph, S, S), (N-331: H, 4-SH-Ph, S, S), (N-332: H, 4-SMe-Ph, S, S), (N-333: H, 3,4-diBr-Ph, S, S), (N-334: H, 4-N(Me)H-Ph, S, S), (N-335: H, 4-N(Me)$_2$-Ph, S, S), (N-336: H, 4-N(Me)$_3$+-Ph, S, S), (N-337: H, 4-Et-Ph, S, S), (N-338: H, 4-iPr-Ph, S, S), (N-339: H, 4-nPr-Ph, S, S), (N-340: H, 4-nBu-Ph, S, S), (N-341: H, 4-iBu-Ph, S, S), (N-342: H, 3,4-diMe-Ph, S, S), (N-343: H, 1,3-Benzodioxole-5-yl, S, S), (N-344: H, N-Me-pyridinium-4-yl, S, S), (N-345: H, N-Me-pyridinium-3-yl, S, S), (N-346: H, 5-Me-Pyridine-2-yl, S, S), (N-347: H, 2-Pyrazinyl, S, S), (N-348: H, 3-Pyrrolyl, S, S), (N-349: H, 1-Me-pyrrole-3-yl, S, S), (N-350: H, Pyridine N-oxide-4-yl, S, S), (N-351: H, Pyridine N-oxide-3-yl, S, S), (N-352: H, 6-OH-pyridine-3-yl, S, S), (N-353: H, 6-SH-pyridine-3-yl, S, S), (N-354: H, 1-Ac-pyrrole-3-yl, S, S), (N-355: H. 4-CF$_3$-Ph, S, S), (N-356: H, 4- CN-Ph, S, S), (N-357: H, 4-CHO-Ph, S, S), (N-358: H, 3-Cl-Ph, S, S), (N-359: H, 3-Br-Ph, S, S), (N-360: H, 3-F-Ph, S, S), (N-361: H, 3-I-Ph, S, S), (N-362: H, 4-I-Ph, S, S), (N-363: H, 4-OCF$_3$-Ph, S, S), (N-364: H, 3,4-diI-Ph, S, S), (N-365: H, Indole-6-yl, S, S), (N-366: H, 1-Ac-indole-6-yl, S, S), (N-367: H, 1-Me- indole-6-yl, S, S), (N-368: H, 4-(1-Imidazolyl)-Ph, S, S), (N-369: H, 4-Morphorino-Ph, S, S), (N-370: H, 4-(1-Piperazinyl)-Ph, S, S), (N-371: H, 2:5- diMe-thiopbene-3-yl, S, S), (N-372: H, 2-Furyl, S, S), (N-373: H, 5-Me-furan- 2-yl, S, S), (N-374: H, 5-Me-furan-2-yl, S, S), (N-375: H, 2-Thiazolyl, S, S), (N-376: H, 1:4-Benzodioxin-6-yl, S, S), (N-377: H, Benzo[b]furan-2-yl, S, S), (N-378: H, 4-NH$_2$CH$_2$-Ph, S, S), (N-379: H, 4-N(Me)HCH$_2$-Ph, S, S), (N-380: H, 4-N(Me)$_2$CH$_2$-Ph, S, S), (N-381: H, 6-Cl-pyridine-3-yl, S, S), (N-382: H, 5,6- diCl-pyridine-3-yl, S, S), (N-383: H, 5-Cl-pyridine-2-yl, S, S), (N-384: 1H, 4:5- diCl-pyridine-2-yl, S, S), (N-385: H, 4-ClCH$_2$-Bn, S, S), (N-386: H, Bn, S, S), (N-387: H, 4-Cl-Bn, S, S), (N-388: H, 4-Br-Bn, S, S), (N-389: H, 4-F-Bn, S, S), (N-390: H, 3,4-diCl-Bn, S, S), (N-391: H, 3,4-diBr-Bn, S, S), (N-392: H, 3,4- diF-Bn, S, S), (N-393: H, 4-Cl-Bz, S, S), (N-394: H, 3,4-diCl-Bz, S, S), (N-395: H, 4-Br-Bz, S, S), (N-396: H, 3,4-diBr-Bz, S, S), (N-397: H, 4-F-Bz, S, S), (N- 398: H, 3,4-diF-Bz, S, S), (N-399: H, 4-NO$_2$-Bn, S, S), (N-400: H, 4-CN-Bn, S, S), (N-401: Me, Ph, S, S), (N-402: Me, 4-F-Ph, S, S), (N-403: Me, 4-Br-Ph, S, S), (N-404: Me, 4-Me-Ph, S, S), (N-405: Me, 4-Ph-Ph, S, S), (N-406: Me, 4-OMe-Ph, S, S), (N-407: Me, 4-tBu-Ph, S, S), (N-408: Me, 4-COOMe-Ph, S, S), (N-409: Me, 4-Pen-Ph, S, S), (N-410: Me, 4-NO$_2$-Ph, S, S), (N-411: Me, 5-Cl-thiophene-2-yl, S, S), (N-412: Me, 3-Thienyl, S, S), (N-413: Me, 2-Py, S, S), (N-414: Me, 3-Py, S, S), (N-415: Me, 4-Py, S, S), (N-416: Me, 3,4-diF-Ph, S, S), (N-417: Me, 5-Br- thiophene-2-yl, S, S), (N-418: Me, 4-CONH$_2$-Pb, S, S), (N-419: Me, 4- CON(Me)H-Ph, S, S), (N-420: Me, 4-CON(Me)$_2$-Ph, S, S), (N-421: Me, 4- iPrOC(=O)-Ph, S, S), (N-422: Me, 4-nBuOC(=O)-Ph, S, S), (N-423: Me, 6-Me- pyridine-3-yl, S, S), (N-424: Me, Quinoline-3-yl, S, S), (N-425: Me, 4-NH$_2$-Ph, S, S), (N-426: Me, 4-N(Ac)H-Ph, S, S), (N-427: Me, 4-OH-Ph, S, S), (N-428: Me, 3,4-di(OH)$_2$-Ph, S, S), (N-429: Me, 3,4-di(NH$_2$)-Ph, S, S), (N-430: Me, 3:4- [N(Ac)H]$_2$-Ph, S, S), (N-431: Me, 4-SH-Ph, S, S), (N-432: Me, 4-SMe-Ph, S, S), (N-433: Me, 3,4-diBr-Ph, S, S), (N-434: Me, 4-N(Me)H-Ph, S, S), (N-435: Me, 4-N(Me)$_2$-Ph, S, S), (N-436: Me, 4-N(Me)$_3$+-Ph, S, S), (N-437: Me, 4-Et-Ph, S, S), (N-438: Me, 4-iPr-Ph, S, S), (N-439: Me, 4-nPr-Ph, S, S), (N-440: Me, 4-nBu-Ph, S, S), (N-441: Me, 4-iBu-Ph, S, S), (N-442: Me, 3,4-diMe-Pb, S, S), (N-443: Me, 1,3-Benzodioxole-5-yl, S, S), (N-444: Me, N-Me-pyridinium-4-yl, S, S), (N-445: Me, N-Me-pyridinium-3-yl, S, S), (N-446: Me, 6-Me-Pyridine-2-yl, S, S), (N- 447: Me, 2-Pyrazinyl, S, S), (N-448: Me, 3-Pyrrolyl, S, S), (N-449: Me, 1-Me- pyrrole-3-yl, S, S), (N-450: Me, Pyridine N-oxide-4-yl, S, S), (N-451: Me, Pyridine N-oxide-3-yl, S, S), (N-452: Me, 6-OH-pyridine-3-yl, S, S), (N-453: Me, 6-SH-pyridine-3-yl, S, S), (N-454: Me, 1-Ac-pyrrole-3-yl, S, S), (N-455: Me, 4- CF$_3$-Ph, S, S), (N-456: Me, 4-CN-Ph, S, S), (N-457: Me, 4-CHO-Ph, S, S), (N- 458: Me, 3-Cl-Ph, S, S), (N-459: Me, 3-Br-Ph, S, S), (N-460: Me, 3-F-Ph, S, S), (N-461: Me, 3-I-Ph, S, S), (N-462: Me, 4-I-Ph, S, S), (N-463: Me, 4-OCF$_3$-Ph, S, S), (N-464: Me, 3,4-diI-Ph, S, S), (N-465: Me, Indole-6-yl, S, S), (N-466: Me, 1-Ac-indole-6-yl, S, S), (N-467: Me, 1-Me-indole-6-yl, S, S), (N-468: Me, 4-(1- Imidazolyl)-Ph, S, S), (N-469: Me, 4-Morphorino-Ph, S, S), (N-470: Me, 4-(1-Piperazinyl)-Ph, S, S), (N-471: Me, 2:5-diMe-thiophene-3-yl, S, S), (N-472: Me, 2-Furyl, S, S), (N-473: Me, 5-Me-furan-2-yl, S, S), (N-474: Me, 5-Me-furan-2- yl, S, S), (N-475: Me, 2-Thiazolyl, S, S), (N-476: Me, 1:4-Benzodioxin-6-yl, S, S), (N-477: Me, Benzo[b]furan-2-yl, S, S), (N-478: Me, 4-NH$_2$CH$_2$-Ph, S, S), (N- 479: Me, 4-N(Me)HICH$_2$-Ph, S, S), (N-480: Me, 4-N(Me)2CH$_2$-Ph, S, S), (N-481: Me, 6-Cl-pyridine-3-yl, S, S), (N-482: Me, 5,6-diCl-pyridine-3-yl, S, S), (N-483: Me, 5-Cl-pyridine-2-yl, S, S), (N-484: Me, 4:5-diCl-pyridine-2-yl, S, S), (N-485: Me, 4-ClCH$_2$-Bn, S, S), (N-486: Me, Bn, S, S), (N-487: Me, 4-Cl-Bn, S, S), (N- 488: Me, 4-Br-Bn, S, S), (N-489: Me, 4-F-Bn, S, S), (N-490: Me, 3,4-diCl-Bn, S, S), (N-491: Me, 3,4-diBr-Bn, S, S), (N-492: Me, 3,4-diF-Bn, S, S), (N-493: Me, 4-Cl-Bz, S, S), (N-494: Me, 3,4-diCl-Bz, S, S), (N-495: Me, 4-Br-Bz, S, S), (N- 496: Me, 3,4-diBr-Bz, S, S), (N-497: Me, 4-F-Bz, S, S), (N-498: Me, 3,4-diF-Bz, S, S), (N-499: Me, 4-NO$_2$-Bn, S, S), (N-500: Me, 4-CN-Bn, S, S), (N-501: Et, Ph, S, S), (N-502: Et, 4-F-Ph, S, S), (N-503: Et, 4-Br-Ph, S, S), (N-504: Et, 4-Me-Ph, S, S), (N-505: Et, 4-Ph-Ph, S, S), (N-506: Et, 4-OMe-Ph, S, S), (N-507: Et, 4- tBu-Ph, S, S), (N-508: Et, 4-COOMe-Ph, S, S), (N-509: Et, 4-Pcn-Ph, S, S), (N-510: Et, 4-NO$_2$-Ph, S, S), (N-511: Et, 5-Cl-thiophene-2-yl, S, S), (N-612: Et, 3-Thienyl, S, S), (N-513: Et, 2-Py, S, S), (N-514: Et, 3-Py, S, S), (N-515: Et, 4- Py, S, S), (N-516: Et, 3,4-diF-Ph, S, S), (N-517: Et, 5-Br-thiophene-2-yl, S, S), (N-518: Et, 4-CONH$_2$-Ph, S, S), (N-519: Et, 4-CON(Me)H-Ph, S, S), (N-520: Et, 4-CON(Me)$_2$-Ph, S, S), (N-521: Et, 4-iPrOC(=O)-Ph, S, S), (N-522: Et, 4- nBuOC(=O)-Ph, S, S), (N-523: Et, 6-Me-pyridine-3-yl, S, S), (N-524: Et, Quinoline-3-yl, S, S), (N-525: Et, 4-NH$_2$-Ph, S, S), (N-526: Et, 4-N(Ac)H-Ph, S, S), (N-527: Et, 4-OH-Ph, S, S), (N-528: Et, 3,4-di(OH)$_2$-Ph, S, S), (N-529: Et, 3,4-di(NH$_2$)-Ph, S, S), (N-530: Et, 3:4-[N(Ac)H]$_2$-Ph, S, S), (N-531: Et, 4-SH-Ph, S, S), (N-532: Et, 4-SMe-Ph, S, S), (N-533: Et, 3,4-diBr-Pb, S, S), (N-534: Et, 4-N(Me)H-Ph, S, S), (N-535: Et, 4-N(Me)$_2$-Ph, S, S), (N-536: Et, 4-N(Me)$_3$+-Ph, S, S), (N-537: Et, 4-Et-Ph, S, S), (N-538: Et, 4-iPr-Ph, S, S), (N-539: Et, 4-nPr-Ph, S, S),.(N-540: Et, 4-nBu-Ph, S, S), (N-541: Et, 4-iBu-Ph, S, S), (N-542: Et, 3,4-diMe-Ph, S, S), (N-543: Et, 1,3-Benzodioxole-5-yl, S, S), (N-544: Et, N-Me-pyridinium-4-yl, S, S), (N-545: Et, N-Me-pyridinium-3-yl, S, S), (N-546: Et, 5-Me-Pyridine-2-yl, S, S), (N-547: Et, 2-Pyrazinyl, S, S), (N-548: Et, 3- Pyrrolyl, S, S), (N-549: Et, 1-Me-pyrrole-3-yl, S, S), (N-550: Et, Pyridine N- oxide-4-yl, S, S), (N-551: Et, Pyridinc N-oxide-3-yl, S, S), (N-552: Et, 6-OH- pyridine-3-yl, S, S), (N-553: Et, 6-SH-pyridine-3-yl, S, S), (N-554: Et, 1-Ac- pyrrole-3-yl, S, S), (N-555: Et, 4-CF$_3$-Ph, S, S), (N-556: Et, 4-CN-Ph, S, S), (N-557: Et, 4-CHO-Ph, S, S), (N-558: Et, 3-Cl-Ph, S, S), (N-559: Et, 3-Br-Ph, S, S), (N-560: Et, 3-F-Ph, S, S), (N-561: Et, 3-I-Ph, S, S), (N-562: Et, 4-I-Ph, S, S), (N-563: Et, 4-OCF$_3$-Ph, S, S), (N-564: Et, 3,4-diI-Ph, S, S), (N-565: Et, Indole- 6-yl, S, S), (N-566: Et, 1-Ac-indole-6-yl, S, S), (N-567: Et, 1-Me-indole-6-yl, S, S), (N-568: Et, 4-(1-Imidazolyl)-Ph, S, S), (N-569: Et, 4-Morphorino-Ph, S, S), (N-570: Et, 4-(1-Piperazinyl)-Ph, S, S), (N-571: Et, 2:5-diMe-thiophene-3-yl, S, S), (N-572: Et, 2-Furyl, S, S), (N-573: Et, 5-Me-furan-2-yl, S, S), (N-574: Et, 5-Me-furan-2-yl, S, S), (N-475: Et, 2-Thiazolyl, S, S), (N-576: Et, 1:4- Benzodioxin-6-yl, S, S), (N-577: Et, Benzo[b]furan-2-yl, S, S), (N-578: Et, 4-NH$_2$CH$_2$-Ph, S, S), (N-579: Et, 4-N(Me)H-Ph, S, S), (N-580: Et, 4- N(Me)$_2$CH$_2$-Ph, S, S), (N-581: Et, 6-Cl-pyridine-3-yl, S, S), (N-582: Et, 5,6- diCl-pyridine-3-yl, S, S), (N-583: Et, 5-Cl-pyridine-2-yl, S, S), (N-584: Et, 4:5- diCl-pyridine-2-yl, S, S), (N-586: Et, 4-ClCH$_2$-Bn, S, S), (N-586: Et, Bn, S, S), (N-587: Et, 4-Cl-Bn, S, S), (N-588: Et, 4-Br-Bn, S, S), (N-589: Et, 4-F-Bn, S, S), (N-590: Et, 3,4-diCl-Bn, S, S), (N-591: Et, 3,4-diBr-Bn, S, S), (N-592: Et, 3,4-diF-Bn, S, S), (N-593: Et, 4-Cl-Bz, S, S), (N-694: Et, 3,4-diCl-Bz, S, S), (N-595: Et, 4-Br-Bz, S, S), (N-596: Et, 3,4-diBr-Bz, S, S), (N-597: Et, 4-F-Bz, S, S), (N-598: Et, 3,4-diF-Bz, S, S), (N-599: Et, 4-NO$_2$-Bn, S, S), (N-600: Et, 4-CN-Bn, S, S), (N-601: COOMe, Ph, S, S), (N-602: COOMe, 4-F-Ph, S, S), (N- 603: COOMe, 4-Br-Ph, S, S), (N-604: COOMe, 4-Me-Ph, S, S), (N-605: COOMe, 4-Ph-Ph, S, S), (N-606: COOMe, 4-OMe-Ph, S, S), (N-607: COOMe, 4-tBu-Ph, S, S), (N-608: COOMe, 4-COOMe-Ph, S, S), (N-609: COOMe, 4-Pen-Ph, S, S), (N- 510: COOMe, 4-NO$_2$-Ph, S, S), (N-611: COOMe, 5-Cl-thiophene-2-yl, S, S), (N-612: COOMe, 3-Thienyl, S, S), (N-513: COOMe, 2-Py, S, S), (N-614: COOMe, 3-Py, S, S), (N-615: COOMe, 4-Py, S, S), (N-616: COOMe, 3,4-diF-Ph, S, S), (N-617: COOMe, 5-Br-thiophene-2-yl, S, S), (N-618: COOMe, 4-CONH$_2$-Ph, S, S), (N-619: COOMe, 4-CON(Me)H-Ph, S, S), (N- 620: COOMe, 4-CON(MC)$_2$-Ph, S, S), (N-621: COOMe, 4-iPrOC(=O)-Ph, S, S), (N-622: COOMe, 4-nBuOC(=O)-Ph, S, S), (N-623: COOMe, 6-Me-pyridine-3-yl, S, S), (N-624: COOMe, Quinoline-3-yl, S, S), (N-625: COOMe, 4-NH$_2$-Ph, S, S), (N-626: COOMe, 4-N(Ac)H-Ph, S, S), (N-627: COOMe, 4-OH-Ph, S, S), (N-628: COOMe, 3,4-di(OH)$_2$-Ph, S, S), (N-629: COOMe, 3,4-di(NH$_2$)-Ph, S, S), (N-630: COOMe, 3:4-[N(Ac)H]$_2$-Ph, S, S), (N-631: COOMe, 4-SH-Ph, S, S), (N-632: COOMe, 4- SMe-Ph, S, S), (N-633: COOMe, 3,4-diBr-Ph, S, S), (N-634: COOMe, 4- N(Me)H-Ph, S, S), (N-636: COOMe, 4-N(Me)$_2$-Ph, S, S), (N-636: COOMc, 4- N(Me)$_3$+-Ph, S, S), (N-637: COOMe, 4-Et-Ph, S, S), (N-638: COOMe, 4-iPr-Ph, S, S), (N-639: COOMe, 4-nPr-Ph, S, S), (N-640: COOMe, 4-nBu-Ph, S, S), (N-641: COOMe, 4-iBu-Ph, S, S), (N-642: COOMe, 3,4-diMe-Ph, S, S), (N-643: COOMe, 1,3-Benzodioxole-5-yl, S, S), (N-644: COOMe, N-Me-pyridinium-4-yl, S, S), (N-645: COOMe, N-Me-pyridinium-3-yl, S, S), (N-646: COOMe, 5-Me- Pyridine-2-yl, S, S), (N-647: COOMe, 2-Pyrazinyl, S, S), (N-648: COOMe, 3- Pyrrolyl, S, S), (N-649: COOMe, 1-Me-pyrrole-3-yl, S, S), (N-650: COOMe, Pyridine N-oxide-4-yl, S, S), (N-651: COOMe, Pyridine N-oxide-3-yl, S, S), (N-652: COOMe, 6-OH-pyridine-3-yl, S, S), (N-653: COOMe, 6-SH-pyridine-3- yl, S, S), (N-664: COOMe, 1-Ac-pyrrole-3-yl, S, S), (N-655: COOMe, 4-CF$_3$-Ph, S, S), (N-656: COOMe, 4-CN-Ph, S, S), (N-667: COOMe, 4-CHO-Ph, S, S), (N- 658: COOMe, 3-Cl-Ph, S, S), (N-659: COOMe, 3-Br-Ph, S, S), (N-660: COOMe, 3-F-Ph, S, S), (N-661: COOMe, 3-I-Ph, S, S), (N-662: COOMe, 4-I-Ph, S, S), (N-663: COOMe, 4-OCF$_3$-Ph, S, S), (N-664: COOMe, 3,4-diI-Ph, S, S), (N-665: COOMe, Indole-6-yl, S, S), (N-666: COOMe, 1-Ac-indole-6-yl, S, S), (N-667: COOMe, 1-Me-indole-6-yl, S, S), (N-668: COOMe, 4-(1-Imidazolyl)-Ph, S, S), (N-669: COOMe, 4-Morphorino-Ph, S, S), (N-670: COOMe, 4-(1-Piperazinyl) Ph, S, S), (N-671: COOMe, 2:5-diMe-thiophene-3-yl, S, S), (N-G72: COOMe, 2- Furyl, S, S), (N-673: COOMe, 5-Me-furan-2-yl, S, S), (N-674: COOMe, 5-Me- furan-2-yl, S, S), (N-675: COOMe, 2-Thiazolyl, S, S), (N-676: COOMe, 1:4- Benzodioxin-6-yl, S, S), (N-577: COOMe, Benzo[b]furan-2-yl, S, S), (N-678: COOMe, 4-NH$_2$CH$_2$-Ph, S, S), (N-679: COOMe, 4-N(Me)HCH$_2$-Ph, S, S), (N- 680: COOMe, 4-N(Me)$_2$CH$_2$-Ph, S, S), (N-681: COOMe, 6-Cl-pyridine-3-yl, S, S), (N-682: COOMe, 5,6-diCl-pyridine-3-yl, S, S), (N-683: COOMe, 5-Cl-pyridine-2-yl, S, S), (N-684: COOMe, 4:5-diCl-pyridine-2-yl, S, S), (N-685: COOMe, 4- ClCH$_2$-Bn, S, S), (N-686: COOMe, Bn, S, S), (N-687: COOMe, 4-Cl-Bn, S, S), (N-688: COOMe, 4-Br-Bn, S, S), (N-689: COOMe, 4-F-Bn, S, S), (N-690: COOMe, 3,4-diCl-Bn, S, S), (N-691: COOMe, 3,4-diBr-Bn, S, S), (N-692: COOMe, 3,4-diF-Bn, S. S), (N-693: COOMe, 4-Cl-Bz, S, S), (N- 694: COOMe, 3,4-diCl-Bz, S, S), (N- 695: COOMe, 4-Br-Bz, S, S), (N- 696: COOMe, 3,4-diBr- Bz, S, S), (N-697: COOMe, 4-F-Bz, S, S), (N-698: COOMe, 3,4-diF-Bz, S, S), (N-699: COOMe, $_4$-NO$_2$-Bn, S. S), (N-700: COOMe, 4-CN-Bn, S, S), (N-701: Ph, H, O, S), (N-702: 4-F-Ph, H, O, S), (N-703: 4-Br-Ph, H, O, S), (N-704: 4-Me-Ph, H, O, S), (N-705: 4-Ph-Ph, H, O, S), (N-706: 4-OMe-Ph, H, O, S), (N-707: 4- tBu-Ph, H, O, S), (N-708: 4-COOMe-Ph, H, O, S), (N-709: 4-Pen-Ph, H, O, S), (N-710: 4-NO$_2$-Ph, H, O, S), (N-711: 5-Cl-thiophene-2-yl, H, O, S), (N-712: 3- Thienyl, H, O, S), (N-713: 2-Py, H, O, S), (N-714: 3-Py, H, O, S), (N-715: 4-Py, H, O, S), (N-716: 3,4-diF-Ph, H, O, S), (N-717: 5-Br-thiophene-2-yl, H, O, S), (N-718: 4-CONH2-Ph, H, O, S), (N-719: 4-CON(Me)H-Ph, H, O, S), (N-720: 4- CON(Me)$_2$-Ph, H, O, S), (N-721: 4-iPrOC(=O)-Ph, H, O, S), (N-722: 4- nBuOC(=O)-Ph, H, O, S), (N-723: 6-Me-pyridine-3-yl, H, O, S), (N-724: Quinoline-3-yl, H, O, S), (N-725: 4-NH$_2$-Ph, H, O, S), (N-726: 4-N(Ac)H-Ph, H, O, S), (N-727: 4-OH-Ph, H, O, S), (N-728: 3,4-di(OH)$_2$-Ph, H, O, S), (N-729: 3,4-di(NH$_2$)-Ph, H, O, S), (N-730: 3:4-[N(Ac)H]$_2$-Ph, H, O, S), (N-731: 4-SH-Ph, H, O, S), (N-732: 4-SMe-Ph, H, O, S), (N-733: 3,4-diBr-Ph, H, O, S), (N-734: 4-N(Me)H-Ph, H, O, S), (N-735: 4-N(Me)2-Ph, H, O, S), (N-736: 4-N(Me)$_3$+-Ph, H, O, S), (N-737: 4-Et-Ph, H, O, S), (N-738: 4-iPr-Ph, H, O, S), (N-739: 4-nPr- Ph, H, O, S), (N-740: 4-nBu-Ph, H, O, S), (N-741: 4-iBu-Ph, H, O, S), (N-742: 3,4-diMe-Ph, H, O, S), (N-743: 1,3-Benzodioxole-5-yl, H, O, S), (N-744: N-Me-pyridinium-4-yl, H, O, S), (N-745: N-Me-pyridinium-3-yl, H, O, S), (N-746: 5- Me-Pyridine-2-yl, H, O, S), (N-747: 2-Pyrazinyl, H, O, S), (N-748: 3-Pyrrolyl, H, O, S), (N-749: 1-Me-pyrrole-3-yl, H, O, S), (N-750: Pyridine N-oxide-4-yl, H, O, S), (N-751: Pyridine N-oxide-3-yl, H, O, S), (N-752: 6-OH-pyridine-3-yl, H, O, S), (N-753: 6-SH-pyridine-3-yl, H, O, S), (N-754: 1-Ac-pyrrole-3-yl, H, O, S), (N-755: 4-CF$_3$-Ph, H, O, S), (N-756: 4-CN-Ph, H, O, S), (N-757: 4-CHO-Ph, H, O, S), (N-758: 3-Cl-Ph, H, O, S), (N-759: 3-Br-Ph, H, O, S), (N-760: 3-F-Ph, H, O, S), (N-761: 3-I-Ph, H, O, S), (N-762: 4-I-Ph, H, O, S), (N-763: 4-OCF$_3$-Ph, H, O, S), (N-764: 3,4-diI-Ph, H, O, S), (N-765: Indole-6-yl, H, O, S), (N-766: 1-Ac- indole-6-yl, H, O, S), (N-767: 1-Me-indole-6-yl, H, O, S), (N-768: 4-(1- Imidazolyl)-Ph, H, O, S), (N-769: 4-Morphorino-Ph, H, O, S), (N-770: 4-(1-Piperazinyl)-Ph, H, O, S), (N-771: 2:5-diMe-thiophene-3-yl, H, O, S), (N-772: 2-Furyl, H, O, S), (N-773: 5-Me-furan-2-yl, H, O, S), (N-774: 5-Me-furan-2-yl, H, O, S), (N-775: 2-Thiazolyl, H, O, S), (N-776: 1:4-Benzodioxin-6-yl, H, O, S), (N-777: Benzo[b]furan-2-yl, H, O, S), (N-778: 4-NH$_2$CH$_2$-Ph, H, O, S), (N-779: 4-N(Me)HCH$_2$-Ph, H, O, S), (N-780: 4-N(Me)$_2$CH$_2$-Ph, H, O, S), (N-781: 6-Cl-pyridine-3-yl, H, O, S), (N-782: 5,6-diCl-pyridine-3-yl, H, O, S), (N-783: 5-Cl- pyridine-2-yl, H, O, S), (N-784: 4:5-diCl-pyridine-2-yl, H, O, S), (N-785: 4- ClCH$_2$-Bn, H, O, S), (N-786: Bn, H, O, S), (N-787: 4-Cl-Bn, H, O, S), (N-788: 4-Br-Bn, H, O, S), (N-789: 4-F-Bn, H, O, S), (N-790: 3,4-diCl-Bn, H, O, S), (N- 791: 3,4-diBr-Bn, H, O, S), (N-792: 3,4-diF-Bn, H, O, S), (N-793: 4-Cl-Bz, H, O, S), (N-794: 3,4-diCl-Bz, H, O, S), (N-795: 4-Br-Bz, H, O, S), (N-796: 3,4-diBr- Bz, H, O, S), (N-797: 4-F-Bz, H, O, S), (N-798: 3,4-diF-Bz, H, O, S), (N-799: 4- NO$_2$-Bn, H, O, S), (N-800: 4-CN-Bn, H, O, S), (N-801: Ph, Me, O, S), (N-802: 4-F-Pb, Me, O, S), (N-803: 4-Br-Ph, Me, O, S), (N-804: 4-Me-Ph, Me, O, S), (N-805: 4-Ph-Ph, Me, O, S), (N-806: 4-OMe-Ph, Me, O, S), (N-807: 4-tBu-Ph, Me, O, S), (N-808: 4-COOMe-Ph, Me, O, S), (N-809: 4-Pen-Ph, Me, O, S), (N- 810: 4-NO$_2$-Ph, Me, O, S), (N-811: 5-Cl-thiophene-2-yl, Me, O, S), (N-812: 3- Thienyl, Me, O, S), (N-813: 2-Py, Me, O, S), (N-814: 3-Py, Me, O, S), (N-815: 4-Py, Me, O, S), (N-816: 3,4-diF-Ph, Me, O, S), (N-817: 5-Br-thiophene-2-yl, Me, O, S), (N-818: 4-CONH$_2$-Ph, Me, O, S), (N-819: 4-CON(Me)H-Ph, Me, O, S), (N-820: 4-CON(Me)$_2$-Ph, Me, O, S), (N-821: 4-iPrOC(=O)-Ph, Me, O, S), (N-822: 4-nBuOC(=O)-Ph, Me, O, S), (N-823: 6-Me-pyridine-3-yl, Me, O, S), (N-824: Quinoline-3-yl, Me, O, S), (N-825: 4-NH$_2$-Ph, Me, O, S), (N-826: 4-N(Ac)H-Ph, Me, O, S), furan-2-yl, Me, O, S), (N-875: 2-Thiazolyl, Me, O, S), (N-876: 1:4-Benzodioxin-6-yl, Me, O, S), (N-877: Benzo[b]furan-2-yl, Me, O, S), (N-878: 4-NH₂CH₂-Ph, Me, O, S), (N-879: 4-N(Me)HCH₂-Ph, Me, O, S), (N-880: 4-N(Me)₂CH₂-Ph, Me, O, S), (N-881: 6-Cl-pyridine-3-yl, Me, O, S), (N-882: 5,6-diCl-pyridine-3-yl, Me, O, S), (N-883: 5-Cl-pyridine-2-yl, Me, O, S), (N-884: 4:5-diCl-pyridine-2-yl, Me, O, S), (N-885: 4-ClCH₂-Bn, Me, O, S), (N-886: Bn, Me, O, S), (N-887: 4-Cl-Bn, Me, O, S), (N-888: 4-Br-Bn, Me, O, S), (N-889: 4-F-Bn, Me, O, S), (N-890: 3,4-diCl-Bn, Me, O, S), (N-891: 3,4-diBr-Bn, Me, O, S), (N-892: 3,4-diF-Bn, Me, O, S), (N-893: 4-Cl-Bz, Me, O, S), (N-894: 3,4-diCl-Bz, Me, O, S), (N-895: 4-Br-Bz, Me, O, S), (N-896: 3,4-diBr-Bz, Me, O, S), (N-897: 4-F-Bz, Me, O, S), (N-898: 3,4-diF-Bz, Me, O, S), (N-899: 4.NO₂-Bn, Me, O, S), (N-900: 4-CN-Bn, Me, O, S), (N-901: Ph, Et, O, S), (N-902: 4-F-Ph, Et, O, S), (N-903: 4-Br-Ph, Et, O, S), (N-904: 4-Me-Ph, Et, O, S), (N-905: 4-Ph-Ph, Et, O, S), (N-906: 4-OMe-Ph, Et, O, S), (N-907: 4-tBu-Ph, Et, O, S), (N-908: 4-COOMe-Ph, Et, O, S), (N-909: 4-Pen-Ph, Et, O, S), (N-910: 4-NO₂-Ph, Et, O, S), (N-911: 5-Cl-thiophene-2-yl, Et, O, S), (N-912: 3-Thienyl, Et, O, S), (N-913: 2-Py, Et, O, S), (N-914: 3-Py, Et, O, S), (N-915: 4-Py, Et, O, S), (N-916: 3,4-diF-Ph, Et, O, S), (N-917: 5-Br-thiophene-2-yl, Et, O, S), (N-918: 4-CONH₂-Ph, Et, O, S), (N-919: 4-CON(Me)H-Ph, Et, O, S), (N-920: 4-CON(Me)₂-Ph, Et, O, S), (N-921: 4-iPrOC(=O)-Ph, Et, O, S), (N-922: 4-nBuOC(=O)-Ph, Et, O, S), (N-923: 6-Me-pyridine-3-yl, Et, O, S), (N-924: Quinoline-3-yl, Et, O, S), (N-925: 4-NH₂-Ph, Et, O, S), (N-926: 4-N(Ac)H-Ph, Et, O, S), (N-927: 4-OH-Ph, Et, O, S), (N-928: 3,4-di(OH)₂-Ph, Et, O, S), (N-929: 3,4-di(NH₂)-Ph, Et, O, S), (N-930: 3:4-[N(Ac)H]₂-Ph, Et, O, S), (N-931: 4-SH-Ph, Et, O, S), (N-932: 4-SMe-Ph, Et, O, S), (N-933: 3,4-diBr-Ph, Et, O, S), (N-934: 4-N(Me)H-Ph, Et, O, S), (N-935: 4-N(Me)₂-Ph, Et, O, S), (N-936: 4-N(Me)₃⁺-Ph, Et, O, S), (N-937: 4-Et-Ph, Et, O, S), (N-938: 4-iPr-Ph, Et, O, S), (N-939: 4-nPr-Ph, Et, O, S), (N-940: 4-nBu-Ph, Et, O, S), (N-941: 4-iBu-Ph, Et, O, S), (N-942: 3,4-diMe-Ph, Et, O, S), (N-943: 1,3-Benzodioxole-5-yl, Et, O, S), (N-944: N-Me-pyridinium-4-yl, Et, O, S), (N-945: N-Me-pyridinium-3-yl, Et, O, S), (N-946: 5-Me-Pyridine-2-yl, Et, O, S), (N-947: 2-Pyrazinyl, Et, O, S), (N-948: 3-Pyrrolyl, Et, O, S), (N-949: 1-Me-pyrrole-3-yl, Et, O, S), (N-950: Pyridine N-oxide-4-yl, Et, O, S), (N-951: Pyridine N-oxide-3-yl, Et, O, S), (N-952: 6-OH-pyridine-3-yl, Et, O, S), (N-953: 6-SH-pyridine-3-yl, Et, O, S), (N-954: 1-Ac-pyrrole-3-yl, Et, O, S), (N-955: 4-CF₃-Ph, Et, O, S), (N-956: 4-CN-Ph, Et, O, S), (N-957: 4-CHO-Ph, Et, O, S), (N-958: 3-Cl-Ph, Et, O, S), (N-959: 3-Br-Ph, Et, O, S), (N-960: 3-F-Ph, Et, O, S), (N-961: 3-I-Ph, Et, O, S), (N-962: 4-I-Ph, Et, O, S), (N-963: 4-OCF₃-Ph, Et, O, S), (N-964: 3,4-diI-Ph, Et, O, S), (N-965: Indole-6-yl, Et, O, S), (N-966: 1-Ac-indole-6-yl, Et, O, S), (N-967: 1-Me-indole-6-yl, Et, O, S), (N-968: 4-(1-Imidazolyl)-Ph, Et, O, S), (N-969: 4-Morphorino-Ph, Et, O, S), (N-970: 4-(1-Piperazinyl)-Ph, Et, O, S), (N-971: 2:5-diMe-thiophene-3-yl, Et, O, S), (N-972: 2-Furyl, Et, O, S), (N-973: 5-Me-furan-2-yl, Et, O, S), (N-974: 5-Me-furan-2-yl, Et, O, S), (N-975: 2-Thiazolyl, Et, O, S), (N-976: 1:4-Benzodioxin-6-yl, Et, O, S), (N-977: Benzo[b]furan-2-yl, Et, O, S), (N-978: 4-NH₂CH₂-Ph, Et, O, S), (N-979: 4-N(Me)HCH₂-Ph, Et, O, S), (N-980: 4-N(Me)₂CH₂-Ph, Et, O, S), (N-981: 6-Cl-pyridine-3-yl, Et, O, S), (N-982: 5,6-diCl-pyridine-3-yl, Et, O, S), (N-983: 5-Cl-pyridine-2-yl, Et, O, S), (N-984: 4:5-diCl-pyridine-2-yl, Et, O, S), (N-985: 4-ClCH₂-Bn, Et, O, S), (N-986: Bn, Et, O, S), (N-987: 4-Cl-Bn, Et, O, S), (N-988: 4-Br-Bn, Et, O, S), (N-989: 4-F-Bn, Et, O, S), (N-990: 3,4-diCl-Bn, Et, O, S), (N-991: 3,4-diBr-Bn, Et, O, S), (N-992: 3,4-diF-Bn, Et, O, S), (N-993: 4-Cl-Bz, Et, O, S), (N-994: 3,4-diCl-Bz, Et, O, S), (N-995: 4-Br-Bz, Et, O, S), (N-996: 3,4-diBr-Bz, Et, O, S), (N-997: 4-F-Bz, Et, O, S), (N-998: 3,4-diF-Bz, Et, O, S), (N-999: 4-NO₂-Bn, Et, O, S), (N-1000: 4-CN-Bn, Et, O, S), (N-1001: Ph, COOMe, O, S), (N-1002: 4-F-Ph, COOMe, O, S), (N-1003: 4-Br-Ph, COOMe, O, S), (N-1004: 4-Me-Ph, COOMe, O, S), (N-1005: 4-Ph-Ph, COOMe, O, S), (N-1006: 4-OMe-Ph, COOMe, O, S), (N-1007: 4-tBu-Ph, COOMe, O, S), (N-1008: 4-COOMe-Ph, COOMe, O, S), (N-1009: 4-Pen-Ph, COOMe, O, S), (N-1010: 4-NO₂-Ph, COOMe, O, S), (N-1011: 5-Cl-thiophene-2-yl, COOMe, O, S), (N-1012: 3-Thienyl, COOMe, O, S), (N-1013: 2-Py, COOMe, O, S), (N-1014: 3-Py, COOMe, O, S), (N-1015: 4-Py, COOMe, O, S), (N-1016: 3,4-diF-Ph, COOMe, O, S), (N-1017: 5-Br-thiophene-2-yl, COOMe, O, S), (N-1018: 4-CONH₂-Ph, COOMe, O, S), (N-1019: 4-CON(Me)H-Ph, COOMe, O, S), (N-1020: 4-CON(Me)₂-Ph, COOMe, O, S), (N-1021: 4-iPrOC(=O)-Ph, COOMe, O, S), (N-1022: 4-nBuOC(=O)-Ph, COOMe, O, S), (N-1023: 6-Me-pyridine-3-yl, COOMe, O, S), (N-1024: Quinoline-3-yl, COOMe, O, S), (N-1025: 4-NH₂-Ph, COOMe, O, S), (N-1026: 4-N(Ac)H-Ph, COOMe, O, S), (N-1027: 4-OH-Ph, COOMe, O, S), (N-1028: 3,4-di(OH)₂-Ph, COOMe, O, S), (N-1029: 3,4-di(NH₂)-Ph, COOMe, O, S), (N-1030: 3:4-[N(Ac)H]₂-Ph, COOMe, O, S), (N-1031: 4-SH-Ph, COOMe, O, S), (N-1032: 4-SMe-Ph, COOMe, O, S), (N-1033: 3,4-diBr-Ph, COOMe, O, S), (N-1034: 4-N(Me)H-Ph, COOMe, O, S), (N-1035: 4-N(Me)₂-Ph, COOMe, O, S), (N-1036: 4-N(Me)₃⁺-Ph, COOMe, O, S), (N-1037: 4-Et-Ph, COOMe, O, S), (N-1038: 4-iPr-Ph, COOMe, O, S), (N-1039: 4-nPr-Ph, COOMe, O, S), (N-1040: 4-nBu-Ph, COOMe, O, S), (N-1041: 4-iBu-Ph, COOMe, O, S), (N-1042: 3,4-diMe-Ph, COOMe, O, S), (N-1043: 1,3-Benzodioxole-5-yl, COOMe, O, S), (N-1044: N-Me-pyridinium-4-yl, COOMe, O, S), (N-1045: N-Me-pyridinium-3-yl, COOMe, O, S), (N-1046: 5-Me-Pyridine-2-yl, COOMe, O, S), (N-1047: 2-Pyrazinyl, COOMe, O, S), (N-1048: 3-Pyrrolyl, COOMe, O, S), (N-1049: 1-Me-pyrrole-3-yl, COOMe, O, S), (N-1050: Pyridine N-oxide-4-yl, COOMe, O, S), (N-1051: Pyridine N-oxide-3-yl, COOMe, O, S), (N-1052: 6-OH-pyridine-3-yl, COOMe, O, S), (N-1053: 6-SH-pyridine-3-yl, COOMe, O, S), (N-1054: 1-Ac-pyrrole-3-yl, COOMe, O, S), (N-1055: 4-CF₃-Ph, COOMe, O, S), (N-1056: 4-CN-Ph, COOMe, O, S), (N-1057: 4-CHO-Ph, COOMe, O, S), (N-1058: 3-Cl-Ph, COOMe, O, S), (N-1059: 3-Br-Ph, COOMe, O, S), (N-1060: 3-F-Ph, COOMe, O, S), (N-1061: 3-I-Ph, COOMe, O, S), (N-1062: 4-I-Ph, COOMe, O, S), (N-1063: 4-OCF₃-Ph, COOMe, O, S), (N-1064: 3,4-diI-Ph, COOMe, O, S), (N-1065: Indole-6-yl, COOMe, O, S), (N-1066: 1-Ac-indole-6-yl, COOMe, O, S), (N-1067: 1-Me-indole-6-yl, COOMe, O, S), (N-1068: 4-(1-Imidazolyl)-Ph, COOMe, O, S), (N-1069: 4-Morphorino-Ph, COOMe, O, S), (N-1070: 4-(1-Piperazinyl)-Ph, COOMe, O, S), (N-1071: 2:5-diMe-thiophene-3-yl, COOMe, O, S), (N-1072: 2-Furyl, COOMe, O, S), (N-1073: 5-Me-furan-2-yl, COOMe, O, S), (N-1074: 5-Me-furan-2-yl, COOMe, O, S), (N-1075: 2-Thiazolyl, COOMe, O, S), (N-1076: 1:4-Benzodioxin-6-yl, COOMe, O, S), (N-1077: Benzo[b]furan-2-yl, COOMe, O, S), (N-1078: 4-NH₂CH₂-Ph, COOMe, O, S), (N-1079: 4-N(Me)HCH₂-Ph, COOMe, O, S), (N-1080: 4-N(Me)₂CH₂-Ph, COOMe, O, S), (N-1081: 6-Cl-pyridine-3-yl, COOMe, O, S), (N-1082: 5,6-diCl-pyridine-3-yl, COOMe, O, S), (N-1083: 5-Cl-pyridine-2-yl, COOMe, O, S), (N-1084: 4:5-diCl-pyridine-2-yl, COOMe, O, S), (N-1085: 4-ClCH₂-Bn, COOMe, O, S), (N-1086: Bn, COOMe, O, S), (N-1087: 4-Cl-Bn, COOMe, O, S), (N-1088: 4-Br-Bn, COOMe, O, S), (N-1089: 4-F-Bn, COOMe, O, S), (N-1090: 3,4-diCl-Bn, COOMe, O, S), (N-1091: 3,4-diBr-Bn, COOMe, O, S), (N-1092: 3,4-diF-Bn, COOMe, O, S), (N-1093: 4-Cl-Bz, COOMe, O, S), (N-1094: 3,4-diCl-Bz, COOMe, O, S), (N-1095: 4-Br-Bz, COOMe, O, S), (N-1096: 3,4-diBr-Bz, COOMe, O, S), (N-1097: 4-F-Bz, COOMe, O, S), (N-1098: 3,4-diF-Bz, COOMe, O, S), (N-1099: 4-NO$_2$-Bn, COOMe, O, S), (N-1100: 4-CN-Bn, COOMe, O, S), (N-1101: H, Ph, O, S), (N-1102: H, 4-F-Ph, O, S), (N-1103: H, 4-Br-Ph, O, S), (N-1104: H, 4-Me-Ph, O, S), (N-1105: H, 4-Ph-Ph, O, S), (N-1106: H, 4-OMe-Ph, O, S), (N-1107: H, 4-tBu-Ph, O, S), (N-1108: H, 4-COOMe-Ph, O, S), (N-1109: H, 4-Pen-Ph, O, S), (N-1110: H, 4-NO$_2$-Ph, O, S), (N-1111: H, 5-Cl-thiophene-2-yl, O, S), (N-1112: H, 3-Thienyl, O, S), (N-1113: H, 2-Py, O, S), (N-1114: H, 3-Py, O, S), (N-1115: H, 4-Py, O, S), (N-1116: H, 3,4-diF-Ph, O, S), (N-1117: H, 5-Br-thiophene-2-yl, O, S), (N-1118: H, 4-CONH$_2$-Ph, O, S), (N-1119: H, 4-CON(Me)H-Ph, O, S), (N-1120: H, 4-CON(Me)2-Ph, O, S), (N-1121: H, 4-iPrOC(=O)-Ph, O, S), (N-1122: H, 4-nBuOC(=O)-Ph, O, S), (N-1123: H, 6-Me-pyridine-3-yl, O, S), (N-1124: H, Quinoline-3-yl, O, S), (N-1125: H, 4-NH$_2$-Ph, O, S), (N-1126: H, 4-N(Ac)H-Ph, O, S), (N-1127: H, 4-OH-Ph, O, S), (N-1128: H, 3,4-di(OH)$_2$-Ph, O, S), (N-1129: H, 3,4-di(NH$_2$)-Ph, O, S), (N-1130: H, 3:4-[N(Ac)H]$_2$-Ph, O, S), (N-1131: H, 4-SH-Ph, O, S), (N-1132: H, 4-SMe-Ph, O, S), (N-1133: H, 3,4-diBr-Ph, O, S), (N-1134: H, 4-N(Me)H-Ph, O, S), (N-1135: H, 4-N(Me)$_2$-Ph, O, S), (N-1136: H, 4-N(Me)$_3^+$-Ph, O, S), (N-1137: H, 4-Et-Ph, O, S), (N-1138: H, 4-iPr-Ph, O, S), (N-1139: H, 4-nPr-Ph, O, S), (N-1140: H, 4-nBu-Ph, O, S), (N-1141: H, 4-iBu-Ph, O, S), (N-1142: H, 3,4-diMe-Ph, O, S), (N-143: H, 1,3-Benzodioxole-5-yl, O, S), (N-1144: H, N-Me-pyridinium-4-yl, O, S), (N-1145: H, N-Me-pyridinium-3-yl, O, S), (N-1146: H, 5-Me-Pyridine-2-yl, O, S), (N-1147: H, 2-Pyrazinyl, O, S), (N-1148: H, 3-Pyrrolyl, O, S), (N-1149: H, 1-Me-pyrrole-3-yl, O, S), (N-1150: H, Pyridine N-oxide-4-yl, O, S), (N-1151: H, Pyridine N-oxide-3-yl, O, S), (N-1152: H, 6-OH-pyridine-3-yl, O, S), (N-1153: H, 6-SH-pyridine-3-yl, O, S), (N-1154: H, 1-Ac-pyrrole-3-yl, O, S), (N-1155: H, 4-CF$_3$-Ph, O, S), (N-1156: H, 4-CN-Ph, O, S), (N-1157: H, 4-CHO-Ph, O, S), (N-1158: H, 3-Cl-Ph, O, S), (N-1159: H, 3-Br-Ph, O, S), (N-1160: H, 3-F-Ph, O, S), (N-1161: H, 3-I-Ph, O, S), (N-1162: H, 4-I-Ph, O, S), (N-1163: H, 4-OCF$_3$-Ph, O, S), (N-1164: H, 3,4-diI-Ph, O, S), (N-1165: H, Indole-6-yl, O, S), (N-1166: H, 1-Ac-indole-6-yl, O, S), (N-1167: H, 1-Me-indole-6-yl, O, S), (N-1168: H, 4-(1-Imidazolyl)-Ph, O, S), (N-1169: H, 4-Morphorino-Ph, O, S), (N-1170: H, 4-(1-Piperazinyl)-Ph, O, S), (N-1171: H. 2:5-diMe-thiophene-3-yl, O, S), (N-1172: H, 2-Furyl, O, S), (N-1173: H, 5-Me-furan-2-yl, O, S), (N-1174: H, 5-Me-furan-2-yl, O, S), (N-1175: H, 2-Thiazolyl, O, S), (N-1176: H, 1:4-Benzodioxin-6-yl, O, S), (N-1177: H, Benzo[b]furan-2-yl, O, S), (N-1178: H, 4-NH$_2$CH$_2$-Ph, O, S), (N-1179: H, 4-N(Me)HCH$_2$-Ph, O, S), (N-1180: H, 4-N(Me)$_2$CH$_2$-Ph, O, S), (N-1181: H, 6-Cl-pyridine-3-yl, O, S), (N-1182: H, 5,6-diCl-pyridine-3-yl, O, S), (N-1183: H, 5-Cl-pyridine-2-yl, O, S), (N-1184: H, 4:5-diCl-pyridine-2-yl, O, S), (N-1185: H, 4-ClCH$_2$-Bn, O, S), (N-1186: H, Bn, O, S), (N-1187: H, 4-Cl-Bn, O, S), (N-1188: H, 4-Br-Bn, O, S), (N-1189: H, 4-F-Bn, O, S), (N-1190: H, 3,4-diCl-Bn, O, S), (N-1191: H, 3,4-diBr-Bn, O, S), (N-1192: H, 3,4-diF-Bn, O, S), (N-1193: H, 4-Cl-Bz, O, S), (N-1194: H, 3,4-diCl-Bz, O, S), (N-1195: H, 4-Br-Bz, O, S), (N-1196: H, 3,4-diBr-Bz, O, S), (N-1197: H, 4-F-Bz, O, S), (N-1198: H, 3,4-diF-Bz, O, S), (N-1199: H, 4-NO$_2$-Bn, O, S), (N-1200: H, 4-CN-Bn, O, S), (N-1201: Me, Ph, O, S), (N-1202: Me, 4-F-Ph, O, S), (N-1203: Me, 4-Br-Ph, O, S), (N-1204: Me, 4-Me-Ph, O, S), (N-1205: Me, 4-Ph-Ph, O, S), (N-1206: Me, 4-OMe-Ph, O, S), (N-1207: Me, 4-tBu-Ph, O, S), (N-1208: Me, 4-COOMe-Ph, O, S), (N-1209: Me, 4-Pen-Ph, O, S), (N-1210: Me, 4-NO$_2$-Ph, O, S), (N-1211: Me, 5-Cl-thiophene-2-yl, O, S), (N-1212: Me, 3-Thienyl, O, S), (N-1213: Me, 2-Py, O, S), (N-1214: Me, 3-Py, O, S), (N-1215: Me, 4-Py, O, S), (N-1216: Me, 3,4-diF-Ph, O, S), (N-1217: Me, 5-Br-thiophene-2-yl, O, S), (N-1218: Me, 4-CONH$_2$-Ph, O, S), (N-1219: Me, 4-CON(Me)H-Ph, O, S), (N-1220: Me, 4-CON(Me)$_2$-Ph, O, S), (N-1221: Me, 4-iPrOC(=O)-Ph, O, S), (N-1222: Me, 4-nBuOC(=O)-Ph, O, S), (N-1223: Me, 6-Me-pyridine-3-yl, O, S), (N-1224: Me, Quinoline-3-yl, O, S), (N-1225: Me, 4-NH$_2$-Ph, O, S), (N-1226: Me, 4-N(Ac)H-Ph, O, S), (N-1227: Me, 4-OH-Ph, O, S), (N-1228: Me, 3,4-di(OH)$_2$-Ph, O, S), (N-1229: Me, 3,4-di(NH$_2$)-Ph, O, S), (N-1230: Me, 3:4-[N(Ac)H]$_2$-Ph, O, S), (N-1231: Me, 4-SH-Ph, O, S), (N-1232: Me, 4-SMe-Ph, O, S), (N-1233: Me, 3,4-diBr-Ph, O, S), (N-1234: Me, 4-N(Me)H-Ph, O, S), (N-1235: Me, 4-N(Me)2-Ph, O, S), (N-1236: Me, 4-N(Me)$_3^+$-Ph, O, S), (N-1237: Me, 4-Et-Pb, O, S), (N-1238: Me, 4-iPr-Ph, O, S), (N-1239: Me, 4-nPr-Ph, O, S), (N-1240: Me, 4-nBu-Ph, O, S), (N-1241: Me, 4-iBu-Ph, O, S), (N-1242: Me, 3,4-diMe-Ph, O, S), (N-1243: Me, 1,3-Benzodioxole-5-yl, O, S), (N-1244: Me, N-Me-pyridinium-4-yl, O, S), (N-1245: Me, N-Me-pyridinium-3-yl, O, S), (N-1246: Me, 5-Me-Pyridine-2-yl, O, S), (N-1247: Me, 2-Pyrazinyl, O, S), (N-1248: Me, 3-Pyrrolyl, O, S), (N-1249: Me, 1-Me-pyrrole-3-yl, O, S), (N-1250: Me, Pyridine N-oxide-4-yl, O, S), (N-1251: Me, Pyridine N-oxide-3-yl, O, S), (N-1252: Me, 6-OH-pyridine-3-yl, O, S), (N-1253: Me, 6-SH-pyridine-3-yl, O, S), (N-1254: Me, 1-Ac-pyrrole-3-yl, O, S), (N-1255: Me, 4-CF$_3$-Ph, O, S), (N-1256: Me, 4-CN-Ph, O, S), (N-1257: Me, 4-CHO-Ph, O, S), (N-1258: Me, 3-Cl-Ph, O, S), (N-1259: Me, 3-Br-Ph, O, S), (N-1260: Me, 3-F-Ph, O, S), (N-1261: Me, 3-I-Ph, O, S), (N-1262: Me, 4-I-Ph, O, S), (N-1263: Me, 4-OCF$_3$-Ph, O, S), (N-1264: Me, 3,4-diI-Ph, O, S), (N-1265: Me, Indole-6-yl, O, S), (N-1266: Me, 1-Ac-indole-6-yl, O, S), (N-1267: Me, 1-Me-indole-6-yl, O, S), (N-1268: Me, 4-(1-Imidazolyl)-Ph, O, S), (N-1269: Me, 4-Morphorino-Ph, O, S), (N-1270: Me, 4-(1-Piperazinyl)-Ph, O, S), (N-1271: Me, 2,5-diMe-thiophene-3-yl, O, S), (N-1272: Me, 2-Furyl, O, S), (N-1273: Me, 5-Me-furan-2-yl, O, S), (N-1274: Me, 5-Me-furan-2-yl, O, S), (N-1275: Me, 2-Thiazolyl, O, S), (N-1276: Me, 1:4-Benzodioxin-6-yl, O, S), (N-1277: Me, Benzo[b]furan-2-yl, O, S), (N-1278: Me, 4-NH$_2$CH$_2$-Ph, O, S), (N-1279: Me, 4-N(Me)HCH$_2$-Ph, O, S), (N-1280: Me, 4-N(Me)$_2$CH$_2$-Ph, O, S), (N-1281: Me, 6-Cl-pyridine-3-yl, O, S), (N-1282: Me, 5,6-diCl-pyridine-3-yl, O, S), (N-1283: Me, 5-Cl-pyridine-2-yl, O, S), (N-1284: Me, 4:5-diCl-pyridine-2-yl, O, S), (N-1285: Me, 4-ClCH$_2$-Bn, O, S), (N-1286: Me, Bn, O, S), (N-1287: Me, 4-Cl-Bn, O, S), (N-1288: Me, 4-Br-Bn, O, S), (N-1289: Me, 4-F-Bn, O, S), (N-1290: Me, 3,4-diCl-Bn, O, S), (N-1291: Me, 3,4-diBr-Bn, O, S), (N-1292: Me, 3,4-diF-Bn, O, S), (N-1293: Me, 4-Cl-Bz, O, S), (N-1294: Me, 3,4-diCl-Bz, O, S), (N-1295: Me, 4-Br-Bz, O, S), (N-1296: Me, 3,4-diBr-Bz, O, S), (N-1297: Me, 4-F-Bz, O, S), (N-1298: Me, 3,4-diF-Bz, O, S), (N-1299: Me, 4-NO$_2$-Bn, O, S), (N-1300: Me, 4-CN-Bn, O, S), (N-1301: Et, Ph, O, S), (N-1302: Et, 4-F-Ph, O, S), (N-1303: Et, 4-Br-Ph, O, S), (N-1304: Et, 4-Me-Ph, O, S), (N-1305: Et, 4-Ph-Ph, O, S), (N-1306: Et, 4-OMe-Ph, O, S), (N-1307: Et, 4-tBu-Ph, O, S), (N-1308: Et, 4-COOMe-Ph, O, S), (N-1309: Et, 4-Pen-Ph, O, S), (N-1310: Et, 4-NO$_2$-Ph, O, S), (N-1311: Et, 5-Cl-thiophene-2-yl, O, S), (N-1312: Et, 3-Thienyl, O, S), (N-1313: Et, 2-Py, O, S), (N-1314: Et, 3-Py, O, S), (N-1315: Et, 4-Py, O, S), (N-1316: Et, 3,4-diF-Ph, O, S), (N-1317: Et, 5-Br-thiophene-2-yl, O, S), (N-1318: Et, 4-CONH$_2$-Ph, O, S), (N-1319: Et, 4-CON(Me)H-Ph, O, S), (N-1320: Et, 4-CON(Me)$_2$-Ph, O, S), (N-1321: Et, 4-iPrOC(=O)-Ph, O, S), (N-1322: Et, 4-nBuOC(=O)-Ph, O, S), (N-1323: Et, 6-Me-pyridine-3-yl, O, S), (N-1324: Et, Quinoline-3-yl, O, S), (N-1325: Et, 4-NH$_2$-Ph, O, S), (N-1326: Et, 4-N(Ac)H-Ph, O, S), (N-1327: Et, 4-OH-Ph, O, S), (N-1328: Et, 3,4-di(OH)$_2$-Ph, O, S), (N-1329: Et, 3,4-di(NH$_2$)$_2$-Ph, O, S), (N-1330: Et, 3:4-[N(Ac)H]$_2$-Ph, O, S), (N-1331: Et, 4-SH-Ph, O, S), (N-1332: Et, 4-SMe-Ph, O, S), (N-1333: Et, 3,4-diBr-Ph, O, S), (N-1334: Et, 4-N(Me)H-Ph, O, S), (N-1335: Et, 4-N(Me)$_2$-Ph, O, S), (N-1336: Et, 4-N(Me)$_3$$^+$-Ph, O, S), (N-1337: Et, 4-Et-Ph, O, S), (N-1338: Et, 4-iPr-Ph, O, S), (N-1339: Et, 4-nPr-Ph, O, S), (N-1340: Et, 4-nBu-Ph, O, S), (N-1341: Et, 4-iBu-Ph, O, S), (N-1342: Et, 3,4-diMe-Ph, O, S), (N-1343: Et, 1,3-Benzodioxole-5-yl, O, S), (N-1344: Et, N-Me-pyridinium-4-yl, O, S), (N-1345: Et, N-Me-pyridinium-3-yl, O, S), (N-1346: Et, 5-Me-Pyridine-2-yl, O, S), (N-1347: Et, 2-Pyrazinyl, O, S), (N-1348: Et, 3-Pyrrolyl, O, S), (N-1349: Et, 1-Me-pyrrole-3-yl, O, S), (N-1350: Et, Pyridine N-oxide-4-yl, O, S), (N-1351: Et, Pyridine N-oxide-3-yl, O, S), (N-1352: Et, 6-OH-pyridine-3-yl, O, S), (N-1353: Et, 6-SH-pyridine-3-yl, O, S), (N-1354: Et, 1-Ac-pyrrole-3-yl, O, S), (N-1355: Et, 4-CF$_3$-Ph, O, S), (N-1356: Et, 4-CN-Ph, O, S), (N-1357: Et, 4-CHO-Ph, O, S), (N-1358: Et, 3-Cl-Ph, O, S), (N-1359: Et, 3-Br-Ph, O, S), (N-1360: Et, 3-F-Ph, O, S), (N-1361: Et, 3-I-Ph, O, S), (N-1362: Et, 4-I-Ph, O, S), (N-1363: Et, 4-OCF$_3$-Ph, O, S), (N-1364: Et, 3,4-diI-Ph, O, S), (N-1365: Et, Indole-6-yl, O, S), (N-1366: Et, 1-Ac-indole-6-yl, O, S), (N-1367: Et, 1-Me-indole-6-yl, O, S), (N-1368: Et, 4-(1-Imidazolyl)-Ph, O, S), (N-1369: Et, 4-Morphorino-Ph, O, S), (N-1370: Et, 4-(1-Piperazinyl)-Ph, O, S), (N-1371: Et, 2:5-diMe-thiophene-3-yl, O, S), (N-1372: Et, 2-Furyl, O, S), (N-1373: Et, 5-Me-furan-2-yl, O, S), (N-1374: Et, 5-Me-furan-2-yl, O, S), (N-1375: Et, 2-Thiazolyl, O, S), (N-1376: Et, 1:4-Benzodioxin-6-yl, O, S), (N-1377: Et, Benzo[b]furan-2-yl, O, S), (N-1378: Et, 4-NH$_2$CH$_2$-Ph, O, S), (N-1379: Et, 4-N(Me)HCH$_2$-Ph, O, S), (N-1380: Et, 4-N(Me)$_2$CH$_2$-Ph, O, S), (N-1381: Et, 6-Cl-pyridine-3-yl, O, S), (N-1382: Et, 5,6-diCl-pyridine-3-yl, O, S), (N-1383: Et, 5-Cl-pyridine-2-yl, O, S), (N-1384: Et, 4:5-diCl-pyridine-2-yl, O, S), (N-1385: Et, 4-ClCH$_2$-Bn, O, S), (N-1386: Et, Bn, O, S), (N-1387: Et, 4-Cl-Bn, O, S), (N-1388: Et, 4-Br-Bn, O, S), (N-1389: Et, 4-F-Bn, O, S), (N-1390: Et, 3,4-diCl-Bn, O, S), (N-1391: Et, 3,4-diBr-Bn, O, S), (N-1392: Et, 3,4-diF-Bn, O, S), (N-1393: Et, 4-Cl-Bz, O, S), (N-1394: Et, 3,4-diCl-Bz, O, S), (N-1395: Et, 4-Br-Bz, O, S), (N-1396: Et, 3,4-diBr-Bz, O, S), (N-1397: Et, 4-F-Bz, O, S), (N-1398: Et, 3,4-diF-Bz, O, S), (N-1399: Et, 4-NO$_2$-Bn, O, S), (N-1400: Et, 4-CN-Bn, O, S), (N-1401: COOMe, Ph, O, S), (N-1402: COOMe, 4-F-Ph, O, S), (N-1403: COOMe, 4-Br-Ph, O, S), (N-1404: COOMe, 4-Me-Ph, O, S), (N-1405: COOMe, 4-Ph-Ph, O, S), (N-1406: COOMe, 4-OMe-Ph, O, S), (N-1407: COOMe, 4-tBu-Ph, O, S), (N-1408: COOMe, 4-COOMe-Ph, O, S), (N-1409: COOMe, 4-Pen-Ph, O, S), (N-1410: COOMe, 4-NO$_2$-Ph, O, S), (N-1411: COOMe, 5-Cl-thiophene-2-yl, O, S), (N-1412: COOMe, 3-Thienyl, O, S), (N-1413: COOMe, 2-Py, O, S), (N-1414: COOMe, 3-Py, O, S), (N-1415: COOMe, 4-Py, O, S), (N-1416: COOMe, 3,4-diF-Ph, O, S), (N-1417: COOMe, 5-Br-thiophene-2-yl, O, S), (N-1418: COOMe, 4-CONH$_2$-Ph, O, S), (N-1419: COOMe, 4-CON(Me)H-Ph, O, S), (N-1420: COOMe, 4-CON(Me)$_2$-Ph, O, S), (N-1421: COOMe, 4-iPrOC(=O)-Ph, O, S), (N-1422: COOMe, 4-nBuOC(=O)-Ph, O, S), (N-1423: COOMe, 6-Me-pyridine-3-yl, O, S), (N-1424: COOMe, Quinoline-3-yl, O, S), (N-1425: COOMe, 4-NH$_2$-Ph, O, S), (N-1426: COOMe, 4-N(Ac)H-Ph, O, S), (N-1427: COOMe, 4-OH-Ph, O, S), (N-1428: COOMe, 3,4-di(OH)$_2$-Ph, O, S), (N-1429: COOMe, 3,4-di(NH$_2$)$_2$-Ph, O, S), (N-1430: COOMe, 3:4-[N(Ac)H]$_2$-Ph, O, S), (N-1431: COOMe, 4-SH-Ph, O, S), (N-1432: COOMe, 4-SMe-Ph, O, S), (N-1433: COOMe, 3,4-diBr-Ph, O, S), (N-1434: COOMe, 4-N(Me)H-Ph, O, S), (N-1435: COOMe, 4-N(Me)$_2$-Ph, O, S), (N-1436: COOME, 4-N(Me)$_3$$^+$-Ph, O, S), (N-1437: COOMe, 4-Et-Ph, O, S), (N-1438: COOMe, 4-iPr-Ph, O, S), (N-1439: COOMe, 4-nPr-Ph, O, S), (N-1440: COOMe, 4-nBu-Ph, O, S), (N-1441: COOMe, 4-iBu-Ph, O, S), (N-1442: COOMe, 3,4-diMe-Ph, O, S), (N-1443: COOMe, 1,3-Benzodioxole-5-yl, O, S), (N-1444: COOMe, N-Me-pyridinium-4-yl, O, S), (N-1445: COOMe, N-Me-pyridinium-3-yl, O, S), (N-1446: COOMe, 5-Me-Pyridine-2-yl, O, S), (N-1447: COOMe, 2-Pyrazinyl, O, S), (N-1448: COOMe, 3-Pyrrolyl, O, S), (N-1449: COOMe, 1-Me-pyrrole-3-yl, O, S), (N-1450- COOMe, Pyridine N-oxide-4-yl, O, S), (N-1451: COOMe, Pyridine N-oxide-3-yl, O, S), (N-1452: COOMe, 6-OH-pyridine-3-yl, O, S), (N-1453: COOMe, 6-SH-pyridine-3-yl, O, S), (N-1454: COOMe, 1-Ac-pyrrole-3-yl, O, S), (N-1455: COOMe, 4-CF$_3$-Ph, O, S), (N-1456: COOMe, 4-CN-Ph, O, S), (N-1457: COOMe, 4-CHO-Ph, O, S), (N-1458: COOMe, 3-Cl-Ph, O, S), (N-1459: COOMe, 3-Br-Ph, O, S), (N-1460: COOMe, 3-F-Ph, O, S), (N-1461: COOMe, 3-I-Ph, O, S), (N-1462: COOMe, 4-I-Ph, O, S), (N-1463: COOMe, 4-OCF$_3$-Ph, O, S), (N-1464: COOMe, 3,4-diI-Ph, O, S), (N-1465: COOMe, Indole-6-yl, O, S), (N-1466: COOMe, 1-Ac-indole-6-yl, O, S), (N-1467: COOMe, 1-Me-indole-6-yl, O, S), (N-1468: COOMe, 4-(1-Imidazolyl)-Ph, O, S), (N-1469: COOMe, 4-Morphorino-Ph, O, S), (N-1470: COOMe, 4-(1-Piperazinyl)-Ph, O, S), (N-1471: COOMe, 2:5-diMe-thiophene-3-yl, O, S), (N-1472: COOMe, 2-Furyl, O, S), (N-1473: COOMe, 5-Me-furan-2-yl, O, S), (N-1474: COOMe, 5-Me-furan-2-yl, O, S), (N-1475: COOMe, 2-Thiazolyl, O, S), (N-1476: COOMe, 1:4-Benzodioxin-6-yl, O, S), (N-1477: COOMe, Benzo[b]furan-2-yl, O, S), (N-1478: COOMe, 4-NH$_2$CH$_2$-Ph, O, S), (N-1479: COOMe, 4-N(Me)HCH$_2$-Ph, O, S), (N-1480: COOMe, 4-N(Me)$_2$CH$_2$-Ph, O, S), (N-1481: COOMe, 6-Cl-pyridine-3-yl, O, S), (N-1482: COOMe, 5,6-diCl-pyridine-3-yl, O, S), (N-1483: COOMe, 5-Cl-pyridine-2-yl, O, S), (N-1484: COOMe, 4:5-diCl-pyridine-2-yl, O, S), (N-1485: COOMe, 4-ClCH2-Bn, O, S), (N-1486: COOMe, Bn, O, S), (N-1487: COOMe, 4-Cl-Bn, O, S), (N-1488: COOMe, 4-Br-Bn, O, S), (N-1489: COOMe, 4-F-Bn, O, S), (N-1490: COOMe, 3,4-diCl-Bn, O, S), (N-1491: COOMe, 3,4-diBr-Bn, O, S), (N-1492: COOMe, 3,4-diF-Bn, O, S), (N-1493: COOMe, 4-Cl-Bz, O, S), (N-1494: COOMe, 3,4-diCl-Bz, O, S), (N-1495: COOMe, 4-Br-Bz, O, S), (N-1496: COOMe, 3,4-diBr-Bz, O, S), (N-1497: COOMe, 4-F-Bz, O, S), (N-1498: COOMe, 3,4-diF-Bz, O, S), (N-1499: COOMe, 4-NO$_2$-Bn, O, S), (N-1500: COOMe, 4-CN-Bn, O, S), (N-1501: Ph, Me, S, O), (N-1502: 4-F-Ph, Me, S, O), (N-1503: 4-Br-Ph, Me, S, O), (N-1504: 4-Me-Ph, Me, S, O), (N-1505: 4-Ph-Ph, Me, S, O), (N-1506: 4-OMe-Ph, Me, S, O), (N-1507: 4-tBu-Ph, Me, S, O), (N-1508: 4-COOMe-Ph, Me, S, O), (N-1509: 4-Pen-Ph, Me, S, O), (N-1510: 4-NO$_2$-Ph, Me, S, O), (N-1511: 5-Cl-thiophene-2-yl, Me, S, O), (N-1512: 3-Thienyl, Me, S, O), (N-1513: 2-Py, Me, S, O), (N-1514: 3-Py, Me, S, O), (N-1515: 4-Py, Me, S, O), (N-1516: 3,4-diF-Ph, Me, S, O), (N-1517: 5-Br-thiophene-2-yl, Me, S, O), (N-1518: 4-CONH$_2$-Ph, Me, S, O), (N-1519: 4-CON(Me)H-Ph, Me, S, O), (N-1520: 4-CON(Me)$_2$-Ph, Me, S, O), (N-1521: 4-iPrOC(=O)-Ph, Me, S, O), (N-1522: 4-nBuOC (=O)-Ph, Me, S, O), (N-1523: 6-Me-pyridine-3-yl, Me, S, O), (N-1524: Quinoline-3-yl, Me, S, O), (N-1525: 4-NH₂-Ph, Me, S, O), (N-1526: 4-N(Ac)H-Ph, Me, S, O), (N-1527: 4-OH-Ph, Me, S, O), (N-1528: 3,4-di(OH)₂-Ph, Me, S, O), (N-1529: 3,4-di(NH₂)-Ph, Me, S, O), (N-1530: 3:4-[N(Ac)H]₂-Ph, Me, S, O), (N-1531: 4-SH-Ph, Me, S, O), (N-1532: 4-SMe-Ph, Me, S, O), (N-1533: 3,4-diBr-Ph, Me, S, O), (N-1534: 4-N(Me)H-Ph, Me, S, O), (N-1535: 4-N(Me)₂-Ph, Me, S, O), (N-1536: 4-N(Me)₃⁺-Ph, Me, S, O), (N-1537: 4-Et-Ph, Me, S, O), (N-1538: 4-iPr-Ph, Me, S, O), (N-1539: 4-nPr-Ph, Me, S, O), (N-1540: 4-nBu-Ph, Me, S, O), (N-1541: 4-iBu-Ph, Me, S, O), (N-1542: 3,4-diMe-Ph, Me, S, O), (N-1543: 1,3-Benzodioxole-5-yl, Me, S, O), (N-1544: N-Me-pyridinium-4-yl, Me, S, O), (N-1545: N-Me-pyridinium-3-yl, Me, S, O), (N-1546: 5-Me-Pyridine-2-yl, Me, S, O), (N-1547: 2-Pyrazinyl, Me, S, O), (N-1548: 3-Pyrrolyl, Me, S, O), (N-1549: 1-Me-pyrrole-3-yl, Me, S, O), (N-1550: Pyridine N-oxide-4-yl, Me, S, O), (N-1551: Pyridine N-oxide-3-yl, Me, S, O), (N-1552: 6-OH-pyridine-3-yl, Me, S, O), (N-1553: 6-SH-pyridine-3-yl, Me, S, O), (N-1554: 1-Ac-pyrrole-3-yl, Me, S, O), (N-1555: 4-CF3-Ph, Me, S, O), (N-1556: 4-CN-Ph, Me, S, O), (N-1557: 4-CHO-Ph, Me, S, O), (N-1558: 3-Cl-Ph, Me, S, O), (N-1559: 3-Br-Ph, Me, S, O), (N-1560: 3-F-Ph, Me, S, O), (N-1561: 3-I-Ph, Me, S, O), (N-1562: 4-I-Ph, Me, S, O), (N-1563: 4-OCF₃-Ph, Me, S, O), (N-1564: 3,4-diI-Ph, Me, S, O), (N-1565: Indole-6-yl, Me, S, O), (N-1566: 1-Ac-indole-6-yl, Me, S, O), (N-1567: 1-Me-indole-6-yl, Me, S, O), (N-1568: 4-(1-Imidazolyl)-Ph, Me, S, O), (N-1569: 4-Morphorino-Ph, Me, S, O), (N-1570: 4-(1-Piperazinyl)-Ph, Me, S, O), (N-1571: 2:5-diMe-thiophene-3-yl, Me, S, O), (N-1572: 2-Furyl, Me, S, O), (N-1573: 5-Me-furan-2-yl, Me, S, O), (N-1574: 5-Me-furan-2-yl, Me, S, O), (N-1575: 2-Thiazolyl, Me, S, O), (N-1576: 1:4-Benzodioxin-6-yl, Me, S, O), (N-1577: Benzo[b]furan-2-yl, Me, S, O), (N-1578: 4-NH₂CH₂-Ph, Me, S, O), (N-1579: 4-N(Me)HCH₂-Ph, Me, S, O), (N-1580: 4-N(Me)₂CH₂-Ph, Me, S, O), (N-1581: 6-Cl-pyridine-3-yl, Me, S, O), (N-1582: 5,6-diCl-pyridine-3-yl, Me, S, O), (N-1583: 5-Cl-pyridine-2-yl, Me, S, O), (N-1584: 4:5-diCl-pyridine-2-yl, Me, S, O), (N-1585: 4-ClCH₂-Bn, Me, S, O), (N-1586: Bn, Me, S, O), (N-1587: 4-Cl-Bn, Me, S, O), (N-1588: 4-Br-Bn, Me, S, O), (N-1589: 4-F-Bn, Me, S, O), (N-1590: 3,4-diCl-Bn, Me, S, O), (N-1591: 3,4-diBr-Bn, Me, S, O), (N-1592: 3,4-diF-Bn, Me, S, O), (N-1593: 4-Cl-Bz, Me, S, O), (N-1594: 3,4-diCl-Bz, Me, S, O), (N-1595: 4-Br-Bz, Me, S, O), (N-1596: 3,4-diBr-Bz, Me, S, O), (N-1597: 4-F-Bz, Me, S, O), (N-1598: 3,4-diF-Bz, Me, S, O), (N-1599: 4-NO₂-Bn, Me, S, O), (N-1600: 4-CN-Bn, Me, S, O), (N-1602: 4-F-Ph, Et, S, O), (N-1603: 4-Br-Ph, Et, S, O), (N-1604: 4-Me-Ph, Et, S, O), (N-1605: 4-Ph-Ph, Et, S, O), (N-1606: 4-OMe-Ph, Et, S, O), (N-1607: 4-tBu-Ph, Et, S, O), (N-1608: 4-COOMe-Ph, Et, S, O), (N-1609: 4-Pen-Ph, Et, S, O), (N-1610: 4-NO₂-Ph, Et, S, O), (N-1611: 5-Cl-thiophene-2-yl, Et, S, O), (N-1612: 3-Thienyl, Et, S, O), (N-1613: 2-Py, Et, S, O), (N-1614: 3-Py, Et, S, O), (N-1615: 4-Py, Et, S, O), (N-1616: 3,4-diF-Ph, Et, S, O), (N-1617: 5-Br-thiophene-2-yl, Et, S, O), (N-1618: 4-CONH₂-Ph, Et, S, O), (N-1619: 4-CON(Me)H-Ph, Et, S, O), (N-1620: 4-CON(Me)₂-Ph, Et, S, O), (N-1621: 4-iPrOC(=O)-Ph, Et, S, O), (N-1622: 4-nBuOC(=O)-Ph, Et, S, O), (N-1623: 6-Me-pyridine-3-yl, Et, S, O), (N-1624: Quinoline-3-yl, Et, S, O), (N-1625: 4-NH₂-Ph, Et, S, O), (N-1626: 4-N(Ac)H-Ph, Et, S, O), (N-1627: 4-OH-Ph, Et, S, O), (N-1628: 3,4-di(OH)₂-Ph, Et, S, O), (N-1629: 3,4-di(NH₂)-Ph, Et, S, O), (N-1630: 3:4-[N(Ac)H]₂-Ph, Et, S, O), (N-1631: 4-SH-Ph, Et, S, O), (N-1632: 4-SMe-Ph, Et, S, O), (N-1633: 3,4-diBr-Ph, Et, S, O), (N-1634: 4-N(Me)H-Ph, Et, S, O), (N-1635: 4-N(Me)₂-Ph, Et, S, O), (N-1636: 4-N(Me)₃⁺-Ph, Et, S, O), (N-1637: 4-Et-Ph, Et, S, O), (N-1638: 4-iPr-Ph, Et, S, O), (N-1639: 4-nPr-Ph, Et, S, O), (N-1640: 4-nBu-Ph, Et, S, O), (N-1641: 4-iBu-Ph, Et, S, O), (N-1642: 3,4-diMe-Ph, Et, S, O), (N-1643: 1,3-Benzodioxole-5-yl, Et, S, O), (N-1644: N-Me-pyridinium-4-yl, Et, S, O), (N-1645: N-Me-pyridinium-3-yl, Et, S, O), (N-1646: 5-Me-Pyridine-2-yl, Et, S, O), (N-1647: 2-Pyrazinyl, Et, S, O), (N-1648: 3-Pyrrolyl, Et, S, O), (N-1649: 1-Me-pyrrole-3-yl, Et, S, O), (N-1650: Pyridine N-oxide-4-yl, Et, S, O), (N-1651: Pyridine N-oxide-3-yl, Et, S, O), (N-1652: 6-OH-pyridine-3-yl, Et, S, O), (N-1653: 6-SH-pyridine-3-yl, Et, S, O), (N-1654: 1-Ac-pyrrole-3-yl, Et, S, O), (N-1655: 4-CF₃-Ph, Et, S, O), (N-1656: 4-CN-Ph, Et, S, O), (N-1657: 4-CHO-Ph, Et, S, O), (N-1658: 3-Cl-Ph, Et, S, O), (N-1659: 3-Br-Ph, Et, S, O), (N-1660: 3-F-Ph, Et, S, O), (N-1661: 3-I-Ph, Et, S, O), (N-1662: 4-I-Ph, Et, S, O), (N-1663: 4-OCF₃-Ph, Et, S, O), (N-1664: 3,4-diI-Ph, Et, S, O), (N-1665: Indole-6-yl, Et, S, O), (N-1666: 1-Ac-indole-6-yl, Et, S, O), (N-1667: 1-Me-indole-6-yl, Et, S, O), (N-1668: 4-(1-Imidazolyl)-Ph, Et, S, O), (N-1669: 4-Morphorino-Ph, Et, S, O), (N-1670: 4-(1-Piperazinyl)-Ph, Et, S, O), (N-1671: 2:5-diMe-thiophene-3-yl, Et, S, O), (N-1672: 2-Furyl, Et, S, O), (N-1673: 5-Me-furan-2-yl, Et, S, O), (N-1674: 5-Me-furan-2-yl, Et, S, O), (N-1675: 2-Thiazolyl, Et, S, O), (N-1676: 1:4-Benzodioxin-6-yl, Et, S, O), (N-1677: Benzo[b]furan-2-yl, Et, S, O), (N-1678: 4-NH₂CH₂-Ph, Et, S, O), (N-1679: 4-N(Me)HCH₂-Ph, Et, S, O), (N-1680: 4-N(Me)₂CH₂-Ph, Et, S, O), (N-1681: 6-Cl-pyridine-3-yl, Et, S, O), (N-1682: 5,6-diCl-pyridine-3-yl, Et, S, O), (N-1683: 5-Cl-pyridine-2-yl, Et, S, O), (N-1684: 4:5-diCl-pyridine-2-yl, Et, S, O), (N-1685: 4-ClCH₂-Bn, Et, S, O), (N-1686: Bn, Et, S, O), (N-1687: 4-Cl-Bn, Et, S, O), (N-1688: 4-Br-Bn, Et, S, O), (N-1689: 4-F-Bn, Et, S, O), (N-1690: 3,4-diCl-Bn, Et, S, O), (N-1691: 3,4-diBr-Bn, Et, S, O), (N-1692: 3,4-diF-Bn, Et, S, O), (N-1693: 4-Cl-Bz, Et, S, O), (N-1694: 3,4-diCl-Bz, Et, S, O), (N-1695: 4-Br-Bz, Et, S, O), (N-1696: 3,4-diBr-Bz, Et, S, O), (N-1697: 4-F-Bz, Et, S, O), (N-1698: 3,4-diF-Bz, Et, S, O), (N-1699: 4-NO₂-Bn, Et, S, O), (N-1700: 4-CN-Bn, Et, S, O), (N-1701: Ph, COOMe, S, O), (N-1702: 4-F-Ph, COOMe, S, O), (N-1703: 4-Br-Ph, COOMe, S, O), (N-1704: 4-Me-Ph, COOMe, S, O), (N-1705: 4-Ph-Ph, COOMe, S, O), (N-1706: 4-OMe-Ph, COOMe, S, O), (N-1707: 4-tBu-Ph, COOMe, S, O), (N-1708: 4-COOMe-Ph, COOMe, S, O), (N-1709: 4-Pen-Ph, COOMe, S, O), (N-1710: 4-NO₂-Ph, COOMe, S, O), (N-1711: 5-Cl-thiophene-2-yl, COOMe, S, O), (N-1712: 3-Thienyl, COOMe, S, O), (N-1713: 2-Py, COOMe, S, O), (N-1714: 3-Py, COOMe, S, O), (N-1715: 4-Py, COOMe, S, O), (N-1716: 3,4-diF-Ph, COOMe, S, O), (N-1717: 5-Br-thiophene-2-yl, COOMe, S, O), (N-1718: 4-CONH₂-Ph, COOMe, S, O), (N-1719: 4-CON(Me)H-Ph, COOMe, S, O), (N-1720: 4-CON(Me)₂-Ph, COOMe, S, O), (N-1721: 4-iPrOC(=O)-Ph, COOMe, S, O), (N-1722: 4-nBuOC(=O)-Ph, COOMe, S, O), (N-1723: 6-Me-pyridine-3-yl, COOMe, S, O), (N-1724: Quinoline-3-yl, COOMe, S, O), (N-1725: 4-NH₂-Ph, COOMe, S, O), (N-1726: 4-N(Ac)H-Ph, COOMe, S, O), (N-1727: 4-OH-Ph, COOMe, S, O), (N-1728: 3,4-di(OH)₂-Ph, COOMe, S, O), (N-1729: 3,4-di(NH₂)-Ph, COOMe, S, O), (N-1730: 3:4-[N(Ac)H]₂-Ph, COOMe, S, O), (N-1731: 4-SH-Ph, COOMe, S, O), (N-1732: 4-SMe-Ph, COOMe, S, O), (N-1733: 3,4-diBr-Ph, COOMe, S, O), (N-1734: 4-N(Me)H-Ph, COOMe, S, O), (N-1735: 4-N(Me)₂-Ph, COOMe, S, O), (N-1736: 4-N(Me)₃⁺-Ph, COOMe, S, O), (N-1737: 4-Et-Ph, COOMe, S, O), (N-1738: 4-iPr-Ph, COOMe, S, O), (N-1739: 4-nPr-Ph, COOMe, S, O), (N-1740: 4-nBu-Ph, COOMe, S, O), (N-1741: 4-iBu-Ph, COOMe, S, O), (N-1742: 3,4-diMe-Ph, COOMe, S, O), (N-1743: 1,3-Benzodioxole-5-yl, COOMe, S, O), (N-1744: N-Me-pyridinium-4-yl, COOMe, S, O), (N-1745: N-Me-pyridinium-3-yl, COOMe, S, O), (N-1746: 5-Me-Pyridine-2-yl, COOMe, S, O), (N-1747: 2-Pyrazinyl, COOMe, S, O), (N-1748: 3-Pyrrolyl, COOMe, S, O), (N-1749: 1-Me-pyrrole-3-yl, COOMe, S, O), (N-1750: Pyridine N-oxide-4-yl, COOMe, S, O), (N-1751: Pyridine N-oxide-3-yl, COOMe, S, O), (N-1752: 6-OH-pyridine-3-yl, COOMe, S, O), (N-1753: 6-SH-pyridine-3-yl, COOMe, S, O), (N-1754: 1-Ac-pyrrole-3-yl, COOMe, S, O), (N-1755: 4-$CF_3$-Ph, COOMe, S, O), (N-1756 4-CN-Ph, COOMe, S, O), (N-1757: 4-CHO-Ph, COOMe, S, O), (N-1758: 3-Cl-Ph, COOMe, S, O), (N-1759: 3-Br-Ph, COOMe, S, O), (N-1760: 3-F-Ph, COOMe, S, O), (N-1761: 3-I-Ph, COOMe, S, O), (N-1762: 4-I-Ph, COOMe, S, O), (N-1763: 4-$OCF_3$-Ph, COOMe, S, O), (N-1764: 3,4-diI-Ph, COOMe, S, O), (N-1765: Indole-6-yl, COOMe, S, O), (N-1766: 1-Ac-indole-6-yl, COOMe, S, O), (N-1767: 1-Me-indole-6-yl, COOMe, S, O), (N-1768: 4-(1-Imidazolyl)-Ph, COOMe, S, O), (N-1769: 4-Morphorino-Ph, COOMe, S, O), (N-1770: 4-(1-Piperazinyl)-Ph, COOMe, S, O), (N-1771: 2:5-diMe-thiophene-3-yl, COOMe, S, O), (N-1772: 2-Furyl, COOMe, S, O), (N-1773: 5-Me-furan-2-yl, COOMe, S, O), (N-1774: 5-Me-furan-2-yl, COOMe, S, O), (N-1775: 2-Thiazolyl, COOMe, S, O), (N-1776: 1:4-Benzodioxin-6-yl, COOMe, S, O), (N-1777: Benzo[b]furan-2-yl, COOMe, S, O), (N-1778: 4-$NH_2CH_2$-Ph, COOMe, S, O), (N-1779: 4-N(Me)$HCH_2$-Ph, COOMe, S, O), (N-1780: 4-$N(Me)_2$$CH_2$-Ph, COOMe, S, O), (N-1781: 6-Cl-pyridine-3-yl, COOMe, S, O), (N-1782: 5,6-diCl-pyridine-3-yl, COOMe, S, O), (N-1783: 5-Cl-pyridine-2-yl, COOMe, S, O), (N-1784: 4:5-diCl-pyridine-2-yl, COOMe, S, O), (N-1785: 4-$ClCH_2$-Bn, COOME, S, O), (N-1786: Bn, COOMe, S, O), (N-1787: 4-Cl-Bn, COOMe, S, O), (N-1788: 4-Br-Bn, COOMe, S, O), (N-1789: 4-F-Bn, COOMe, S, O), (N-1790: 3,4-diCl-Bn, COOMe, S, O), (N-1791: 3,4-diBr-Bn, COOMe, S, O), (N-1792: 3,4-diF-Bn, COOMe, S, O), (N-1793: 4-Cl-Bz, COOMe, S, O), (N-1794: 3,4-diCl-Bz, COOMe, S, O), (N-1795: 4-Br-Bz, COOMe, S, O), (N-1796: 3,4-diBr-Bz, COOMe, S, O), (N-1797: 4-F-Bz, COOMe, S, O), (N-1798: 3,4-diF-Bz, COOMe, S, O), (N-1799: 4-$NO_2$-Bn, COOMe, S, O), (N-1800: 4-CN-Bn, COOMe, S, O), (N-1801: H, Ph, S, O), (N-1802: H, 4-F-Ph, S, O), (N-1803: H, 4-Br-Ph, S, O), (N-1804: H, 4-Me-Ph, S, O), (N-1805: H, 4-Ph-Ph, S, O), (N-1806: H, 4-OMe-Ph, S, O), (N-1807: H, 4-tBu-Ph, S, O), (N-1808: H, 4-COOMe-Ph, S, O), (N-1809: H, 4-Pen-Ph, S, O), (N-1810: H, 4-$NO_2$-Ph, S, O), (N-1811: H, 5-Cl-thiophene-2-yl, S, O), (N-1812: H, 3-Thienyl, S, O), (N-1813: H, 2-Py, S, O), (N-1814: H, 3-Py, S, O), (N-1815: H, 4-Py, S, O), (N-1816: H, 3,4-diF-Pb, S, O), (N-1817: H, 5-Br-thiophene-2-yl, S, O), (N-1818: H, 4- $CONH_2$-Ph, S, O), (N-1819: H, 4-CON(Me)H-Ph, S, O), (N-1820: H, 4-CON(Me)2-Ph, S, O), (N-1821: H, 4-iPrOC(=O)-Ph, S, O), (N-1822: H, 4-nBuOC(=O)-Ph, S, O), (N-1823: H, 6-Me-pyridine-3-yl, S, O), (N-1824: H, Quinoline-3-yl, S, O), (N-1825: H, 4-$NH_2$-Ph, S, O), (N-1826: H, 4-N(Ac)H-Ph, S, O), (N-1827: H, 4-OH-Ph, S, O), (N-1828: H, 3,4-di(OH)2-Ph, S, O), (N-1829: H, 3,4-di(NH2)-Ph, S, O), (N-1830: H, 3:4-[N(Ac)H]2-Ph, S, O), (N-1831: H, 4-SH-Ph, S, O), (N-1832: H, 4-SMe-Ph, S, O), (N-1833: H, 3,4-diBr-Ph, S, O), (N-1834: H, 4-N(Me)H-Ph, S, O), (N-1835: H, 4-N(Me)2-Ph, S, O), (N-1836: H, 4-N(Me)3+-Ph, S, O), (N-1837: H, 4-Et-Ph, S, O), (N-1838:1I, 4-iPr-Ph, S, O), (N-1839: H, 4-nPr-Ph, S, O), (N-1840: H, 4-nBu-Ph, S, O), (N-1841: H, 4-iBu-Ph, S, O), (N-1842: H, 3,4-diMe-Ph, S, O), (N-1843: H, 1,3-Benzodioxole-5-yl, S, O), (N-1844: H, N-Me-pyridinium-4-yl, S, O), (N-1845: H, N-Me-pyridinium-3-yl, S, O), (N-1846: H, 5-Me-Pyridine-2-yl, S, O), (N-1847: H, 2-Pyrazinyl, S, O), (N-1848: H, 3-Pyrrolyl, S, O), (N-1849: H, 1-Me-pyrrole-3-yl, S, O), (N-1850: H, Pyridine N-oxide-4-yl, S, O), (N-1851: H, Pyridine N-oxide-3-yl, S, O), (N-1853: H, 6-OH-pyridine-3-yl, S, O), (N-1853: H, 6-SH-pyridine-3-yl, S, O), (N-1854: H, 1-Ac-pyrrole-3-yl, S, O), (N-1855: H, 4-CFs-Ph, S, O), (N-1856: H, 4-CN-Ph, S, O), (N-1857: H, 4-CHO-Ph, S, O), (N-1858: H, 3-Cl-Ph, S, O), (N-1859: H, 3-Br-Ph, S, O), (N-1860: H, 3-F-Ph, S, O), (N-1861: H, 3-I-Ph, S, O), (N-1862: H, 4-1-Ph, S, O), (N-1863: H, 4-$OCF3$-Ph, S, O), (N-1864: H, 3,4-diI-Ph, S, O), (N-1865: H, Indole-6-yl, S, O), (N-1866: H, 1-Ac-indole-6-yl, S, O), (N-1867: H, 1-Me-indole-6-yl, S, O), (N-1868: H, 4-(1-Imidazolyl)-Ph, S, O), (N-1869: 1-, 4-Morphorino-Ph, S, O), (N-1870: H, 4-(1-Piperazinyl)-Ph, S, O), (N-1871: H, 2:5-diMe-thiophene-3-yl, S, O), (N-1872: 1-, 2-Furyl, S, O), (N-1873: H, 5-Me-furan-2-yl, S, O), (N-1874: H, 5-Me-furan-2-yl, S, O), (N-1875: H, 2-Thiazolyl, S, O), (N-1876: H, 1:4-Benzodioxin-6-yl, S, O), (N-1877: H, Benzo[blfuran-2-yl, S, O), (N-1878: H, 4-$NH_2CH2$-Ph, S, O), (N-1879: H, 4-N(Me)$HCH_2$-Ph, S, O), (N-1880: H, 4-N(Me)$2CH2$-Ph, S, O), (N-1881: H, 6-Cl-pyridine-3-yl, S, O), (N-1882: H, 5,6-diCl-pyridine-3-yl, S, O), (N-1883: H, 5-Cl-pyridine-2-yl, S, O), (N-1884: H, 4:5-diCl-pyridine-2-yl, S, O), (N-1885: H, 4-$ClCH2$-Bn, S, O), (N-1886: H, Bn, S, O), (N-1887: H, 4-Cl-Bn, S, O), (N-1888: H, 4-Br-Bn, S, O), (N-1889: H, 4-F-Bn, S, O), (N-1890: H, 3,4-diCl-Bn, S, O), (N-1891: H, 3,4-diBr-Bn, S, O), (N-1892: H, 3,4-diF-Bn, S, O), (N-1893: H, 4-Cl-Bz, S, O), (N-1894: H, 3,4-diCl-Bz, S, O), (N-1895: H, 4-Br-Bz, S, O), (N-1896: H, 3,4-diBr-Bz, S, O), (N-1897: H, 4-F-Bz, S, O), (N-1898: H, 3,4-diF-Bz, S, O), (N-1899: H, 4-$NO2$-Bn, S, O), (N-1900: H, 4-CN-Bn, S, O), (N-1901: Et, Pb, S, O), (N-1902: Et, 4-F-Ph, S, O), (N-1903: Et, 4-Br-Ph, S, O), (N-1904: Et, 4-Me-Ph, S, O), (N-1905: Et, 4-Ph-Ph, S, O), (N-1906: Et, 4-OMe-Ph, S, O), (N-1907: Et, 4-tBu-Ph, S, O), (N-1908: Et, 4-COOMe-Ph, S, O), (N-1909: Et, 4-Pen-Ph, S, O), (N-1910: Et, 4-$NO2$-Ph, S, O), (N-1911: Et, 5-Cl-thiophene-2-yl, S, O), (N-1912: Et, 3-Thienyl, S, O), (N-1913: Et, 2-Py, S, O), (N-1914: Et, 3-Py, S, O), (N-1915: Et, 4-Py, S, O), (N-1916: Et, 3,4-diF-Ph, S, O), (N-1917: Et, 5-Br-thiophene-2-yl, S, O), (N-1918: Et, 4-$CONH_2$-Ph, S, O), (N-1919: Et, 4-CON(Me)H-Ph, S, O), (N-1920: Et, 4-CON(Me)2-Ph, S, O), (N-1921: Et, 4-iPrOC(=O)-Ph, S, O), (N-1922: Et, 4-nBuOC(=O)-Ph, S, O), (N-1923: Et, 6-Me-pyridine-3-yl, S, O), (N-1924: Et, Quinoline-3-yl, S, O), (N-1925: Et, 4-$NH2$-Ph, S, O), (N-1926: Et, 4-N(Ac)H-Ph, S, O), (N-1927: Et, 4-OH-Ph, S, O), (N-1928: Et, 3,4-di(OH)2-Ph, S, O), (N-1929: Et, 3,4-di($NH_2$)-Ph, S, O), (N-1930: Et, 3:4-tN(Ac)H]2-Ph, S, O), (N-1931: Et, 4-SH-Ph, S, O), (N-1932: Et, 4-SMe-Ph, S, O), (N-1933: Et, 3,4-diBr-Ph, S, O), (N-1934: Et, 4-N(Me)H-Ph, S, O), (N-1935: Et, 4-N(Me)2-Ph, S, O), (N-1936: Et, 4-N(Mc)3+-Ph, S, O), (N-1937: Et, 4-Et-Ph, S, O), (N-1938: Et, 4-iPr-Ph, S, O), (N-1939: Et, 4-nPr-Ph, S, O), (N-1940: Et, 4-nBu-Ph, S, O), (N-1941: Et, 4-iBu-Ph, S, O), (N-1942: Et, 3,4-diMe-Ph, S, O), (N-1943: Et, 1,3-Benzodioxole-5-yl, S, O), (N-1944: Et, N-Me-pyridinium-4-yl, S, O), (N-1945: Et, N-Me-pyridinium-3-yl, S, O), (N-1946: Et, 5-Me-Pyridine-2-yl, S, O), (N-1947: Et, 2-Pyrazinyl, S, O), (N-1948: Et, 3-Pyrrolyl, S, O), (N-1949: Et, 1-Me-pyrrole-3-yl, S, O), (N-1960: Et, Pyridine N-oxide-4-yl, S, O), (N-1951: Et, Pyridine N-oxide-3-yl, S, O), (N-1953: Et, 6-OH-pyridine-3-yl, S8 0), (N-1953: Et, 6-SH-pyridine-3-yl, S, O), (N-1954: Et, 1-Ac-pyrrole-3-yl, S, O), (N-1955: Et, 4-$CF_3$-

Ph, S, O), (N-1956: Et, 4-CN-Ph, S, O), (N-1957: Et, 4-CHO-Ph, S, O), (N-1958: Et, 3-Cl-Ph, S, O), (N-1959: Et, 3-Br-Ph, S, O), (N-1960: Et, 3-F-Ph, S, O), (N-1961: Et, 3-I-Ph, S, O), (N-1962: Et, O 4-I-Ph, S, O), (N-1963: Et, 4-OCF$_3$-Ph, S, O), (N-1964: Et, 3,4-diI-Ph, S, O), (N-1965: Et, Indole-6-yl, S, O), (N-1966: Et, 1-Ac-indole-6-yl, S, O), (N-1967: Et, 1-Me-indole-6-yl, S, O), (N-1968: Et, 4-(1-Imidazolyl)-Ph, S, O), (N-1969: Et, 4-Morphorino-Ph, S, O), (N-1970: Et, 4-(1-Piperazinyl)-Ph, S, O), (N-1971: Et, 2:5-diMe-thiophene-3-yl, S, O), (N-1972: Et, 2-Furyl, S, O), (N-1973: Et, 5-Me-furan-2-yl, S, O), (N-1974: Et, 5-Me-furan-2-yl, S, O), (N-1975: Et, 2-Thiazolyl, S, O), (N-1976: Et, 1:4-Benzodioxin-6-yI, S, O), (N-1977: Et, Benzoibjfuran-2-yl, S, O), (N-1978: Et, 4-NH2CH2-Ph, S, O), (N-1979: Et, 4-N(Me)HCl-12-Ph, S, O), (N-1980: Et, 4-N(Me)2CH$_2$-Ph, S, O), (N-1981: Et, 6-Cl-pyridine-3-yl, S, O), (N-1982: Et, 5,6-diCl-pyridine-3-yl, S, O), (N-1983: Et, 5-Cl-pyridine-2-yl, S, O), (N-1984: Et, 4:5-diCl-pyridine-2-yl, S, O), (N-1985: Et, 4-CICH2-Bn, S, O), (N-1986: Et, Bn, S, O), (N-1987: Et, 4-Cl-Bn, S, O), (N-1988: Et, 4-Br-Bn, S, O), (N-1989: Et, 4-F-Bn, S, O), (N-1990: Et, 3,4-diCl-Bn, S, O), (N-1991: Et, 3,4-diBr-Bn, S, O), (N-1992: Et, 3,4-diF-Bn, S, O), (N-1993: Et, 4-Cl-Bz, S, O), (N-1994: Et, 3,4-diCl-Bz, S, O), (N-1995: Et, 4-Br-Bz, S, O), (N-1996: Et, 3,4-diBr-Bz, S, O), (N-1997: Et, 4-F-Bz, S, O), (N-1998: Et, 3,4-diF-Bz, S, O), (N-1999: Et, 4-NO2-Bn, S, O), (N-2000: Et, 4-CN-Bn, S, O), (N-2001: COOMe, Ph, S, O), (N-2002: COOMe, 4-F-Ph, S, O), (N-2003: COOMe, 4-Br-Ph, S, O), (N-2004: COOMe, 4-Me-Ph, S, O), (N-2005: COOMe, 4-Ph-Ph, S, O), (N-2006: COOMe, 4-OMe-Ph, S, O), (N-2007: COOMe, 4-tBu-Ph, S, O), (N-2008: COOMe, 4-COOMe-Ph, S, O), (N-2009: COOMe, 4-Pen-Ph, S, O), (N-2010: COOMe, 4-NO2-Ph, S, O), (N-2011: COOMe, 5-Cl-thiophene-2-yl, S, O), (N-2012: COOMe, 3-Thienyl, S, O), (N-2013: COOMe, 2-Py, S, O), (N-2014: COOMe, 3-Py, S, O), (N-2015: COOMe, 4-Py, S, O), (N-2016: COOMe, 3,4-diF-Ph, S, O), (N-2017: COOMe, 6-Br-tbiophene-2-yl, S, O), (N-2018: COOMe, 4-CONH2-Ph, S, O), (N-2019: COOMe, 4-CON(Me)H-Ph, S, O), (N-2020: COOMe, 4-CON(Me)2-Ph, S, O), (N-2021: COOMe, 4-iPrOC(=O)-Ph, S, O), (N-2022: COOMe, 4-nBuOC(=O)-Ph, S, O), (N-2023: COOMc, 6-Me-pyridine-3-yl, S, O), (N-2024: COOMe, Quinoline-3-yl, S, O), (N-2025: COOMe, 4-NH$_2$-Ph, S, O), (N-2026: COOMe, 4-N(Ac)H-Ph, S, O), (N-2027: COOMe, 4-OH-Ph, S, O), (N-2028: COOMe, 3,4-di(OH)$_2$-Ph, S, O), (N-2029: COOMe, 3,4-di(NH2)-Ph, S, O), (N-2030: COOMe, 3:4-[N(Ac)H]2-Ph, S, O), (N-2031: COOMe, 4-SH-Ph, S, O), (N-2032: COOMe, 4-SMe-Ph, S, O), (N-2033: COOMe, 3,4-diBr-Ph, S, O), (N-2034: COOMe, 4-N(Me)H-Ph, S, O), (N-2035: COOMe, 4-N(Me)2-Ph, S, O), (N-2036: COOMe, 4-N(Me)3+-Ph, S, O), (N-2037: COOMe, 4-Et-Ph, S, O), (N-2038: COOMe, 4-iPr-Ph, S, O), (N-2039: COOMe, 4-nPr-Ph, S, O), (N-2040: COOMe, 4-nBu-Ph, S, O), (N-2041: COOMe, 4-iBu-Ph, S, O), (N-2042: COOMe, 3,4-diMe-Ph, S, O), (N-2043: COOMe, 1,3-Benzodioxole-5-yl, S, O), (N-2044: COOMe, N-Me-pyridinium-4-yl, S, O), (N-2045: COOMe, N-Me-pyridinium-3-yl, S, O), (N-2046: COOMe, 5-Me-Pyridine-2-yl, S, O), (N-2047: COOMe, 2-Pyrazinyl, S, O), (N-2048: COOMe, 3-Pyrrolyl, S, O), (N-2049: COOMe, 1-Me-pyrrole-3-yl, S, O), (N-2050: COOMe, Pyridine N-oxide-4-yl, S, O), (N-2051: COOMe, Pyridine N-oxide-3-yl, S, O), (N-2052: COOMe, 6-OH-pyridine-3-yI, S, O), (N-2053: COOMe, 6-SH-pyridinc-3-yI, S, O), (N-2054: COOMe, l-Ac-pyrrole-3-yl, S, O), (N-2055: COOMe, 4-CF3-Ph, S, O), (N-2056: COOMe, 4-CN-Ph, S, O), (N-2057: COOMe, 4-CHO-Ph, S, O), (N-2058: COOMe, 3-Cl-Ph, S, O), (N-2059: COOMe, 3-Br-Ph, S, O), (N-2060: COOMe, 3-F-Ph, S, O), (N-2061: COOMe, 3-I-Ph, S, O), (N-2062: COOMe, 4-I-Ph, S, O), (N-2063: COOMe, 4-OCF3-Ph, S, O), (N-2064: COOMe, 3,4-diI-Ph, S, O), (N-2065: COOMe, Indole-6-yl, S, O), (N-2066: COOMe, 1-Ac-indole-6-yl, S, O), (N-2067: COOMe, 1-Me-indole-G-yl, S, O), (N-2068: COOMe, 4-(1-Imidazolyl)-Ph, S, O), (N-2069: COOMe, 4-Morphorino-Ph, S, O), (N-2070: COOMe, 4-(1-Piperazinyl)-Ph, S, O), (N-2071: COOMe, 2:5-diMe-thiophene-3-yl, S, O), (N-2072: COOMe, 2-Furyl, S, O), (N-2073: COOMe, 5-Me-furan-2-yl, S, O), (N-2074: COOMe, 5-Me-furan-2--yl , O), (N-2075: COOMe, 2-Thiazolyl, S, O), (N-2076: COOMe, 1:4-Benzodioxin-6-yl, S, O), (N-2077: COOMe, Benzo[b]furan-2-yl, S, O), (N-2078: COOMe, 4-NH$_2$CH$_2$-Ph, S, O), (N-2079: COOMe, 4-N(Me)HCH2-Ph, S, O), (N-2080: COOMe, 4-N(Me)2CH2-Ph, S, O), (N-2081: COOMe, 6-Cl-pyridine-3-yl, S, O), (N-2082: COOMe, 5,6-diCl-pyridine-3-yi, S, O), (N-2083: COOMe, 5-Cl-pyridine-2-yl, S, O), (N-2084: COOMe, 4:5-diCl-pyridine-2-yl, S, O), (N-2085: COOMe, 4-CICH2-Bn, S, O), (N-2086: COOMe, Bn, S, O), (N-2087: COOMe, 4-Cl-Bn, S, O), (N-2088: COOMe, 4-Br-Bn, S, O), (N-2089: COOMe, 4-F-Bn, S, O), (N-2090: COOMe, 3,4-diCl-Bn, S, O), (N-2091: COOMe, 3,4-diBr-Bn, S, O), (N-2092: COOMe, 3,4-diF-Bn, S, O), (N-2093: COOMe, 4-Cl-Bz, S, O), (N-2094: COOMe, 3,4-diCl-Bz, S, O), (N-2095: COOMe, 4-Br-Bz, S, O), (N-2096: COOMe, 3,4-diBr-Bz, S, O), (N-2097: COOMe, 4-F-Bz, S, O), (N-2098: COOMe, 3,4-diF-Bz, S, O), (N-2099: COOMe, 4-NO$_2$-Bn, S, O), (N-2100: COOMe, 4-CN-Bn, S, O), (N-2101: Ph, Me, O, O), (N-2102: 4-F-Ph, Me, O, O), (N-2103: 4-Br-Ph, Me, O, O), (N-2104: 4-Me-Ph, Me, O, O), (N-2105: 4-Ph-Ph, Me, O, O), (N-2106: 4-OMe-Ph, Me, O, O), (N-2107: 4-tBu-Ph, Me, O, O), (N-2108: 4-COOMe-Ph, Me, O, O), (N-2109: 4-Pen-Ph, Me, O, O), (N-2110: 4-NO2-Ph, Me, O, O), (N-2111: 5-Cl-thiophene-2-yl, Me, O, O), (N-2112: 3-Thienyl, Me, O, O), (N-2113: 2-Py, Me, O, O), (N-2114: 3-Py, Me, O, O), (N-2115: 4-Py, Me, O, O), (N-2116: 3,4-diF-Ph, Me, O, O), (N-2117: 5-Br-thiophene-2-yl, Mc, O, O), (N-2118: 4-CONH2-Ph, Me, O, O), (N-2119: 4-CON(Me)H-Ph, Me, O, O), (N-2120: 4-5 CON(Me)2-Ph, Me, O, O), (N-2121: 4-iPrOC(=O)-Ph, Me, O, O), (N-2122: 4-nBuOC(=O)-Ph, Me, O, O), (N-2123: 6-Me-pyridine-3-yl, Me, O, O), (N-2124: Quinoline-3-yl, Me, O, O), (N-2125: 4-NH2-Ph, Me, O, O), (N-2126: 4-N(Ac)H-Ph, Me, O, O), (N-2127: 4-OH-Ph, Me, O, O), (N-2128: 3,4-di(OH)$_2$-Ph, Me, O, O), (N-2129: 3,4-di(NH2)-Ph, Me, O, O), (N-2130: 3:4-[N(Ac)H]$_2$-Ph, Me, O, O), (N-2131: 4-SH-Ph, Me, O, O), (N-2132: 4-SMe-Ph, Me, O, O), (N-2133: 3,4-diBr-Ph, Me, O, O), (N-2134: 4-N(Me)H-Ph, Me, O, O), (N-2135: 4-N(Me)2-Ph, Me, O, O), (N-2136: 4-N(Me)3+-Ph, Me, O, O), (N-2137: 4-Et-Ph, Me, O, O), (N-2138: 4-iPr-Ph, Me, O, O), (N-2139: 4-nPr-Ph, Me, O, O), (N-2140: 4-nBu-Ph, Me, O, O), (N-2141: 4-iBu-Ph, Me, O, O), (N-2142: 3,4-diMe-Ph, Me, O, O), 15 (N-2143: 1,3-Benzodioxole-5-yl, Me, O, O), (N-2144: N-Me-pyridinium-4-yl, Me, O, O), (N-2145: N-Me-pyridinium-3-yl, Me, O, O), (N-2146: 5-Me-Pyridine-2-yl, Me, O, O), (N-2147: 2-Pyrazinyl, Me, O, O), (N-2148: 3-Pyrrolyl, Me, O, O), (N-2149: I-Me-pyrrole-3-yl, Me, O, O), (N-2150: Pyridine N-oxide-4-yl, Me, O, O), (N-2151: Pyridine N-oxide-3-yl, Me, O, O), (N-2152: 6-OH-pyridine-3-yl, 20. Me, O, O), (N-2153: 6-SH-pyridine-3-yl, Me, O, O), (N-2154: 1-Ac-pyrrole-3-yl, Me, O, O), (N-2155: 4-CF3-Ph, Me, O, O), (N-2156: 4-CN-Ph, Me, O, O), (N-2157: 4-CHO-Ph, Me, O, O), (N-2168: 3-Cl-Ph, Me, O, O), (N-2159: 3-Br-Ph, Me, O, O), (N-2160: 3-F-Ph, Me, O, O), (N-2161: 3-1-Ph, Me, 9, 0), (N-2162: 4-I-Ph, Me, O, O), (N-2163: 4-OCF3-Ph, Me, O, O), (N-2164: 3,4-diI-Ph, Mc, O, O), (N-25 2165: Indole-6-yi, Me, O, O), (N-2166: 1-Ac-indole-6-yl, Me, O, O), (N-2167: 1-Me-indole-6-yl, Me, O, O), (N-2168: 4-(1-Imidazolyl)-Ph, Me, O, O), (N-2169: 4-Morphorino-Ph, Me, O, O), (N-2170: 4-(1-Piperazinyl)-Ph, Me, O, O), (N-2171: 2:5-diMe-thiophene-3-yl, Me, O, O), (N-2172: 2-Furyl, Me, O, O), (N-2173: 5-Me-furan-2-yl, Me, O, O), (N-2174: 5-Me-furan-2-yl, Me, O, O), (N-2175: 2-Thiazolyl, Me, O, O), (N-2176: 1:4-Benzodioxin-6-yl, Me, O, O), (N-2177: Benzo[bjfuran-2-yl, Me, O, O), (N-2178: 4-NH2CH2-Ph, Me, O, O), (N-2179: 4-N(Me)HCH2-Ph, Me, O, O), (N-2180: 4-N(Me)2CH2-Ph, Me, O, O), (N-2181: 6-Cl-pyridine-3-yl, Me, O, O), (N-2182: 5,6-diCl-pyridine-3-yl, Me, O, O), (N-2183: 6-Cl-pyridine-2-yl, Me, O, O), (N-2184: 4:5-diCl-pyridine-2-yl, Me, O, O), (N-2185: 4-ClCH2-Bn, Me, O, O), (N-2186: Bn, Me, O, O), (N-2187: 4-Cl-Bn, Me, O, O), (N-2188: 4-Br-Bn, Me, O, O), (N-2189: 4-F-Bn, Me, O, O), (N-2190: 3,4-diCl-Bn, Me, O, O), (N-2191: 3,4-diBr-Bn, Me, O, O), (N-2192: 3,4-diF-Bn, Me, O, O), (N-2193: 4-Cl-Bz, Me, O, O), (N-2194: 3,4-diCl-Bz, Me, O, O), (N-2195: 4-Br-Bz, Me, O, O), (N-2196: 3,4-diBr-Bz, Me, O, O), (N-2197: 4-F-Bz, Me, O, O), (N-2198: 3,4-diF-Bz, Me, O, O), (N-2199: 4-NO2-Bn, Me, O, O), (N-2200: 4-CN-Bn, Me, O, O), (N-2201: Ph, Et, O, O), (N-2202: 4-F-Ph, Et, O, O), (N-2203: 4-Br-Ph, Et, O, O), (N-2204: 4-Me-Ph, Et, O, O), (N-2205: 4-Ph-Ph, Et, O, O), (N-2206: 4-OMe-Ph, Et, O, O), (N-2207: 4-tBu-Ph, Et, O, O), (N-2208: 4-COOMe-Ph, Et, O, O), (N-2209: 4-Pen-Ph, Et, O, O), (N-2210: 4-NO2-Ph, Et, O, O), (N-2211: 5-Cl-thiopbene-2-yl, Et, O, O), (N-2212: 3-Thienyl, Et, O, O), (N-2213: 2-Py, Et, O, O), (N-2214: 3-Py, Et, O, O), (N-2215: 4-Py, Et, O, O), (N-2216: 3,4-diF-Ph, Et, O, O), (N-2217: 5-Br-thiophene-2-yl, Et, O, O), (N-2218: 4-CONH2-Ph, Et, O, O), (N-2219: 4-CON(Me)H-Ph, Et, O, O), (N-2220: 4-CON(Me)2-Ph, Et, O, O), (N-2221: 4-iPrOC(=O)-Pb, Et, O, O), (N-2222: 4-nBuOC(=O)-Ph, Et, O, O), (N-2223: 6-Me-pyridine-3-yl, Et, O, O), (N-2224: Quinoline-3-yl, Et, O, O), (N-2225: 4-NH2-Ph, Et, O, O), (N-2226: 4-N(Ac)H-Ph, Et, O, O), (N-2227: 4-OH-Ph, Et, O, O), (N-2228: 3,4-di(OH)2-Ph, Et, O, O), (N-2229: 3,4-di(NH-12)-Ph, Et, O, O), (N-2230: 3:4-[N(Ac)H]2-Ph, Et, O, O), (N-2231: 4-SH-Ph, Et, O, O), (N-2232: 4-SMe-Ph, Et, O, O), (N-2233: 3,4-diBr-Ph, Et, O, O), (N-2234: 4-N(Me)H-Ph, Et, O, O), (N-2235: 4-N(Me)2-Ph, Et, O, O), (N-2236: 4-N(Me)3+-Ph, Et, O, O), (N-2237: 4-Et-Ph, Et, O, O), (N-2238: 4-iPr-Ph, Et, O, O), (N-2239: 4-nPr-Ph, Et, O, O), (N-2240: 4-nBu-Ph, Et, O, O), (N-2241: 4-iBu-Ph, Et, O, O), (N-2242: 3,4-diMe-Ph, Et, O, O), (N-2243: 1,3-Benzodioxole-5-yl, Et, O, O), (N-2244: N-Me-pyridinium-4-yl, Et, O, O), (N-2245: N-Me-pyridinium-3-yl, Et, O, O), (N-2246: 5-Me-Pyridine-2-yl, Et, O, O), (N-2247: 2-Pyrazinyl, Et, O, O), (N-2248: 3-Pyrrolyl, Et, O, O), (N-2249: 1-Me-pyrrole-3-yl, Et, O, O), (N-2250: Pyridine N-oxide-4-yl, Et, O, O), (N-2251: Pyridine N-oxide-3-yl, Et, O, O), (N-2262: 6-OH-pyridine-3-yl, Et, O, O), (N-2253: 6-SH-pyridine-3-yl, Et, O, O), (N-2254: 1-Ac-pyrrole-3-yl, Et, O, O), (N-2256: 4-CF3-Ph, Et, O, O), (N-2256: 4-CN-Ph, Et, O, O), (N-2257: 4-CHO-Ph, Et, O, O), (N-2258: 3-Cl-Ph, Et, O, O), (N-2259: 3-Br-Ph, Et, O, O), (N-2260: 3-F-Ph, Et, O, O), (N-2261: 3-I-Ph, Et, O, O), (N-2262: 4-I-Ph, Et, O, O), (N-2263: 4-OCF3-Ph, Et, O, O), (N-2264: 3,4-diI-Ph, Et, O, O), (N-2265: Indole-6-yl, Et, O, O), (N-2266: 1-Ac-indole-6-yl, Et, O, O), (N-2267: 1-Me-indole-6-yl, Et, O O), (N-2268: 4-(l-Imidazolyl)-Ph, Et, O, O), (N-2269: 4-Morphorino-Ph, Et, O, O), (N-2270: 4-(1-Piperazinyl)-Ph, Et, O, O), (N-2271: 2:5-diMe-thiophene-3-yl, Et, O, O), (N-2272: 2-Furyl, Et, O, O), (N-2273: 5-Me-furan-2-yl, Et, O, O), (N-2274: 5-Me-furan-2-yl, Et, O, O), (N-2275: 2-Thiazolyl, Et, O, O), (N-2276: 1:4-Benzodioxin-6-yl, Et, O, O), (N-2277: Benzo[b]furan-2-yl, Et, O, O), (N-2278: 4-NH2CH2-Ph, Et, O, O), (N-2279: 4-N(Me)HCH2-Ph, Et, O, O), (N-2280: 4-N(Me)2CH2-Ph, Et, O, O), (N-2281: 6-Cl-pyridine-3-yl, Et, O, O), (N-2282: 5,6-diCl-pyridine-3-yl, Et, O, O), (N-2283: 5-Cl-pyridine-2-yl, Et, O, O), (N-2284: 4:5-diCl-pyridine-2-yl, Et, O, O), (N-2285: 4-ClCH2-Bn, Et; O, O), (N-2286: Bn, Et, O, O), (N-2287: 4-Cl-Bn, Et, O, O), (N-2288: 4-Br-Bn, Et, O, O), (N-2289: 4-F-Bn, Et, O, O), (N-2290: 3,4-diCl-Bn, Et, O, O), (N-2291: 3,4-diBr-Bn, Et, O, O), (N-2292: 3,4-diF-Bn, Et, O, O), (N-2293: 4-Cl-Bz, Et, O, O), (N-2294: 3,4-diCl-Bz, Et, O, O), (N-2295: 4-Br-Bz, Et, O, O), (N-2296: 3,4-diBr-Bz, Et, O, O), (N-2297: 4-F-Bz, Et, O, O), (N-2298: 3,4-diF-Bz, Et, O, O), (N-2299: 4-NO2-Bn, Et, O, O), (N-2300: 4-CN-Bn, Et, O, O), (N-2301: Ph, COOMe, O, O), (N-2302: 4-F-Ph, COOMe, O, O), (N-2303: 4-Br-Ph, COOMe, O, O), (N-2304: 4-Me-Ph, COOMe, O, O), (N-2305: 4-Ph-Ph, COOMe, O, O), (N-2306: 4-OMe-Ph, COOMe, O, O), (N-2307: 4-tBu-Ph, COOMe, O, O), (N-2308: 4-COOMe-Ph, COOMe, O, O), (N-2309: 4-Pen-Ph, COOMe, O, O), (N-2310: 4-NO2-Ph, COOMe, O, O), (N-2311: 5-Cl-tbiophene-2-yl, COOMe, O, O), (N-2312: 3-Thienyl, COOMe, O, O), (N-2313: 2-Py, COOMe, O, O), (N-2314: 3-Py, COOMe, O, O), (N-2315: 4-Py, COOMe, O, O), (N-2316: 3,4-diF-Ph, COOMe, O, O), (N-2317: 5-Br-thiophene-2-yl, COOMe, O, O), (N-2318: 4-CONH2-Ph, COOMe, O, O), (N-2319: 4-CON(Me)H-Ph, COOMe, O, O), (N-2320: 4-CON(Me)2-Ph, COOMe, O, O), (N-2321: 4-iPrOC(=O)-Ph, COOMe, O, O), (N-2322: 4-nBuOC(=O)-Ph, COOMe, O, O), (N-2323: 6-Me-pyridine-3-yI, COOMe, O, O), (N-2324: Quinoline-3-yl, COOMe, O, O), (N-2325: 4-NH2-Ph, COOMe, O, O), (N-2326: 4-N(Ac)H-Ph, COOMe, O, O), (N-2327: 4-OH-Ph, COOMe, O, O), (N-2328: 3,4-di(OH)2-Ph, COOMe, O, O), (N-2329: 3,4-di(NH2)-Ph, COOMe, O, O), (N-2330: 3:4-[N(Ac)H]2-Ph, COOMe, O, O), (N-2331: 4-SH-Ph, COOMe, O, O), (N-2332: 4-SMe-Ph, COOMe, O, O), (N-2333: 3,4-diBr-Ph, COOMe, O, O), (N-2334: 4-N(Me)H-Ph, COOMe, O, O), (N-2335: 4-N(Me)2-Ph, COOMe, O, O), (N-2336: 4-N(Me)3+-Ph, COOMe, O, O), (N-2337: 4-Et-Ph, COOMe, O, O), (N-2338: 4-iPr-Ph, COOMe, O, O), (N-2339: 4-nPr-Ph, COOMe, O, O), (N-2340: 4-nBu-Ph, COOMe, O, O), (N-2341: 4-iBu-Ph, COOMe, O, O), (N-2342: 3,4-diMe-Ph, COOMe, O, O), (N-2343: 1,3-Benzodioxole-5-yl, COOMe, O, O), (N-2344: N-Me-pyridinium-4-yl, COOMe, O, O), (N-2345: N-Me-pyridinium-3-yl, COOMe, O, O), (N-2346: 5-Me-Pyridine-2-yl, COOMe, O, O), (N-2347: 2-Pyrazinyl, COOMe, O, O), (N-2348: 3-Pyrrolyl, COOMe, O, O), (N-2349: 1-Me-pyrrole-3-yl, COOMe, O, O), (N-2350: Pyridine N-oxide-4-yl, COOMe, O, O), (N-2351: Pyridine N-oxide-3-yl, COOMe, O, O), (N-2353: 6-OH-pyridine-3-yl, COOMe, O, O), (N-2353: 6-SH-pyridine-3-yl, COOMe, O, O), (N-2354: 1-Ac-pyrrole-3-yl, COOMe, O, O), (N-2355: 4-CF3-Ph, COOMe, O, O), (N-2356: 4-CN-Ph, COOMe, O, O), (N-2357: 4-CHO-Ph, COOMe, O, O), (N-2358: 3-Cl-Ph, COOMe, O, O), (N-2359: 3-Br-Ph, COOMe, O, O), (N-2360: 3-F-Ph, COOMe, O, O), (N-2361: 3-1-Ph, COOMe, O, O), (N-2362: 4-I-Ph, COOMe, O, O), (N-2363: 4-OCF$_3$-Ph, COOMe, O, O), (N-2364: 3,4-diI-Ph, COOMe, O, O), (N-2365: Indole-6-yl, COOMe, O, O), (N-2366: 1-Ac-indole-6-yl, COOMe, O, O), (N-2367: I-Me-indole-6-yl, COOMe, O, O), (N-2368: 4-(I-Imidazolyl)-Ph, COOMe, O, O), (N-2369: 4-Morphorino-Ph, COOMe, O, O), (N-2370: 4-(1-Piperazinyl)-Ph, COOMe, O, O), (N-2371: 2:5-diMe-thiophene-3-yl, COOMe, O, O), (N-2372: 2-Furyl, COOMe, O, O), (N-2373: 5-Me-furan-2-yl, COOMe, O, O), (N-2374: 5-Me-furan-2-yl, COOMe, O, O), (N-2375: 2-Thiazolyl, COOMe, O, O), (N-2376: 1:4-Benzodioxin-6-yl, COOMe, O, O), (N-2377: Benzo[b]furan-2-yl, COOMe, O, O), (N-2378: 4-NH2CH2-Ph, COOMe, O, O), (N-2379: 4-N(Me)HCH2-Ph, COOMe, O, O), (N-2380: 4-N(Me)2CH2-Ph, COOMe, O, O), (N-2381: 6-Cl-pyridine-3-yl, COOMe, O, O), (N-2382: 5,6-diCl-pyridine-3-yl, COOMe, O, O), (N-2383: 5-Cl-pyridine-2-yl, COOMe, O, O), (N-2384: 4:5-diCl-pyridine-2-yl, COOMe, O, O), (N-2385: 4-ClCH2-Bn, COOMe, O, O), (N-2386: Bn, COOMe, O, O), (N-2387: 4-Cl-Bn, COOMe, O, O), (N-2388: 4-Br-Bn, COOMe, O, O), (N-2389: 4-F-Bn, COOMe, O, O), (N-2390: 3,4-diCl-Bn, COOMe, O, O), (N-2391: 3,4-diBr-Bn, COOMe, O, O), (N-2392: 3,4-diF-Bn, COOMe, O, O), (N-2393: 4-Cl-Bz, COOMe, O, O), (N-2394: 3,4-diCl-Bz, COOMe, O, O), (N-2395: 4-Br-Bz, COOMe, O, O), (N-2396: 3,4-diBr-Bz, COOMe, O, O), (N-2397: 4-F-Bz, COOMe, O, O), (N-2398: 3,4-diF-Bz, COOMe, O, O), (N-2399: 4-NO2-Bn, COOMe, O, O), (N-2400: 4-CN-Bn, COOMe, O, O), (N-2401: H, Ph, O, O), (N-2402: H, 4-F-Ph, O, O), (N-2403: H, 4-Br-Ph, O, O), (N-2404: H, 4-Me-Pb, O, O), (N-2405: H, 4-Ph-Ph, O, O), (N-2406: H, 4-OMe-Ph, O, O), (N-2407: H, 4-tBu-Ph, O, O), (N-2408: H, 4-COOMe-Ph, O, O), (N-2409: H, 4-Pen-Ph, O, O), (N-2410: H, 4-NO$_2$-Ph, O, O), (N-2411: H, 5-Cl-thiophene-2-yl, O, O), (N-2412: H, 3-Thienyl, O, O), (N-2413: H, 2-Py, O, O), (N-2414: H, 3-Py, O, O), (N-2415: H, 4-Py, O, O), (N-2416: H, 3,4-diF-Ph, O, O), (N-2417: H, 5-Br-thiophene-2-yl, O, O), (N-2418: H, 4-CONH2-Ph, O, O), (N-2419: H, 4-CON(Me)H-Ph, O, O), (N-2420: H, 4-CON(Me)2-Ph, O, O), (N-2421: H, 4-iPrOC(=O)-Ph, O, O), (N-2422: H, 4-nBuOC(=O)-Ph, O, O), (N-2423: H, 6-Me-pyridine-3-yl, O, O), (N-2424: H, Quinoline-3-yl, O, O), (N-2425: H, 4-NH$_2$-Ph, O, O), (N-2426: H, 4-N(Ac)H-Ph, O, O), (N-2427: H, 4-OH-Ph, O, O), (N-2428: H, 3,4-di(OH)$_2$-Ph, O, O), (N-2429: H, 3,4-di(NH2)-Ph, O, O), (N-2430: H, 3:4-[N(Ac)H]2-Ph, O, O), (N-2431: H, 4-SH-Ph, O, O), (N-2432: H, 4-SMe-Ph, O, O), (N-2433: H, 3,4-diBr-Ph, O, O), (N-2434: H, 4-N(Me)H-Ph, O, O), (N-2435: H, 4-N(Me)2-Ph, O, O), (N-2436: H, 4-N(Me)3+-Ph, O, O), (N-2437: H, 4-Et-Ph, O, O), (N-2438: H, 4-iPr-Ph, O, O), ! (N-2439: H, 4-nPr-Ph, O, O), (N-2440: H, 4-nBu-Ph, O, O), (N-2441: H, 4-iBu-Ph, O, O), (N-2442: H, 3,4-diMe-Ph, O, O), (N-2443: H, 1,3-Benzodioxole-5-yl, O, O), (N-2444: H, N-Me-pyridinium-4-yl, O, O), (N-2445: H, N-Me-pyridinium-3-yl, O, O), (N-2446: H, 5-Mc-Pyridine-2-yl, O, O), (N-2447: H, 2-Pyrazinyl, O, O), (N-2448: H, 3-Pyrrolyl, O, O), (N-2449: H, 1-Me-pyrrole-3-yl, O, O), (N-2450: H, Pyridine N-oxide-4-yl, O, O), (N-2451: H, Pyridine N-oxide-3-yl, O, O), (N-2453: H, 6-OH-pyridine-3-yl, O, O), (N-2453: H, 6-SH-pyridine-3-yl, O, O), (N-2454: H, 1-Ac-pyrrole-3-yl, O, O), (N-2455: H, 4-CF$_3$-Ph, O, O), (N-2456: H, 4-CN-Ph, O, O), (N-2457: H, 4-CHO-Ph, O, O), (N-2458: H, 3-Cl-Ph, O, O), (N-2459: H, 3-Br-Ph, O, O), (N-2460: H, 3-F-Ph, O, -O), (N-2461: H, 3-1-Ph, O, O), (N-2462: H, 4-I-Ph, O, O), (N-2463: H, 4-OCF3-Ph, O, O), (N-2464: H, 3,4-diI-Ph, O, O), (N-2465: H, Indole-6-yl, O, O), (N-2466: 11, 1-11.5 Ac-indole-6-yl, O, O), (N-2467: H, 1-Me-indole-6-yl, O, O), (N-2468: H, 4-(1-Imidazolyl)-Ph, O, O), (N-2469: H, 4-Morphorino-Ph, O, O), (N-2470: H, 4-(1-Piperazinyl)-Ph, O, O), (N-2471: H, 2:5-diMe-thiophene-3-yl, O, O), (N-2472: H, 2-Furyl, O, O), (N-2473: H, 5-Me-furan-2-yl, O, O), (N-2474: H, 5-Me-furan-2-yl, O, O), (N-2475: H, 2-Thiazolyl, O, O), (N-2476: H, 1:4-Benzodioxin-6-yl, O, O), (N-2477: H, Benzo[b]furan-2-yl, O, O), (N-2478: H, 4-NH2CH2-Ph, O, O), (N-2479: H, 4-N(Me)HCH2-Ph, O, O), (N-2480: H, 4-N(MC)2CH2-Ph, O, O), (N-2481: H, 6-Cl-pyridine-3-yl, O, O), (N-2482: H, 5,6-diCl-pyridine-3-yl, O, O), (N-2483: H, 5-Cl-pyridine-2-yl, O, O), (N-2484: H, 4:5-diCl-pyridine-2-yl, O, O), (N-2485: H, 4-ClCH2-Bn, O, O), (N-2486: H, Bn, O, O), (N-2487: H, 4-Cl-Bn, O, O), (N-2488: H, 4-Br-Bn, O, O), (N-2489: H, 4-F-Bn, O, O), (N-2490: H, 3,4-diC]-Bn, O, O), (N-2491: H, 3,4-diBr-Bn, O, O), (N-2492: H, 3,4-diF-Bn, O, O), (N-2493: H, 4-Cl-Bz, O, O), (N-2494: H, 3,4-diCl-Bz, O, O), (N-2495: H, 4-Br-Bz, O, O), (N-2496: H, 3,4-diBr-Bz, O, O), (N-2497: H, 4-F-Bz, O, O), (N-2498: H, 3,4-diF-Bz, O, O), (N-2499: H, 4-NO$_2$-Bn, O, O), (N-2500: H, 4-CN-Bn, O, O), (N-2501: Me, Ph, O, O), (N-2502: Me, 4-F-Ph, O, O), (N-2503: Me, 4-Br-Ph, O, O), (N-2504: Me, 4-Me-Ph, O, O), (N-2505: Me, 4-Ph-Ph, O, O), (N-2506: Me, 4-OMe-Ph, O, O), (N-2507: Me, 4-tBu-Ph, O, O), (N-2508: Me, 4-COOMe-Ph, O, O), (N-2509: Me, 4-Pen-Ph, O, O), (N-2510: Me, 4-NO2-Ph, O, O), (N-2511: Me, 5-CI-tbiophene-2-yl, O, O), (N-2512: Me, 3-Thienyl, O, O), (N-2513: Me, 2-Py, O, O), (N-2514: Me, 3-Py, O, O), (N-2616: Me, 4-Py, O, O), (N-2516: Me, 3,4-diF-Ph, O, O), (N-2517: Me, 5-Br-thiophene-2-yl, O, O), (N-2518: Me, 4-CONH2-Ph, O, O), (N-2519: Me, 4-CON(Me)H-Ph, O, O), (N-2520: Me, 4-CON(Me)2-Ph, O, O), (N-2521: Me, 4-iPrOC(=O)-Ph, O, O), (N-2522: Me, 4-nBuOC(=O)-Ph, O, O), (N-2523: Me, 6-Me-pyridine-3-yl, O, O), (N-2524: Me, Quinoline-3-yl, O, O), (N-2525: Me, 4-NH$_2$-Ph, O, O), (N-2526: Me, 4-N(Ac)H-Ph, O, O), (N-2527: Me, 4-OH-Ph, O, O), (N-2528: Me, 3,4-di(OH)2-Ph, O, O), (N-2529: Me, 3,4-di(NH$_2$)-Ph, O, O), (N-2530: Me, 3:4-[N(Ac)H]$_2$-Ph, O, O), (N-2531: Me, 4-SH-Ph, O, O), (N-2532: Me, 4-SMe-Ph, O, O), (N-2533: Me, 3,4-diBr-Ph, O, O), (N-2534: Me, 4-N(Me)H-Ph, O, O), (N-2535: Me, 4-N(Me)2-Ph, O, O), (N-2536: Me, 4-N(Me)3+-Ph, O, O), (N-2537: Me, 4-Et-Ph, O, O), (N-2538: Me, 4-iPr-Ph, O, O), (N-2539: Me, 4-nPr-Ph, O, O), (N-2540: Me, 4-nBu-Ph, O, O), (N-2541: Me, 4-iBu-Ph, O, O), (N-2542: Me, 3,1-diMe-Ph, O, O), (N-2643: Me, 1,3-Benzodioxole-5-yl, O, O), (N-2544: Me, N-Me-pyridinium-4-yl, O, O), (N-2545: Me, N-Me-pyridinium-3-yl, O, O), (N-2546: Me, 5-Me-Pyridine-2-yl, O, O), (N-2547: Me, 2-Pyrazinyl, O, O), (N-2548: Me, 3-Pyrrolyl, O, O), (N-2549: Me, 1-Me-pyrrole-3-yl, O, O), (N-2550: Me, Pyridine N-oxide-4-yl, O, O), (N-2551: Me, Pyridine N-oxide-3-yl, O, O), (N-2553: Me, 6-OH-pyridine-3-yl, O, O), (N-2553: Me, 6-SH-pyridine-3-yl, O, O), (N-2554: Me, 1-Ac-pyrrole-3-yl, O, O), (N-2555: Me, 4-CF$_3$-Ph, O, O), (N-2556: Me, 4-CN-Ph, O, O), (N-2557: Me, 4-CHO-Ph, O, O), (N-2558: Me, 3-Cl-Ph, O, O), (N-2559: Mc, 3-Br-Ph, O, O), (N-2660: Mc, 3-F-Ph, O, O), (N-2561: Me, 3-I-Ph, O, O), (N-2562: Me, 4-I-Ph, O, O), (N-2563: Me, 4-OCF3-Ph, O, O), (N-2564: Me, 3,4-diI-Ph, O, O), (N-2565: Me, Indole-6-yl, O, O), (N-2566: Me, 1-Ac-indole-6-yl, O, O), (N-2567: Me, 1-Me-indole-6-yl, O, O), (N-2568: Me, 4-(1-Imidazolyl)-Ph, O, O), (N-2569: Me, 4-Morphorino-Ph, O, O), (N-2570: Me, 4-(1-Piperazinyl)-Ph, O, O), (N-2571: Me, 2:5-diMe-thiophene-3-yl, O, O), (N-2572: Me, 2-Furyl, O, O), (N-2573: Me, 5-Me-furan-2-yl, O, O), (N-2574: Me, 5-Me-furan-2-yl, O, O), (N-2575: Me, 2-Thiazolyl, O, O), (N-2576: Me, 1:4-Benzodioxin-6-yl, O, O), (N-2577: Me, Benzo[b]furan-2-yl, O, O), (N-2578: Me, 4-NH2CH2-Ph, O, O), (N-2579: Me, 4-N(Me)HCH2-Ph, O, O), (N-2580: Me, 4-N(Me)2CH2-Ph, O, O), (N-2581: Me, 6-Cl-pyridine-3-yl, O, O), (N-2582: Me, 5,6-diCl-pyridine-3-yl, O, O), (N-2583: Me, 5-Cl-pyridine-2-yl, O, O), (N-2584: Me, 4:5-diCl-pyridine-2-yl, O, O), (N-2585: Me, 4-ClCH2-Bn, O, O), (N-2586: Me, Bn, O, O), (N-2587: Me, 4-Cl-Bn, O, O), (N-2588: Me, 4-Br-Bn, O, O), (N-2689: Me, 4-F-Bn, O, O), (N-2590: Me, 3,4-diCl-Bn, O, O), (N-2591: Me, 3,4-diBr-Bn, O, O), (N-2592: Me, 3,4-diF-Bn, O, O), (N-2593: Me, 4-Cl-Bz, O, O), (N-2594: Me, 3,4-diCl-Bz, O, O), (N-2595: Me, 4-Br-Bz, O, O), (N-2596: Me, 3,4-diBr-Bz, O, O), (N-2597: Me, 4-F-Bz, O, O), (N-2598: Me, 3,4-diF-Bz, O, O), (N-2599: Me, 4-NO2-Bn, O, O), (N-2600: Me, 4-CN-Bn, O, O), (N-2601: Et, Ph, O, O), (N-2602: Et, 4-F-Ph, O, O), (N-2603: Et, 4-Br-Ph, O, O), (N-2604: Et, 4-Me-Ph, O, O), (N-2605: Et, 4-Ph-Ph, O, O), (N-2606: Et, 4-OMe-Ph, O, O), (N-2607: Et, 4-tBu-Ph, O, O), (N-2608: Et, 47 COOMe-Ph, O, O), (N-2609: Et, 4-Pen-Ph, O, O), (N-2610: Et, 4-NO2-Ph, O, O), (N-2611: Et, 5-Cl-thiophene-2-yl, O, O), (N-2612: Et, 3-Thienyl, O, O), (N-2613: Et, 2-Py, O, O), (N-2614: Et, 3-Py, O, O), (N-2615: Et, 4-Py, O, O), (N-2616: Et, 3,4-(IiF-Ph, O, O), (N-2617: Et, 5-Br-thiophene-2-yl, O, O), (N-2618: Et, 4-CONH$_2$-Ph, O, O), (N-2619: Et, 4-CON(Me)H-Ph, O, O), (N-2620: Et, 4-CON(Me)2-Ph, O, O), (N-2621: Et, 4-iPrOC(=O)-Ph, O, O), (N-2622: Et, 4-nBuOC(=O)-Ph. O, O), (N-2623: Et, 6-Me-pyridine-3-yl, O, O), (N-2624: Et, Quinoline-3-yl, O, O), (N-2625: Et, 4-NH$_2$-Ph, O, O), (N-2626: Et, 4-N(Ac)H-Ph, O, O), (N-2627: Et, 4-OH-Ph, O, O), (N-2628: Et, 3,4-di(OH)$_2$-Ph, O, O), (N-2629: Et, 3,4-di(NH$_2$)-Ph, O, O), (N-2630: Et, 3:4-[N(Ac)H]$_2$-Ph, O, O), (N-2631: Et, 4-SH-Ph, O, O), (N-2632: Et, 4-SMe-Ph, O, O), (N-2633: Et, 3,4-diBr-Ph, O, O), (N-2634: Et, 4-N(Me)H-Ph, O, O), (N-2635: Et, 4-N(Me)2-Ph, O, O), (N-2636: Et, 4-N(Me)3+-Ph, O, O), (N-2637: Et, 4-Et-Ph, O, O), (N-2638: Et, 4-iPr-Ph, O, O), (N-2639: Et, 4-nPr-Ph, O, O), (N-2640: Et, 4-nBu-Ph, O, O), (N-2641: Et, 4-iBu-Ph, O, O), (N-2642: Et, 3,4-diMe-Ph, O, O), (N-2643: Et, 1,3-Benzodioxole-5-yl, O, O), (N-2644: Et, N-Me-pyridinium-4-yl, O, O), (N-2645: Et, N-Me-pyridinium-3-yl, O, O), (N-2646: Et, 5-Me-Pyridine-2-yl, O, O), (N-2647: Et, 2-Pyrazinyl, O, O), (N-2648: Et, 3-Pyrrolyl, O, O), (N-2649: Et, 1-Me-pyrrole-3-yl, 0, 0), (N-2650: Et, Pyridine N-oxide-4-yl, O, O), (N-2651: Et, Pyridine N-oxide-3-yl, O, O), (N-2653: Et, 6-OH-pyridine-3-yl, O, O), (N-2653: Et, 6-SH-pyridine-3-yl, O, O), (N-2654: Et, 1-Ac-pyrrole-3-yl, O, O), (N-2655: Et, 4-CF.-Ph, O, O), (N-2656: Et, 4-CN-Ph, O, O), (N-2657: Et, 4-CHO-Ph, O, O), (N-2658: Et, 3-Cl-Ph, O, O), (N-2659: Et, 3-Br-Ph, O, O), (N-2660: Et, 3-F-Ph, O, O), (N-2661: Et, 3-I-Ph, O, O), (N-2662: Et, 4-I-Ph, O, O), (N-2663: Et, 4-OCF3-Ph, O, O), (N-2664: Et, 3,4-diT-Ph, O, O), (N-2665: Et, Indole-6-yl, O, O), (N-2666: Et, 1-Ac-indole-6-yl, O, O), (N-2667: Et, 1-Me-indole-6-yl, O, O), (N-2668: Et, 4-(1-Imidazolyl)-Ph, O, O), (N-2669: Et, 4-Morphorino-Ph, O, O), (N-2670: Et, 4-(1-Piperazinyl)-Ph, O, O), (N-2671: Et, 2:5-diMe-thiophene-3-yl, O, O), (N-2672: Et, 2-Furyl, O, O), (N-2673: Et, 5-Me-furan-2-yl, O, O), (N-2674: Et, 5-Me-furan-2-yl, O, O), (N-2675: Et, 2-Thiazolyl, O, O), (N-2676: Et, 1:4-Benzodioxin-6-yl, O, O), (N-2677: Et, Benzo[b]furan-2-yl, O, O), (N-2678: Et, 4-NI-I$_2$CH2-Ph, O, O), (N-2679: Et, 4-N(Me)HCH2-Ph, O, O), (N-2680: Et, 4-N(Me)2CH2-Ph, O, O), (N-2681: Et, 6-Cl-pyridine-3-yl, O, O), (N-2682: Et, 5,6-diCl-pyridine-3-yl, O, O), (N-2683: Et, 5-Cl-pyridine-2-yl, O, O), (N-2684: Et, 4:5-diCl-pyridine-2-yl, O, O), (N-2685: Et, 4-ClCH2-Bn, O, O), (N-2686: Et, Bn, O, O), (N-2687: Et, 4-Cl-Bn, O, O), (N-2688: Et, 4-Br-Bn, O, O), (N-2689: Et, 4-F-Bn, O, O), (N-2690: Et, 3,4-diCl-Bn, O, O), (N-2691: Et, 3,4-diBr-Bn, O, O), (N-2692: Et, 3,4-diF-Bn, O, O), (N-2693: Et, 4-Cl-Bz, O, O), (N-2694: Et, 3,4-diCl-Bz, O, O), (N-2695: Et, 4-Br-Bz, O, O), (N-2696: Et, 3,4-diBr-Bz, O, O), (N-2697: Et, 4-F-Bz, O, O), (N-2698: Et, 3,4-diF-Bz, O, O), (N-2699: Et, 4-NO2-Bn, O, O), (N-2700: Et, 4-CN-Bn, O, O), (N-2701: COOMe, Ph, O, O), (N-2702: COOMe, 4-F-Ph, O, O), (N-2703: COOMe, 4-Br-Ph, O, O), (N-2704: COOMe, 4-Me-Ph, O, O), (N-2705: COOMe, 4-Ph-Ph, O, O), (N-2706: COOMe, 4-OMe-Ph, O, O), (N-2707: COOMe, 4-tBu-Ph, O, O), (N-2708: COOMe, 4-COOMe-Ph, O, O), (N-2709: COOMe, 4-Pen-Ph, O, O), (N-2710: COOMe, 4-NO2-Ph, O, O), (N-2711: COOMe, 5-Cl-thiophene-2-yl, O, O), (N-2712: COOMe, 3-Thienyl, O, O), (N-2713: COOMe, 2-Py, O, O), (N-2714: COOMe, 3-Py, O, O), (N-2715: COOMe, 4-Py, O, O), (N-2716: COOMe, 3,4-diF-Ph, O, O), (N-2717: COOMe, 5-Br-thiophene-2-yl, O, O), (N-2718: COOMe, 4-CONH$_2$-Ph, O, O), (N-2719: COOMe, 4-CON(Me)H-Ph, O, O), (N-2720: COOMe, 4-CON(Me)$_2$-Ph, O, O), (N-2721: COOMe, 4-iPrOC(=O)-Ph, O, O), (N-2722: COOMe, 4-nBuOC(=O)-Ph, O, O), (N-2723: COOMe, 6-Me-pyridine-3-yl, O, O), (N-2724: COOMe, Quinoline-3-yl, O, O), (N-2725: COOME, 4-NH$_2$-Ph, O, O), (N-2726: COOMe, 4-N(Ac)H-Ph, O, O), (N-2727: COOMe, 4-OH-Ph, O, O), (N-2728: COOMe, 3,4-di(OH)$_2$-Ph, O, O), (N-2729: COOMe, 3,4-di(NH$_2$)-Ph, O, O), (N-2730: COOMe, 3:4-[N(Ac)H]$_2$-Ph, O, O), (N-2731: COOMe, 4-SH-Ph, O, O), (N-2732: COOMe, 4-SMe-Ph, O, O), (N-2733: COOMe, 3,4-diBr-Ph, O, O), (N-2734: COOMe, 4-N(Me)H-Ph, O, O), (N-2735: COOMe, 4-N(Me)$_2$-Ph, O, O), (N-2736: COOMe, 4-N(Me)$_3$+-Ph, O, O), (N-2737: COOMe, 4-Et-Ph, O, O), (N-2738: COOMe, 4-iPr-Ph, O, O), (N-2739: COOMe, 4-nPr-Ph, O, O), (N-2740: COOMe, 4-nBu-Ph, O, O), (N-2741: COOMe, 4-iBu-Ph, O, O), (N-2742: COOMe, 3,4-diMe-Ph, O, O), (N-2743: COOMe, 1,3-Benzodioxole-5-yl, O, O), (N-2744: COOMe, N-Me-pyridinium-4-yl, O, O), (N-2745: COOMe, N-Me-pyridinium-3-yl, O, O), (N-2746: COOMe, 5-Me-Pyridine-2-yl, O, O), (N-2747: COOMe, 2-Pyrazinyl, O, O), (N-2748: COOMe, 3-Pyrrolyl, O, O), (N-2749: COOMe, 1-Me-pyrrole-3-yl, O, O), (N-2750: COOMe, Pyridine N-oxide-4-yl, O, O), (N-2751: COOMe, Pyridine N-oxide-3-yl, O, O), (N-2752: COOMe, 6-OH-pyridine-3-yl, O, O), (N-2753: COOMe, 6-SH-pyridine-3-yl, O, O), (N-2754: COOMe, 1-Ac-pyrrole-3-yl, O, O), (N-2755: COOMe, 4-CF$_3$-Ph, O, O), (N-2756: COOMe, 4-CN-Ph, O, O), (N-2757: COOMe, 4-CHO-Ph, O, O), (N-2758: COOMe, 3-Cl-Ph, O, O), (N-2759: COOMe, 3-Br-Ph, O, O), (N-2760: COOMe, 3-F-Ph, O, O), (N-2761: COOMe, 3-I-Ph, O, O), (N-2762: COOMe, 4-I-Ph, O, O), (N-2763: COOMe, 4-OCF$_3$-Ph, O, O), (N-2764: COOMe, 3,4-diI-Ph, O, O), (N-2765: COOMe, Indole-6-yl, O, O), (N-2766: COOMe, 1-Ac-indole-6-yl, O, O), (N-2767: COOMe, 1-Me-indole-6-yl, O, O), (N-2768: COOMe, 4-(1-lmidazolyl)-Ph, O, O), (N-2769: COOMe, 4-Morphorino-Ph, O, O), (N-2770: COOMe, 4-(1-Piperazinyl)-Ph, O, O), (N-2771: COOMe, 2:5-diMe-thiophene-3-yl, O, O), (N-2772: COOMe, 2-Furyl, O, O), (N-2773: COOMe, 5-Me-furan-2-yl, O, O), (N-2774: COOMe, 5-Me-furan-2-yl, O, O), (N-2775: COOMe, 2-Thiazolyl, O, O), (N-2776: COOMe, 1:4-Benzodioxin-6-yl, O, O), (N-2777: COOMe, Benzo[b]furan-2-yl, O, O), (N-2778: COOMe, 4-NH$_2$CH$_2$-Ph, O, O), (N-2779: COOMe, 4-N(Me)HCH$_2$-Ph, O, O), (N-2780: COOMe, 4-N(Me)$_2$CH$_2$-Ph, O, O), (N-2781: COOMe, 6-Cl-pyridine-3-yl, O, O), (N-2782: COOMe, 5,6-diCl-pyridine-3-yl, O, O), (N-2783: COOMe, 5-Cl-pyridine-2-yl, O, O), (N-2784: COOMe, 4:5-diCl-pyridine-2-yl, O, O), (N-2785: COOMe, 4-ClCH$_2$-Bn, O, O), (N-2786: COOMe, Bn, O, O), (N-2787: COOMe, 4-Cl-Bn, O, O), (N-2788: COOMe, 4-Br-Bn, O, O), (N-2789: COOMe, 4-F-Bn, O, O), (N-2790: COOMe, 3,4-diCl-Bn, O, O), (N-2791: COOMe, 3,4-diBr-Bn, O, O), (N-2792: COOMe, 3,4-diF-Bn, O, O), (N-2793: COOMe, 4-Cl-Bz, O, O), (N-2794: COOMe, 3,4-diCl-Bz, O, O), (N-2795: COOMe, 4-Br-Bz, O, O), (N-2796: COOMe, 3,4-diBr-Bz, O, O), (N-2797: COOMe, 4-F-Bz, O, O), (N-2798: COOMe, 3,4-diF-Bz, O, O), (N-2799: COOMe, 4-NO$_2$-Bn, O, O), (N-2800: COOMe, 4-CN-Bn, O, O), (N-2801: 4-F-Ph, CONH$_2$, S, S), (N-2802: 4-Br-Ph, CONH$_2$, S, S), (N-2803: 5-Cl-thiophene-2-yl, CONH$_2$, S, S), (N-2804: 3,4-diF-Ph, CONH$_2$, S, S), (N-2805: 5-Br-thiophene-2-yl, CONH$_2$, S, S), (N-2806: 3,4-diBr-Ph, CONH$_2$, S, S), (N-2807: 4-CF$_3$-Ph, CONH$_2$, S, S), (N-2808: 3-Cl-Ph, CONH$_2$, S, S), (N-2809: 3-Br-Ph, CONH$_2$, S, S), (N-2810: 3-F-Ph, CONH$_2$, S, S), (N-2811: 4-F-Ph, CO$_2$NHCH$_3$, S, S), (N-2812: 4-Br-Ph, CO$_2$NHCH$_3$, S, S), (N-2813: 5-Cl-thiophene-2-yl, CO$_2$NHCH$_3$, S, S), (N-2814: 3,4-diF-Ph, CO$_2$NHCH$_3$, S, S), (N-2815: 5-Br-thiophene-2-yl, CO$_2$NHCH$_3$, S, S), (N-2816: 3,4-diBr-Ph, CO$_2$NHCH$_3$, S, S), (N-2817: 4-CF$_3$-Ph, CO$_2$NHCH$_3$, S, S), (N-2818: 3-Cl-Ph, CO$_2$NHCH$_3$, S, S), (N-2819: 3-Br-Ph, CO$_2$NHCH$_3$, S, S), (N-2820: 3-F-Ph, CO$_2$NHCH$_3$, S, S), (N-2821: 4-F-Ph, CO$_2$N(CH$_3$)$_2$, S, S), (N-2822: 4-Br-Ph, CO$_2$N(CH$_3$)$_2$, S, S), (N-2823: 5-Cl-thiophene-2-yl, CO$_2$N(CH$_3$)$_2$, S, S), (N-2824: 3,4-diF-Ph, CO$_2$N(CH$_3$)$_2$, S, S), (N-2825: 5-Br-thiophene-2-yl, CO$_2$N(CH$_3$)$_2$, S, S), (N-2826: 3,4-diBr-Ph, CO$_2$N(CH$_3$)$_2$, S, S), (N-2827: 4-CF$_3$-Ph, CO$_2$N(CH$_3$)$_2$, S, S), (N-2828: 3-Cl-Ph, CO$_2$N(CH$_3$)$_2$, S, S), (N-2829: 3-Br-Ph, CO$_2$N(CH$_3$)$_2$, S, S), (N-2830: 3-F-Ph, CO$_2$N(CH$_3$)$_2$, S, S), (N-2831: 4-F-Ph, CO$_2$H, S, S), (N-2832: 4-Br-Ph, CO$_2$H, S, S), (N-2833: 5-Cl-thiophene-2-yl, CO$_2$H, S, S), (N-2834: 3,4-diF-Ph, CO$_2$H, S, S), (N-2835: 5-Br-thiophene-2-yl, CO$_2$H, S, S), (N-2836: 3,4-diBr-Ph, CO$_2$H, S, S), (N-2837: 4-CF$_3$-Ph, CO$_2$H, S, S), (N-2838: 3-Cl-Ph, CO$_2$H, S, S), (N-2839: 3-Br-Ph, CO$_2$H, S, S), (N-2840: 3-F-Ph, CO$_2$H, S, S), (N-2841: 4-F-Ph, NH$_2$, S, S), (N-2842: 4-Br-Ph, NH$_2$, S, S), (N-2843: 5-Cl-thiophene-2-yl, NH$_2$, S, S), (N-2844: 3,4-diF-Ph, NH$_2$, S, S), (N-2845: 5-Br-thiophene-2-yl, NH$_2$, S, S), (N-2846: 3,4-diBr-Ph, NH$_2$, S, S), (N-2847: 4-CF3-Ph, NH$_2$, S, S), (N-2848: 3-Cl-Ph, NH$_2$, S, S), (N-2849: 3-Br-Ph, NH$_2$, S, S), (N-2850: 3-F-Ph, NH$_2$, S, S), (N-2851: 4-F-Ph, CH$_2$COOMe, S, S), (N-2852: 4-Br-Ph, CH$_2$COOMe, S, S), (N-2853: 5-Cl-thiophene-2-yl, CH$_2$COOMe, S, S), (N-2854: 3,4-diF-Ph, CH$_2$COOMe, S, S), (N-2855: 5-Br-thiophene-2-yl, CH$_2$COOMe, S, S), (N-2866: 3,4-diBr-Ph, CH$_2$COOMe, S, S), (N-2857: 4-CF$_3$-Ph, CH$_2$COOMe, S, S), (N-2858: 3-Cl-Ph, CH$_2$COOMe, S, S), (N-2859: 3-Br-Ph, CH$_2$COOMe, S, S), (N-2860: 3-F-Ph, CH$_2$COOMe, S, S), (N-2861: 4-F-Ph, CH$_2$CH$_2$COOMe, S, S), (N-2862: 4-Br-Ph, CH$_2$CH$_2$COOMe, S, S), (N-2863: 5-Cl-thiophene-2-yl, CH$_2$CH$_2$COOMe, S, S), (N-2864: 3,4-diF-Ph, CH$_2$CH$_2$COOMe, S, S), (N-2865: 5-Br-thiophene-2-yl, CH$_2$CH$_2$COOMe, S, S), (N-2866: 3,4-diBr-Ph, CH$_2$CH$_2$COOMe, S, S), (N-2867: 4-CF$_3$-Ph, CH$_2$CH$_2$COOMe, S, S), (N-2868: 3-Cl-Ph, CH$_2$CH$_2$COOMe, S, S), (N-2869: 3-Br-Ph, CH$_2$CH$_2$COOMe, S, S), (N-2870: 3-F-Ph, CH$_2$CH$_2$COOMe, S, S), (N-2871: 4-F-Ph, CH$_2$COONH$_2$, S, S), (N-2872: 4-Br-Ph, CH$_2$COONH$_2$, S, S), (N-2873: 5-Cl-thiophene-2-yl, CH$_2$COONH$_2$, S, S), (N-2874: 3,4-diF-Ph, CH$_2$COONH$_2$, S, S), (N-2875: 5-Br-thiophene-2-yl, CH$_2$COONH$_2$, S, S), (N-2876: 3,4-diBr-Ph, CH$_2$COONH$_2$, S, S), (N-2877: 4-CF$_3$-Ph, CH$_2$COONH$_2$, S, S), (N-2878: 3-Cl-Ph, CH$_2$COONH$_2$, S, S), (N-2879: 3-Br-Ph, CH$_2$COONH$_2$, S, S), (N-2880: 3-F-Ph, CH$_2$COONH$_2$, S, S), (N-2881: 4-F-Ph, CH$_2$COONHCH$_3$, S, S), (N-2882: 4-Br-Ph, CH$_2$COONHCH$_3$, S, S), (N-2883: 5-Cl-thiophene-2-yl, CH$_2$COONHCH$_3$, S, S), (N-2884: 3,4-diF-Ph, CH$_2$COONHCH$_3$, S, S), (N-2886: 5-Br-thiophene-2-yl, CH$_2$COONHCH$_3$, S, S), (N-2886: 3,4-diBr-Ph, CH$_2$COONHCH$_3$, S, S), (N-2887: 4-CF$_3$-Ph, CH$_2$COONHCH$_3$, S, S), (N-2888: 3-Cl-Ph, CH$_2$COONHCH$_3$, S, S), (N-2889: 3-Br-Ph, CH$_2$COONHCH$_3$, S, S), (N-2890: 3-F-Ph, CH$_2$COONHCH$_3$, S, S), (N-2893: 5-Cl-thiophene-2-yl, CH$_2$CH$_2$Cl, S, S), (N-2894: 3,4-diF-Ph, CH$_2$CH$_2$Cl, S, S), (N-2895: 5-Br-thiophene-2-yl, CH$_2$CH$_2$Cl, S, S), (N-2896: 3,4-diBr-Ph, CH$_2$CH$_2$Cl, S, S), (N-2897: 4-CF$_3$-Ph, CH$_2$CH$_2$Cl, S, S), (N-2898: 3-Cl-Ph, CH$_2$CH$_2$Cl, S, S), (N-2899: 3-Br-Ph, CH$_2$CH$_2$Cl, S, S), (N-2900: 3-F-Ph, CH$_2$CH$_2$Cl, S, S), (N-2901: 4-F-Ph, CONH$_2$, O, S), (N-2902: 4-Br-Ph, CONH$_2$, O, S), (N-2903: 5-Cl-thiophene-2-yl, CONH$_2$, O, S), (N-2904: 3,4-diF-Ph, CONH$_2$, O, S), (N-2905: 5-Br-thiophene-2-yl, CONH$_2$O, S), (N-2906: 3,4-diBr-Ph, CONH$_2$O, S), (N-2907: 4-CF$_3$-Ph, CONH$_2$, O, S), (N-2908: 3-Cl-Ph, CONH$_2$, O, S), (N-2909: 3-Br-Ph, CONH$_2$, O, S), (N-2910: 3-F-Ph, CONH$_2$, O, S), (N-2911: 4-F-Ph, CO$_2$NHCH$_3$, O, S), (N-2912: 4-Br-Ph, CO$_2$NHCH$_3$, O, S), (N-2913: 5-Cl-thiophene-2-yl, CO$_2$NHCH$_3$O, S), (N-2914: 3,4-diF-Ph, CO$_2$NHCH$_3$O, S), (N-2915: 5-Br-thiophene-2-yl, CO$_2$NHCH$_3$, O, S), (N-2916: 3,4-diBr-Ph, CO$_2$NHCH$_3$, O, S), (N-2917: 4-CF$_3$-Ph, CO$_2$NHCH$_3$, O, S), (N-2918: 3-Cl-Ph, CO$_2$NHCH$_3$, O, S), (N-2919: 3-Br-Ph, CO$_2$NHCH$_3$, O, S), (N-2920: 3-F-Ph, CO$_2$NHCH$_3$, O, S), (N-2921: 4-F-Ph, CO$_2$N(CH$_3$)$_2$, O, S), (N-2922: 4-Br-Ph, CO$_2$N(CH$_3$)$_2$, O, S), (N-2923: 5-Cl-thiophene-2-yl, CO$_2$N(CH$_3$)$_2$, O, S), (N-2924: 3,4-diF-Ph, CO$_2$N(CH$_3$)$_2$, O, S), (N-2925: 5-Br-thiophene-2-yl, CO$_2$N(CH$_3$)$_2$, O, S), (N-2926: 3,4-diBr-Ph, CO$_2$N(CH$_3$)$_2$, O, S), (N-2927: 4-CF$_3$-Ph, CO$_2$N(CH$_3$)$_2$, O, S), (N-2928: 3-Cl-Ph, CO$_2$N(CH$_3$)$_2$, O, S), (N-2929: 3-Br-Ph, CO$_2$N(CH$_3$)$_2$, O, S), (N-2930: 3-F-Ph, CO$_2$N(CH$_3$)$_2$, O, S), (N-2931: 4-F-Ph, CO$_2$H, O, S), (N-2932: 4-Br-Ph, CO$_2$H, O, S), (N-2933: 5-Cl-thiophene-2-yl, CO$_2$H, O, S), (N-2934: 3,4-diF-Ph, CO$_2$H, O, S), (N-2935: 5-Br-thiophene-2-yl, CO$_2$H, O, S), (N-2936: 3,4-diBr-Ph, CO$_2$H, O, S), (N-2937: 4-CF$_3$-Ph, CO$_2$H, O, S), (N-2938: 3-Cl-Ph, CO$_2$H, O, S), (N-2939: 3-Br-Ph, CO$_2$H, O, S), (N-2940: 3-F-Ph, CO$_2$H, O, S), (N-2941: 4-F-Ph, NH$_2$, O, S), (N-2942: 4-Br-Ph, NH$_2$, O, S), (N-2943: 5-Cl-thiophene-2-yl, NH$_2$, O, S), (N-2944: 3,4-diF-Ph, NH$_2$, O, S), (N-2945: 5-Br-thiophene-2-yl, NH$_2$, O, S), (N-296: 3,4-diBr-Ph, NH$_2$, O, S), (N-2947: 4-CF$_3$-Ph, NH$_2$, O, S), (N-2948: 3-Cl-Ph, NH$_2$, O, S), (N-2949: 3-Br-Ph, NH$_2$, O, S), (N-2950: 3-F-Ph, NH$_2$, O, S), (N-2951: 4-F-Ph, CH$_2$COOMe, O, S), (N-2952: 4-Br-Ph, CH$_2$COOMe, O, S), (N-2953: 5-Cl-thiophene-2-yl, CH$_2$COOMe, O, S), (N-2954: 3,4-diF-Ph, CH$_2$COOMe, O, S), (N-2955: 5-Br-thiophene-2-yl, CH$_2$COOMe, O, S), (N-2956: 3,4-diBr-Ph, CH$_2$COOMe, O, S), (N-2957: 4-CF$_3$-Ph, CH$_2$COOMe, O, S), (N-2958: 3-Cl-Ph, CH$_2$COOMe, O, S), (N-2959: 3-Br-Ph, CH$_2$COOMe, O, S), (N-2960: 3-F-Ph, CH$_2$COOMe, O, S), (N-2961: 4-F-Ph, CH$_2$CH$_2$COOMe, O, S), (N-2962: 4-Br-Ph, CH$_2$CH$_2$COOMe, O, S), (N-2963: 5-Cl-thiophene-2-yl, CH$_2$CH$_2$COOMe, O, S), (N-2964: 3,4-diF-Ph, CH$_2$CH$_2$COOMe, O, S), (N-2965: 5-Br-thiophene-2-yl, CH$_2$CH$_2$COOMe, O, S), (N-2966: 3,4-diBr-Ph, CH$_2$CH$_2$COOMe, O, S), (N-2967: 4-CF$_3$-Ph, CH$_2$CH$_2$COOMe, O, S), (N-2968: 3-Cl-Ph, CH$_2$CH$_2$COOMe, O, S), (N-2969: 3-Br-Ph, CH$_2$CH$_2$COOMe, O, S), (N-2970: 3-F-Ph, CH$_2$CH$_2$COOMe, O, S), (N-2971: 4-F-Ph, CH$_2$COONH$_2$, O, S), (N-2972: 4-Br-Ph, CH$_2$COONH$_2$, O, S), (N-2973: 5-Cl-thiophene-2-yl, CH$_2$COONH$_2$, O, S), (N-2974: 3,4-diF-Ph, CH$_2$COONH$_2$, O, S), (N-2975: 5-Br-thiophene-2-yl, CH$_2$COONH$_2$, O, S), (N-2976: 3,4-diBr-Ph, CH$_2$COONH$_2$, O, S), (N-2977: 4-CF$_3$-Ph, CH$_2$COONH$_2$, O, S), (N-2978: 3-Cl-Ph, CH$_2$COONH$_2$, O, S), (N-2979: 3-Br-Ph, CH$_2$COONH$_2$, O, S), (N-2980: 3-F-Ph, CH$_2$COONH$_2$, O, S), (N-2981: 4-F-Ph, CH$_2$COONHCH$_3$, O, S), (N-2982: 4-Br-Ph, CH$_2$COONHCH$_3$, O, S), (N-2983: 5-Cl-thiophene-2-yl, CH$_2$COONHCH$_3$, O, S), (N-2984: 3,4-diF-Ph, CH$_2$COONHCH$_3$, O, S), (N-2985: 5-Br-thiophene-2-yl, CH$_2$COONHCH$_3$, O, S), (N-2986: 3,4-diBr-Ph, CH$_2$COONHCH$_3$, O, S), (N-2987: 4-CF$_3$-Ph, CH$_2$COONHCH$_3$, O, S), (N-2988: 3-Cl-Ph, CH$_2$COONHCH$_3$, O, S), (N-2989: 3-Br-Ph, CH$_2$COONHCH$_3$, O, S), (N-2990: 3-F-Ph, CH$_2$COONHCH$_3$, O, S), (N-2991: 4-F-Ph, CH$_2$CH$_2$Cl, O, S), (N-2992: 4-Br-Ph, CH$_2$CH$_2$Cl, O, S), (N-2993: 5-Cl-thiophene-2-yl, CH$_2$CH$_2$Cl, O, S), (N-2994: 3,4-diF-Ph, CH$_2$CH$_2$Cl, O, S), (N-2995: 5-Br-thiophene-2-yl, CH$_2$CH$_2$Cl, O, S), (N-2996: 3,4-diBr-Ph, CH$_2$CH$_2$Cl, O, S), (N-2997: 4-CF$_3$-Ph, CH$_2$CH$_2$Cl, O, S), (N-2998: 3-Cl-Ph, CH$_2$CH$_2$Cl, O, S), (N-2999: 3-Br-Ph, CH$_2$CH$_2$Cl, O, S), (N-3000: 3-F-Ph, CH$_2$CH$_2$Cl, O, S), (N-3001: 4-F-Ph, CONH$_2$, S, O), (N-3002: 4-Br-Ph, CONH$_2$, S, O), (N-3003: 5-Cl-thiophene-2-yl, CONH$_2$, S, O), (N-3004: 3,4-diF-Ph, CONH$_2$, S, O), (N-3005: 5-Br-thiophene-2-yl, CONH$_2$, S, O), (N-3006: 3,4-diBr-Ph, CONH$_2$, S, O), (N-3007: 4-CF$_3$-Ph, CONH$_2$, S, O), (N-300: 3-Cl-Ph, CONH$_2$, S, O), (N-3009: 3-Br-Ph, CONH$_2$, S, O), (N-3010: 3-F-Ph, CONH$_2$, S, O), (N-3011: 4-F-Ph, CO$_2$NHCH$_3$, S, O), (N-3012: 4-Br-Ph, CO$_2$NHCH$_3$, S, O), (N-3013: 5-Cl-thiophene-2-yl, CO$_2$NHCH$_3$, S, O), (N-3014: 3,4-diF-Ph, CO$_2$NHCH$_3$, S, O), (N-3015: 5-Br-thiophene-2-yl, CO$_2$NHCH$_3$, S, O), (N-3016: 3,4-diBr-Ph, CO$_2$NHCH$_3$, S, O), (N-3017: 4-CF$_3$-Ph, CO$_2$NHCH$_3$, S, O), (N-3018: 3-Cl-Ph, CO$_2$NHCH$_3$, S, O), (N-3019: 3-Br-Ph, CO$_2$NHCH$_3$, S, O), (N-3020: 3-F-Ph, CO$_2$NHCH$_3$, S, O), (N-3021: 4-F-Ph, CO$_2$N(CH$_3$)$_2$, S, O), (N-3022: 4-Br-Ph, CO$_2$N(CH$_3$)$_2$, S, O), (N-3023: 5-Cl-thiophene-2-yl, CO$_2$N(CH$_3$)$_2$, S, O), (N-3024: 3,4-diF-Ph, CO$_2$N(CH$_3$)$_2$, S, O), (N-3025: 5-Br-thiophene-2-yl, CO$_2$N(CH$_3$)$_2$, S, O), (N-3026: 3,4-diBr-Ph, CO$_2$N(CH$_3$)$_2$, S, O), (N-3027: 4-CF$_3$-Ph, CO$_2$N(CH$_3$)$_2$, S, O), (N-3028: 3-Cl-Ph, CO$_2$N(CH$_3$)$_2$, S, O), (N-3029: 3-Br-Ph, CO$_2$N(CH$_3$)$_2$, S, O), (N-3030: 3-F-Ph, CO$_2$N(CH$_3$)$_2$, S, O), (N-3031: 4-F-Ph, CO$_2$H, S, O), (N-3032: 4-Br-Ph, CO$_2$H, S, O), (N-3033: 5-Cl-thiophene-2-yl, CO$_2$H, S, O), (N-3034: 3,4-diF-Ph, CO$_2$H, S, O), (N-3035: 5-Br-thiophene-2-yl, CO$_2$H, S, O), (N-3036: 3,4-diBr-Ph, CO$_2$H, S, O), (N-3037: 4-CF$_3$-Ph, CO$_2$H, S, O), (N-3038: 3-Cl-Ph, CO$_2$H, S, O), (N-3039: 3-Br-Ph, CO$_2$H, S, O), (N-3040: 3-F-Ph, CO$_2$H, S, O), (N-3041: 4-F-Ph, NH$_2$, S, O), (N-3042: 4-Br-Ph, NH$_2$, S, O), (N-3043: 5-Cl-thiophene-2-yl, NH$_2$, S, O), (N-3044: 3,4-diF-Ph, NH$_2$, S, O), (N-3045: 5-Br-thiophene-2-yl, NH$_2$, S, O), (N-3046: 3,4-diBr-Ph, NH$_2$, S, O), (N-3047: 4-CF$_3$-Ph, NH$_2$, S, O), (N-3048: 3-Cl-Ph, NH$_2$, S, O), (N-3049: 3-Br-Ph, NH$_2$, S, O), (N-3050: 3-F-Ph, NH$_2$, S, O), (N-3051: 4-F-Ph, CH$_2$COOMe, S, O), (N-3052: 4-Br-Ph, CH$_2$COOMe, S, O), (N-3053: 5-Cl-thiophene-2-yl, CH$_2$COOMe, S, O ), (N-3054: 3,4-diF-Ph, CH$_2$COOMe, S, O), (N-3055: 5-Br-thiophene-2-yl, CH$_2$COOMe, S, O), (N-3056: 3,4-diBr-Ph, CH$_2$COOMe, S, O), (N-3057: 4-CF$_3$-Ph, CH$_2$COOMe, S, O), (N-3058: 3-Cl-Ph, CH$_2$COOMe, S, O), (N-3059: 3-Br-Ph, CH$_2$COOMe, S, O), (N-3060: 3-F-Ph, CH$_2$COOMe, S, O), (N-3061: 4-F-Ph, CH$_2$CH$_2$COOMe, S, O), (N-3062: 4-Br-Ph, CH$_2$CH$_2$COOMe, S, O), (N-3063: 5-Cl-thiophene-2-yl, CH$_2$CH$_2$COOMe, S, O), (N-3064: 3,4-diF-Ph, CH$_2$CH$_2$COOMe, S, O), (N-3065: 5-Br-thiophene-2-yl, CH$_2$CH$_2$COOMe, S, O), (N-3066: 3,4-diBr-Ph, CH$_2$CH$_2$COOMe, S, O), (N-3067: 4-CF$_3$-Ph, CH$_2$CH$_2$COOMe, S, O), (N-3068: 3-Cl-Ph, CH$_2$CH$_2$COOMe, S, O), (N-3069: 3-Br-Ph, CH$_2$CH$_2$COOMe, S, O), (N-3070: 3-F-Ph, CH$_2$CH$_2$COOMe, S, O), (N-3071: 4-F-Ph, CH$_2$COONH$_2$, S, O), (N-3072: 4-Br-Ph, CH$_2$COONH$_2$, S, O), (N-3073: 5-Cl-thiophene-2-yl, CH$_2$COONH$_2$, S, O), (N-3074: 3,4-diF-Ph, CH$_2$COONH$_2$, S, O), (N-3075: 5-Br-thiophene-2-yl, CH$_2$COONH$_2$, S, O), (N-3076: 3,4-diBr-Ph, CH$_2$COONH$_2$, S, O), (N-3077: 4-CF$_3$-Ph, CH$_2$COONH$_2$, S, O), (N-3078: 3-Cl-Ph, CH$_2$COONH$_2$, S, O), (N-3079: 3-Br-Ph, CH$_2$COONH$_2$, S, O), (N-3080: 3-F-Ph, CH$_2$COONH$_2$, S, O), (N-3081: 4-F-Ph, CH$_2$COONHCH$_3$, S, O), (N-3082: 4-Br-Ph, CH$_2$COONHCH$_3$, S, O), (N-3083: 5-Cl-thiophene-2-yl, CH$_2$COONHCH$_3$, S, O), (N-3084: 3,4-diF-Ph, CH$_2$COONHCH$_3$, S, O), (N-3085: 5-Br-thiophene-2-yl, CH$_2$COONHCH$_3$, S, O), (N-3086: 3,4-diBr-Ph, CH$_2$COONHCH$_3$, S, O), (N-3087: 4-CF$_3$-Ph, CH$_2$COONHCH$_3$, S, O), (N-3088: 3-Cl-Ph, CH$_2$COONHCH$_3$, S, O), (N-3089: 3-Br-Ph, CH$_2$COONHCH$_3$, S, O), (N-3090: 3-F-Ph, CH$_2$COONHCH$_3$, S, O), (N-3091: 4-F-Ph, CH$_2$CH$_2$Cl, S, O), (N-3092: 4-Br-Ph, CH$_2$CH$_2$Cl, S, O), (N-3093: 5-Cl-thiophene-2-yl, CH$_2$CH$_2$Cl, S, O), (N-3094: 3,4-diF-Ph, CH$_2$CH$_2$Cl, S, O), (N-3095: 5-Br-thiophene-2-yl, CH$_2$CH$_2$Cl, S, O), (N-3096: 3,4-diBr-Ph, CH$_2$CH$_2$Cl, S, O), (N-3097: 4-CF$_3$-Ph, CH$_2$CH$_2$Cl, S, O), (N-3098: 3-Cl-Ph, CH$_2$CH$_2$Cl, S, O), (N-3099: 3-Br-Ph, CH$_2$CH$_2$Cl, S, O), (N-3100: 3-F-Ph, CH$_2$CH$_2$Cl, S, O), (N-3101: 4-F-Ph, CONH$_2$, O, O), (N-3102: 4-Br-Ph, CONH$_2$, O, O), (N-3103: 5-Cl-thiophene-2-yl, CONH$_2$, O, O), (N-3104: 3,4-diF-Ph, CONH$_2$, O, O), (N-3105: 5-Br-thiophene-2-yl, CONH$_2$, O, O), (N-3106: 3,4-diBr-Ph, CONH$_2$, O, O), (N-3107: 4-CF$_3$-Ph, CONH$_2$, O, O), (N-3108: 3-Cl-Ph, CONH$_2$, O, O), (N-3109: 3-Br-Ph, CONH$_2$, O, O), (N-3110: 3-F-Ph, CONH$_2$, O, O), (N-3111: 4-F-Ph, CO$_2$NHCH$_3$, O, O), (N-3112: 4-Br-Ph, CO$_2$NHCH$_3$, O, O), (N-3113: 5-Cl-thiophene-2-yl, CO$_2$NHCH$_3$, O, O), (N-3114: 3,4-diF-Ph, CO$_2$NHCH$_3$, O, O), (N-3115: 5-Br-thiophene-2-yl, CO$_2$NHCH$_3$, O, O), (N-3116: 3,4-diBr-Ph, CO$_2$NHCH$_3$, O, O), (N-3117: 4-CF$_3$-Ph, CO$_2$NHCH$_3$, O, O), (N-3118: 3-Cl-Ph, CO$_2$NHCH$_3$, O, O), (N-3119: 3-Br-Ph, CO$_2$NHCH$_3$, O, O), (N-3120: 3-F-Ph, CO$_2$NHCH$_3$, O, O), (N-3121: 4-F-Ph, CO$_2$N(CH$_3$)$_2$, O, O), (N-3122: 4-Br-Ph, CO$_2$N(CH$_3$)$_2$, O, O), (N-3123: 5-Cl-thiophene-2-yl, CO$_2$N(CH$_3$)$_2$, O, O), (N-3124: 3,4-diF-Ph, CO$_2$N(CH$_3$)$_2$, O, O), (N-3125: 5-Br-thiophene-2-yl, CO$_2$N(CH$_3$)$_2$, O, O), (N-3126: 3,4-diBr-Ph, CO$_2$N(CH$_3$)$_2$, O, O), (N-3127: 4-CF$_3$-Ph, CO$_2$N(CH$_3$)$_2$, O, O), (N-3128: 3-Cl-Ph, CO$_2$N(CH$_3$)$_2$, O, O), (N-3129: 3-Br-Ph, CO$_2$N(CH$_3$)$_2$, O, O), (N-3130: 3-F-Ph, CO$_2$N(CH$_3$)$_2$, O, O), (N-3131: 4-F-Ph, CO$_2$H, O, O), (N-3132: 4-Br-Ph, CO$_2$H, O, O), (N-3133: 5-Cl-thiophene-2-yl, CO$_2$H, O, O), (N-3134: 3,4-diF-Ph, CO$_2$H, O, O), (N-3135: 5-Br-thiophene-2-yl, CO$_2$H, O, O), (N-3136: 3,4-diBr-Ph, CO$_2$H, O, O), (N-3137: 4-CF$_3$-Ph, CO$_2$H, O, O), (N-3138: 3-Cl-Ph, CO$_2$H, O, O), (N-3139: 3-Br-Ph, CO$_2$H, O, O), (N-3140: 3-F-Ph, CO$_2$H, O, O), (N-3141: 4-F-Ph, NH$_2$, O, O), (N-3142: 4-Br-Ph, NH$_2$, O, O), (N-3143: 5-Cl-thiophene-2-yl, NH$_2$, O, O), (N-3144: 3,4-diF-Ph, NH$_2$, O, O), (N-3145: 5-Br-thiophene-2-yl, NH$_2$, O, O), (N-3146: 3,4-diBr-Ph, NH$_2$, O, O), (N-3147: 4-CF$_3$-Ph, NH$_2$, O, O), (N-3148: 3-Cl-Ph, NH$_2$, O, O), (N-3149: 3-Br-Ph, NH$_2$, O, O), (N-3150: 3-F-Ph, NH$_2$, O, O), (N-3151: 4-F-Ph, CH$_2$COOMe, O, O), (N-3152: 4-Br-Ph, CH$_2$COOMe, O, O), (N-3153: 5-Cl-thiophene-2-yl, CH$_2$COOMe, O, O), (N-3154: 3,4-diF-Ph, CH$_2$COOMe, O, O), (N-3155: 5-Br-thiophene-2-yl, CH$_2$COOMe, O, O), (N-3156: 3,4-diBr-Ph, CH$_2$COOMe, O, O), (N-3157: 4-CF$_3$-Ph, CH$_2$COOMe, O, O), (N-3158: 3-Cl-Ph, CH₂COOMe, O, O), (N-3159: 3-Br-Ph, CH₂COOMe, O, O), (N-3160: 3-F-Ph, CH₂COOMe, O, O), (N-3161: 4-F-Ph, CH₂CH₂COOMe, O, O), (N-3162: 4-Br-Ph, CH₂CH₂COOMe, O, O), (N-3163: 5-Cl-thiophene-2-yl, CH₂CH₂COOMe, O, O), (N-3164: 3,4-diF-Ph, CH₂CH₂COOMe, O, O), (N-3165: 5-Br-thiophene-2-yl, CH₂CH₂COOMe, O, O), (N-3166: 3,4-diBr-Ph, CH₂CH₂COOMe, O, O), (N-3167: 4-CF₃-Ph, CH₂CH₂COOMe, O, O), (N-3168: 3-Cl-Ph, CH₂CH₂COOMe, O, O), (N-3169: 3-Br-Ph, CH₂CH₂COOMe, O, O), (N-3170: 3-F-Ph, CH₂CH₂COOMe, O, O), (N-3171: 4-F-Ph, CH₂COONH₂, O, O), (N-3172: 4-Br-Ph, CH₂COONH₂, O, O), (N-3173: 5-Cl-thiophene-2-yl, CH₂COONH₂, O, O), (N-3174: 3,4-diF-Ph, CH₂COONH₂, O, O), (N-3175: 5-Br-thiophene-2-yl, CH₂COONH₂, O, O), (N-3176: 3,4-diBr-Ph, CH₂COONH₂, O, O), (N-3177: 4-CF₃-Ph, CH₂COONH₂, O, O), (N-3178: 3-Cl-Ph, CH₂COONH₂, O, O), (N-3179: 3-Br-Ph, CH₂COONH₂, O, O), (N-3180: 3-F-Ph, CH2COONH₂, O, O), (N-3181: 4-F-Ph, CH₂COONHCH₃, O, O), (N-3182: 4-Br-Ph, CH₂COONHCH₃, O, O), (N-3183: 5-Cl-thiophene-2-yl, CH₂COONHCH₃, O, O), (N-3184: 3,4-diF-Ph, CH₂COONHCH₃, O, O), (N-3185: 5-Br-thiophene-2-yl, CH₂COONHCH₃, O, O), (N-3186: 3,4-diBr-Ph, CH₂COONHCH₃, O, O), (N-3187: 4-CF₃-Ph, CH₂COONHCH₃, O, O), (N-3188: 3-Cl-Ph, CH₂COONHCH₃, O, O), (N-3189: 3-Br-Ph, CH₂COONHCH₃, O, O), (N-3190: 3-F-Ph, CH₂COONHCH₃, O, O), (N-3192: 4-Br-Ph, CH₂CH₂Cl, O, O), (N-3193: 5-Cl-thiophene-2-yl, CH₂CH₂Cl, O, O), (N-3194: 3,4-diF-Ph, CH₂CH₂Cl, O, O), (N-3195: 5-Br-thiophene-2-yl, CH₂CH₂Cl, O, O), (N-3196: 3,4-diBr-Ph, CH₂CH₂Cl, O, O), (N-3197: 4-CF₃-Ph, CH₂CH₂Cl, O, O), (N-3198: 3-Cl-Ph, CH₂CH₂Cl, O, O), (N-3199: 3-Br-Ph, CH₂CH₂Cl, O, O), (N-3200: 3-F-Ph, CH₂CH₂Cl, O, O), (N-3301: CONH₂, 4-F-Ph, S, S), (N-3302: CONH₂, 4-Br-Ph, S, S), (N-3303: CONH₂, 5-Cl-thiophene-2-yl, S, S), (N-3304: CONH₂, 3,4-diF-Ph, S, S), (N-3305: CONH₂, 5-Br-thiophene-2-yl, S, S), (N-3306: CONH₂, 3,4-diBr-Ph, S, S), (N-3307: CONH₂, 4-CF₃-Ph, S, S), (N-3308: CONH₂, 3-Cl-Ph, S, S), (N-3309: CONH₂, 3-Br-Ph, S, S), (N-3310: CONH₂, 3-F-Ph, S, S), (N-3311: CO₂NHCH₃4-F-Ph, S, S), (N-3312: CO₂NHCH₃, 4-Br-Ph, S, S), (N-3313: CO₂NHCH₃, 5-Cl-thiophene-2-yl, S, S), (N-3314: CO₂NHCH₃, 3,4-diF-Ph, S, S), (N-3315: CO₂NHCH₃, 5-Br-thiophene-2-yl, S, S), (N-3316: CO₂NHCH₃, 3,4-diBr-Ph, S, S), (N-3317: CO₂NHCH₃, 4-CF₃-Ph, S, S), (N-3318: CO₂NHCH₃, 3-Cl-Ph, S, S), (N-3319: CO₂NHCH₃, 3-Br-Ph, S, S), (N-3320: CO₂NHCH₃, 3-F-Ph, S, S), (N-3321: CO₂N(CH₃)₂, 4-F-Ph, S, S), (N-3322: CO₂N(CH₃)₂, 4-Br-Ph, S, S), (N-3323: CO₂N(CH₃)₂, 5-Cl-thiophene-2-yl, S, S), (N-3324: CO₂N(CH₃)₂, 3,4-diF-Ph, S, S), (N-3325: CO₂N(CH₃)₂, 5-Br-thiophene-2-yl, S, S), (N-3326: CO₂N(CH₃)₂, 3,4-diBr-Ph, S, S), (N-3327: CO₂N(CH₃)₂, 4-CF₃-Ph, S, S), (N-3328: CO₂N(CH₃)₂, 3-Cl-Ph, S, S), (N-3329: CO₂N(CH₃)₂, 3-Br-Ph, S, S), (N-3330: CO₂N(CH₃)₂, 3-F-Ph, S, S), (N-3331: CO₂H, 4-F-Ph, S, S), (N-3332: CO₂H, 4-Br-Ph, S, S), (N-3333: CO₂H, 5-Cl-thiophene-2-yl, S, S), (N-3334: CO₂H, 3,4-diF-Ph, S, S), (N-3335: CO₂H, 5-Br-thiophene-2-yl, S, S), (N-3336: CO₂H, 3,4-diBr-Ph, S, S), (N-3337: CO₂H, 4-CF₃-Ph, S, S), (N-3338: CO₂H, 3-Cl-Ph, S, S), (N-3339: CO₂H, 3-Br-Ph, S, S), (N-3340: CO₂H, 3-F-Ph, S, S), (N-3341: NH₂, 4-F-Ph, S, S), (N-3342: NH₂, 4-Br-Ph, S, S), (N-3343: NH₂, 5-Cl-thiophene-2-yl, S, S), (N-3344: NH₂, 3,4-diF-Ph, S, S), (N-3345: NH₂, 5-Br-thiophene-2-yl, S, S), (N-3346: NH₂, 3,4-diBr-Ph, S, S), (N-3347: NH₂, 4-CF₃-Ph, S, S), (N-3348: NH₂, 3-Cl-Ph, S, S), (N-3349: NH₂, 3-Br-Ph, S, S), (N-3350: NH₂, 3-F-Ph, S, S), (N-3351: CH₂COOMe, 4-F-Ph, S, S), (N-3352: CH₂COOMe, 4-Br-Ph, S, S), (N-3353: CH₂COOMe, 5-Cl-thiophene-2-yl, S, S), (N-3354: CH₂COOMe, 3,4-diF-Ph, S, S), (N-3355: CH₂COOMe, 5-Br-thiophene-2-yl, S, S), (N-3356: CH₂COOMe, 3,4-diBr-Ph, S, S), (N-3357: CH₂COOMe, 4-CF₃-Ph, S, S), (N-3358: CH₂COOMe, 3-Cl-Ph, S, S), (N-3359: CH₂COOMe, 3-Br-Ph, S, S), (N-3360: CH₂COOMe, 3-F-Ph, S, S), (N-3361: CH₂CH₂COOMe, 4-F-Ph, S, S), (N-3362: CH₂CH₂COOMe, 4-Br-Ph, S, S), (N-3363: CH₂CH₂COOMe, 5-Cl-thiophene-2-yl, S, S), (N-3364: CH₂CH₂COOMe, 3,4-diF-Ph, S, S), (N-3365: CH₂CH₂COOMe, 5-Br-thiophene-2-yl, S, S), (N-3366: CH₂CH₂COOMe, 3,4-diBr-Ph, S, S), (N-3367: CH₂CH₂COOMe, 4-CF₃-Ph, S, S), (N-3368: CH₂CH₂COOMe, 3-Cl-Ph, S, S), (N-3369: CH₂CH₂COOMe, 3-Br-Ph, S, S), (N-3370: CH₂CH₂COOMe, 3-F-Ph, S, S), (N-3371: CH₂COONH₂, 4-F-Ph, S, S), (N-3372: CH₂COONH₂, 4-Br-Ph, S, S), (N-3373: CH₂COONH₂, 5-Cl-thiophene-2-yl, S, S), (N-3374: CH₂COONH₂, 3,4-diF-Ph, S, S), (N-3375: CH₂COONH₂, 5-Br-thiophene-2-yl, S, S), (N-3376: CH₂COONH₂, 3,4-diBr-Ph, S, S), (N-3377: CH₂COONH₂, 4-CF₃-Ph, S, S), (N-3378: CH₂COONH₂, 3-Cl-Ph, S, S), (N-3379: CH₂COONH₂, 3-Br-Ph, S, S), (N-3380: CH₂COONH₂, 3-F-Ph, S, S), (N-3381: CH₂COONHCH₃, 4-F-Ph, S, S), (N-3382: CH₂COONHCH₃, 4-Br-Ph, S, S), (N-3383: CH₂COONHCH₃, 5-Cl-thiophene-2-yl, S, S), (N-3384:CH₂COONHCH₃, 3,4-diF-Ph, S, S), (N-3385: CH₂COONHCH₃, 5-Br-thiophene-2-yl, S, S), (N-3386: CH₂COONHCH₃, 3,4-diBr-Ph, S, S), (N-3387: CH₂COONHCH₃, 4-CF₃-Ph, S, S), (N-3388: CH₂COONHCH₃, 3-Cl-Ph, S, S), (N-3389: CH₂COONHCH₃, 3-Br-Ph, S, S), (N-3390: CH₂COONHCH₃, 3-F-Ph, S, S), (N-3391: CH₂CH₂Cl, 4-F-Ph, S, S), (N-3392: CH₂CH₂Cl, 4-Br-Ph, S, S), (N-3393: CH₂CH₂Cl, 5-Cl-thiophene-2-yl, S, S), (N-3394: CH₂CH₂Cl, 3,4-diF-Ph, S, S), (N-3395: CH₂CH₂Cl, 5-Br-thiophene-2-yl, S, S), (N-3396: CH₂CH₂Cl, 3,4-diBr-Ph, S, S), (N-3397: CH₂CH₂Cl, 4-CF₃-Ph, S, S), (N-3398: CH₂CH₂Cl, 3-Cl-Ph, S, S), (N-3399: CH₂CH₂Cl, 3-Br-Ph, S, S), (N-3400: CH₂CH₂Cl, 3-F-Ph, S, S), (N-3401: CONH₂, 4-F-Ph, S, O), (N-3402: CONH₂, 4-Br-Ph, S, O), (N-3403: CONH₂, 5-Cl-thiophene-2-yl, S, O), (N-3404: CONH₂, 3,4-diF-Ph, S, O), (N-3405: CONH₂, 5-Br-thiophene-2-yl, S, O), (N-3406: CONH₂, 3,4-diBr-Ph, S, O), (N-3407: CONH₂, 4-CF₃-Ph, S, O), (N-3408: CONH₂, 3-Cl-Ph, S, O), (N-3409: CONH₂, 3-Br-Ph, S, O), (N-3410: CONH₂, 3-F-Ph, S, O), (N-3411: CO₂NHCH₃, 4-F-Ph, S, O), (N-3412: CO₂NHCH₃, 4-Br-Ph, S, O), (N-3413: CO₂NHCH₃, 5-Cl-thiophene-2-yl, S, O), (N-3414: CO₂NHCH₃, 3,4-diF-Ph, S, O), (N-3415: CO₂NHCH₃, 5-Br-thiophene-2-yl, S, O), (N-3416: CO₂NHCH₃, 3,4-diBr-Ph, S, O), (N-3417: CO₂NHCH₃, 4-CF₃-Ph, S, O), (N-3418: CO₂NHCH₃, 3-Cl-Ph, S, O), (N-3419: CO₂NHCH₃, 3-Br-Ph, S, O), (N-3420: CO₂NHCH₃, 3-F-Ph, S, O), (N-3421: CO₂N(CH₃)₂, 4-F-Ph, S, O), (N-3422: CO₂N(CH₃)₂, 4-Br-Ph, S, O), (N-3423: CO₂N(CH₃)₂, 5-Cl-thiophene-2-yl, S, O), (N-3424: CO₂N(CH₃)₂, 3,4-diF-Ph, S, O), (N-3425: CO₂N(CH₃)₂, 5-Br-thiophene-2-yl, S, O), (N-3426: CO₂N(CH₃)₂, 3,4-diBr-Ph, S, O), (N-3427: CO₂N(CH₃)₂, 4-CF₃-Ph, S, O), (N-3428: CO₂N(CH₃)₂, 3-Cl-Ph, S, O), (N-3429: CO₂N(CH₃)₂, 3-Br-Ph, S, O), (N-3430: CO₂N(CH₃)₂, 3-F-Ph, S, O), (N-3431: CO₂H, 4-F-Ph, S, O), (N-3432: CO₂H, 4-Br-Ph, S, O), (N-3433: CO₂H, 5-Cl-thiophene-2-yl, S, O), (N-3434: CO₂H, 3,4-diF-Ph, S, O), (N-3435: CO₂H, 5-Br-thiophene-2-yl, S, O), (N-3436: CO₂H, 3,4-diBr-Ph, S, O), (N-3437: CO₂H, 4-CF₃-Ph, S, O), (N-3438: CO₂H, 3-Cl-Ph, S, O), (N-3439: CO₂H, 3-Br-Ph, S, O), (N-3440: CO₂H, 3-F-Ph, S, O), (N-3441: NH₂, 4-F-Ph, S, O), (N-3442: NH₂, 4-Br-Ph, S, O), (N-3443: NH₂, 5-Cl-thiophene-2-yl, S, O), (N-3444: NH₂, 3,4-diF-Ph, S, O), (N-3445: NH₂, 5-Br-thiophene-2-yl, S, O), (N-3446: NH₂, 3,4-diBr-Ph, S, O), (N-3447: NH₂, 4-CF₃-Ph, S, O), (N-3448: NH₂, 3-Cl-Ph, S, O), (N-3449: NH₂, 3-Br-Ph, S, O), (N-3450: NH₂, 3-F-Ph, S, O), (N-3451: CH₂COOMe, 4-F-Ph, S, O), (N-3452: CH₂COOMe, 4-Br-Ph, S, O), (N-3453: CH₂COOMe, 5-Cl-thiophene-2-yl, S, O), (N-3454: CH₂COOMe, 3,4-diF-Ph, S, O), (N-3455: CH₂COOMe, 5-Br-thiophene-2-yl, S, O), (N-3456: CH₂COOMe, 3,4-diBr-Ph, S, O), (N-3457: CH₂COOMe, 4-CF₃-Ph, S, O), (N-3458: CH₂COOMe, 3-Cl-Ph, S, O), (N-3459: CH₂COOMe, 3-Br-Ph, S, O), (N-3460: CH₂COOMe, 3-F-Ph, S, O), (N-3461: CH₂CH₂COOMe, 4-F-Ph, S, O), (N-3462: CH₂CH₂COOMe, 4-Br-Ph, S, O), (N-3463: CH₂CH₂COOMe, 5-Cl-thiophene-2-yl, S, O), (N-3464: CH₂CH₂COOMe, 3,4-diF-Ph, S, O), (N-3465: CH₂CH₂COOMe, 5-Br-thiophene-2-yl, S, O), (N-3466: CH₂CH₂COOMe, 3,4-diBr-Ph, S, O), (N-3467: CH₂CH₂COOMe, 4-CF₃-Ph, S, O), (N-3468: CH₂CH₂COOMe, 3-Cl-Ph, S, O), (N-3469: CH₂CH₂COOMe, 3-Br-Ph, S, O), (N-3470: CH₂CH₂COOMe, 3-F-Ph, S, O), (N-3471: CH₂COONH₂, 4-F-Ph, S, O), (N-3472: CH₂COONH₂, 4-Br-Ph, S, O), (N-3473: CH₂COONH₂, 5-Cl-thiophene-2-yl, S, O), (N-3474: CH₂COONH₂, 3,4-diF-Ph, S, O), (N-3475: CH₂COONH₂, 5-Br-thiophene-2-yl, S, O), (N-3476: CH₂COONH₂, 3,4-diBr-Ph, S, O), (N-3477: CH₂COONH₂, 4-CF₃-Ph, S, O), (N-3478: CH₂COONH₂, 3-Cl-Ph, S, O), (N-3479: CH₂COONH₂, 3-Br-Ph, S, O), (N-3480: CH₂COONH₂, 3-F-Ph, S, O), (N-3481: CH₂COONHCH₃, 4-F-Ph, S, O), (N-3482: CH₂COONHCH₃, 4-Br-Ph, S, O), (N-3483: CH₂COONHCH₃, 5-Cl-thiophene-2-yl, S, O), (N-3484: CH₂COONHCH₃, 3,4-diF-Ph, S, O), (N-3485: CH₂COONHCH₃, 5-Br-thiophene-2-yl, S, O), (N-3486: CH₂COONHCH₃, 3,4-diBr-Ph, S, O), (N-3487: CH₂COONHCH₃, 4-CF₃-Ph, S, O), (N-3488: CH₂COONHCH₃, 3-Cl-Ph, S, O), (N-3489: CH₂COONHCH₃, 3-Br-Ph, S, O), (N-3490: CH₂COONHCH₃, 3-F-Ph, S, O), (N-3491: CH₂CH₂Cl, 4-F-Ph, S, O), (N-3492: CH₂CH₂Cl, 4-Br-Ph, S, O), (N-3493: CH₂CH₂Cl, 5-Cl-thiophene-2-yl, S, O), (N-3494: CH₂CH₂Cl, 3,4-diF-Ph, S, O), (N-3495: CH₂CH₂Cl, 5-Br-thiophene-2-yl, S, O), (N-3496: CH₂CH₂Cl, 3,4-diBr-Ph, S, O), (N-347: CH₂CH₂Cl, 4-CF₃-Ph, S, O), (N-3498: CH₂CH₂Cl, 3-Cl-Ph, S, O), (N-3499: CH₂CH₂Cl, 3-Br-Ph, S, O), (N-3500: CH₂CH₂Cl, 3-F-Ph, S, O), (N-3501: CONH₂, 4-F-Ph, O, S), (N-3502: CONH₂, 4-Br-Ph, O, S), (N-3503: CONH₂, 5-Cl-thiophene-2-yl, O, S), (N-3504: CONH₂, 3,4-diF-Ph, O, S), (N-3505: CONH₂, 5-Br-thiophene-2-yl, O, S), (N-3506: CONH₂, 3,4-diBr-Ph, O, S), (N-3507: CONH₂, 4-CF₃-Ph, O, S), (N-3508: CONH₂, 3-Cl-Ph, O, S), (N-3509: CONH₂, 3-Br-Ph, O, S), (N-3510: CONH₂, 3-F-Ph, O, S), (N-3511: CO₂NHCH₃, 4-F-Ph, O, S), (N-3512: CO₂NHCH₃, 4-Br-Ph, O, S), (N-3513: CO₂NHCH₃, 5-Cl-thiophene-2-yl, O, S), (N-3514: CO₂NHCH₃, 3,4-diF-Ph, O, S), (N-3515: CO₂NHCH₃, 5-Br-thiophene-2-yl, O, S), (N-3516: CO₂NHCH₃, 3,4-diBr-Ph, O, S), (N-3517: CO₂NHCH₃, 4-CF₃-Ph, O, S), (N-3518: CO₂NHCH₃, 3-Cl-Ph, O, S), (N-3519: CO₂NHCH₃, 3-Br-Ph, O, S), (N-3520: CO₂NHCH₃, 3-F-Ph, O, S), (N-3521: CO₂N(CH₃)₂, 4-F-Ph, O, S), (N-3522: CO₂N(CH₃)₂, 4-Br-Ph, O, S), (N-3523: CO₂N(CH₃)₂, 5-Cl-thiophene-2-yl, O, S), (N-3524: CO₂N(CH₃)₂, 3,4-diF-Ph, O, S), (N-3625: CO₂N(CH₃)₂, 5-Br-thiophene-2-yl, O, S), (N-3526: CO₂N(CH₃)₂, 3,4-diBr-Ph, O, S), (N-3527: CO₂N(CH₃)₂, 4-CF₃-Ph, O, S), (N-3528: CO₂N(CH₃)₂, 3-Cl-Ph, O, S), (N-3529: CO₂N(CH₃)₂, 3-Br-Ph, O, S), (N-3530: CO₂N(CH₃)₂, 3-F-Ph, O, S), (N-3531: CO₂H, 4-F-Ph, O, S), (N-3532: CO₂H, 4-Br-Ph, O, S), (N-353: CO₂H, 5-Cl-thiophene-2-yl, O, S), (N-3534: CO₂H, 3,4-diF-Ph, O, S), (N-3535: CO₂H, 5-Br-thiophene-2-yl, O, S), (N-3536: CO₂H, 3,4-diBr-Ph, O, S), (N-3537: CO₂H, 4-CF₃-Ph, O, S), (N-3538: CO₂H, 3-Cl-Ph, O, S), (N-3539: CO₂H, 3-Br-Ph, O, S), (N-3540: CO₂H, 3-F-Ph, O, S), (N-3541: NH₂, 4-F-Ph, O, S), (N-3542: NH₂, 4-Br-Ph, O, S), (N-3543: NH₂, 5-Cl-thiophene-2-yl, O, S), (N-3544: NH₂, 3,4-diF-Ph, O, S), (N-3545: NH₂, 5-Br-thiophene-2-yl, O, S), (N-3546: NH₂, 3,4-diBr-Ph, O, S), (N-3547: NH₂, 4-CF₃-Ph, O, S), (N-3548: NH₂, 3-Cl-Ph, O, S), (N-3549: NH₂, 3-Br-Ph, O, S), (N-3550: NH₂, 3-F-Ph, O, S), N35-51: CH₂COOMe, 4-F-Ph, O, S), (N-3552: CH₂COOMe, 4-Br-Ph, O, S), (N-3553: CH₂COOMe, 5-Cl-thiophene-2-yl, O, S), (N-3554: CH₂COOMe, 3,4-diF-Ph, O, S), (N-355: CH₂COOMe, 5-Br-thiophene-2-yl, O, S), (N-3556: CH₂COOMe, 3,4-diBr-Ph, O, S), (N-3557: CH₂COOMe, 4-CF₃-Ph, O, S), (N-3558: CH₂COOMe, 3-Cl-Ph, O, S), (N-3559: CH₂COOMe, 3-Br-Ph, O, S), (N-3560: CH₂COOMe, 3-F-Ph, O, S), (N-3561: CH₂CH₂COOMe, 4-F-Ph, O, S), (N-3562: CH₂CH₂COOMe, 4-Br-Ph, O, S), (N-3563: CH₂CH₂COOMe, 5-Cl-thiophene-2-yl, O, S), (N-3564: CH₂CH₂COOMe, 3,4-diF-Ph, O, S), (N-3565: CH₂CH₂COOMe, 5-Br-thiophene-2-yl, O, S), (N-3566: CH₂CH₂COOMe, 3,4-diBr-Ph, O, S), (N-3567: CH₂CH₂COOMe, 4-CF₃-Ph, O, S), (N-3568: CH₂CH₂COOMe, 3-Cl-Ph, O, S), (N-3569: CH₂CH₂COOMe, 3-Br-Ph, O, S), (N-3570: CH₂CH₂COOMe, 3-F-Ph, O, S), (N-3571: CH₂COONH₂, 4-F-Ph, O, S), (N-3572: CH₂COONH₂, 4-Br-Ph, O, S), (N-3573: CH₂COONH₂, 5-Cl-thiophene-2-yl, O, S), (N-3574: CH₂COONH₂, 3,4-diF-Ph, O, S), (N-3575: CH₂COONH₂, 5-Br-thiophene-2-yl, O, S), (N-3576: CH₂COONH₂, 3,4-diBr-Ph, O, S), (N-3577: CH₂COONH₂, 4-CF₃-Ph, O, S), (N-3578: CH₂COONH₂, 3-Cl-Ph, O, S), (N-3579: CH₂COONH₂, 3-Br-Ph, O, S), (N-3580: CH₂COONH₂, 3-F-Ph, O, S), (N-3581: CH₂COONHCH₃, 4-F-Ph, O, S), (N-3582: CH₂COONHCH₃, 4-Br-Ph, O, S), (N-3583: CH₂COONHCH₃, 5-Cl-thiophene-2-yl, O, S), (N-3584: CH₂COONHCH₃, 3,4-diF-Ph, O, S), (N-3585: CH₂COONHCH₃, 5-Br-thiophene-2-yl, O, S), (N-3586: CH₂COONHCH₃, 3,4-diBr-Ph, O, S), (N-3587: CH₂COONHCH₃, 4-CF₃-Ph, O, S), (N-3588: CH₂COONHCH₃, 3-Cl-Ph, O, S), (N-3589: CH₂COONHCH₃, 3-Br-Ph, O, S), (N-3590: CH₂COONHCH₃, 3-F-Ph, O, S), (N-3591: CH₂CH₂Cl, 4-F-Ph, O, S), (N-3592: CH₂CH₂Cl, 4-Br-Ph, O, S), (N-3593: CH₂CH₂Cl, 5-Cl-thiophene-2-yl, O, S), (N-3594: CH₂CH₂Cl, 3,4-diF-Ph, O, S), (N-3595: CH₂CH₂Cl, 5-Br-thiophene-2-yl, O, S), (N-356: CH₂CH₂Cl, 3,4-diBr-Ph, O, S), (N-3597: CH₂CH₂Cl, 4-CF₃-Ph, O, S), (N-3598: CH₂CH₂Cl, 3-Cl-Ph, O, S), (N-3599: CH₂CH₂Cl, 3-Br-Ph, O, S), (N-3600: CH₂CH₂Cl, 3-F-Ph, O, S), (N-3601: CONH₂, 4-F-Ph, O, O), (N-3602: CONH₂, 4-Br-Ph, O, O), (N-3603: CONH₂, 5-Cl-thiophene-2-yl, O, O), (N-3604: CONH₂, 3,4-diF-Ph, O, O), (N-3605: CONH₂, 5-Br-thiophene-2-yl, O, O), (N-3606: CONH₂, 3,4-diBr-Ph, O, O), (N-3607: CONH₂, 4-CF₃-Ph, O, O), (N-3608: CONH₂, 3-Cl-Ph, O, O), (N-3609: CONH₂, 3-Br-Ph, O, O), (N-3610: CONH₂, 3-F-Ph, O, O), (N-3611: CO₂NHCH₃, 4-F-Ph, O, O), (N-3612: CO₂NHCH₃, 4-Br-Ph, O, O), (N-3613: CO₂NHCH₃, 5-Cl-thiophene-2-yl, O, O), (N-3614:

CO₂NHCH₃, 3,4-diF-Ph, O, O), (N-3615: CO₂NHCH₃, 5-Br-thiophene-2-yl, O, O), (N-3616: CO₂NHCH₃, 3,4-diBr-Ph, O, O), (N-3617: CO₂NHCH₃, 4-CF₃-Ph, O, O), (N-3618: CO₂NHCH₃, 3-Cl-Ph, O, O), (N-3619: CO₂NHCH₃, 3-Br-Ph, O, O), (N-3620: CO₂NHCH₃, 3-F-Ph, O, O), (N-3621: CO₂N(CH₃)₂, 4-F-Ph, O, O), (N-3622: CO₂N(CH₃)₂, 4-Br-Ph, O, O), (N-3623: CO₂N(CH₃)₂, 5-Cl-thiophene-2-yl, O, O), (N-3624: CO₂N(CH₃)₂, 3,4-diF-Ph, O, O), (N-3625: CO₂N(CH₃)₂, 5-Br-thiophene-2-yl, O, O), (N-3626: CO₂N(CH₃)₂, 3,4-diBr-Ph, O, O), (N-3627: CO₂N(CH₃)₂, 4-CF₃-Ph, O, O), (N-3628: CO₂N(CH₃)₂, 3-Cl-Ph, O, O), (N-3629: CO₂N(CH₃)₂, 3-Br-Ph, O, O), (N-3630: CO₂N(CH₃)₂, 3-F-Ph, O, O), (N-3631: CO₂H, 4-F-Ph, O, O), (N-3632: CO₂H, 4-Br-Ph, O, O), (N-3633: CO₂H, 5-Cl-thiophene-2-yl, O, O), (N-3634: CO₂H, 3,4-diF-Ph, O, O), (N-3635: CO₂H, 5-Br-thiophene-2-yl, O, O), (N-3636: CO₂H, 3,4-diBr-Ph, O, O), (N-3637: CO₂H, 4-CF₃-Ph, O, O), (N-3638: CO₂H, 3-Cl-Ph, O, O), (N-3639: CO₂H, 3-Br-Ph, O, O), (N-3640: CO₂H, 3-F-Ph, O, O), (N-3641: NH₂, 4-F-Ph, O, O), (N-3642: NH₂, 4-Br-Ph, O, O), (N-3643: NH₂, 5-Cl-thiophene-2-yl, O, O), (N-3644: NH₂, 3,4-diF-Ph, O, O), (N-3645: NH₂, 5-Br-thiophene-2-yl, O, O), (N-3646: NH₂, 3,4-diBr-Ph, O, O), (N-3647: NH₂, 4-CF₃-Ph, O, O), (N-3648: NH₂, 3-Cl-Ph, O, O), (N-3649: NH₂, 3-Br-Ph, O, O), (N-3650: NH₂, 3-F-Ph, O, O), (N-3651: CH₂COOMe, 4-F-Ph, O, O), (N-3652: CH₂COOMe, 4-Br-Ph, O, O), (N-3653: CH₂COOMe, 5-Cl-thiophene-2-yl, O, O), (N-3654: CH₂COOMe, 3,4-diF-Ph, O, O), (N-3655: CH₂COOMe, 5-Br-thiophene-2-yl, O, O), (N-3656: CH₂COOMe, 3,4-diBr-Ph, O, O), (N-3657: CH₂COOMe, 4-CF₃-Ph, O, O), (N-3658: CH₂COOMe, 3-Cl-Ph, O, O), (N-3659: CH₂COOMe, 3-Br-Ph, O, O), (N-3660: CH₂COOMe, 3-F-Ph, O, O), (N-3661: CH₂CH₂COOMe, 4-F-Ph, O, O), (N-3662: CH₂CH₂COOMe, 4-Br-Ph, O, O), (N-3663: CH₂CH₂COOMe, 5-Cl-thiophene-2-yl, O, O), (N-3664: CH₂CH₂COOMe, 3,4-diF-Ph, O, O), (N-3665: CH₂CH₂COOMe, 5-Br-thiophene-2-yl, O, O), (N-3666: CH₂CH₂COOMe, 3,4-diBr-Ph, O, O), (N-3667: CH₂CH₂COOMe, 4-CF₃-Ph, O, O), (N-3668: CH₂CH₂COOMe, 3-Cl-Ph, O, O), (N-3669: CH₂CH₂COOMe, 3-Br-Ph, O, O), (N-3670: CH₂CH₂COOMe, 3-F-Ph, O, O), (N-3671: CH₂COONH₂, 4-F-Ph, O, O), (N-3672: CH₂COONH₂, 4-Br-Ph, O, O), (N-3673: CH₂COONH₂, 5-Cl-thiophene-2-yl, O, O), (N-3674: CH₂COONH₂, 3,4-diF-Ph, O, O), (N-3675: CH₂COONH₂, 5-Br-thiophene-2-yl, O, O), (N-3676: CH₂COONH₂, 3,4-diBr-Ph, O, O), (N-3677: CH₂COONH₂, 4-CF₃-Ph, O, O), (N-3678: CH₂COONH₂, 3-Cl-Ph, O, O), (N-3679: CH₂COONH₂, 3-Br-Ph, O, O), (N-3680: CH₂COONH₂, 3-F-Ph, O, O), (N-3681: CH₂COONHCH₃, 4-F-Ph, O, O), (N-3682: CH₂COONHCH₃, 4-Br-Ph, O, O), (N-3683: CH₂COONHCH₃, 5-Cl-thiophene-2-yl, O, O), (N-3684: CH₂COONHCH₃, 3,4-diF-Ph, O, O), (N-3685: CH₂COONHCH₃, 5-Br-thiophene-2-yl, O, O), (N-3686: CH₂COONHCH₃, 3,4-diBr-Ph, O, O), (N-3687: CH₂COONHCH₃, 4-CF₃-Ph, O, O), (N-3688: CH₂COONHCH₃, 3-Cl-Ph, O, O), (N-3689: CH₂COONHCH₃, 3-Br-Ph, O, O), (N-3690: CH₂COONHCH₃, 3-F-Ph, O, O), (N-3691: CH₂CH₂Cl, 4-F-Ph, O, O), (N-3692: CH₂CH₂Cl, 4-Br-Ph, O, O), (N-3693: CH₂CH₂Cl, 5-Cl-thiophene-2-yl, O, O), (N-3694: CH₂CH₂Cl, 3,4-diF-Ph, O, O), (N-3695: CH₂CH₂Cl, 5-Br-thiophene-2-yl, O, O), (N-3696: CH₂CH₂Cl, 3,4-diBr-Ph, O, O), (N-3697: CH₂CH₂Cl, 4-CF₃-Ph, O, O), (N-3698: CH₂CH₂Cl, 3-Cl-Ph, O, O), (N-3699: CH₂CH₂Cl, 3-Br-Ph, O, O), (N-3700: CH₂CH₂Cl, 3-F-Ph, O, O), (N-3701: 4-NH₂-Ph, H, S, S), (N-3702: 4-N(Ac)H-Ph, H, S, S), (N-3703: 4-OH-Ph, H, S, S), (N-3704: 3,4-di(OH)₂-Ph, H, S, S), (N-3705: 3,4-di(NH₂)₂-Ph, H, S, S), (N-3706: 3:4-[N(Ac)H]₂-Ph, H, S, S), (N-3707: 4-SH-Ph, H, S, S), (N-3708: 4-SMe-Ph, H, S, S), (N-3709: 3,4-diBr-Ph, H, S, S), (N-3710: 4-N(Me)H-Ph, H, S, S), (N-3711: 4-N(Me)₂-Ph, H, S, S), (N-3712: 4-N(Me)₃+-Ph, H, S, S), (N-3713: 4-Et-Ph, H, S, S), (N-3714: 4-iPr-Ph, H, S, S), (N-3715: 4-nPr-Ph, H, S, S), (N-3716: 4-nBu-Ph, H, S, S), (N-3717: 4-iBu-Ph, H, S, S), (N-3718: 3,4-diMe-Ph, H, S, S), (N-3719: 1,3-Benzodioxole-5-yl, H, S, S), (N-3720: N-Me-pyridinium-4-yl, H, S, S), (N-3721: N-Me-pyridinium-3-yl, H, S, S), (N-3722: 5-Me-Pyridine-2-yl, H, S, S), (N-3723: 2-Pyrazinyl, H, S, S), (N-3724: 3-Pyrrolyl, H, S, S), (N-3725: 1-Me-pyrrole-3-yl, H, S, S), (N-3726: Pyridine N-oxide-4-yl, H, S, S), (N-3727: Pyridine N-oxide-3-yl, H, S, S), (N-3728: 6-OH-pyridine-3-yl, H, S, S), (N-3729: 6-SH-pyridine-3-yl, H, S, S), (N-3730: 1-Ac-pyrrole-3-yl, H, S, S), (N-3731: 4-CF₃-Ph, H, S, S), (N-3732: 4-CN-Ph, H, S, S), (N-3733: 4-CHO-Ph, H, S, S), (N-3734: 3-Cl-Ph, H, S, S), (N-3735: 3-Br-Ph, H, S, S), (N-3736: 3-F-Ph, H, S, S), (N-3737: 3-I-Ph, H, S, S), (N-3738: 4-I-Ph, H, S, S), (N-3739: 4-OCF₃-Ph, H, S, S), (N-3740: 3,4-diI-Ph, H, S, S), (N-3741: Indole-6-yl, H, S, S), (N-3742: 1-Ac-indole-6-yl, H, S, S), (N-3743: 1-Me-indole-6-yl, H, S, S), (N-3744: 4-(1-Imidazolyl)-Ph, H, S, S), (N-3745: 4-Morphorino-Ph, H, S, S), (N-3746: 4-(1-Piperazinyl)-Ph, H, S, S), (N-3747: 2:5-diMe-thiophene-3-yl, H, S, S), (N-3748: 2-Furyl, H, S, S), (N-3749: 5-Me-furan-2-yl, H, S, S), (N-3750: 5-Me-furan-2-yl, H, S, S), (N-3751: 2-Thiazolyl, H, S, S), (N-3752: 1:4-Benzodioxin-6-yl, H, S, S), (N-3753: Benzo[b]furan-2-yl, H, S, S), (N-3754: 4-NH₂CH₂-Ph, H, S, S), (N-3755: 4-N(Me)HCH₂-Ph, H, S, S), (N-3756: 4-N(Me)₂CH₂-Ph, H, S, S), (N-3757: 6-Cl-pyridine-3-yl, H, S, S), (N-3758: 5,6-diCl-pyridine-3-yl, H, S, S), (N-3759: 5-Cl-pyridine-2-yl, H, S, S), (N-3760: 4:5-diCl-pyridine-2-yl, H, S, S), (N-3761: 4-ClCH₂-Bn, H, S, S), (N-3762: Bn, H, S, S), (N-3763: 4-Cl-Bn, H, S, S), (N-3764: 4-Br-Bn, H, S, S), (N-3765: 4-F-Bn, H, S, S), (N-3766: 3,4-diCl-Bn, H, S, S), (N-3767: 3,4-diBr-Bn, H, S, S), (N-3768: 3,4-diF-Bn, H, S, S), (N-3769: 4-Cl-Bz, H, S, S), (N-3770: 3,4-diCl-Bz, H, S, S), (N-3771: 4-Br-Bz, H, S, S), (N-3772: 3,4-diBr-Bz, H, S, S), (N-3773: 4-F-Bz, H, S, S), (N-3774: 3,4-diF-Bz, H, S, S), (N-3775: 4-NH₂-Ph, H, S, O), (N-3776: 4-N(Ac)H-Ph, H, S, O), (N-3777: 4-OH-Ph, H, S, O), (N-3778: 3,4-di(OH)₂-Ph, H, S, O), (N-3779: 3,4-di(NH₂)-Ph, H, S, O), (N-3780: 3:4-[N(Ac)H]₂-Ph, H, S, O), (N-3781: 4-SH-Ph, H, S, O), (N-3782: 4-SMe-Ph, H, S, O), (N-3783: 3,4-diBr-Ph, H, S, O), (N-3784: 4-N(Me)H-Ph, H, S, O), (N-3785: 4-N(Me)₂-Ph, H, S, O), (N-3786: 4-N(Me)₃+-Ph, H, S, O), (N-3787: 4-Et-Ph, H, S, O), (N-3788: 4-iPr-Ph, H, S, O), (N-3789: 4-nPr-Ph, H, S, O), (N-3790: 4-nBu-Ph, H, S, O), (N-3791: 4-iBu-Ph, H, S, O), (N-3792: 3,4-diMe-Ph, H, S, O), (N-3793: 1,3-Benzodioxole-5-yl, H, S, O), (N-3794: N-Me-pyridinium-4-yl, H, S, O), (N-3795: N-Me-pyridinium-3-yl, H, S, O), (N-3796: 5-Me-Pyridine-2-yl, H, S, O), (N-3797: 2-Pyrazinyl, H, S, O), (N-3798: 3-Pyrrolyl, H, S, O), (N-3799: 1-Me-pyrrole-3-yl, H, S, O), (N-3800: Pyridine N-oxide-4-yl, H, S, O), (N-3801: Pyridine N-oxide-3-yl, H, S, O), (N-3802: 6-OH-pyridine-3-yl, H, S, O), (N-3803: 6-SH-pyridine-3-yl, H, S, O), (N-3804: 1-Ac-pyrrole-3-yl, H, S, O), (N-3805: 4-CF₃-Ph, H, S, O), (N-3806: 4-CN-Ph, H, S, O), (N-3807: 4-CHO-Ph, H, S, O), (N-3808: 3-Cl-Ph, H, S, O), (N-3809: 3-Br-Ph, H, S, O), (N-3810: 3-F-Ph, H, S, O), (N-3811: 3-I-Ph, H, S, O), (N-3812: 4-I-Ph, H, S, O), (N-3813: 4-OCF₃-Ph, H, S, O), (N-3814: 3,4-diI-Ph, H, S, O), (N-3815: Indole-6-yl, H, S, O), (N-3816: 1-Ac-indole-6-yl, H, S, O), (N-3817: 1-Me-indole-6-yl, H, S, O), (N-3818: 4-(1- Imidazolyl)-Ph, H, S, O), (N-3819: 4-Morphorino-Ph, H, S, O), (N-3820: 4-(1-Piperazinyl)-Ph, H, S, O), (N-3821: 2:5-diMe-thiophene-3-yl, H, S, O), (N-3822: 2-Furyl, H, S, O), (N-3823: 5-Me-furan-2-yl, H, S, O), (N-3824: 5-Me-furan-2-yl, H, S, O), (N-3825: 2-Thiazolyl, H, S, O), (N-3826: 1:4-Benzodioxin-6-yl, H, S, O), (N-3827: Benzo[b]furan-2-yl, H, S, O), (N-3828: 4-$NH_2CH_2$-Ph, H, S, O), (N-3829: 4-N(Me)$HCH_2$-Ph, H, S, O), (N-3830: 4-N(Me)$_2CH_2$-Ph, H, S, O), (N-3831: 6-Cl-pyridine-3-yl, H, S, O), (N-3832: 5,6-diCl-pyridine-3-yl, H, S, O), (N-3833: 5-Cl-pyridine-2-yl, H, S, O), (N-3834: 4:5-diCl-pyridine-2-yl, H, S, O), (N-3835: 4-$ClCH_2$-Bn, H, S, O), (N-3836: Bn, H, S, O), (N-3837: 4-Cl-Bn, H, S, O), (N-3838: 4-Br-Bn, H, S, O), (N-3839: 4-F-Bn, H, S, O), (N-3840: 3,4-diCl-Bn, H, S, O), (N-3841: 3,4-diBr-Bn, H, S, O), (N-3842: 3,4-diF-Bn, H, S, O), (N-3843: 4-Cl-Bz, H, S, O), (N-3844: 3,4-diCl-Bz, H, S, O), (N-3845: 4-Br-Bz, H, S, O), (N-3846: 3,4-diBr-Bz, H, S, O), (N-3847: 4-F-Bz, H, S, O), (N-3848: 3,4-diF-Bz, H, S, O), (N-3849: 4-$NO_2$-Bn, H, S, O), (N-3850: 4-CN-Bn, H, S, O)

Test Example 1
Isolation and Purification of Thrombopoietin (TPO)

Human TPO (hTPO) and murine TPO (mTPO) were purchased from R&D Systems.

Test Example 2 The increasing effect in vitro of the megakaryocyte colonies with the compound (A-1), (B-17), and (C-1)

We examined the ability of the compound in promoting differentiation of human hematopoietic progenitor cells into mature megakaryocytes. Human bone marrow cells (2.2+$10^5$ cells) were plated in 3-cm dishes and cultured in methylcellulose in Iscove's Modified Dulbecco's medium in the presence of 1% of the compound (A-1, B-17, C-1) dissolved in 10% ethanol. After incubation at 37° C. for 7 days in the 5% $CO_2$ incubator, the megakaryocyte colonies were counted. The result is shown in FIG. 1.

Test Example 3 The Thrombopoietic Activity of the Compound (B-17)

Figure 2:
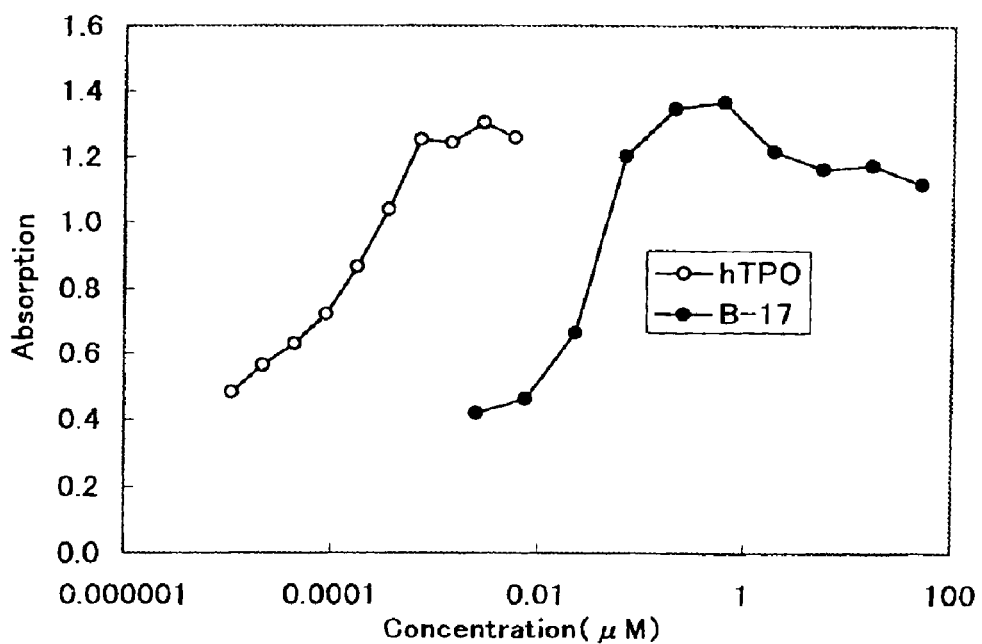
FIG. 2: The chart represents proliferation of the human TPO dependent cells manifesting human TPO receptors by the present invention compound, wherein the x-axis is concentration of the present invention compound, and the y-axis is absorption as an indicator of cell proliferation. White circle is a response of human TPO, and black circle is a response of the compound (B-17).
Figure 3:
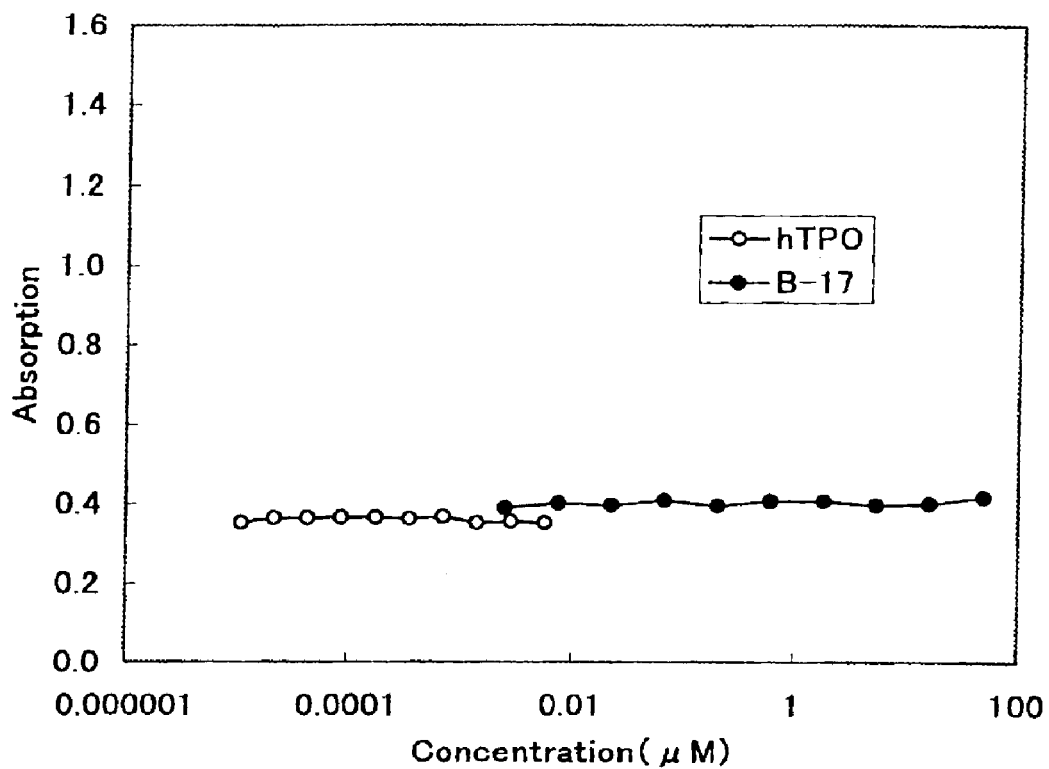
FIG. 3: The chart represents proliferation of the human TPO independent cell manifesting no human TPO receptor by the present invention compound, wherein the x-axis is a concentration of the present invention compound, and the y-axis is absorption as an indicator of cell proliferation. White circle is a response of human TPO, and black circle is a response of the compound (B-17).
Figure 4:
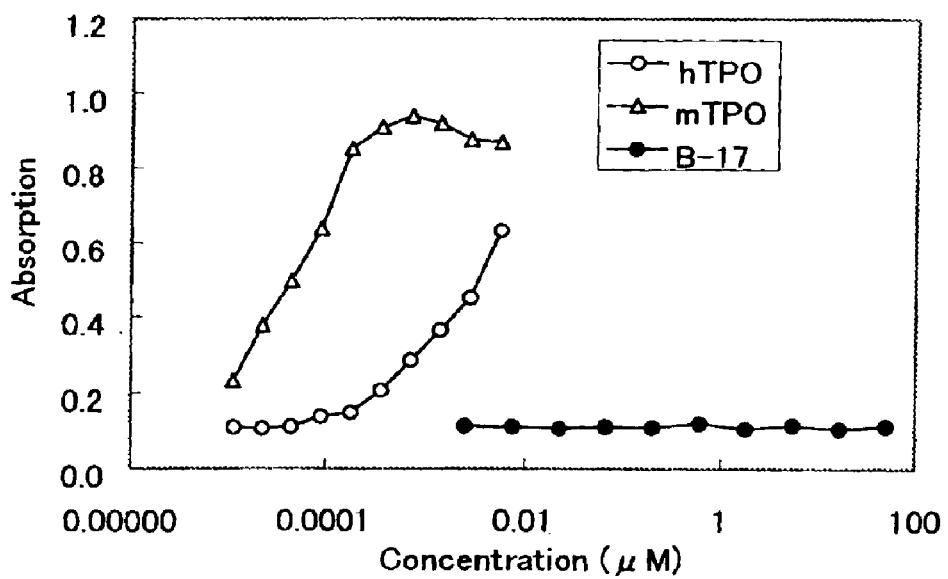
FIG. 4: The chart represents proliferation of the murine TPO independent cell manifesting murine TPO receptor by the present invention compound, wherein the x-axis is a concentration of the present invention compound, and the y-axis is absorption as an indicator of cell proliferation. White circle is a response of human TPO, and black circle is a response of the compound (B-17)

The TPO dependent BaF/hTPOR cell line which was established by introducing human TPO receptor (hTPOR) into BaF-BO3 cells according to Collins et al (J. Cell. Physiol., 137:293–298 (1988)) was used to test the thrombopoietic activity of the present compound (B-17). The DNA sequences and encoded peptide sequences for human hTPOR have been described by Vigon et al (Proc. Natl. Acad. Sci. USA, 89:5640–5644 (1992)). TPO dose not have any ability to support proliferation of interlukin-3 dependent parental cell line BaF-BO3. BAF/hTPOR cells were maintained in RPMI medium and WEHI-3B conditioned medium as a source of murine interleukin-3 (IL-3). These cells were washed and resuspended in RPMI medium without a source of murine IL-3 and seeded into each well of 96-well microtiter plates at a density of 5+$10^4$ cells per well in the absence or presence of various concentration of hTPO or the present compound. After incubation at 37° C. for 20 hours in the 5% $CO_2$ incubator, 10% WST-1 reagent (Takara Biomedicals, Japan) was added to each wells and the cells were further incubated for 4 hours. The absorbance at 450 nm was measured and the result is shown in FIG. 2. Effect of the present compound on the growth of the parental cell line BaF-BO3 not expressing TPOR is shown in FIG. 3. Effect of the present compound on the growth of the BaF-BO3 expressing murine TPOR is shown in FIG. 4. Table 24 exemplifies the $ED_{50}$ for tested compounds of the present invention, wherein the $ED_{50}$ is the half concentration of the concentration showing the maximum thrombopoietic activity

TABLE 24

| Compound No. | $ED_{50}$ (μM) |
|---|---|
| A-1 | 0.012 |
| A-2 | 0.058 |
| A-3 | 0.017 |
| A-4 | 0.036 |
| A-5 | 0.022 |
| A-6 | 0.045 |
| A-7 | 0.060 |
| A-11 | 0.031 |
| A-12 | 0.011 |
| A-13 | 0.021 |
| A-14 | 0.015 |
| A-15 | 0.026 |
| A-16 | 0.049 |
| A-20 | 0.029 |
| A-21 | 0.041 |
| A-25 | 0.099 |
| A-26 | 0.072 |
| A-32 | 0.077 |
| A-37 | 0.027 |
| A-38 | 0.047 |
| A-42 | 0.072 |
| A-43 | 0.073 |
| A-49 | 0.035 |
| A-50 | 0.026 |
| A-53 | 0.023 |
| A-56 | 0.096 |
| A-59 | 0.084 |
| A-61 | 0.069 |
| A-63 | 0.016 |
| A-64 | 0.047 |
| A-67 | 0.050 |
| A-70 | 0.020 |
| A-71 | 0.080 |
| A-72 | 0.035 |
| A-73 | 0.070 |
| B-1 | 0.071 |
| B-2 | 0.011 |
| B-3 | 0.047 |
| B-4 | 0.037 |
| B-5 | 0.047 |
| B-6 | 0.072 |
| B-14 | 0.023 |
| B-15 | 0.077 |
| B-16 | 0.020 |
| B-17 | 0.030 |
| B-18 | 0.016 |
| B-21 | 0.084 |
| C-1 | 0.068 |
| E-2 | 0.062 |
| H-5 | 0.047 |

Test Example 4 The Compound(B-17)-Induced Signal Transduction via hTPOR

Drachman et al (J. Biol. Chem, 270: 4979–4982 (1995)) reported that TPO induced tyrosine phosphorylation of Jak2, Shc, and c-Mpl. To compare the signaling pathway of TPO and the compound of the present invention, we analyzed the tyrosine phosphorylation of signal transducers by stimulation of the compound according to the method reported by Drachman. Briefly, BaF/hTPOR cells suspended in the RPMI medium (1+$10^7$ cells/ml) without WEHI-3B were incubated for 4 hours at 37° C. 25 ng/ml of TPO or 200 nM of the compound (B-17) was added to cells and incubated for 10 min at 37° C. After the cells were washed twice with PBS then lysed in a buffer composed of 1% Triton X-100. After the sample were spun in a centrifuge and the supernatant were immunoprecipitated by using antibodies against several proteins related to intracellular signal transduction. Immune complexes were separated by SDS-polyacrylamide gel electrophoresis. Protein was electrophoretically transferred to nitrocellulose sheets and tyrosine phosphorylated protein was detected by anti-phosphotyrosine antibody. Results were summarized in Table 25.

TABLE 25

|  | Vehicle | Compound (B-17) | TPO |
|---|---|---|---|
| Jak1 | − | − | − |
| Jak2 | − | + | + |
| Jak3 | − | − | − |
| Tyk2 | − | + | + |
| STAT1 | − | − | − |
| STAT3 | − | + | + |
| STAT5 | − | + | + |
| STAT6 | − | − | − |
| Mpl | − | + | + |
| Shc | − | + | + |
| Cbl | − | + | + |
| Vav | − | + | + |
| Ship | − | − | − |
| SHPTP2 | − | + | + |
| PI3K | − | − | − |
| PLCγ1 | − | + | + |
| MAPK | − | + | + |
| SAPK | − | + | + |
| p38MAPK | − | + | + |

As shown in FIG. 1, addition of the compounds of the present invention induced forming megakaryocyte colonies and the number of colonies increased depending on the concentration of the compounds. This result revealed that the compounds of the present invention induced the differentiation of human bone marrow cells and produce megakaryocytes having ability of producing platelet.

The compound supported the proliferation of TPO-dependent BaF/hTPOR in a dose-dependent manner as shown in FIG. 2. Parental BaF cells bearing no TPOR was not induced the proliferation by compounds as shown in FIG. 3. BaF/mTPOR expressing murine TPOR was not induced the proliferation by compounds as shown in FIG. 4. These results suggest that the compound of the present invention exert the thrombopoietic activity by interacting with hTPOR because it is active only in cells expressing hTPOR.

As shown in Table 25, the compound induced phosphorylation of following the same intracellular signal transducing molecules as TPO did: Jak2, Tyk2, STAT3, STAT5, Shc, Vav, SHPTP2, Mpl, PLCγ1, Cbl, MAPK, SAPK, and p38MAPK. Therefore, the compounds elicit thrombopoietic activity by stimulating the signal transduction pathways identical to those of TPO.

Formulation Example
Formulation Example 1
Granules are prepared using the following ingredients.

| Ingredients | The compound represented by the formula (I) | 10 mg |
|---|---|---|
|  | Lactose | 700 mg |
|  | Corn starch | 274 mg |
|  | HPC-L | 16 mg |
|  |  | 1000 mg |

The compound represented by the formula (I) and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation 2
Powders for filling capsules are prepared using the following ingredients.

| Ingredients | The compound represented by the formula (I) | 10 mg |
|---|---|---|
|  | Lactose | 79 mg |
|  | Corn starch | 10 mg |
|  | Magnesium stearate | 1 mg |
|  |  | 100 mg |

The compound represented by the formula (I) and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation 3
Granules for filling capsules are prepared using the following ingredients.

| Ingredients | The compound represented by the formula (I) | 15 mg |
|---|---|---|
|  | Lactose | 90 mg |
|  | Corn starch | 42 mg |
|  | HPC-L | 3 mg |
|  |  | 150 mg |

The compound represented by the formula (I) and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

Formulation 4
Tablets are prepared using the following ingredients.

| Ingredients | The compound represented by the formula (I) | 10 mg |
|---|---|---|
|  | Lactose | 90 mg |
|  | Microcrystal cellulose | 30 mg |
|  | CMC-Na | 15 mg |
|  | Magnesium stearate | 5 mg |
|  |  | 150 mg |

The compound represented by the formula (I), lactose, microcrystal cellulose, and CMC—Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

INDUSTRIAL APPLICABILITY

The compounds of the present invention have thrombopoietin receptor agonism and are useful as the treating or preventing agent for hemopathy accompanied with unusual count of platelet, for example, thrombocytopenia and the like.

What is claimed is:

1. A compound represented by the formula (II):

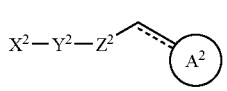
(II)

or its prodrug; or a pharmaceutically acceptable salt or solvate thereof, wherein $X^2$ is an optionally substituted 5-member thiazole ring:

$Y^2$ is $-NR^GCO-(CH_2)_{0-2}-$, wherein $R^G$ is a hydrogen atom or an optionally substituted lower alkyl;

$Z^2$ is an optionally substituted phenylene;

$A^2$ is a thiazolidine ring represented by the formula:

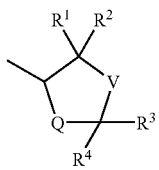

wherein $R^1$ and $R^2$ are both hydrogen atoms or taken together may form an oxygen atom or a sulfur atom, $R^3$ and $R^4$ are both hydrogen atoms or taken together may form an oxygen atom or a sulfur atom, Q and V are chosen from $-S-$, and $-NR-$, wherein $R^B$ is a hydrogen atom or lower alkyl; and a broken line ( - - - ) represents the presence or absence of a bond.

2. A compound according to claim 1, wherein $X^2$ is a group represented by the formula:

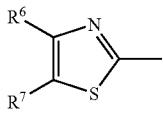

wherein $R^6$ and $R^7$ are each independently a hydrogen atom, an optionally substituted lower alkyl, carboxy, a lower alkyloxycarbonyl, an optionally substituted aminocarbonyl, an optionally substituted thienyl, or an optionally substituted phenyl.

3. A compound according to claim 1, wherein $X^2$ is a group represented by the formula:

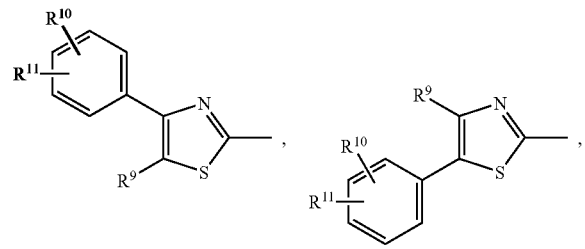

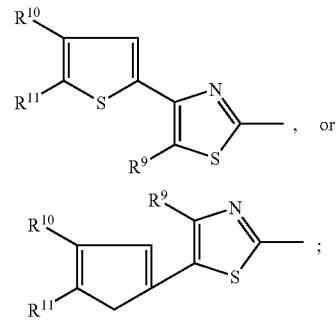

$R^9$ is a hydrogen atom, an optionally substituted lower alkyl, a carboxy, a lower alkyloxycarbonyl, or an optionally substituted aminocarbonyl;

$R^{10}$ and $R^{11}$ are each independently a hydrogen atom, halogen, carboxy, lower alkyloxycarbonyl, optionally substituted aminocarbonyl, nitro, or optionally substituted amino.

4. A compound according to any one of claims 1 to 3, wherein $Y^2$ is $-NHCO-$.

5. A compound according to any one of claims 1 to 3, wherein $Z^2$ is 1,4-phenylene.

6. A compound of any one of claims 1 to 3, wherein $A^2$ is a ring represented by the formula:

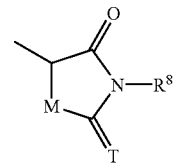

wherein $R^8$ is a hydrogen atom or lower alkyl; M is $-S-$; and T is an oxygen atom or a sulfur atom.

7. A compound according to any one of claims 1 to 3, wherein the broken line represents the presence of a bond.

8. A compound represented by the formula III-A:

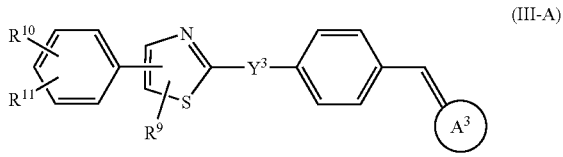
(III-A)

or its prodrug; or a pharmaceutically acceptable salt or solvate thereof, wherein $R^9$ is a hydrogen atom, an optionally substituted lower alkyl, a carboxy, a lower alkyloxycarbonyl, or an optionally substituted aminocarbonyl; $R^{10}$ and $R^{11}$ are each independently a hydrogen atom, halogen, carboxy, lower alkyloxycarbonyl, optionally substituted aminocarbonyl, nitro, or optionally substituted amino;

$Y^3$ is $-NHCO-$; and $A^3$ is a ring represented by the formula:

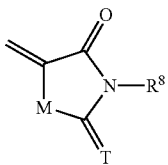

wherein $R^8$ is a hydrogen atom or lower alkyl; M is —S—; and T is an oxygen atom or a sulfur atom.

9. A compound represented by the formula III-B:

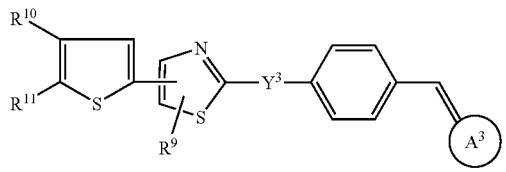

(III-B)

or its prodrug; or a pharmaceutically acceptable salt or solvate thereof, wherein $R^9$ is a hydrogen atom, an optionally substituted lower alkyl, a carboxy, a lower alkyloxycarbonyl, or an optionally substituted aminocarbonyl;

$R^{10}$ and $R^{11}$ are each independently a hydrogen atom, halogen, carboxy, lower alkyloxycarbonyl, optionally substituted aminocarbonyl, nitro, or optionally substituted amino;

$Y^3$ is —NHCO—; and $A^3$ is a ring represented by the formula:

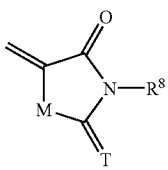

wherein $R^8$ is a hydrogen atom or lower alkyl; M is —S—; and T is an oxygen atom or a sulfur atom.

10. A pharmaceutical composition containing at least one compound according to any one of claims 1 to 3, 8, or 9 as an active ingredient.

11. A pharmaceutical composition for exhibiting thrombopoietin agonism comprising as an active ingredient at least one compound according to any one of claims 1 to 3, 8, or 9.

12. A pharmaceutical composition comprising at least one compound according to any one of claims 1 to, 3, 8 or 9, wherein the compound is a platelet production modifier.

13. A thrombopoietin receptor agonist composition comprising as an active ingredient a compound of the formula (I):

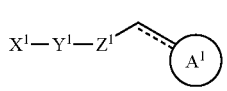

(I)

or its prodrug; or a pharmaceutically acceptable salt or solvate thereof, wherein $X^1$ is an optionally substituted thiazole ring;

$Y^1$ is —$NR^4CO$—$(CH_2)_{0-2}$—, wherein $R^4$ is a hydrogen atom, an optionally substituted lower alkyl, an optionally substituted aryl, an optionally substituted aralkyl, an optionally substituted heteroaryl, or an optionally substituted heteroarylalkyl;

$Z^1$ is an optionally substituted phenylene;

$A^1$ is a thiazolidine ring represented by the formula:

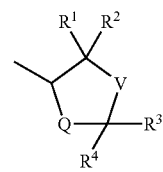

wherein $R^1$ and $R^2$ are both hydrogen atoms or taken together may form an oxygen atom or a sulfur atom; $R^3$ and $R^4$ are both hydrogen atoms or taken together may form an oxygen atom or a sulfur atom; $R^5$ is a hydrogen atom or lower alkyl; Q and V are chosen from —S— and —$NR^8$—, wherein $R^8$ is a hydrogen atom or lower alkyl; and a broken line ( - - - ) represents the presence or absence of a bond.

14. A thrombopoietin receptor agonist composition according to claim 13, wherein $X^1$ is a group represented by the formula:

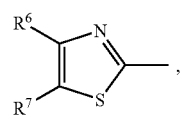

wherein $R^6$ and $R^7$ are each independently a hydrogen atom, optionally substituted lower alkyl, carboxy, lower alkyloxycarbonyl, optionally substituted aminocarbonyl, optionally substituted thienyl, or optionally substituted phenyl.

15. A thrombopoietin receptor agonist composition according to any one of claim 13 or 14, wherein $Y^1$ is —NHCO—.

16. A thrombopoietin receptor agonist composition according to any one of claim 13 or 14, wherein $Z^1$ is 1,4-phenylene.

17. A thrombopoietin receptor agonist composition according to of any one of claim 13 or 14, wherein $A^1$ is a ring represented by the formula:

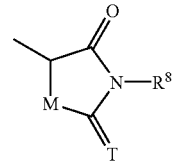

wherein $R^8$ is a hydrogen atom or lower alkyl; M is —S—;

and T is an oxygen atom or a sulfur atom.

18. A thrombopoietin receptor agonist composition according to any one of claim 13 or 14, wherein the broken line represents the presence of a bond.

* * * * *

UNITED STATES PATENT AND TRADEMARK OFFICE
CERTIFICATE OF CORRECTION

PATENT NO. : 7,026,334 B1 Page 1 of 1
APPLICATION NO. : 10/048008
DATED : April 11, 2006
INVENTOR(S) : Hiroshi Takemoto et al.

It is certified that error appears in the above-identified patent and that said Letters Patent is hereby corrected as shown below:

In claim 1, column 107, line 13, "ring:" should read --ring;--.

In claim 1, column 107, line 34, "atom," should read --atom;--.

In claim 1, column 107, line 35, "-NR-," should read -- -NR$^B$-, --.

In claim 3, column 107, line 56, "formula" should read --formulae--.

In claim 12, column 109, line 55, "claims 1 to, 3, 8 or 9," should read --claims 1 to 3, 8, or 9,--.

In claim 13, column 110, line 23, "-NR$^8$-, wherein R$^8$" should read -- -NR$^B$-, wherein R$^B$--.

In claim 15, column 110, line 43, "claim" should read --claims--.

In claim 16, column 110, line 46, "claim" should read --claims--.

In claim 17, column 110, line 49, "to of any" should read --to any--.

In claim 17, column 110, line 49, "claim" should read --claims--.

In claim 18, column 110, line 64, "claim" should read --claims--.

Signed and Sealed this

Fifth Day of September, 2006

JON W. DUDAS
*Director of the United States Patent and Trademark Office*